US012774485B2

(12) United States Patent
Mellor et al.

(10) Patent No.: US 12,774,485 B2
(45) Date of Patent: Oct. 27, 2026

(54) COMPOSITIONS AND METHODS FOR SEQUENCING NUCLEIC ACIDS

(71) Applicant: seqWell, Inc., Beverly, MA (US)

(72) Inventors: Joseph C. Mellor, Melrose, MA (US); Jack T. Leonard, South Hamilton, MA (US)

(73) Assignee: seqWell, Inc., Beverly, MA (US)

( * ) Notice: Subject to any disclaimer, the term of this patent is extended or adjusted under 35 U.S.C. 154(b) by 49 days.

(21) Appl. No.: 16/486,091

(22) PCT Filed: Feb. 14, 2018

(86) PCT No.: PCT/US2018/018235
§ 371 (c)(1),
(2) Date: Aug. 14, 2019

(87) PCT Pub. No.: WO2018/152244
PCT Pub. Date: Aug. 23, 2018

(65) Prior Publication Data

US 2020/0002746 A1 Jan. 2, 2020

Related U.S. Application Data

(60) Provisional application No. 62/458,893, filed on Feb. 14, 2017.

(51) Int. Cl.
*C12Q 1/6806* (2018.01)
*C12N 15/10* (2006.01)
*C12Q 1/6869* (2018.01)

(52) U.S. Cl.
CPC ....... *C12Q 1/6806* (2013.01); *C12N 15/1082* (2013.01); *C12Q 1/6869* (2013.01)

(58) Field of Classification Search
CPC .... C12N 15/1065; C12N 15/10; C12N 15/11; C12N 15/1082; C12Q 1/68; C12Q 1/6869; C12Q 1/6806; C40B 40/06; C40B 40/08
See application file for complete search history.

(56) References Cited

U.S. PATENT DOCUMENTS 5,750,341 A 5/1998 Macevicz
5,925,545 A 7/1999 Reznikoff et al.
5,965,443 A 10/1999 Reznikoff et al.
6,159,736 A 12/2000 Reznikoff et al.
6,255,475 B1 7/2001 Kwiatkowski
6,355,431 B1 3/2002 Chee et al.
6,613,752 B2 9/2003 Kay et al.
6,831,166 B2 12/2004 Manoharan et al.
7,181,122 B1 2/2007 Levene et al.
7,302,146 B2 11/2007 Turner et al.
7,313,308 B2 12/2007 Turner et al.
7,323,305 B2 1/2008 Leamon et al.
7,985,739 B2 7/2011 Kay et al.
8,399,643 B2 3/2013 Ostertag et al.
8,546,128 B2 10/2013 Schultz et al.
8,574,835 B2 11/2013 Hinz et al.
8,673,627 B2 3/2014 Nobile et al.
8,748,102 B2 6/2014 Berka et al.
8,765,380 B2 7/2014 Berka et al.
8,795,965 B2 8/2014 Zhang
9,074,251 B2 * 7/2015 Steemers ............. C12Q 1/6869
9,228,180 B2 1/2016 Izsvak et al.
9,234,190 B2 1/2016 Savilahti et al.
9,243,290 B2 1/2016 Edwards
9,388,430 B2 7/2016 Liu et al.
2003/0158129 A1 8/2003 Plasterk et al.
2004/0152076 A1 * 8/2004 Willson ............... C12N 15/101 536/25.4
2010/0120098 A1 5/2010 Grunenwald et al.
2010/0298170 A1 * 11/2010 Heredia ............... C12Q 1/6804 506/26
2010/0304982 A1 * 12/2010 Hinz ....................... C40B 40/08 506/17
2011/0177493 A1 7/2011 Lu
2013/0203605 A1 8/2013 Shendure et al.
2015/0111788 A1 4/2015 Fernandez et al.
2015/0291965 A1 10/2015 Zhang et al.
2016/0060691 A1 * 3/2016 Giresi .................... G16B 30/00 506/7
2016/0076092 A1 3/2016 Jayasinghe et al.
2016/0177304 A1 6/2016 Collingwood et al.
2016/0208243 A1 7/2016 Zhang et al.

(Continued)

FOREIGN PATENT DOCUMENTS

WO WO-98/40510 A1 9/1998
WO WO-99/25817 A2 5/1999

(Continued)

OTHER PUBLICATIONS

Shapiro "Molecular model for the transposition and replication of bacteriophage Mu and other transposable elements" Proc. Natl. Acad. Sci. USA, vol. 76, No. 4, pp. 1933-1937, Apr. 1979 (Year: 1979).*

(Continued)

*Primary Examiner* — Sahana S Kaup
(74) *Attorney, Agent, or Firm* — Clark & Elbing LLP

(57) ABSTRACT

The invention provides compositions including artificial nucleic acids, multivalent transposase reagents that include multivalent cores linked to artificial nucleic acids, tethered synaptic complexes (TSCs), and kits, as well as methods of using the same, for example, for preparation of nucleic acid libraries and sequencing.

26 Claims, 21 Drawing Sheets

Specification includes a Sequence Listing.

(56) References Cited

U.S. PATENT DOCUMENTS

| | | | |
|---|---|---|---|
| 2016/0251650 | A1 | 9/2016 | Steemers et al. |
| 2019/0169602 | A1 | 6/2019 | Mellor et al. |

FOREIGN PATENT DOCUMENTS

| | | | | | |
|---|---|---|---|---|---|
| WO | WO-2014/108810 | A2 | 7/2014 | | |
| WO | WO-2014/121091 | A1 | 8/2014 | | |
| WO | WO-2014142850 | A1 * | 9/2014 | ......... | C12N 15/1065 |
| WO | WO-2014/190214 | A1 | 11/2014 | | |
| WO | WO-2015/069374 | A1 | 5/2015 | | |
| WO | WO-2016061517 | A2 * | 4/2016 | ............. | C12N 15/10 |
| WO | WO-2016/196358 | A1 | 12/2016 | | |
| WO | WO-2017/015075 | A1 | 1/2017 | | |
| WO | WO-2017/123758 | A1 | 7/2017 | | |

OTHER PUBLICATIONS

Hickman et al. "DNA Transposition at Work" Chem. Rev. 2016, 116, 12758-12784; DOI: 10.1021/acs.chemrev.6b00003 (Year: 2016).*

Extended European Search Report for European Patent Application No. 18753866.5, dated Mar. 10, 2021 (7 pages).

Green et al., "Insertion site preference of Mu, Tn5, and Tn7 transposons," Mob DNA. 3(1):3 (2012).

Syed et al., "Optimized library preparation method for next-generation sequencing," Nature Methods, Nature Pub. Group. 6(10): i-ii (2009).

Abudayyeh et al., "C2c2 is a single-component programmable RNA-guided RNA-targeting CRISPR effector," Available in PMC Nov. 29, 2016, published in final edited form: Science. 353(6299):aaf5573 (2016) (23 pages).

Bhakta et al., "The generation of zinc finger proteins by modular assembly," Availble in PMC Feb. 11, 2015, published in final edited form as: Methods Mol Biol. 649:3-30 (2010) (25 pages).

Bhasin et al., "Hairpin formation in Tn5 transposition," J Biol Chem. 274(52):37021-9 (1999) (10 pages).

Boch et al., "Breaking the code of DNA binding specificity of TAL-type III effectors," Science. 326(5959):1509-1512 (2009) (5 pages).

Broom et al., "Sequence of a transposon identified as Tn1000 (gamma delta)," DNA Seq. 5(3): 185-189 (1995).

Brunner et al., "Distinct DNA methylation patterns characterize differentiated human embryonic stem cells and developing human fetal liver," Genome Res. 19(6):1044-56 (2009).

Buenrostro et al., "Transposition of native chromatin for multimodal regulatory analysis and personal epigenomics," Available in PMC Jun. 1, 2014, published in final edited form as: Nat Methods. 10(12):1213-8 (2013) (15 pages).

Cary et al., "Transposon mutagenesis of baculoviruses: Analysis of *Trichoplusia ni* transposon IFP2 insertions within the FP-locus of nuclear polyhedrosis viruses," Virology. 172(1): 156-169 (1989).

Chin et al., "Nonhybrid, finished microbial genome assemblies from long-read SMRT sequencing data," Nat Methods. 10(6): 563-569 (2013) (9 pages).

Cirulli et al., "Uncovering the roles of rare variants in common disease through whole-genome sequencing," Nat Rev Genet. 11(6): 415-425 (2010).

Cloonan et al., "Stem cell transcriptome profiling via massive-scale mRNA sequencing," Nat Mathods. 5(7):613-9 (2008).

Cockroft et al., "A single-molecule nanopore device detects DNA polymerase activity with single-nucleotide resolution," Available in PMC Jul. 10, 2008, published in final edited form as: J Am Chem Soc. 130(3):818-20 (2008) (9 pages).

Corey et al., "Sequence-selective hydrolysis of duplex DNA by an oligonucleotide-directed nuclease," J Am Chem Soc. 111(22): 8523-5 (1989).

Eid et al., "Real-time DNA sequencing from single polymerase molecules," Science. 323(5910):133-8 (2009) (7 pages).

Feng et al., "Nanopore-based fourth-generation DNA sequencing technology," Genomics Proteomics Bioinformatics. 13(1):4-16 (2015).

Feng et al., "Precise targeted integration by a chimaeric transposase zinc-finger fusion protein," Nucleic Acids Res. 38(4):1204-1216 (2010).

Fuller et al., "Real-time single-molecule electronic DNA sequencing by synthesis using polymer-tagged nucleotides on a nanopore array," Proc Natl Acad Sci U S A. 113(19):5233-8 (2016).

Gao et al., "DNA-guided genome editing using the *Natronobacterium gregoryi* Argonaute," Nat Biotechnol. 34(7): 768-773 (2016) (ePublication, DOI: 10.1038/nbt.3547) (Retracted) (7 pages).

Gawad et al., "Single-cell genome sequencing: current state of the science," Nat Rev Genet. 17(3): 175-188 (2016).

Goldhaber-Gordon et al., "DNA recognition sites activate MuA transposase to perform transposition of non-Mu DNA," J Biol Chem. 277(10):7694-702 (2002) (10 pages).

Goldhaber-Gordon et al., "Sequence and positional requirements for DNA sites in a Mu transpososome," J Biol Chem. 277(10):7703-12 (2002) (11 pages).

Goryshin et al., "DNA length, bending, and twisting constraints on IS50 transposition," Proc Natl Acad Sci U S A. 91(23):10834-8 (1994).

Guilinger et al., "Fusion of catalytically inactive Cas9 to *FokI* nuclease improves the specificity of genome modification," Available in PMC Dec. 11, 2014, published in final edited form as: Nat Biotechnol. 32(6):577-82 (2014) (17 pages).

Harshey, "Transposable phage Mu," Available in PMC Jun. 30, 2015, published in final edited form as: Microbiol Spectr. 2(5) (2014) (36 pages).

Ichikawa et al., "Specific binding of transposase to terminal inverted repeats of transposable element Tn3," Proc Natl Acad Sci U S A. 84(23):8220-4 (1987).

Imre et al., "Site-directed (IS30-FljA) transposon mutagenesis system to produce nonflagellated mutants of *Salmonella enteritidis*," FEMS Microbiol Lett. 317(1):52-9 (2011).

International Search Report and Written Opinion for International Application No. PCT/US18/18235, mailed Apr. 30, 2018 (14 pages).

Ivics et al., "Molecular reconstruction of Sleeping Beauty, a Tc1-like transposon from fish, and its transposition in human cells," Cell. 91(4):501-510 (1997).

Ivics et al., "Targeted sleeping beauty transposition in human cells," Mol Ther. 15(6):1137-44 (2007).

Jilk et al., "The organization of the outside end of transposon Tn5," J Bacteriol. 178(6):1671-9 (1996).

Johnson et al., "DNA sequences at the ends of transposon Tn5 required for transposition," Nature. 304(5923): 280-282 (1983).

Kim et al., "Genome-wide analysis reveals specificities of Cpf1 endonucleases in human cells," Nat Biotechnol. 34(8): 863-868 (2016) (ePublication, DOI: 10.1038/nbt.3609) (7 pages).

Kleinstiver et al., "Genome-wide specificities of CRISPR-Cas Cpf1 nucleases in human cells," Nat Biotechnol. Available in PMC Dec. 27, 2016, published in final edited form as: 34(8):869-74 (2016) (14 pages).

Levene et al., "Zero-mode waveguides for single-molecule analysis at high concentrations," Science. 299(5607):682-6 (2003).

Li et al., "Multi-platform and cross-methodological reproducibility of transcriptome profiling by RNA-seq in the ABRF Next-Generation Sequencing Study," Available in PMC Dec. 1, 2014, published in final edited form as: Nat Biotechnol. 32(9):915-25 (2014) (24 pages).

Lu et al., "Isolation and characterization of Tn7 transposase gain-of-function mutants: a model for transposase activation," EMBO J. 19(13):3446-57 (2000).

Maeder et al., "Rapid "open-source" engineering of customized zinc-finger nucleases for highly efficient gene modification," Available in PMC Sep. 13, 2008, published in final edited form as: Mol Cell. 31(2):294-301 (2008) (13 pages).

Maekawa et al., "Identification of the region that determines the specificity of binding of the transposases encoded by Tn3 and gamma delta to the terminal inverted repeat sequences," Jpn J Genet. 69(3):269-85 (1994).

Mali et al., "CAS9 transcriptional activators for target specificity screening and paired nickases for cooperative genome engineering," Available in PMC Mar. 1, 2014, published in final edited form as: Nat Biotechnol. 31(9):833-8 (2013) (17 pages).

(56) References Cited

OTHER PUBLICATIONS

Maragathavally et al., "Chimeric Mos1 and piggyBac transposases result in site-directed integration," FASEB J. 20(11): 1880-1882 (2006) (Summary and full text article included) (11 pages).
Margulies et al., "Genome sequencing in open microfabricated high-density picoliter reactors," available in PMC Sep. 15, 2006, published in final edited form as: Nature. 437(7057):376-80 (2005) (14 pages).
Mellor et al., "Phased NGS library generation via tethered synaptic complexes," <http://seqwell.com/wp-content/uploads/2017/02/seqWell_LongBow_poster_AGBT2017.pdf>, retrieved Aug. 15, 2017 (1 page).
Mellor et al., "Phased NGS Library Generation via Tethered Synaptic Complexes," AGBT 2017, Poster No. 303, http://seqwell.com/phased-ngs-library-generation-via-tethered-synaptic-complexes/, retreived May 4, 2017 (1 page).
Merriman et al., "Progress in ion torrent semiconductor chip based sequencing," Electrophoresis. 33(23):3397-417 (2012).
Mitra et al., "Fluorescent in situ sequencing on polymerase colonies," Anal Biochem. 320(1): 55-65 (2003).
Miyoshi et al., "Structural basis for the recognition of guide RNA and target DNA heteroduplex by Argonaute," Nat Commun. 7:11846 (2016) (10 pages).
Mizuuchi, "Transpositional recombination: mechanistic insights from studies of Mu and other elements," Annu Rev Biochem. 61(1): 1011-1051 (1992).
Naumann et al., "Trans catalysis in Tn5 transposition," Proc Natl Acad Sci U S A. 97(16):8944-9 (2000).
NCBI GenBank Accession No. AF083977.1, dated Mar. 21, 2002, accessed Sep. 28, 2018 (16 pages).
NCBI GenBank Accession No. D16449.1, dated Dec. 20, 2010, accessed Sep. 28, 2018 (3 pages).
NCBI GenBank Accession No. U00004, dated Mar. 9, 2017, accessed Sep. 28, 2018 (5 pages).
NCBI GenBank Accession No. V00613.1, dated Apr. 18, 2005, accessed Sep. 28, 2018 (3 pages).
NCBI GenBank Accession No. X61695.1, dated Jun. 12, 2006, accessed Sep. 28, 2018 (2 pages).
Park, "ChIP-seq: advantages and challenges of a maturing technology," Available in PMC Oct. 12, 2011, published in final edited form as: Nat Rev Genet. 10(10):669-80 (2009) (21 pages).
Parks et al., "Tn7 elements: engendering diversity from chromosomes to episomes," Available in PMC Jan. 1, 2010, published in final edited form as: Plasmid. 61(1):1-14 (2009) (25 pages).
Pavlopoulos et al., "The DNA transposon Minos as a tool for transgenesis and functional genomic analysis in vertebrates and invertebrates," Genome Biol. 8 Suppl 1:S2 (2007) (7 pages).
Picelli et al., "Tn5 transposase and tagmentation procedures for massively scaled sequencing projects," Genome Res. 24(12):2033-40 (2014).
Reznikoff, "Tn5 as a model for understanding DNA transposition," Mol Microbiol. 47(5):1199-206 (2003).
Roh et al., "Engineering DNA-based functional materials," Chem Soc Rev. 40(12): 5730-5744 (2011).
Rothberg et al., "The development and impact of 454 sequencing," Nature Biotechnol. 26(10): 1117-1124 (2008).
Savilahti et al., "The phage Mu transpososome core: DNA requirements for assembly and function," EMBO J. 14(19):4893-903 (1995).
Shendure et al., "Accurate multiplex polony sequencing of an evolved bacterial genome," Science. 309(5741):1728-32 (2005).
Snyder et al., "Haplotype-resolved gneome sequencing: experimental methods and application," Nat Rev Genet. 16(6): 344-358 (2015) (ePublication, DOI: 10.1038/nrg3903) (15 pages).
Swarts et al., "DNA-guided DNA interference by a prokaryotic Argonaute," available in PMC Jan. 1, 2016, published in final edited form as: Nature. 507(7491):258-61 (2014) (32 pages).
Szabó et al., "Transposition and targeting of the prokaryotic mobile element IS30 in zebrafish," FEBS Lett. 550(1-3):46-50 (2003).
Takeda et al., "Site-specific conjugation of oligonucleotides to the C-terminus of recombinant protein by expressed protein ligation," Bioorg Med Chem Lett. 14(10): 2407-2410 (2004).
UniProt Accession No. P03008, dated Jul. 21, 1986, accessed Sep. 28, 2018 (1 page).
UniProt Accession No. P03012, dated Jul. 21, 1986, accessed Sep. 28, 2018 (3 pages).
UniProt Accession No. P07636; P06021, dated Apr. 1, 1988, accessed Sep. 28, 2018 (9 pages).
UniProt Accession No. P0ADI2; P03011, dated Jul. 21, 1986, accessed Sep. 28, 2018 (2 pages).
UniProt Accession No. P13988; Q47662, dated Jan. 1, 1990, accessed Sep. 28, 2018 (3 pages).
UniProt Accession No. P13989; Q9R5R8, dated Jan. 1, 1990, accessed Sep. 28, 2018 (3 pages).
UniProt Accession No. Q00037, dated Dec. 1, 2000, accessed Sep. 28, 2018 (2 pages).
UniProt Accession No. Q27026, dated Nov. 1, 1996, accessed Sep. 28, 2018 (1 page).
UniProt Accession No. Q46731 et al., dated Oct. 14, 2008, accessed Sep. 28, 2018 (7 pages).
UniProt Accession No. Q70BL4, dated Jul. 5, 2004, accessed Sep. 28, 2018 (5 pages).
UniProt Accession No. Q9U986, dated May 1, 2000, accessed Sep. 28, 2018 (1 page).
Vojta et al., "Repurposing the CRISPR-Cas9 system for targeted DNA methylation," Nucleic Acid Res. 44(12):5615-28 (2016).
Wang et al., "CRISPR/Cas9 in Genome Editing and Beyond," Annu Rev Biochem. 85:227-64 (2016) (41 pages).
Way et al., "New Tn10 derivatives for transposon mutagenesis and for contruction of IacZ operon fusions by transposition," Gene. 32(3): 369-379 (1984).
Wilson et al., "Functional zinc finger/sleeping beauty transposase chimeras exhibit attenuated overproduction inhibition," FEBS Lett. 579(27):6205-9 (2005).
Wu et al., "piggyBac is a flexible and highly active transposon as compared to sleeping beauty, Tol2, and Mos1 in mammalian cells," Proc Natl Acad Sci U S A. 103(41):15008-13 (2006).
Yant et al., "Site-directed transposon integration in human cells," Nucleic Acids Res. 35(7):e50 (2007) (13 pages).
Yusa et al., "A hyperactive piggyBac transposase for mammalian applications," Proc Natl Acad Sci USA. 108(4):1531-6 (2011).
Yusa, "piggyBac Transposon," Microbiol Spectr. 3(2):MDNA3-0028-2014 (2015) (16 pages).
Zentner et al., "High-resolution digital profiling of the epigenome," Nat Rev Genet. 15(12): 814-827 (2014) (ePublication, DOI: 10.1038/nrg3798) (14 pages).
Zetsche et al., "Cpf1 is a single RNA-guided endonuclease of a class 2 CRISPR-Cas system," Available in PMC Oct. 22, 2016, published in final edited form as: Cell. 163(3):759-71 (2015) (26 pages).
Zhu et al., "Controlling integration specificity of a yeast retrotransposon," Proc Natl Acad Sci U S A. 100(10):5891-5 (2003).
Kolb et al., "Click Chemistry: Diverse Chemical Function from a Few Good Reactions," Angew Chem Int Ed. 40(11):2004-21 (2001).
Lu et al., "Effective Antisense Gene Regulation via Noncationic, Polyethylene Glycol Brushes," J Am Chem Soc. 138(29):9097-100 (Jul. 2016).

* cited by examiner

TSC Manufacturing Workflow

5-Azido-PEG4-dCTP

Step 1. PCR generation of azido ct308 scaffold (approx. 180 azide per dsDNA molecule)

TSC Manufacturing Workflow

Step 2. SPAAC (click) attachment of poly-T TAG1 splint primer to universal scaffold

SEQUENCE LISTING

```
<160> NUMBER OF SEQ ID NOS: 518

<210> SEQ ID NO 1
<211> LENGTH: 54
<212> TYPE: DNA
<213> ORGANISM: Artificial Sequence
<220> FEATURE:
<223> OTHER INFORMATION: Synthetic Construct

<400> SEQUENCE: 1

caagcagaag acggcatacg agatgtacca tgtggtctcg tgggctcgga gatg          54


<210> SEQ ID NO 2
<211> LENGTH: 54
<212> TYPE: DNA
<213> ORGANISM: Artificial Sequence
```

<220> FEATURE:
<223> OTHER INFORMATION: Synthetic Construct

<400> SEQUENCE: 2
caagcagaag acggcatacg agatgttgct tccagtctcg tgggctcgga gatg 54

<210> SEQ ID NO 3
<211> LENGTH: 54
<212> TYPE: DNA
<213> ORGANISM: Artificial Sequence
<220> FEATURE:
<223> OTHER INFORMATION: Synthetic Construct

<400> SEQUENCE: 3
caagcagaag acggcatacg agatgtcggt tgttgtctcg tgggctcgga gatg 54

<210> SEQ ID NO 4
<211> LENGTH: 54
<212> TYPE: DNA
<213> ORGANISM: Artificial Sequence
<220> FEATURE:
<223> OTHER INFORMATION: Synthetic Construct

<400> SEQUENCE: 4
caagcagaag acggcatacg agatgtgctg ttgtgtctcg tgggctcgga gatg 54

<210> SEQ ID NO 5
<211> LENGTH: 54
<212> TYPE: DNA
<213> ORGANISM: Artificial Sequence
<220> FEATURE:
<223> OTHER INFORMATION: Synthetic Construct

<400> SEQUENCE: 5
caagcagaag acggcatacg agatgtcttg gatggtctcg tgggctcgga gatg 54

<210> SEQ ID NO 6
<211> LENGTH: 54
<212> TYPE: DNA
<213> ORGANISM: Artificial Sequence
<220> FEATURE:
<223> OTHER INFORMATION: Synthetic Construct

<400> SEQUENCE: 6
caagcagaag acggcatacg agatgtgctt cgaagtctcg tgggctcgga gatg 54

<210> SEQ ID NO 7
<211> LENGTH: 54
<212> TYPE: DNA
<213> ORGANISM: Artificial Sequence
<220> FEATURE:
<223> OTHER INFORMATION: Synthetic Construct

<400> SEQUENCE: 7
caagcagaag acggcatacg agatgtctct actcgtctcg tgggctcgga gatg 54

<210> SEQ ID NO 8
<211> LENGTH: 54
<212> TYPE: DNA
<213> ORGANISM: Artificial Sequence
<220> FEATURE:
<223> OTHER INFORMATION: Synthetic Construct

<400> SEQUENCE: 8
caagcagaag acggcatacg agatgtgaac atcggtctcg tgggctcgga gatg 54

<210> SEQ ID NO 9
<211> LENGTH: 54
<212> TYPE: DNA
<213> ORGANISM: Artificial Sequence
<220> FEATURE:
<223> OTHER INFORMATION: Synthetic Construct

<400> SEQUENCE: 9
caagcagaag acggcatacg agatgttgac gcatgtctcg tgggctcgga gatg 54

<210> SEQ ID NO 10
<211> LENGTH: 54
<212> TYPE: DNA
<213> ORGANISM: Artificial Sequence
<220> FEATURE:
<223> OTHER INFORMATION: Synthetic Construct

<400> SEQUENCE: 10
caagcagaag acggcatacg agatgtgagc ttgtgtctcg tgggctcgga gatg 54

<210> SEQ ID NO 11
<211> LENGTH: 54
<212> TYPE: DNA
<213> ORGANISM: Artificial Sequence
<220> FEATURE:
<223> OTHER INFORMATION: Synthetic Construct

<400> SEQUENCE: 11
caagcagaag acggcatacg agatgtatgc ctgtgtctcg tgggctcgga gatg 54

<210> SEQ ID NO 12
<211> LENGTH: 54
<212> TYPE: DNA
<213> ORGANISM: Artificial Sequence
<220> FEATURE:
<223> OTHER INFORMATION: Synthetic Construct

<400> SEQUENCE: 12
caagcagaag acggcatacg agatgttctt gacggtctcg tgggctcgga gatg 54

<210> SEQ ID NO 13
<211> LENGTH: 54
<212> TYPE: DNA
<213> ORGANISM: Artificial Sequence
<220> FEATURE:
<223> OTHER INFORMATION: Synthetic Construct

<400> SEQUENCE: 13
caagcagaag acggcatacg agatctagaa cgaggtctcg tgggctcgga gatg 54

<210> SEQ ID NO 14
<211> LENGTH: 54
<212> TYPE: DNA
<213> ORGANISM: Artificial Sequence
<220> FEATURE:
<223> OTHER INFORMATION: Synthetic Construct

<400> SEQUENCE: 14
caagcagaag acggcatacg agatctgaca tggtgtctcg tgggctcgga gatg 54

<210> SEQ ID NO 15
<211> LENGTH: 54
<212> TYPE: DNA
<213> ORGANISM: Artificial Sequence
<220> FEATURE:
<223> OTHER INFORMATION: Synthetic Construct

<400> SEQUENCE: 15
caagcagaag acggcatacg agatcttcac gttcgtctcg tgggctcgga gatg 54

<210> SEQ ID NO 16
<211> LENGTH: 54
<212> TYPE: DNA
<213> ORGANISM: Artificial Sequence
<220> FEATURE:
<223> OTHER INFORMATION: Synthetic Construct

<400> SEQUENCE: 16
caagcagaag acggcatacg agatctttgg tgaggtctcg tgggctcgga gatg 54

<210> SEQ ID NO 17
<211> LENGTH: 54
<212> TYPE: DNA
<213> ORGANISM: Artificial Sequence
<220> FEATURE:
<223> OTHER INFORMATION: Synthetic Construct

<400> SEQUENCE: 17
caagcagaag acggcatacg agatcttgtg aagcgtctcg tgggctcgga gatg 54

<210> SEQ ID NO 18
<211> LENGTH: 54
<212> TYPE: DNA
<213> ORGANISM: Artificial Sequence
<220> FEATURE:
<223> OTHER INFORMATION: Synthetic Construct

<400> SEQUENCE: 18
caagcagaag acggcatacg agatcttgga gagtgtctcg tgggctcgga gatg 54

<210> SEQ ID NO 19
<211> LENGTH: 54
<212> TYPE: DNA
<213> ORGANISM: Artificial Sequence
<220> FEATURE:
<223> OTHER INFORMATION: Synthetic Construct

<400> SEQUENCE: 19
caagcagaag acggcatacg agatctgtga gcttgtctcg tgggctcgga gatg 54

<210> SEQ ID NO 20
<211> LENGTH: 54
<212> TYPE: DNA
<213> ORGANISM: Artificial Sequence
<220> FEATURE:
<223> OTHER INFORMATION: Synthetic Construct

<400> SEQUENCE: 20
caagcagaag acggcatacg agatctttgt gtgcgtctcg tgggctcgga gatg 54

<210> SEQ ID NO 21
<211> LENGTH: 54
<212> TYPE: DNA
<213> ORGANISM: Artificial Sequence
<220> FEATURE:
<223> OTHER INFORMATION: Synthetic Construct

<400> SEQUENCE: 21
caagcagaag acggcatacg agatctcttc gttcgtctcg tgggctcgga gatg 54

<210> SEQ ID NO 22

<211> LENGTH: 54
<212> TYPE: DNA
<213> ORGANISM: Artificial Sequence
<220> FEATURE:
<223> OTHER INFORMATION: Synthetic Construct

<400> SEQUENCE: 22
caagcagaag acggcatacg agatctcgtt gagtgtctcg tgggctcgga gatg 54

<210> SEQ ID NO 23
<211> LENGTH: 54
<212> TYPE: DNA
<213> ORGANISM: Artificial Sequence
<220> FEATURE:
<223> OTHER INFORMATION: Synthetic Construct

<400> SEQUENCE: 23
caagcagaag acggcatacg agatctccat acgtgtctcg tgggctcgga gatg 54

<210> SEQ ID NO 24
<211> LENGTH: 54
<212> TYPE: DNA
<213> ORGANISM: Artificial Sequence
<220> FEATURE:
<223> OTHER INFORMATION: Synthetic Construct

<400> SEQUENCE: 24
caagcagaag acggcatacg agatctatga ccaggtctcg tgggctcgga gatg 54

<210> SEQ ID NO 25
<211> LENGTH: 54
<212> TYPE: DNA
<213> ORGANISM: Artificial Sequence
<220> FEATURE:
<223> OTHER INFORMATION: Synthetic Construct

<400> SEQUENCE: 25
caagcagaag acggcatacg agattggagt ggttgtctcg tgggctcgga gatg 54

<210> SEQ ID NO 26
<211> LENGTH: 54
<212> TYPE: DNA
<213> ORGANISM: Artificial Sequence
<220> FEATURE:
<223> OTHER INFORMATION: Synthetic Construct

<400> SEQUENCE: 26
caagcagaag acggcatacg agattgcgca tgatgtctcg tgggctcgga gatg 54

<210> SEQ ID NO 27
<211> LENGTH: 54
<212> TYPE: DNA
<213> ORGANISM: Artificial Sequence
<220> FEATURE:
<223> OTHER INFORMATION: Synthetic Construct

<400> SEQUENCE: 27
caagcagaag acggcatacg agattgacca tccagtctcg tgggctcgga gatg 54

<210> SEQ ID NO 28
<211> LENGTH: 54
<212> TYPE: DNA
<213> ORGANISM: Artificial Sequence
<220> FEATURE:
<223> OTHER INFORMATION: Synthetic Construct

<400> SEQUENCE: 28
caagcagaag acggcatacg agattgtagt tgcggtctcg tgggctcgga gatg 54

<210> SEQ ID NO 29
<211> LENGTH: 54
<212> TYPE: DNA
<213> ORGANISM: Artificial Sequence
<220> FEATURE:
<223> OTHER INFORMATION: Synthetic Construct

<400> SEQUENCE: 29
caagcagaag acggcatacg agattgtatt ccgggtctcg tgggctcgga gatg 54

<210> SEQ ID NO 30
<211> LENGTH: 54
<212> TYPE: DNA
<213> ORGANISM: Artificial Sequence
<220> FEATURE:
<223> OTHER INFORMATION: Synthetic Construct

<400> SEQUENCE: 30
caagcagaag acggcatacg agattgtacc aggagtctcg tgggctcgga gatg 54

<210> SEQ ID NO 31
<211> LENGTH: 54
<212> TYPE: DNA
<213> ORGANISM: Artificial Sequence
<220> FEATURE:
<223> OTHER INFORMATION: Synthetic Construct

<400> SEQUENCE: 31
caagcagaag acggcatacg agattgctgc acttgtctcg tgggctcgga gatg 54

<210> SEQ ID NO 32
<211> LENGTH: 54
<212> TYPE: DNA
<213> ORGANISM: Artificial Sequence
<220> FEATURE:
<223> OTHER INFORMATION: Synthetic Construct

<400> SEQUENCE: 32
caagcagaag acggcatacg agattgtgga tcacgtctcg tgggctcgga gatg 54

<210> SEQ ID NO 33
<211> LENGTH: 54
<212> TYPE: DNA
<213> ORGANISM: Artificial Sequence
<220> FEATURE:
<223> OTHER INFORMATION: Synthetic Construct

<400> SEQUENCE: 33
caagcagaag acggcatacg agattggcaa tggagtctcg tgggctcgga gatg 54

<210> SEQ ID NO 34
<211> LENGTH: 54
<212> TYPE: DNA
<213> ORGANISM: Artificial Sequence
<220> FEATURE:
<223> OTHER INFORMATION: Synthetic Construct

<400> SEQUENCE: 34
caagcagaag acggcatacg agattgtccg tatggtctcg tgggctcgga gatg 54

<210> SEQ ID NO 35
<211> LENGTH: 54
<212> TYPE: DNA

<213> ORGANISM: Artificial Sequence
<220> FEATURE:
<223> OTHER INFORMATION: Synthetic Construct

<400> SEQUENCE: 35
caagcagaag acggcatacg agattgactc agacgtctcg tgggctcgga gatg 54

<210> SEQ ID NO 36
<211> LENGTH: 54
<212> TYPE: DNA
<213> ORGANISM: Artificial Sequence
<220> FEATURE:
<223> OTHER INFORMATION: Synthetic Construct

<400> SEQUENCE: 36
caagcagaag acggcatacg agattgaagt gtcggtctcg tgggctcgga gatg 54

<210> SEQ ID NO 37
<211> LENGTH: 54
<212> TYPE: DNA
<213> ORGANISM: Artificial Sequence
<220> FEATURE:
<223> OTHER INFORMATION: Synthetic Construct

<400> SEQUENCE: 37
caagcagaag acggcatacg agatagaact gagcgtctcg tgggctcgga gatg 54

<210> SEQ ID NO 38
<211> LENGTH: 54
<212> TYPE: DNA
<213> ORGANISM: Artificial Sequence
<220> FEATURE:
<223> OTHER INFORMATION: Synthetic Construct

<400> SEQUENCE: 38
caagcagaag acggcatacg agatagctgt gttggtctcg tgggctcgga gatg 54

<210> SEQ ID NO 39
<211> LENGTH: 54
<212> TYPE: DNA
<213> ORGANISM: Artificial Sequence
<220> FEATURE:
<223> OTHER INFORMATION: Synthetic Construct

<400> SEQUENCE: 39
caagcagaag acggcatacg agatagtcct tagcgtctcg tgggctcgga gatg 54

<210> SEQ ID NO 40
<211> LENGTH: 54
<212> TYPE: DNA
<213> ORGANISM: Artificial Sequence
<220> FEATURE:
<223> OTHER INFORMATION: Synthetic Construct

<400> SEQUENCE: 40
caagcagaag acggcatacg agataggatt ggaggtctcg tgggctcgga gatg 54

<210> SEQ ID NO 41
<211> LENGTH: 54
<212> TYPE: DNA
<213> ORGANISM: Artificial Sequence
<220> FEATURE:
<223> OTHER INFORMATION: Synthetic Construct

<400> SEQUENCE: 41
caagcagaag acggcatacg agatagacgt tcaggtctcg tgggctcgga gatg 54

<210> SEQ ID NO 42
<211> LENGTH: 54
<212> TYPE: DNA
<213> ORGANISM: Artificial Sequence
<220> FEATURE:
<223> OTHER INFORMATION: Synthetic Construct

<400> SEQUENCE: 42
caagcagaag acggcatacg agataggcgt tctagtctcg tgggctcgga gatg 54

<210> SEQ ID NO 43
<211> LENGTH: 54
<212> TYPE: DNA
<213> ORGANISM: Artificial Sequence
<220> FEATURE:
<223> OTHER INFORMATION: Synthetic Construct

<400> SEQUENCE: 43
caagcagaag acggcatacg agatagattg cgtggtctcg tgggctcgga gatg 54

<210> SEQ ID NO 44
<211> LENGTH: 54
<212> TYPE: DNA
<213> ORGANISM: Artificial Sequence
<220> FEATURE:
<223> OTHER INFORMATION: Synthetic Construct

<400> SEQUENCE: 44
caagcagaag acggcatacg agataggtcg gtaagtctcg tgggctcgga gatg 54

<210> SEQ ID NO 45
<211> LENGTH: 54
<212> TYPE: DNA
<213> ORGANISM: Artificial Sequence
<220> FEATURE:
<223> OTHER INFORMATION: Synthetic Construct

<400> SEQUENCE: 45
caagcagaag acggcatacg agatagagag gttggtctcg tgggctcgga gatg 54

<210> SEQ ID NO 46
<211> LENGTH: 54
<212> TYPE: DNA
<213> ORGANISM: Artificial Sequence
<220> FEATURE:
<223> OTHER INFORMATION: Synthetic Construct

<400> SEQUENCE: 46
caagcagaag acggcatacg agatagttga ggcagtctcg tgggctcgga gatg 54

<210> SEQ ID NO 47
<211> LENGTH: 54
<212> TYPE: DNA
<213> ORGANISM: Artificial Sequence
<220> FEATURE:
<223> OTHER INFORMATION: Synthetic Construct

<400> SEQUENCE: 47
caagcagaag acggcatacg agatagtctg ctctgtctcg tgggctcgga gatg 54

<210> SEQ ID NO 48
<211> LENGTH: 54
<212> TYPE: DNA
<213> ORGANISM: Artificial Sequence
<220> FEATURE:

<223> OTHER INFORMATION: Synthetic Construct

<400> SEQUENCE: 48
caagcagaag acggcatacg agatagtgga gttggtctcg tgggctcgga gatg 54

<210> SEQ ID NO 49
<211> LENGTH: 54
<212> TYPE: DNA
<213> ORGANISM: Artificial Sequence
<220> FEATURE:
<223> OTHER INFORMATION: Synthetic Construct

<400> SEQUENCE: 49
caagcagaag acggcatacg agattcgcct tgttgtctcg tgggctcgga gatg 54

<210> SEQ ID NO 50
<211> LENGTH: 54
<212> TYPE: DNA
<213> ORGANISM: Artificial Sequence
<220> FEATURE:
<223> OTHER INFORMATION: Synthetic Construct

<400> SEQUENCE: 50
caagcagaag acggcatacg agattctgcc tcttgtctcg tgggctcgga gatg 54

<210> SEQ ID NO 51
<211> LENGTH: 54
<212> TYPE: DNA
<213> ORGANISM: Artificial Sequence
<220> FEATURE:
<223> OTHER INFORMATION: Synthetic Construct

<400> SEQUENCE: 51
caagcagaag acggcatacg agattcctga cacagtctcg tgggctcgga gatg 54

<210> SEQ ID NO 52
<211> LENGTH: 54
<212> TYPE: DNA
<213> ORGANISM: Artificial Sequence
<220> FEATURE:
<223> OTHER INFORMATION: Sequence Listing

<400> SEQUENCE: 52
caagcagaag acggcatacg agattcagat gagggtctcg tgggctcgga gatg 54

<210> SEQ ID NO 53
<211> LENGTH: 54
<212> TYPE: DNA
<213> ORGANISM: Artificial Sequence
<220> FEATURE:
<223> OTHER INFORMATION: Synthetic Construct

<400> SEQUENCE: 53
caagcagaag acggcatacg agattcaggc ataggtctcg tgggctcgga gatg 54

<210> SEQ ID NO 54
<211> LENGTH: 54
<212> TYPE: DNA
<213> ORGANISM: Artificial Sequence
<220> FEATURE:
<223> OTHER INFORMATION: Synthetic Construct

<400> SEQUENCE: 54
caagcagaag acggcatacg agattcctat cgcagtctcg tgggctcgga gatg 54

<210> SEQ ID NO 55
<211> LENGTH: 54
<212> TYPE: DNA
<213> ORGANISM: Artificial Sequence
<220> FEATURE:
<223> OTHER INFORMATION: Synthetic Construct

<400> SEQUENCE: 55
caagcagaag acggcatacg agattcatag cggtgtctcg tgggctcgga gatg 54

<210> SEQ ID NO 56
<211> LENGTH: 54
<212> TYPE: DNA
<213> ORGANISM: Artificial Sequence
<220> FEATURE:
<223> OTHER INFORMATION: Synthetic Construct

<400> SEQUENCE: 56
caagcagaag acggcatacg agattctagc cgaagtctcg tgggctcgga gatg 54

<210> SEQ ID NO 57
<211> LENGTH: 54
<212> TYPE: DNA
<213> ORGANISM: Artificial Sequence
<220> FEATURE:
<223> OTHER INFORMATION: Synthetic Construct

<400> SEQUENCE: 57
caagcagaag acggcatacg agattcatac tccggtctcg tgggctcgga gatg 54

<210> SEQ ID NO 58
<211> LENGTH: 54
<212> TYPE: DNA
<213> ORGANISM: Artificial Sequence
<220> FEATURE:
<223> OTHER INFORMATION: Synthetic Construct

<400> SEQUENCE: 58
caagcagaag acggcatacg agattcttgc agacgtctcg tgggctcgga gatg 54

<210> SEQ ID NO 59
<211> LENGTH: 54
<212> TYPE: DNA
<213> ORGANISM: Artificial Sequence
<220> FEATURE:
<223> OTHER INFORMATION: Synthetic Construct

<400> SEQUENCE: 59
caagcagaag acggcatacg agattcggta tagggtctcg tgggctcgga gatg 54

<210> SEQ ID NO 60
<211> LENGTH: 54
<212> TYPE: DNA
<213> ORGANISM: Artificial Sequence
<220> FEATURE:
<223> OTHER INFORMATION: Synthetic Construct

<400> SEQUENCE: 60
caagcagaag acggcatacg agattctcac agcagtctcg tgggctcgga gatg 54

<210> SEQ ID NO 61
<211> LENGTH: 54
<212> TYPE: DNA
<213> ORGANISM: Artificial Sequence
<220> FEATURE:
<223> OTHER INFORMATION: Synthetic Construct

<400> SEQUENCE: 61
caagcagaag acggcatacg agatacatgg cgaagtctcg tgggctcgga gatg 54

<210> SEQ ID NO 62
<211> LENGTH: 54
<212> TYPE: DNA
<213> ORGANISM: Artificial Sequence
<220> FEATURE:
<223> OTHER INFORMATION: Synthetic Construct

<400> SEQUENCE: 62
caagcagaag acggcatacg agatacacct ggaagtctcg tgggctcgga gatg 54

<210> SEQ ID NO 63
<211> LENGTH: 54
<212> TYPE: DNA
<213> ORGANISM: Artificial Sequence
<220> FEATURE:
<223> OTHER INFORMATION: Synthetic Construct

<400> SEQUENCE: 63
caagcagaag acggcatacg agatactgac tgacgtctcg tgggctcgga gatg 54

<210> SEQ ID NO 64
<211> LENGTH: 54
<212> TYPE: DNA
<213> ORGANISM: Artificial Sequence
<220> FEATURE:
<223> OTHER INFORMATION: Synthetic Construct

<400> SEQUENCE: 64
caagcagaag acggcatacg agatactacg gttggtctcg tgggctcgga gatg 54

<210> SEQ ID NO 65
<211> LENGTH: 54
<212> TYPE: DNA
<213> ORGANISM: Artificial Sequence
<220> FEATURE:
<223> OTHER INFORMATION: Synthetic Construct

<400> SEQUENCE: 65
caagcagaag acggcatacg agataccctt gatcgtctcg tgggctcgga gatg 54

<210> SEQ ID NO 66
<211> LENGTH: 54
<212> TYPE: DNA
<213> ORGANISM: Artificial Sequence
<220> FEATURE:
<223> OTHER INFORMATION: Synthetic Construct

<400> SEQUENCE: 66
caagcagaag acggcatacg agatacatgg tccagtctcg tgggctcgga gatg 54

<210> SEQ ID NO 67
<211> LENGTH: 54
<212> TYPE: DNA
<213> ORGANISM: Artificial Sequence
<220> FEATURE:
<223> OTHER INFORMATION: Synthetic Construct

<400> SEQUENCE: 67
caagcagaag acggcatacg agatacccaa gcaagtctcg tgggctcgga gatg 54

<210> SEQ ID NO 68
<211> LENGTH: 54

<212> TYPE: DNA
<213> ORGANISM: Artificial Sequence
<220> FEATURE:
<223> OTHER INFORMATION: Synthetic Construct

<400> SEQUENCE: 68
caagcagaag acggcatacg agataccagc gattgtctcg tgggctcgga gatg 54

<210> SEQ ID NO 69
<211> LENGTH: 54
<212> TYPE: DNA
<213> ORGANISM: Artificial Sequence
<220> FEATURE:
<223> OTHER INFORMATION: Synthetic Construct

<400> SEQUENCE: 69
caagcagaag acggcatacg agatacaacg acgtgtctcg tgggctcgga gatg 54

<210> SEQ ID NO 70
<211> LENGTH: 54
<212> TYPE: DNA
<213> ORGANISM: Artificial Sequence
<220> FEATURE:
<223> OTHER INFORMATION: Synthetic Construct

<400> SEQUENCE: 70
caagcagaag acggcatacg agatacgagc agtagtctcg tgggctcgga gatg 54

<210> SEQ ID NO 71
<211> LENGTH: 54
<212> TYPE: DNA
<213> ORGANISM: Artificial Sequence
<220> FEATURE:
<223> OTHER INFORMATION: Synthetic Construct

<400> SEQUENCE: 71
caagcagaag acggcatacg agatacgcca gtatgtctcg tgggctcgga gatg 54

<210> SEQ ID NO 72
<211> LENGTH: 54
<212> TYPE: DNA
<213> ORGANISM: Artificial Sequence
<220> FEATURE:
<223> OTHER INFORMATION: Synthetic Construct

<400> SEQUENCE: 72
caagcagaag acggcatacg agatacctga gatcgtctcg tgggctcgga gatg 54

<210> SEQ ID NO 73
<211> LENGTH: 54
<212> TYPE: DNA
<213> ORGANISM: Artificial Sequence
<220> FEATURE:
<223> OTHER INFORMATION: Synthetic Construct

<400> SEQUENCE: 73
caagcagaag acggcatacg agatcaccat tcacgtctcg tgggctcgga gatg 54

<210> SEQ ID NO 74
<211> LENGTH: 54
<212> TYPE: DNA
<213> ORGANISM: Artificial Sequence
<220> FEATURE:
<223> OTHER INFORMATION: Synthetic Construct

<400> SEQUENCE: 74
caagcagaag acggcatacg agatcattct ctcggtctcg tgggctcgga gatg 54

<210> SEQ ID NO 75
<211> LENGTH: 54
<212> TYPE: DNA
<213> ORGANISM: Artificial Sequence
<220> FEATURE:
<223> OTHER INFORMATION: Synthetic Construct

<400> SEQUENCE: 75
caagcagaag acggcatacg agatcaggac ctatgtctcg tgggctcgga gatg 54

<210> SEQ ID NO 76
<211> LENGTH: 54
<212> TYPE: DNA
<213> ORGANISM: Artificial Sequence
<220> FEATURE:
<223> OTHER INFORMATION: Synthetic Construct

<400> SEQUENCE: 76
caagcagaag acggcatacg agatcaggat cttcgtctcg tgggctcgga gatg 54

<210> SEQ ID NO 77
<211> LENGTH: 54
<212> TYPE: DNA
<213> ORGANISM: Artificial Sequence
<220> FEATURE:
<223> OTHER INFORMATION: Synthetic Construct

<400> SEQUENCE: 77
caagcagaag acggcatacg agatcaacac actcgtctcg tgggctcgga gatg 54

<210> SEQ ID NO 78
<211> LENGTH: 54
<212> TYPE: DNA
<213> ORGANISM: Artificial Sequence
<220> FEATURE:
<223> OTHER INFORMATION: Synthetic Construct

<400> SEQUENCE: 78
caagcagaag acggcatacg agatcagatg tgtggtctcg tgggctcgga gatg 54

<210> SEQ ID NO 79
<211> LENGTH: 54
<212> TYPE: DNA
<213> ORGANISM: Artificial Sequence
<220> FEATURE:
<223> OTHER INFORMATION: Synthetic Construct

<400> SEQUENCE: 79
caagcagaag acggcatacg agatcacctg tcatgtctcg tgggctcgga gatg 54

<210> SEQ ID NO 80
<211> LENGTH: 54
<212> TYPE: DNA
<213> ORGANISM: Artificial Sequence
<220> FEATURE:
<223> OTHER INFORMATION: Synthetic Construct

<400> SEQUENCE: 80
caagcagaag acggcatacg agatcactag gtgagtctcg tgggctcgga gatg 54

<210> SEQ ID NO 81
<211> LENGTH: 54
<212> TYPE: DNA
<213> ORGANISM: Artificial Sequence
<220> FEATURE:
<223> OTHER INFORMATION: Synthetic Construct

<400> SEQUENCE: 81
caagcagaag acggcatacg agatcagaag aggtgtctcg tgggctcgga gatg 54

<210> SEQ ID NO 82
<211> LENGTH: 54
<212> TYPE: DNA
<213> ORGANISM: Artificial Sequence
<220> FEATURE:
<223> OTHER INFORMATION: Synthetic Construct

<400> SEQUENCE: 82
caagcagaag acggcatacg agatcagtct tgcagtctcg tgggctcgga gatg 54

<210> SEQ ID NO 83
<211> LENGTH: 54
<212> TYPE: DNA
<213> ORGANISM: Artificial Sequence
<220> FEATURE:
<223> OTHER INFORMATION: Synthetic Construct

<400> SEQUENCE: 83
caagcagaag acggcatacg agatcatagg atgcgtctcg tgggctcgga gatg 54

<210> SEQ ID NO 84
<211> LENGTH: 54
<212> TYPE: DNA
<213> ORGANISM: Artificial Sequence
<220> FEATURE:
<223> OTHER INFORMATION: Synthetic Construct

<400> SEQUENCE: 84
caagcagaag acggcatacg agatcagttc atgggtctcg tgggctcgga gatg 54

<210> SEQ ID NO 85
<211> LENGTH: 54
<212> TYPE: DNA
<213> ORGANISM: Artificial Sequence
<220> FEATURE:
<223> OTHER INFORMATION: Synthetic Construct

<400> SEQUENCE: 85
caagcagaag acggcatacg agatgactcc atgtgtctcg tgggctcgga gatg 54

<210> SEQ ID NO 86
<211> LENGTH: 54
<212> TYPE: DNA
<213> ORGANISM: Artificial Sequence
<220> FEATURE:
<223> OTHER INFORMATION: Synthetic Construct

<400> SEQUENCE: 86
caagcagaag acggcatacg agatgaaacc tcctgtctcg tgggctcgga gatg 54

<210> SEQ ID NO 87
<211> LENGTH: 54
<212> TYPE: DNA
<213> ORGANISM: Artificial Sequence
<220> FEATURE:
<223> OTHER INFORMATION: Synthetic Construct

<400> SEQUENCE: 87
caagcagaag acggcatacg agatgagatt accggtctcg tgggctcgga gatg 54

<210> SEQ ID NO 88
<211> LENGTH: 54
<212> TYPE: DNA
<213> ORGANISM: Artificial Sequence
<220> FEATURE:
<223> OTHER INFORMATION: Synthetic Construct

<400> SEQUENCE: 88
caagcagaag acggcatacg agatgaaccg catagtctcg tgggctcgga gatg 54

<210> SEQ ID NO 89
<211> LENGTH: 54
<212> TYPE: DNA
<213> ORGANISM: Artificial Sequence
<220> FEATURE:
<223> OTHER INFORMATION: Synthetic Construct

<400> SEQUENCE: 89
caagcagaag acggcatacg agatgatggc actagtctcg tgggctcgga gatg 54

<210> SEQ ID NO 90
<211> LENGTH: 54
<212> TYPE: DNA
<213> ORGANISM: Artificial Sequence
<220> FEATURE:
<223> OTHER INFORMATION: Synthetic Construct

<400> SEQUENCE: 90
caagcagaag acggcatacg agatgagtcc acatgtctcg tgggctcgga gatg 54

<210> SEQ ID NO 91
<211> LENGTH: 54
<212> TYPE: DNA
<213> ORGANISM: Artificial Sequence
<220> FEATURE:
<223> OTHER INFORMATION: Synthetic Construct

<400> SEQUENCE: 91
caagcagaag acggcatacg agatgaaacg tggagtctcg tgggctcgga gatg 54

<210> SEQ ID NO 92
<211> LENGTH: 54
<212> TYPE: DNA
<213> ORGANISM: Artificial Sequence
<220> FEATURE:
<223> OTHER INFORMATION: Synthetic Construct

<400> SEQUENCE: 92
caagcagaag acggcatacg agatgaacta ggaggtctcg tgggctcgga gatg 54

<210> SEQ ID NO 93
<211> LENGTH: 54
<212> TYPE: DNA
<213> ORGANISM: Artificial Sequence
<220> FEATURE:
<223> OTHER INFORMATION: Synthetic Construct

<400> SEQUENCE: 93
caagcagaag acggcatacg agatgatacg ccttgtctcg tgggctcgga gatg 54

<210> SEQ ID NO 94
<211> LENGTH: 54
<212> TYPE: DNA
<213> ORGANISM: Artificial Sequence
<220> FEATURE:
<223> OTHER INFORMATION: Synthetic Construct

<400> SEQUENCE: 94
caagcagaag acggcatacg agatgacaat gtgggtctcg tgggctcgga gatg 54

<210> SEQ ID NO 95
<211> LENGTH: 54
<212> TYPE: DNA
<213> ORGANISM: Artificial Sequence
<220> FEATURE:
<223> OTHER INFORMATION: Synthetic Construct

<400> SEQUENCE: 95
caagcagaag acggcatacg agatgaactc tcgagtctcg tgggctcgga gatg 54

<210> SEQ ID NO 96
<211> LENGTH: 54
<212> TYPE: DNA
<213> ORGANISM: Artificial Sequence
<220> FEATURE:
<223> OTHER INFORMATION: Synthetic Construct

<400> SEQUENCE: 96
caagcagaag acggcatacg agatgacatc gtgagtctcg tgggctcgga gatg 54

<210> SEQ ID NO 97
<211> LENGTH: 54
<212> TYPE: DNA
<213> ORGANISM: Artificial Sequence
<220> FEATURE:
<223> OTHER INFORMATION: Synthetic Construct

<400> SEQUENCE: 97
caagcagaag acggcatacg agatgtgtcc ttctgtctcg tgggctcgga gatg 54

<210> SEQ ID NO 98
<211> LENGTH: 54
<212> TYPE: DNA
<213> ORGANISM: Artificial Sequence
<220> FEATURE:
<223> OTHER INFORMATION: Synthetic Construct

<400> SEQUENCE: 98
caagcagaag acggcatacg agatgttgta ccgtgtctcg tgggctcgga gatg 54

<210> SEQ ID NO 99
<211> LENGTH: 54
<212> TYPE: DNA
<213> ORGANISM: Artificial Sequence
<220> FEATURE:
<223> OTHER INFORMATION: Synthetic Construct

<400> SEQUENCE: 99
caagcagaag acggcatacg agatgttgca ccaagtctcg tgggctcgga gatg 54

<210> SEQ ID NO 100
<211> LENGTH: 54
<212> TYPE: DNA
<213> ORGANISM: Artificial Sequence
<220> FEATURE:
<223> OTHER INFORMATION: Synthetic Construct

<400> SEQUENCE: 100
caagcagaag acggcatacg agatgtggag atgagtctcg tgggctcgga gatg 54

<210> SEQ ID NO 101

<211> LENGTH: 54
<212> TYPE: DNA
<213> ORGANISM: Artificial Sequence
<220> FEATURE:
<223> OTHER INFORMATION: Synthetic Construct

<400> SEQUENCE: 101
caagcagaag acggcatacg agatgtcttg ctgtgtctcg tgggctcgga gatg 54

<210> SEQ ID NO 102
<211> LENGTH: 54
<212> TYPE: DNA
<213> ORGANISM: Artificial Sequence
<220> FEATURE:
<223> OTHER INFORMATION: Synthetic Construct

<400> SEQUENCE: 102
caagcagaag acggcatacg agatgtcact gacagtctcg tgggctcgga gatg 54

<210> SEQ ID NO 103
<211> LENGTH: 54
<212> TYPE: DNA
<213> ORGANISM: Artificial Sequence
<220> FEATURE:
<223> OTHER INFORMATION: Synthetic Construct

<400> SEQUENCE: 103
caagcagaag acggcatacg agatgtcagg agatgtctcg tgggctcgga gatg 54

<210> SEQ ID NO 104
<211> LENGTH: 54
<212> TYPE: DNA
<213> ORGANISM: Artificial Sequence
<220> FEATURE:
<223> OTHER INFORMATION: Synthetic Construct

<400> SEQUENCE: 104
caagcagaag acggcatacg agatgtcggc taatgtctcg tgggctcgga gatg 54

<210> SEQ ID NO 105
<211> LENGTH: 54
<212> TYPE: DNA
<213> ORGANISM: Artificial Sequence
<220> FEATURE:
<223> OTHER INFORMATION: Synthetic Construct

<400> SEQUENCE: 105
caagcagaag acggcatacg agatgttccg tgaagtctcg tgggctcgga gatg 54

<210> SEQ ID NO 106
<211> LENGTH: 54
<212> TYPE: DNA
<213> ORGANISM: Artificial Sequence
<220> FEATURE:
<223> OTHER INFORMATION: Synthetic Construct

<400> SEQUENCE: 106
caagcagaag acggcatacg agatgtttac ggctgtctcg tgggctcgga gatg 54

<210> SEQ ID NO 107
<211> LENGTH: 54
<212> TYPE: DNA
<213> ORGANISM: Artificial Sequence
<220> FEATURE:
<223> OTHER INFORMATION: Synthetic Construct

<400> SEQUENCE: 107
caagcagaag acggcatacg agatgtatgg ttgcgtctcg tgggctcgga gatg 54

<210> SEQ ID NO 108
<211> LENGTH: 54
<212> TYPE: DNA
<213> ORGANISM: Artificial Sequence
<220> FEATURE:
<223> OTHER INFORMATION: Synthetic Construct

<400> SEQUENCE: 108
caagcagaag acggcatacg agatgtgtac cttggtctcg tgggctcgga gatg 54

<210> SEQ ID NO 109
<211> LENGTH: 54
<212> TYPE: DNA
<213> ORGANISM: Artificial Sequence
<220> FEATURE:
<223> OTHER INFORMATION: Synthetic Construct

<400> SEQUENCE: 109
caagcagaag acggcatacg agatctggaa ttgcgtctcg tgggctcgga gatg 54

<210> SEQ ID NO 110
<211> LENGTH: 54
<212> TYPE: DNA
<213> ORGANISM: Artificial Sequence
<220> FEATURE:
<223> OTHER INFORMATION: Synthetic Construct

<400> SEQUENCE: 110
caagcagaag acggcatacg agatcttggc atgtgtctcg tgggctcgga gatg 54

<210> SEQ ID NO 111
<211> LENGTH: 54
<212> TYPE: DNA
<213> ORGANISM: Artificial Sequence
<220> FEATURE:
<223> OTHER INFORMATION: Synthetic Construct

<400> SEQUENCE: 111
caagcagaag acggcatacg agatcttggt acaggtctcg tgggctcgga gatg 54

<210> SEQ ID NO 112
<211> LENGTH: 54
<212> TYPE: DNA
<213> ORGANISM: Artificial Sequence
<220> FEATURE:
<223> OTHER INFORMATION: Synthetic Construct

<400> SEQUENCE: 112
caagcagaag acggcatacg agatctagtc aggagtctcg tgggctcgga gatg 54

<210> SEQ ID NO 113
<211> LENGTH: 54
<212> TYPE: DNA
<213> ORGANISM: Artificial Sequence
<220> FEATURE:
<223> OTHER INFORMATION: Synthetic Construct

<400> SEQUENCE: 113
caagcagaag acggcatacg agatctttgg tctcgtctcg tgggctcgga gatg 54

<210> SEQ ID NO 114
<211> LENGTH: 54
<212> TYPE: DNA

<213> ORGANISM: Artificial Sequence
<220> FEATURE:
<223> OTHER INFORMATION: Synthetic Construct

<400> SEQUENCE: 114
caagcagaag acggcatacg agatctaggc ttctgtctcg tgggctcgga gatg 54

<210> SEQ ID NO 115
<211> LENGTH: 54
<212> TYPE: DNA
<213> ORGANISM: Artificial Sequence
<220> FEATURE:
<223> OTHER INFORMATION: Synthetic Construct

<400> SEQUENCE: 115
caagcagaag acggcatacg agatctatcg ccatgtctcg tgggctcgga gatg 54

<210> SEQ ID NO 116
<211> LENGTH: 54
<212> TYPE: DNA
<213> ORGANISM: Artificial Sequence
<220> FEATURE:
<223> OTHER INFORMATION: Synthetic Construct

<400> SEQUENCE: 116
caagcagaag acggcatacg agatctgcta tcctgtctcg tgggctcgga gatg 54

<210> SEQ ID NO 117
<211> LENGTH: 54
<212> TYPE: DNA
<213> ORGANISM: Artificial Sequence
<220> FEATURE:
<223> OTHER INFORMATION: Synthetic Construct

<400> SEQUENCE: 117
caagcagaag acggcatacg agatctatcc agaggtctcg tgggctcgga gatg 54

<210> SEQ ID NO 118
<211> LENGTH: 54
<212> TYPE: DNA
<213> ORGANISM: Artificial Sequence
<220> FEATURE:
<223> OTHER INFORMATION: Synthetic Construct

<400> SEQUENCE: 118
caagcagaag acggcatacg agatctgctt cttggtctcg tgggctcgga gatg 54

<210> SEQ ID NO 119
<211> LENGTH: 54
<212> TYPE: DNA
<213> ORGANISM: Artificial Sequence
<220> FEATURE:
<223> OTHER INFORMATION: Synthetic Construct

<400> SEQUENCE: 119
caagcagaag acggcatacg agatctgtag gagtgtctcg tgggctcgga gatg 54

<210> SEQ ID NO 120
<211> LENGTH: 54
<212> TYPE: DNA
<213> ORGANISM: Artificial Sequence
<220> FEATURE:
<223> OTHER INFORMATION: Synthetic Construct

<400> SEQUENCE: 120
caagcagaag acggcatacg agatctccag tgttgtctcg tgggctcgga gatg 54

<210> SEQ ID NO 121
<211> LENGTH: 54
<212> TYPE: DNA
<213> ORGANISM: Artificial Sequence
<220> FEATURE:
<223> OTHER INFORMATION: Synthetic Construct

<400> SEQUENCE: 121
caagcagaag acggcatacg agattgcgct agtagtctcg tgggctcgga gatg 54

<210> SEQ ID NO 122
<211> LENGTH: 54
<212> TYPE: DNA
<213> ORGANISM: Artificial Sequence
<220> FEATURE:
<223> OTHER INFORMATION: Synthetic Construct

<400> SEQUENCE: 122
caagcagaag acggcatacg agattgggta gtgtgtctcg tgggctcgga gatg 54

<210> SEQ ID NO 123
<211> LENGTH: 54
<212> TYPE: DNA
<213> ORGANISM: Artificial Sequence
<220> FEATURE:
<223> OTHER INFORMATION: Synthetic Construct

<400> SEQUENCE: 123
caagcagaag acggcatacg agattgtcgc gatagtctcg tgggctcgga gatg 54

<210> SEQ ID NO 124
<211> LENGTH: 54
<212> TYPE: DNA
<213> ORGANISM: Artificial Sequence
<220> FEATURE:
<223> OTHER INFORMATION: Synthetic Construct

<400> SEQUENCE: 124
caagcagaag acggcatacg agattgctga tcgtgtctcg tgggctcgga gatg 54

<210> SEQ ID NO 125
<211> LENGTH: 54
<212> TYPE: DNA
<213> ORGANISM: Artificial Sequence
<220> FEATURE:
<223> OTHER INFORMATION: Synthetic Construct

<400> SEQUENCE: 125
caagcagaag acggcatacg agattggttg cgatgtctcg tgggctcgga gatg 54

<210> SEQ ID NO 126
<211> LENGTH: 54
<212> TYPE: DNA
<213> ORGANISM: Artificial Sequence
<220> FEATURE:
<223> OTHER INFORMATION: Synthetic Construct

<400> SEQUENCE: 126
caagcagaag acggcatacg agattgttcg cagtgtctcg tgggctcgga gatg 54

<210> SEQ ID NO 127
<211> LENGTH: 54
<212> TYPE: DNA
<213> ORGANISM: Artificial Sequence
<220> FEATURE:

<223> OTHER INFORMATION: Synthetic Construct

<400> SEQUENCE: 127
caagcagaag acggcatacg agattgcgag actagtctcg tgggctcgga gatg 54

<210> SEQ ID NO 128
<211> LENGTH: 54
<212> TYPE: DNA
<213> ORGANISM: Artificial Sequence
<220> FEATURE:
<223> OTHER INFORMATION: Synthetic Construct

<400> SEQUENCE: 128
caagcagaag acggcatacg agattggaga tacggtctcg tgggctcgga gatg 54

<210> SEQ ID NO 129
<211> LENGTH: 54
<212> TYPE: DNA
<213> ORGANISM: Artificial Sequence
<220> FEATURE:
<223> OTHER INFORMATION: Synthetic Construct

<400> SEQUENCE: 129
caagcagaag acggcatacg agattgttac cgaggtctcg tgggctcgga gatg 54

<210> SEQ ID NO 130
<211> LENGTH: 54
<212> TYPE: DNA
<213> ORGANISM: Artificial Sequence
<220> FEATURE:
<223> OTHER INFORMATION: Synthetic Construct

<400> SEQUENCE: 130
caagcagaag acggcatacg agattggatt cagcgtctcg tgggctcgga gatg 54

<210> SEQ ID NO 131
<211> LENGTH: 54
<212> TYPE: DNA
<213> ORGANISM: Artificial Sequence
<220> FEATURE:
<223> OTHER INFORMATION: Synthetic Construct

<400> SEQUENCE: 131
caagcagaag acggcatacg agattgtcgc tgttgtctcg tgggctcgga gatg 54

<210> SEQ ID NO 132
<211> LENGTH: 54
<212> TYPE: DNA
<213> ORGANISM: Artificial Sequence
<220> FEATURE:
<223> OTHER INFORMATION: Synthetic Construct

<400> SEQUENCE: 132
caagcagaag acggcatacg agattgtgcc attcgtctcg tgggctcgga gatg 54

<210> SEQ ID NO 133
<211> LENGTH: 54
<212> TYPE: DNA
<213> ORGANISM: Artificial Sequence
<220> FEATURE:
<223> OTHER INFORMATION: Synthetic Construct

<400> SEQUENCE: 133
caagcagaag acggcatacg agataggtcc taaggtctcg tgggctcgga gatg 54

<210> SEQ ID NO 134
<211> LENGTH: 54
<212> TYPE: DNA
<213> ORGANISM: Artificial Sequence
<220> FEATURE:
<223> OTHER INFORMATION: Synthetic Construct

<400> SEQUENCE: 134
caagcagaag acggcatacg agataggacg aatggtctcg tgggctcgga gatg 54

<210> SEQ ID NO 135
<211> LENGTH: 54
<212> TYPE: DNA
<213> ORGANISM: Artificial Sequence
<220> FEATURE:
<223> OTHER INFORMATION: Synthetic Construct

<400> SEQUENCE: 135
caagcagaag acggcatacg agatagaagt ccgtgtctcg tgggctcgga gatg 54

<210> SEQ ID NO 136
<211> LENGTH: 54
<212> TYPE: DNA
<213> ORGANISM: Artificial Sequence
<220> FEATURE:
<223> OTHER INFORMATION: Synthetic Construct

<400> SEQUENCE: 136
caagcagaag acggcatacg agataggaag gttcgtctcg tgggctcgga gatg 54

<210> SEQ ID NO 137
<211> LENGTH: 54
<212> TYPE: DNA
<213> ORGANISM: Artificial Sequence
<220> FEATURE:
<223> OTHER INFORMATION: Synthetic Construct

<400> SEQUENCE: 137
caagcagaag acggcatacg agataggatt gctcgtctcg tgggctcgga gatg 54

<210> SEQ ID NO 138
<211> LENGTH: 54
<212> TYPE: DNA
<213> ORGANISM: Artificial Sequence
<220> FEATURE:
<223> OTHER INFORMATION: Synthetic Construct

<400> SEQUENCE: 138
caagcagaag acggcatacg agataggaga tgtcgtctcg tgggctcgga gatg 54

<210> SEQ ID NO 139
<211> LENGTH: 54
<212> TYPE: DNA
<213> ORGANISM: Artificial Sequence
<220> FEATURE:
<223> OTHER INFORMATION: Synthetic Construct

<400> SEQUENCE: 139
caagcagaag acggcatacg agatagacac ggttgtctcg tgggctcgga gatg 54

<210> SEQ ID NO 140
<211> LENGTH: 54
<212> TYPE: DNA
<213> ORGANISM: Artificial Sequence
<220> FEATURE:
<223> OTHER INFORMATION: Synthetic Construct

<400> SEQUENCE: 140
caagcagaag acggcatacg agatagagtc gcttgtctcg tgggctcgga gatg 54

<210> SEQ ID NO 141
<211> LENGTH: 54
<212> TYPE: DNA
<213> ORGANISM: Artificial Sequence
<220> FEATURE:
<223> OTHER INFORMATION: Synthetic Construct

<400> SEQUENCE: 141
caagcagaag acggcatacg agatagctaa ctcggtctcg tgggctcgga gatg 54

<210> SEQ ID NO 142
<211> LENGTH: 54
<212> TYPE: DNA
<213> ORGANISM: Artificial Sequence
<220> FEATURE:
<223> OTHER INFORMATION: Synthetic Construct

<400> SEQUENCE: 142
caagcagaag acggcatacg agatagacga cagagtctcg tgggctcgga gatg 54

<210> SEQ ID NO 143
<211> LENGTH: 54
<212> TYPE: DNA
<213> ORGANISM: Artificial Sequence
<220> FEATURE:
<223> OTHER INFORMATION: Synthetic Construct

<400> SEQUENCE: 143
caagcagaag acggcatacg agatagagca agcagtctcg tgggctcgga gatg 54

<210> SEQ ID NO 144
<211> LENGTH: 54
<212> TYPE: DNA
<213> ORGANISM: Artificial Sequence
<220> FEATURE:
<223> OTHER INFORMATION: Synthetic Construct

<400> SEQUENCE: 144
caagcagaag acggcatacg agataggaac gcttgtctcg tgggctcgga gatg 54

<210> SEQ ID NO 145
<211> LENGTH: 54
<212> TYPE: DNA
<213> ORGANISM: Artificial Sequence
<220> FEATURE:
<223> OTHER INFORMATION: Synthetic Construct

<400> SEQUENCE: 145
caagcagaag acggcatacg agattcgtat tggcgtctcg tgggctcgga gatg 54

<210> SEQ ID NO 146
<211> LENGTH: 54
<212> TYPE: DNA
<213> ORGANISM: Artificial Sequence
<220> FEATURE:
<223> OTHER INFORMATION: Synthetic Construct

<400> SEQUENCE: 146
caagcagaag acggcatacg agattccgca atctgtctcg tgggctcgga gatg 54

<210> SEQ ID NO 147
<211> LENGTH: 54

<212> TYPE: DNA
<213> ORGANISM: Artificial Sequence
<220> FEATURE:
<223> OTHER INFORMATION: Synthetic Construct

<400> SEQUENCE: 147
caagcagaag acggcatacg agattcgtgc ttacgtctcg tgggctcgga gatg 54

<210> SEQ ID NO 148
<211> LENGTH: 54
<212> TYPE: DNA
<213> ORGANISM: Artificial Sequence
<220> FEATURE:
<223> OTHER INFORMATION: Synthetic Construct

<400> SEQUENCE: 148
caagcagaag acggcatacg agattcaacc ttgggtctcg tgggctcgga gatg 54

<210> SEQ ID NO 149
<211> LENGTH: 54
<212> TYPE: DNA
<213> ORGANISM: Artificial Sequence
<220> FEATURE:
<223> OTHER INFORMATION: Synthetic Construct

<400> SEQUENCE: 149
caagcagaag acggcatacg agattcggaa gctagtctcg tgggctcgga gatg 54

<210> SEQ ID NO 150
<211> LENGTH: 54
<212> TYPE: DNA
<213> ORGANISM: Artificial Sequence
<220> FEATURE:
<223> OTHER INFORMATION: Synthetic Construct

<400> SEQUENCE: 150
caagcagaag acggcatacg agattcgtta cgcagtctcg tgggctcgga gatg 54

<210> SEQ ID NO 151
<211> LENGTH: 54
<212> TYPE: DNA
<213> ORGANISM: Artificial Sequence
<220> FEATURE:
<223> OTHER INFORMATION: Synthetic Construct

<400> SEQUENCE: 151
caagcagaag acggcatacg agattccgac gttagtctcg tgggctcgga gatg 54

<210> SEQ ID NO 152
<211> LENGTH: 54
<212> TYPE: DNA
<213> ORGANISM: Artificial Sequence
<220> FEATURE:
<223> OTHER INFORMATION: Synthetic Construct

<400> SEQUENCE: 152
caagcagaag acggcatacg agattcagcg tgttgtctcg tgggctcgga gatg 54

<210> SEQ ID NO 153
<211> LENGTH: 54
<212> TYPE: DNA
<213> ORGANISM: Artificial Sequence
<220> FEATURE:
<223> OTHER INFORMATION: Synthetic Construct

<400> SEQUENCE: 153
caagcagaag acggcatacg agattcacct tctcgtctcg tgggctcgga gatg 54

<210> SEQ ID NO 154
<211> LENGTH: 54
<212> TYPE: DNA
<213> ORGANISM: Artificial Sequence
<220> FEATURE:
<223> OTHER INFORMATION: Synthetic Construct

<400> SEQUENCE: 154
caagcagaag acggcatacg agattccatt gcctgtctcg tgggctcgga gatg 54

<210> SEQ ID NO 155
<211> LENGTH: 54
<212> TYPE: DNA
<213> ORGANISM: Artificial Sequence
<220> FEATURE:
<223> OTHER INFORMATION: Synthetic Construct

<400> SEQUENCE: 155
caagcagaag acggcatacg agattcatct tcgggtctcg tgggctcgga gatg 54

<210> SEQ ID NO 156
<211> LENGTH: 54
<212> TYPE: DNA
<213> ORGANISM: Artificial Sequence
<220> FEATURE:
<223> OTHER INFORMATION: Synthetic Construct

<400> SEQUENCE: 156
caagcagaag acggcatacg agattctgac ttcggtctcg tgggctcgga gatg 54

<210> SEQ ID NO 157
<211> LENGTH: 54
<212> TYPE: DNA
<213> ORGANISM: Artificial Sequence
<220> FEATURE:
<223> OTHER INFORMATION: Synthetic Construct

<400> SEQUENCE: 157
caagcagaag acggcatacg agatacaact ggtggtctcg tgggctcgga gatg 54

<210> SEQ ID NO 158
<211> LENGTH: 54
<212> TYPE: DNA
<213> ORGANISM: Artificial Sequence
<220> FEATURE:
<223> OTHER INFORMATION: Synthetic Construct

<400> SEQUENCE: 158
caagcagaag acggcatacg agatactcaa ggacgtctcg tgggctcgga gatg 54

<210> SEQ ID NO 159
<211> LENGTH: 54
<212> TYPE: DNA
<213> ORGANISM: Artificial Sequence
<220> FEATURE:
<223> OTHER INFORMATION: Synthetic Construct

<400> SEQUENCE: 159
caagcagaag acggcatacg agatacattc gagggtctcg tgggctcgga gatg 54

<210> SEQ ID NO 160
<211> LENGTH: 54
<212> TYPE: DNA
<213> ORGANISM: Artificial Sequence
<220> FEATURE:
<223> OTHER INFORMATION: Synthetic Construct

<400> SEQUENCE: 160
caagcagaag acggcatacg agatacggct attggtctcg tgggctcgga gatg 54

<210> SEQ ID NO 161
<211> LENGTH: 54
<212> TYPE: DNA
<213> ORGANISM: Artificial Sequence
<220> FEATURE:
<223> OTHER INFORMATION: Synthetic Construct

<400> SEQUENCE: 161
caagcagaag acggcatacg agatacccgt atctgtctcg tgggctcgga gatg 54

<210> SEQ ID NO 162
<211> LENGTH: 54
<212> TYPE: DNA
<213> ORGANISM: Artificial Sequence
<220> FEATURE:
<223> OTHER INFORMATION: Synthetic Construct

<400> SEQUENCE: 162
caagcagaag acggcatacg agatacggat accagtctcg tgggctcgga gatg 54

<210> SEQ ID NO 163
<211> LENGTH: 54
<212> TYPE: DNA
<213> ORGANISM: Artificial Sequence
<220> FEATURE:
<223> OTHER INFORMATION: Synthetic Construct

<400> SEQUENCE: 163
caagcagaag acggcatacg agataccgat gcttgtctcg tgggctcgga gatg 54

<210> SEQ ID NO 164
<211> LENGTH: 54
<212> TYPE: DNA
<213> ORGANISM: Artificial Sequence
<220> FEATURE:
<223> OTHER INFORMATION: Synthetic Construct

<400> SEQUENCE: 164
caagcagaag acggcatacg agatactcta acgcgtctcg tgggctcgga gatg 54

<210> SEQ ID NO 165
<211> LENGTH: 54
<212> TYPE: DNA
<213> ORGANISM: Artificial Sequence
<220> FEATURE:
<223> OTHER INFORMATION: Synthetic Construct

<400> SEQUENCE: 165
caagcagaag acggcatacg agatacatgt agcggtctcg tgggctcgga gatg 54

<210> SEQ ID NO 166
<211> LENGTH: 54
<212> TYPE: DNA
<213> ORGANISM: Artificial Sequence
<220> FEATURE:
<223> OTHER INFORMATION: Synthetic Construct

<400> SEQUENCE: 166
caagcagaag acggcatacg agataccaat cgacgtctcg tgggctcgga gatg 54

<210> SEQ ID NO 167
<211> LENGTH: 54
<212> TYPE: DNA
<213> ORGANISM: Artificial Sequence
<220> FEATURE:
<223> OTHER INFORMATION: Synthetic Construct

<400> SEQUENCE: 167
caagcagaag acggcatacg agatacgagg acttgtctcg tgggctcgga gatg 54

<210> SEQ ID NO 168
<211> LENGTH: 54
<212> TYPE: DNA
<213> ORGANISM: Artificial Sequence
<220> FEATURE:
<223> OTHER INFORMATION: Synthetic Construct

<400> SEQUENCE: 168
caagcagaag acggcatacg agatacggtg attcgtctcg tgggctcgga gatg 54

<210> SEQ ID NO 169
<211> LENGTH: 54
<212> TYPE: DNA
<213> ORGANISM: Artificial Sequence
<220> FEATURE:
<223> OTHER INFORMATION: Synthetic Construct

<400> SEQUENCE: 169
caagcagaag acggcatacg agatcataac gagggtctcg tgggctcgga gatg 54

<210> SEQ ID NO 170
<211> LENGTH: 54
<212> TYPE: DNA
<213> ORGANISM: Artificial Sequence
<220> FEATURE:
<223> OTHER INFORMATION: Synthetic Construct

<400> SEQUENCE: 170
caagcagaag acggcatacg agatcacacg ttgtgtctcg tgggctcgga gatg 54

<210> SEQ ID NO 171
<211> LENGTH: 54
<212> TYPE: DNA
<213> ORGANISM: Artificial Sequence
<220> FEATURE:
<223> OTHER INFORMATION: Synthetic Construct

<400> SEQUENCE: 171
caagcagaag acggcatacg agatcatgtt cgaggtctcg tgggctcgga gatg 54

<210> SEQ ID NO 172
<211> LENGTH: 54
<212> TYPE: DNA
<213> ORGANISM: Artificial Sequence
<220> FEATURE:
<223> OTHER INFORMATION: Synthetic Construct

<400> SEQUENCE: 172
caagcagaag acggcatacg agatcatctc tagggtctcg tgggctcgga gatg 54

<210> SEQ ID NO 173
<211> LENGTH: 54
<212> TYPE: DNA
<213> ORGANISM: Artificial Sequence
<220> FEATURE:
<223> OTHER INFORMATION: Synthetic Construct

<400> SEQUENCE: 173
caagcagaag acggcatacg agatcagtgc catagtctcg tgggctcgga gatg 54

<210> SEQ ID NO 174
<211> LENGTH: 54
<212> TYPE: DNA
<213> ORGANISM: Artificial Sequence
<220> FEATURE:
<223> OTHER INFORMATION: Synthetic Construct

<400> SEQUENCE: 174
caagcagaag acggcatacg agatcattaa gcgggtctcg tgggctcgga gatg 54

<210> SEQ ID NO 175
<211> LENGTH: 54
<212> TYPE: DNA
<213> ORGANISM: Artificial Sequence
<220> FEATURE:
<223> OTHER INFORMATION: Synthetic Construct

<400> SEQUENCE: 175
caagcagaag acggcatacg agatcagaag ttgggtctcg tgggctcgga gatg 54

<210> SEQ ID NO 176
<211> LENGTH: 54
<212> TYPE: DNA
<213> ORGANISM: Artificial Sequence
<220> FEATURE:
<223> OTHER INFORMATION: Synthetic Construct

<400> SEQUENCE: 176
caagcagaag acggcatacg agatcataca cgctgtctcg tgggctcgga gatg 54

<210> SEQ ID NO 177
<211> LENGTH: 54
<212> TYPE: DNA
<213> ORGANISM: Artificial Sequence
<220> FEATURE:
<223> OTHER INFORMATION: Synthetic Construct

<400> SEQUENCE: 177
caagcagaag acggcatacg agatcacagt gaaggtctcg tgggctcgga gatg 54

<210> SEQ ID NO 178
<211> LENGTH: 54
<212> TYPE: DNA
<213> ORGANISM: Artificial Sequence
<220> FEATURE:
<223> OTHER INFORMATION: Synthetic Construct

<400> SEQUENCE: 178
caagcagaag acggcatacg agatcactac agtggtctcg tgggctcgga gatg 54

<210> SEQ ID NO 179
<211> LENGTH: 54
<212> TYPE: DNA
<213> ORGANISM: Artificial Sequence
<220> FEATURE:
<223> OTHER INFORMATION: Synthetic Construct

<400> SEQUENCE: 179
caagcagaag acggcatacg agatcagtgg tgttgtctcg tgggctcgga gatg 54

<210> SEQ ID NO 180

<211> LENGTH: 54
<212> TYPE: DNA
<213> ORGANISM: Artificial Sequence
<220> FEATURE:
<223> OTHER INFORMATION: Synthetic Construct

<400> SEQUENCE: 180
caagcagaag acggcatacg agatcacttc accagtctcg tgggctcgga gatg 54

<210> SEQ ID NO 181
<211> LENGTH: 54
<212> TYPE: DNA
<213> ORGANISM: Artificial Sequence
<220> FEATURE:
<223> OTHER INFORMATION: Synthetic Construct

<400> SEQUENCE: 181
caagcagaag acggcatacg agatgaaaga gccagtctcg tgggctcgga gatg 54

<210> SEQ ID NO 182
<211> LENGTH: 54
<212> TYPE: DNA
<213> ORGANISM: Artificial Sequence
<220> FEATURE:
<223> OTHER INFORMATION: Synthetic Construct

<400> SEQUENCE: 182
caagcagaag acggcatacg agatgaaggt cactgtctcg tgggctcgga gatg 54

<210> SEQ ID NO 183
<211> LENGTH: 54
<212> TYPE: DNA
<213> ORGANISM: Artificial Sequence
<220> FEATURE:
<223> OTHER INFORMATION: Synthetic Construct

<400> SEQUENCE: 183
caagcagaag acggcatacg agatgaaacc gttcgtctcg tgggctcgga gatg 54

<210> SEQ ID NO 184
<211> LENGTH: 54
<212> TYPE: DNA
<213> ORGANISM: Artificial Sequence
<220> FEATURE:
<223> OTHER INFORMATION: Synthetic Constuct

<400> SEQUENCE: 184
caagcagaag acggcatacg agatgaagcg gaatgtctcg tgggctcgga gatg 54

<210> SEQ ID NO 185
<211> LENGTH: 54
<212> TYPE: DNA
<213> ORGANISM: Artificial Sequence
<220> FEATURE:
<223> OTHER INFORMATION: Synthetic Construct

<400> SEQUENCE: 185
caagcagaag acggcatacg agatgaaagc cacagtctcg tgggctcgga gatg 54

<210> SEQ ID NO 186
<211> LENGTH: 54
<212> TYPE: DNA
<213> ORGANISM: Artificial Sequence
<220> FEATURE:
<223> OTHER INFORMATION: Synthetic Construct

<400> SEQUENCE: 186
caagcagaag acggcatacg agatgactta cagcgtctcg tgggctcgga gatg 54

<210> SEQ ID NO 187
<211> LENGTH: 54
<212> TYPE: DNA
<213> ORGANISM: Artificial Sequence
<220> FEATURE:
<223> OTHER INFORMATION: Synthetic Construct

<400> SEQUENCE: 187
caagcagaag acggcatacg agatgagcga tagtgtctcg tgggctcgga gatg 54

<210> SEQ ID NO 188
<211> LENGTH: 54
<212> TYPE: DNA
<213> ORGANISM: Artificial Sequence
<220> FEATURE:
<223> OTHER INFORMATION: Synthetic Construct

<400> SEQUENCE: 188
caagcagaag acggcatacg agatgagaac acacgtctcg tgggctcgga gatg 54

<210> SEQ ID NO 189
<211> LENGTH: 54
<212> TYPE: DNA
<213> ORGANISM: Artificial Sequence
<220> FEATURE:
<223> OTHER INFORMATION: Synthetic Construct

<400> SEQUENCE: 189
caagcagaag acggcatacg agatgacaac acctgtctcg tgggctcgga gatg 54

<210> SEQ ID NO 190
<211> LENGTH: 54
<212> TYPE: DNA
<213> ORGANISM: Artificial Sequence
<220> FEATURE:
<223> OTHER INFORMATION: Synthetic Construct

<400> SEQUENCE: 190
caagcagaag acggcatacg agatgaacac cagtgtctcg tgggctcgga gatg 54

<210> SEQ ID NO 191
<211> LENGTH: 54
<212> TYPE: DNA
<213> ORGANISM: Artificial Sequence
<220> FEATURE:
<223> OTHER INFORMATION: Synthetic Construct

<400> SEQUENCE: 191
caagcagaag acggcatacg agatgagctg actagtctcg tgggctcgga gatg 54

<210> SEQ ID NO 192
<211> LENGTH: 54
<212> TYPE: DNA
<213> ORGANISM: Artificial Sequence
<220> FEATURE:
<223> OTHER INFORMATION: Synthetic Construct

<400> SEQUENCE: 192
caagcagaag acggcatacg agatgagaga cgatgtctcg tgggctcgga gatg 54

<210> SEQ ID NO 193
<211> LENGTH: 54
<212> TYPE: DNA

<213> ORGANISM: Artificial Sequence
<220> FEATURE:
<223> OTHER INFORMATION: Synthetic Construct

<400> SEQUENCE: 193
caagcagaag acggcatacg agatgttggt ccttgtctcg tgggctcgga gatg 54

<210> SEQ ID NO 194
<211> LENGTH: 54
<212> TYPE: DNA
<213> ORGANISM: Artificial Sequence
<220> FEATURE:
<223> OTHER INFORMATION: Synthetic Construct

<400> SEQUENCE: 194
caagcagaag acggcatacg agatgtctta ggacgtctcg tgggctcgga gatg 54

<210> SEQ ID NO 195
<211> LENGTH: 54
<212> TYPE: DNA
<213> ORGANISM: Artificial Sequence
<220> FEATURE:
<223> OTHER INFORMATION: Synthetic Construct

<400> SEQUENCE: 195
caagcagaag acggcatacg agatgttcgc attggtctcg tgggctcgga gatg 54

<210> SEQ ID NO 196
<211> LENGTH: 54
<212> TYPE: DNA
<213> ORGANISM: Artificial Sequence
<220> FEATURE:
<223> OTHER INFORMATION: Synthetic Construct

<400> SEQUENCE: 196
caagcagaag acggcatacg agatgtctag caaggtctcg tgggctcgga gatg 54

<210> SEQ ID NO 197
<211> LENGTH: 54
<212> TYPE: DNA
<213> ORGANISM: Artificial Sequence
<220> FEATURE:
<223> OTHER INFORMATION: Synthetic Construct

<400> SEQUENCE: 197
caagcagaag acggcatacg agatgtggtc ttaggtctcg tgggctcgga gatg 54

<210> SEQ ID NO 198
<211> LENGTH: 54
<212> TYPE: DNA
<213> ORGANISM: Artificial Sequence
<220> FEATURE:
<223> OTHER INFORMATION: Synthetic Construct

<400> SEQUENCE: 198
caagcagaag acggcatacg agatgtacgg tcttgtctcg tgggctcgga gatg 54

<210> SEQ ID NO 199
<211> LENGTH: 54
<212> TYPE: DNA
<213> ORGANISM: Artificial Sequence
<220> FEATURE:
<223> OTHER INFORMATION: Synthetic Construct

<400> SEQUENCE: 199
caagcagaag acggcatacg agatgtacga cttggtctcg tgggctcgga gatg 54

<210> SEQ ID NO 200
<211> LENGTH: 54
<212> TYPE: DNA
<213> ORGANISM: Artificial Sequence
<220> FEATURE:
<223> OTHER INFORMATION: Synthetic Construct

<400> SEQUENCE: 200
caagcagaag acggcatacg agatgttgcg aactgtctcg tgggctcgga gatg 54

<210> SEQ ID NO 201
<211> LENGTH: 54
<212> TYPE: DNA
<213> ORGANISM: Artificial Sequence
<220> FEATURE:
<223> OTHER INFORMATION: Synthetic Construct

<400> SEQUENCE: 201
caagcagaag acggcatacg agatgtggac aatcgtctcg tgggctcgga gatg 54

<210> SEQ ID NO 202
<211> LENGTH: 54
<212> TYPE: DNA
<213> ORGANISM: Artificial Sequence
<220> FEATURE:
<223> OTHER INFORMATION: Synthetic Construct

<400> SEQUENCE: 202
caagcagaag acggcatacg agatgtttct cgacgtctcg tgggctcgga gatg 54

<210> SEQ ID NO 203
<211> LENGTH: 54
<212> TYPE: DNA
<213> ORGANISM: Artificial Sequence
<220> FEATURE:
<223> OTHER INFORMATION: Synthetic Construct

<400> SEQUENCE: 203
caagcagaag acggcatacg agatgttaag tggcgtctcg tgggctcgga gatg 54

<210> SEQ ID NO 204
<211> LENGTH: 54
<212> TYPE: DNA
<213> ORGANISM: Artificial Sequence
<220> FEATURE:
<223> OTHER INFORMATION: Synthetic Construct

<400> SEQUENCE: 204
caagcagaag acggcatacg agatgtatcg gtgtgtctcg tgggctcgga gatg 54

<210> SEQ ID NO 205
<211> LENGTH: 54
<212> TYPE: DNA
<213> ORGANISM: Artificial Sequence
<220> FEATURE:
<223> OTHER INFORMATION: Synthetic Construct

<400> SEQUENCE: 205
caagcagaag acggcatacg agatctgctg taaggtctcg tgggctcgga gatg 54

<210> SEQ ID NO 206
<211> LENGTH: 54
<212> TYPE: DNA
<213> ORGANISM: Artificial Sequence
<220> FEATURE:

<223> OTHER INFORMATION: Synthetic Construct

<400> SEQUENCE: 206
caagcagaag acggcatacg agatctgtga agtggtctcg tgggctcgga gatg 54

<210> SEQ ID NO 207
<211> LENGTH: 54
<212> TYPE: DNA
<213> ORGANISM: Artificial Sequence
<220> FEATURE:
<223> OTHER INFORMATION: Synthetic Construct

<400> SEQUENCE: 207
caagcagaag acggcatacg agatctaagg cgttgtctcg tgggctcgga gatg 54

<210> SEQ ID NO 208
<211> LENGTH: 54
<212> TYPE: DNA
<213> ORGANISM: Artificial Sequence
<220> FEATURE:
<223> OTHER INFORMATION: Synthetic Construct

<400> SEQUENCE: 208
caagcagaag acggcatacg agatcttcac tctggtctcg tgggctcgga gatg 54

<210> SEQ ID NO 209
<211> LENGTH: 54
<212> TYPE: DNA
<213> ORGANISM: Artificial Sequence
<220> FEATURE:
<223> OTHER INFORMATION: Synthetic Construct

<400> SEQUENCE: 209
caagcagaag acggcatacg agatctgtct aggtgtctcg tgggctcgga gatg 54

<210> SEQ ID NO 210
<211> LENGTH: 54
<212> TYPE: DNA
<213> ORGANISM: Artificial Sequence
<220> FEATURE:
<223> OTHER INFORMATION: Synthetic Construct

<400> SEQUENCE: 210
caagcagaag acggcatacg agatctcctt gtaggtctcg tgggctcgga gatg 54

<210> SEQ ID NO 211
<211> LENGTH: 54
<212> TYPE: DNA
<213> ORGANISM: Artificial Sequence
<220> FEATURE:
<223> OTHER INFORMATION: Synthetic Construct

<400> SEQUENCE: 211
caagcagaag acggcatacg agatctcatt cggtgtctcg tgggctcgga gatg 54

<210> SEQ ID NO 212
<211> LENGTH: 54
<212> TYPE: DNA
<213> ORGANISM: Artificial Sequence
<220> FEATURE:
<223> OTHER INFORMATION: Synthetic Construct

<400> SEQUENCE: 212
caagcagaag acggcatacg agatctgatg cactgtctcg tgggctcgga gatg 54

<210> SEQ ID NO 213
<211> LENGTH: 54
<212> TYPE: DNA
<213> ORGANISM: Artificial Sequence
<220> FEATURE:
<223> OTHER INFORMATION: Synthetic Construct

<400> SEQUENCE: 213
caagcagaag acggcatacg agatcttgtg cgttgtctcg tgggctcgga gatg 54

<210> SEQ ID NO 214
<211> LENGTH: 54
<212> TYPE: DNA
<213> ORGANISM: Artificial Sequence
<220> FEATURE:
<223> OTHER INFORMATION: Synthetic Construct

<400> SEQUENCE: 214
caagcagaag acggcatacg agatctccaa tagggtctcg tgggctcgga gatg 54

<210> SEQ ID NO 215
<211> LENGTH: 54
<212> TYPE: DNA
<213> ORGANISM: Artificial Sequence
<220> FEATURE:
<223> OTHER INFORMATION: Synthetic Construct

<400> SEQUENCE: 215
caagcagaag acggcatacg agatctgttc ggttgtctcg tgggctcgga gatg 54

<210> SEQ ID NO 216
<211> LENGTH: 54
<212> TYPE: DNA
<213> ORGANISM: Artificial Sequence
<220> FEATURE:
<223> OTHER INFORMATION: Synthetic Construct

<400> SEQUENCE: 216
caagcagaag acggcatacg agatcttggt agctgtctcg tgggctcgga gatg 54

<210> SEQ ID NO 217
<211> LENGTH: 54
<212> TYPE: DNA
<213> ORGANISM: Artificial Sequence
<220> FEATURE:
<223> OTHER INFORMATION: Synthetic Construct

<400> SEQUENCE: 217
caagcagaag acggcatacg agattggtat gctggtctcg tgggctcgga gatg 54

<210> SEQ ID NO 218
<211> LENGTH: 54
<212> TYPE: DNA
<213> ORGANISM: Artificial Sequence
<220> FEATURE:
<223> OTHER INFORMATION: Synthetic Construct

<400> SEQUENCE: 218
caagcagaag acggcatacg agattgcgct taacgtctcg tgggctcgga gatg 54

<210> SEQ ID NO 219
<211> LENGTH: 54
<212> TYPE: DNA
<213> ORGANISM: Artificial Sequence
<220> FEATURE:
<223> OTHER INFORMATION: Synthetic Construct

<400> SEQUENCE: 219
caagcagaag acggcatacg agattgctcc tagagtctcg tgggctcgga gatg 54

<210> SEQ ID NO 220
<211> LENGTH: 54
<212> TYPE: DNA
<213> ORGANISM: Artificial Sequence
<220> FEATURE:
<223> OTHER INFORMATION: Synthetic Construct

<400> SEQUENCE: 220
caagcagaag acggcatacg agattgcttc tgaggtctcg tgggctcgga gatg 54

<210> SEQ ID NO 221
<211> LENGTH: 54
<212> TYPE: DNA
<213> ORGANISM: Artificial Sequence
<220> FEATURE:
<223> OTHER INFORMATION: Synthetic Construct

<400> SEQUENCE: 221
caagcagaag acggcatacg agattgagca gatggtctcg tgggctcgga gatg 54

<210> SEQ ID NO 222
<211> LENGTH: 54
<212> TYPE: DNA
<213> ORGANISM: Artificial Sequence
<220> FEATURE:
<223> OTHER INFORMATION: Synthetic Construct

<400> SEQUENCE: 222
caagcagaag acggcatacg agattgccgt aagagtctcg tgggctcgga gatg 54

<210> SEQ ID NO 223
<211> LENGTH: 54
<212> TYPE: DNA
<213> ORGANISM: Artificial Sequence
<220> FEATURE:
<223> OTHER INFORMATION: Synthetic Construct

<400> SEQUENCE: 223
caagcagaag acggcatacg agattgttga tccggtctcg tgggctcgga gatg 54

<210> SEQ ID NO 224
<211> LENGTH: 54
<212> TYPE: DNA
<213> ORGANISM: Artificial Sequence
<220> FEATURE:
<223> OTHER INFORMATION: Synthetic Construct

<400> SEQUENCE: 224
caagcagaag acggcatacg agattgtgca ggtagtctcg tgggctcgga gatg 54

<210> SEQ ID NO 225
<211> LENGTH: 54
<212> TYPE: DNA
<213> ORGANISM: Artificial Sequence
<220> FEATURE:
<223> OTHER INFORMATION: Synthetic Construct

<400> SEQUENCE: 225
caagcagaag acggcatacg agattgcagg ttaggtctcg tgggctcgga gatg 54

<210> SEQ ID NO 226
<211> LENGTH: 54

<212> TYPE: DNA
<213> ORGANISM: Artificial Sequence
<220> FEATURE:
<223> OTHER INFORMATION: Synthetic Construct

<400> SEQUENCE: 226
caagcagaag acggcatacg agattgtacg ctacgtctcg tgggctcgga gatg 54

<210> SEQ ID NO 227
<211> LENGTH: 54
<212> TYPE: DNA
<213> ORGANISM: Artificial Sequence
<220> FEATURE:
<223> OTHER INFORMATION: Synthetic Construct

<400> SEQUENCE: 227
caagcagaag acggcatacg agattgccag gatagtctcg tgggctcgga gatg 54

<210> SEQ ID NO 228
<211> LENGTH: 54
<212> TYPE: DNA
<213> ORGANISM: Artificial Sequence
<220> FEATURE:
<223> OTHER INFORMATION: Synthetic Construct

<400> SEQUENCE: 228
caagcagaag acggcatacg agattgcgtg tgtagtctcg tgggctcgga gatg 54

<210> SEQ ID NO 229
<211> LENGTH: 54
<212> TYPE: DNA
<213> ORGANISM: Artificial Sequence
<220> FEATURE:
<223> OTHER INFORMATION: Synthetic Construct

<400> SEQUENCE: 229
caagcagaag acggcatacg agataggttg tagcgtctcg tgggctcgga gatg 54

<210> SEQ ID NO 230
<211> LENGTH: 54
<212> TYPE: DNA
<213> ORGANISM: Artificial Sequence
<220> FEATURE:
<223> OTHER INFORMATION: Synthetic Construct

<400> SEQUENCE: 230
caagcagaag acggcatacg agatagcagt cttcgtctcg tgggctcgga gatg 54

<210> SEQ ID NO 231
<211> LENGTH: 54
<212> TYPE: DNA
<213> ORGANISM: Artificial Sequence
<220> FEATURE:
<223> OTHER INFORMATION: Synthetic Construct

<400> SEQUENCE: 231
caagcagaag acggcatacg agatagagca cttcgtctcg tgggctcgga gatg 54

<210> SEQ ID NO 232
<211> LENGTH: 54
<212> TYPE: DNA
<213> ORGANISM: Artificial Sequence
<220> FEATURE:
<223> OTHER INFORMATION: Synthetic Construct

<400> SEQUENCE: 232
caagcagaag acggcatacg agatagactc gttggtctcg tgggctcgga gatg 54

<210> SEQ ID NO 233
<211> LENGTH: 54
<212> TYPE: DNA
<213> ORGANISM: Artificial Sequence
<220> FEATURE:
<223> OTHER INFORMATION: Synthetic Construct

<400> SEQUENCE: 233
caagcagaag acggcatacg agatagtagg tagggtctcg tgggctcgga gatg 54

<210> SEQ ID NO 234
<211> LENGTH: 54
<212> TYPE: DNA
<213> ORGANISM: Artificial Sequence
<220> FEATURE:
<223> OTHER INFORMATION: Synthetic Construct

<400> SEQUENCE: 234
caagcagaag acggcatacg agataggtct gatcgtctcg tgggctcgga gatg 54

<210> SEQ ID NO 235
<211> LENGTH: 54
<212> TYPE: DNA
<213> ORGANISM: Artificial Sequence
<220> FEATURE:
<223> OTHER INFORMATION: Synthetic Construct

<400> SEQUENCE: 235
caagcagaag acggcatacg agatagacag ctcagtctcg tgggctcgga gatg 54

<210> SEQ ID NO 236
<211> LENGTH: 54
<212> TYPE: DNA
<213> ORGANISM: Artificial Sequence
<220> FEATURE:
<223> OTHER INFORMATION: Synthetic Construct

<400> SEQUENCE: 236
caagcagaag acggcatacg agatagccga tgtagtctcg tgggctcgga gatg 54

<210> SEQ ID NO 237
<211> LENGTH: 54
<212> TYPE: DNA
<213> ORGANISM: Artificial Sequence
<220> FEATURE:
<223> OTHER INFORMATION: Synthetic Construct

<400> SEQUENCE: 237
caagcagaag acggcatacg agatagctgt tgacgtctcg tgggctcgga gatg 54

<210> SEQ ID NO 238
<211> LENGTH: 54
<212> TYPE: DNA
<213> ORGANISM: Artificial Sequence
<220> FEATURE:
<223> OTHER INFORMATION: Synthetic Construct

<400> SEQUENCE: 238
caagcagaag acggcatacg agatagtagc gtctgtctcg tgggctcgga gatg 54

<210> SEQ ID NO 239
<211> LENGTH: 54
<212> TYPE: DNA
<213> ORGANISM: Artificial Sequence
<220> FEATURE:
<223> OTHER INFORMATION: Synthetic Construct

<400> SEQUENCE: 239
caagcagaag acggcatacg agatagaacc gaaggtctcg tgggctcgga gatg 54

<210> SEQ ID NO 240
<211> LENGTH: 54
<212> TYPE: DNA
<213> ORGANISM: Artificial Sequence
<220> FEATURE:
<223> OTHER INFORMATION: Synthetic Construct

<400> SEQUENCE: 240
caagcagaag acggcatacg agatagctta cctggtctcg tgggctcgga gatg 54

<210> SEQ ID NO 241
<211> LENGTH: 54
<212> TYPE: DNA
<213> ORGANISM: Artificial Sequence
<220> FEATURE:
<223> OTHER INFORMATION: Synthetic Construct

<400> SEQUENCE: 241
caagcagaag acggcatacg agattcagtt acgggtctcg tgggctcgga gatg 54

<210> SEQ ID NO 242
<211> LENGTH: 54
<212> TYPE: DNA
<213> ORGANISM: Artificial Sequence
<220> FEATURE:
<223> OTHER INFORMATION: Synthetic Construct

<400> SEQUENCE: 242
caagcagaag acggcatacg agattccatc ctctgtctcg tgggctcgga gatg 54

<210> SEQ ID NO 243
<211> LENGTH: 54
<212> TYPE: DNA
<213> ORGANISM: Artificial Sequence
<220> FEATURE:
<223> OTHER INFORMATION: Synthetic Construct

<400> SEQUENCE: 243
caagcagaag acggcatacg agattcgtaa cgacgtctcg tgggctcgga gatg 54

<210> SEQ ID NO 244
<211> LENGTH: 54
<212> TYPE: DNA
<213> ORGANISM: Artificial Sequence
<220> FEATURE:
<223> OTHER INFORMATION: Synthetic Construct

<400> SEQUENCE: 244
caagcagaag acggcatacg agattcgtcg aagagtctcg tgggctcgga gatg 54

<210> SEQ ID NO 245
<211> LENGTH: 54
<212> TYPE: DNA
<213> ORGANISM: Artificial Sequence
<220> FEATURE:
<223> OTHER INFORMATION: Synthetic Construct

<400> SEQUENCE: 245
caagcagaag acggcatacg agattccagt tctggtctcg tgggctcgga gatg 54

<210> SEQ ID NO 246
<211> LENGTH: 54
<212> TYPE: DNA
<213> ORGANISM: Artificial Sequence
<220> FEATURE:
<223> OTHER INFORMATION: Synthetic Construct

<400> SEQUENCE: 246
caagcagaag acggcatacg agattcggtg tcttgtctcg tgggctcgga gatg 54

<210> SEQ ID NO 247
<211> LENGTH: 54
<212> TYPE: DNA
<213> ORGANISM: Artificial Sequence
<220> FEATURE:
<223> OTHER INFORMATION: Synthetic Construct

<400> SEQUENCE: 247
caagcagaag acggcatacg agattcacat tgcggtctcg tgggctcgga gatg 54

<210> SEQ ID NO 248
<211> LENGTH: 54
<212> TYPE: DNA
<213> ORGANISM: Artificial Sequence
<220> FEATURE:
<223> OTHER INFORMATION: Synthetic Construct

<400> SEQUENCE: 248
caagcagaag acggcatacg agattcacgg aacagtctcg tgggctcgga gatg 54

<210> SEQ ID NO 249
<211> LENGTH: 54
<212> TYPE: DNA
<213> ORGANISM: Artificial Sequence
<220> FEATURE:
<223> OTHER INFORMATION: Synthetic Construct

<400> SEQUENCE: 249
caagcagaag acggcatacg agattccctg attggtctcg tgggctcgga gatg 54

<210> SEQ ID NO 250
<211> LENGTH: 54
<212> TYPE: DNA
<213> ORGANISM: Artificial Sequence
<220> FEATURE:
<223> OTHER INFORMATION: Synthetic Construct

<400> SEQUENCE: 250
caagcagaag acggcatacg agattcacgg attcgtctcg tgggctcgga gatg 54

<210> SEQ ID NO 251
<211> LENGTH: 54
<212> TYPE: DNA
<213> ORGANISM: Artificial Sequence
<220> FEATURE:
<223> OTHER INFORMATION: Synthetic Construct

<400> SEQUENCE: 251
caagcagaag acggcatacg agattcttga cagggtctcg tgggctcgga gatg 54

<210> SEQ ID NO 252
<211> LENGTH: 54
<212> TYPE: DNA
<213> ORGANISM: Artificial Sequence
<220> FEATURE:
<223> OTHER INFORMATION: Synthetic Construct

<400> SEQUENCE: 252
caagcagaag acggcatacg agattctgtg gtacgtctcg tgggctcgga gatg 54

<210> SEQ ID NO 253
<211> LENGTH: 54
<212> TYPE: DNA
<213> ORGANISM: Artificial Sequence
<220> FEATURE:
<223> OTHER INFORMATION: Synthetic Construct

<400> SEQUENCE: 253
caagcagaag acggcatacg agatacactc catcgtctcg tgggctcgga gatg 54

<210> SEQ ID NO 254
<211> LENGTH: 54
<212> TYPE: DNA
<213> ORGANISM: Artificial Sequence
<220> FEATURE:
<223> OTHER INFORMATION: Synthetic Construct

<400> SEQUENCE: 254
caagcagaag acggcatacg agatactcga aggtgtctcg tgggctcgga gatg 54

<210> SEQ ID NO 255
<211> LENGTH: 54
<212> TYPE: DNA
<213> ORGANISM: Artificial Sequence
<220> FEATURE:
<223> OTHER INFORMATION: Synthetic Construct

<400> SEQUENCE: 255
caagcagaag acggcatacg agatacagtc tgtggtctcg tgggctcgga gatg 54

<210> SEQ ID NO 256
<211> LENGTH: 54
<212> TYPE: DNA
<213> ORGANISM: Artificial Sequence
<220> FEATURE:
<223> OTHER INFORMATION: Synthetic Construct

<400> SEQUENCE: 256
caagcagaag acggcatacg agatacctag gcatgtctcg tgggctcgga gatg 54

<210> SEQ ID NO 257
<211> LENGTH: 54
<212> TYPE: DNA
<213> ORGANISM: Artificial Sequence
<220> FEATURE:
<223> OTHER INFORMATION: Synthetic Construct

<400> SEQUENCE: 257
caagcagaag acggcatacg agatacaaca accggtctcg tgggctcgga gatg 54

<210> SEQ ID NO 258
<211> LENGTH: 54
<212> TYPE: DNA
<213> ORGANISM: Artificial Sequence
<220> FEATURE:
<223> OTHER INFORMATION: Synthetic Construct

<400> SEQUENCE: 258
caagcagaag acggcatacg agataccgtt gcaagtctcg tgggctcgga gatg 54

<210> SEQ ID NO 259

<211> LENGTH: 54
<212> TYPE: DNA
<213> ORGANISM: Artificial Sequence
<220> FEATURE:
<223> OTHER INFORMATION: Synthetic Construct

<400> SEQUENCE: 259
caagcagaag acggcatacg agatacgcta cgttgtctcg tgggctcgga gatg 54

<210> SEQ ID NO 260
<211> LENGTH: 54
<212> TYPE: DNA
<213> ORGANISM: Artificial Sequence
<220> FEATURE:
<223> OTHER INFORMATION: Synthetic Construct

<400> SEQUENCE: 260
caagcagaag acggcatacg agatacgaca agaggtctcg tgggctcgga gatg 54

<210> SEQ ID NO 261
<211> LENGTH: 54
<212> TYPE: DNA
<213> ORGANISM: Artificial Sequence
<220> FEATURE:
<223> OTHER INFORMATION: Synthetic Construct

<400> SEQUENCE: 261
caagcagaag acggcatacg agatactcga gtgagtctcg tgggctcgga gatg 54

<210> SEQ ID NO 262
<211> LENGTH: 54
<212> TYPE: DNA
<213> ORGANISM: Artificial Sequence
<220> FEATURE:
<223> OTHER INFORMATION: Synthetic Construct

<400> SEQUENCE: 262
caagcagaag acggcatacg agatacaggt tcgagtctcg tgggctcgga gatg 54

<210> SEQ ID NO 263
<211> LENGTH: 54
<212> TYPE: DNA
<213> ORGANISM: Artificial Sequence
<220> FEATURE:
<223> OTHER INFORMATION: Synthetic Construct

<400> SEQUENCE: 263
caagcagaag acggcatacg agataccgtc aatggtctcg tgggctcgga gatg 54

<210> SEQ ID NO 264
<211> LENGTH: 54
<212> TYPE: DNA
<213> ORGANISM: Artificial Sequence
<220> FEATURE:
<223> OTHER INFORMATION: Synthetic Construct

<400> SEQUENCE: 264
caagcagaag acggcatacg agataccgag tatggtctcg tgggctcgga gatg 54

<210> SEQ ID NO 265
<211> LENGTH: 54
<212> TYPE: DNA
<213> ORGANISM: Artificial Sequence
<220> FEATURE:
<223> OTHER INFORMATION: Synthetic Construct

<400> SEQUENCE: 265
caagcagaag acggcatacg agatcatcct acctgtctcg tgggctcgga gatg 54

<210> SEQ ID NO 266
<211> LENGTH: 54
<212> TYPE: DNA
<213> ORGANISM: Artificial Sequence
<220> FEATURE:
<223> OTHER INFORMATION: Synthetic Construct

<400> SEQUENCE: 266
caagcagaag acggcatacg agatcaagcc aagtgtctcg tgggctcgga gatg 54

<210> SEQ ID NO 267
<211> LENGTH: 54
<212> TYPE: DNA
<213> ORGANISM: Artificial Sequence
<220> FEATURE:
<223> OTHER INFORMATION: Synthetic Construct

<400> SEQUENCE: 267
caagcagaag acggcatacg agatcagcgt cattgtctcg tgggctcgga gatg 54

<210> SEQ ID NO 268
<211> LENGTH: 54
<212> TYPE: DNA
<213> ORGANISM: Artificial Sequence
<220> FEATURE:
<223> OTHER INFORMATION: Synthetic Construct

<400> SEQUENCE: 268
caagcagaag acggcatacg agatcacaga atcggtctcg tgggctcgga gatg 54

<210> SEQ ID NO 269
<211> LENGTH: 54
<212> TYPE: DNA
<213> ORGANISM: Artificial Sequence
<220> FEATURE:
<223> OTHER INFORMATION: Synthetic Construct

<400> SEQUENCE: 269
caagcagaag acggcatacg agatcaatcg atcggtctcg tgggctcgga gatg 54

<210> SEQ ID NO 270
<211> LENGTH: 54
<212> TYPE: DNA
<213> ORGANISM: Artificial Sequence
<220> FEATURE:
<223> OTHER INFORMATION: Synthetic Construct

<400> SEQUENCE: 270
caagcagaag acggcatacg agatcatgag gtgtgtctcg tgggctcgga gatg 54

<210> SEQ ID NO 271
<211> LENGTH: 54
<212> TYPE: DNA
<213> ORGANISM: Artificial Sequence
<220> FEATURE:
<223> OTHER INFORMATION: Synthetic Construct

<400> SEQUENCE: 271
caagcagaag acggcatacg agatcagacg atctgtctcg tgggctcgga gatg 54

<210> SEQ ID NO 272
<211> LENGTH: 54
<212> TYPE: DNA

<213> ORGANISM: Artificial Sequence
<220> FEATURE:
<223> OTHER INFORMATION: Synthetic Construct

<400> SEQUENCE: 272
caagcagaag acggcatacg agatcacaac ggatgtctcg tgggctcgga gatg 54

<210> SEQ ID NO 273
<211> LENGTH: 54
<212> TYPE: DNA
<213> ORGANISM: Artificial Sequence
<220> FEATURE:
<223> OTHER INFORMATION: Synthetic Construct

<400> SEQUENCE: 273
caagcagaag acggcatacg agatcaagtc gacagtctcg tgggctcgga gatg 54

<210> SEQ ID NO 274
<211> LENGTH: 54
<212> TYPE: DNA
<213> ORGANISM: Artificial Sequence
<220> FEATURE:
<223> OTHER INFORMATION: Synthetic Construct

<400> SEQUENCE: 274
caagcagaag acggcatacg agatcagatc gagtgtctcg tgggctcgga gatg 54

<210> SEQ ID NO 275
<211> LENGTH: 54
<212> TYPE: DNA
<213> ORGANISM: Artificial Sequence
<220> FEATURE:
<223> OTHER INFORMATION: Synthetic Construct

<400> SEQUENCE: 275
caagcagaag acggcatacg agatcatcag acgagtctcg tgggctcgga gatg 54

<210> SEQ ID NO 276
<211> LENGTH: 54
<212> TYPE: DNA
<213> ORGANISM: Artificial Sequence
<220> FEATURE:
<223> OTHER INFORMATION: Synthetic Construct

<400> SEQUENCE: 276
caagcagaag acggcatacg agatcacacc actagtctcg tgggctcgga gatg 54

<210> SEQ ID NO 277
<211> LENGTH: 54
<212> TYPE: DNA
<213> ORGANISM: Artificial Sequence
<220> FEATURE:
<223> OTHER INFORMATION: Synthetic Construct

<400> SEQUENCE: 277
caagcagaag acggcatacg agatgactct ggttgtctcg tgggctcgga gatg 54

<210> SEQ ID NO 278
<211> LENGTH: 54
<212> TYPE: DNA
<213> ORGANISM: Artificial Sequence
<220> FEATURE:
<223> OTHER INFORMATION: Synthetic Construct

<400> SEQUENCE: 278
caagcagaag acggcatacg agatgatacc acaggtctcg tgggctcgga gatg 54

<210> SEQ ID NO 279
<211> LENGTH: 54
<212> TYPE: DNA
<213> ORGANISM: Artificial Sequence
<220> FEATURE:
<223> OTHER INFORMATION: Synthetic Construct

<400> SEQUENCE: 279
caagcagaag acggcatacg agatgagact tagggtctcg tgggctcgga gatg 54

<210> SEQ ID NO 280
<211> LENGTH: 54
<212> TYPE: DNA
<213> ORGANISM: Artificial Sequence
<220> FEATURE:
<223> OTHER INFORMATION: Synthetic Construct

<400> SEQUENCE: 280
caagcagaag acggcatacg agatgatctg agaggtctcg tgggctcgga gatg 54

<210> SEQ ID NO 281
<211> LENGTH: 54
<212> TYPE: DNA
<213> ORGANISM: Artificial Sequence
<220> FEATURE:
<223> OTHER INFORMATION: Synthetic Construct

<400> SEQUENCE: 281
caagcagaag acggcatacg agatgagttc tcgtgtctcg tgggctcgga gatg 54

<210> SEQ ID NO 282
<211> LENGTH: 54
<212> TYPE: DNA
<213> ORGANISM: Artificial Sequence
<220> FEATURE:
<223> OTHER INFORMATION: Synthetic Construct

<400> SEQUENCE: 282
caagcagaag acggcatacg agatgagctt agctgtctcg tgggctcgga gatg 54

<210> SEQ ID NO 283
<211> LENGTH: 54
<212> TYPE: DNA
<213> ORGANISM: Artificial Sequence
<220> FEATURE:
<223> OTHER INFORMATION: Synthetic Construct

<400> SEQUENCE: 283
caagcagaag acggcatacg agatgagtgg ataggtctcg tgggctcgga gatg 54

<210> SEQ ID NO 284
<211> LENGTH: 54
<212> TYPE: DNA
<213> ORGANISM: Artificial Sequence
<220> FEATURE:
<223> OTHER INFORMATION: Synthetic Construct

<400> SEQUENCE: 284
caagcagaag acggcatacg agatgacata acgggtctcg tgggctcgga gatg 54

<210> SEQ ID NO 285
<211> LENGTH: 54
<212> TYPE: DNA
<213> ORGANISM: Artificial Sequence
<220> FEATURE:

<223> OTHER INFORMATION: Synthetic Construct

<400> SEQUENCE: 285
caagcagaag acggcatacg agatgaacct aagggtctcg tgggctcgga gatg 54

<210> SEQ ID NO 286
<211> LENGTH: 54
<212> TYPE: DNA
<213> ORGANISM: Artificial Sequence
<220> FEATURE:
<223> OTHER INFORMATION: Synthetic Construct

<400> SEQUENCE: 286
caagcagaag acggcatacg agatgatcga catcgtctcg tgggctcgga gatg 54

<210> SEQ ID NO 287
<211> LENGTH: 54
<212> TYPE: DNA
<213> ORGANISM: Artificial Sequence
<220> FEATURE:
<223> OTHER INFORMATION: Synthetic Construct

<400> SEQUENCE: 287
caagcagaag acggcatacg agatgagctc tgtagtctcg tgggctcgga gatg 54

<210> SEQ ID NO 288
<211> LENGTH: 54
<212> TYPE: DNA
<213> ORGANISM: Artificial Sequence
<220> FEATURE:
<223> OTHER INFORMATION: Synthetic Construct

<400> SEQUENCE: 288
caagcagaag acggcatacg agatgaactg ctaggtctcg tgggctcgga gatg 54

<210> SEQ ID NO 289
<211> LENGTH: 54
<212> TYPE: DNA
<213> ORGANISM: Artificial Sequence
<220> FEATURE:
<223> OTHER INFORMATION: Synthetic Construct

<400> SEQUENCE: 289
caagcagaag acggcatacg agatgtagag ccttgtctcg tgggctcgga gatg 54

<210> SEQ ID NO 290
<211> LENGTH: 54
<212> TYPE: DNA
<213> ORGANISM: Artificial Sequence
<220> FEATURE:
<223> OTHER INFORMATION: Synthetic Construct

<400> SEQUENCE: 290
caagcagaag acggcatacg agatgttgct tggtgtctcg tgggctcgga gatg 54

<210> SEQ ID NO 291
<211> LENGTH: 54
<212> TYPE: DNA
<213> ORGANISM: Artificial Sequence
<220> FEATURE:
<223> OTHER INFORMATION: Synthetic Construct

<400> SEQUENCE: 291
caagcagaag acggcatacg agatgtatca cacggtctcg tgggctcgga gatg 54

<210> SEQ ID NO 292
<211> LENGTH: 54
<212> TYPE: DNA
<213> ORGANISM: Artificial Sequence
<220> FEATURE:
<223> OTHER INFORMATION: Synthetic Construct

<400> SEQUENCE: 292
caagcagaag acggcatacg agatgtgttg ttcggtctcg tgggctcgga gatg 54

<210> SEQ ID NO 293
<211> LENGTH: 54
<212> TYPE: DNA
<213> ORGANISM: Artificial Sequence
<220> FEATURE:
<223> OTHER INFORMATION: Synthetic Construct

<400> SEQUENCE: 293
caagcagaag acggcatacg agatgttgcg tagagtctcg tgggctcgga gatg 54

<210> SEQ ID NO 294
<211> LENGTH: 54
<212> TYPE: DNA
<213> ORGANISM: Artificial Sequence
<220> FEATURE:
<223> OTHER INFORMATION: Synthetic Construct

<400> SEQUENCE: 294
caagcagaag acggcatacg agatgtcatg gaacgtctcg tgggctcgga gatg 54

<210> SEQ ID NO 295
<211> LENGTH: 54
<212> TYPE: DNA
<213> ORGANISM: Artificial Sequence
<220> FEATURE:
<223> OTHER INFORMATION: Synthetic Construct

<400> SEQUENCE: 295
caagcagaag acggcatacg agatgtctgt tagggtctcg tgggctcgga gatg 54

<210> SEQ ID NO 296
<211> LENGTH: 54
<212> TYPE: DNA
<213> ORGANISM: Artificial Sequence
<220> FEATURE:
<223> OTHER INFORMATION: Synthetic Construct

<400> SEQUENCE: 296
caagcagaag acggcatacg agatgtggta ctacgtctcg tgggctcgga gatg 54

<210> SEQ ID NO 297
<211> LENGTH: 54
<212> TYPE: DNA
<213> ORGANISM: Artificial Sequence
<220> FEATURE:
<223> OTHER INFORMATION: Synthetic Construct

<400> SEQUENCE: 297
caagcagaag acggcatacg agatgtgcca cttagtctcg tgggctcgga gatg 54

<210> SEQ ID NO 298
<211> LENGTH: 54
<212> TYPE: DNA
<213> ORGANISM: Artificial Sequence
<220> FEATURE:
<223> OTHER INFORMATION: Synthetic Construct

<400> SEQUENCE: 298
caagcagaag acggcatacg agatgttatc agcggtctcg tgggctcgga gatg 54

<210> SEQ ID NO 299
<211> LENGTH: 54
<212> TYPE: DNA
<213> ORGANISM: Artificial Sequence
<220> FEATURE:
<223> OTHER INFORMATION: Synthetic Construct

<400> SEQUENCE: 299
caagcagaag acggcatacg agatgtcttc gactgtctcg tgggctcgga gatg 54

<210> SEQ ID NO 300
<211> LENGTH: 54
<212> TYPE: DNA
<213> ORGANISM: Artificial Sequence
<220> FEATURE:
<223> OTHER INFORMATION: Synthetic Construct

<400> SEQUENCE: 300
caagcagaag acggcatacg agatgtcgaa gaacgtctcg tgggctcgga gatg 54

<210> SEQ ID NO 301
<211> LENGTH: 54
<212> TYPE: DNA
<213> ORGANISM: Artificial Sequence
<220> FEATURE:
<223> OTHER INFORMATION: Synthetic Construct

<400> SEQUENCE: 301
caagcagaag acggcatacg agatctcacc ttacgtctcg tgggctcgga gatg 54

<210> SEQ ID NO 302
<211> LENGTH: 54
<212> TYPE: DNA
<213> ORGANISM: Artificial Sequence
<220> FEATURE:
<223> OTHER INFORMATION: Synthetic Construct

<400> SEQUENCE: 302
caagcagaag acggcatacg agatctacat aggcgtctcg tgggctcgga gatg 54

<210> SEQ ID NO 303
<211> LENGTH: 54
<212> TYPE: DNA
<213> ORGANISM: Artificial Sequence
<220> FEATURE:
<223> OTHER INFORMATION: Synthetic Construct

<400> SEQUENCE: 303
caagcagaag acggcatacg agatcttgtc tgctgtctcg tgggctcgga gatg 54

<210> SEQ ID NO 304
<211> LENGTH: 54
<212> TYPE: DNA
<213> ORGANISM: Artificial Sequence
<220> FEATURE:
<223> OTHER INFORMATION: Synthetic Construct

<400> SEQUENCE: 304
caagcagaag acggcatacg agatctcagt ccaagtctcg tgggctcgga gatg 54

<210> SEQ ID NO 305
<211> LENGTH: 54

<212> TYPE: DNA
<213> ORGANISM: Artificial Sequence
<220> FEATURE:
<223> OTHER INFORMATION: Synthetic Construct

<400> SEQUENCE: 305
caagcagaag acggcatacg agatctgtct ccttgtctcg tgggctcgga gatg 54

<210> SEQ ID NO 306
<211> LENGTH: 54
<212> TYPE: DNA
<213> ORGANISM: Artificial Sequence
<220> FEATURE:
<223> OTHER INFORMATION: Synthetic Construct

<400> SEQUENCE: 306
caagcagaag acggcatacg agatctcaac ctaggtctcg tgggctcgga gatg 54

<210> SEQ ID NO 307
<211> LENGTH: 54
<212> TYPE: DNA
<213> ORGANISM: Artificial Sequence
<220> FEATURE:
<223> OTHER INFORMATION: Synthetic Construct

<400> SEQUENCE: 307
caagcagaag acggcatacg agatctaacg tctggtctcg tgggctcgga gatg 54

<210> SEQ ID NO 308
<211> LENGTH: 54
<212> TYPE: DNA
<213> ORGANISM: Artificial Sequence
<220> FEATURE:
<223> OTHER INFORMATION: Synthetic Construct

<400> SEQUENCE: 308
caagcagaag acggcatacg agatctcctc agttgtctcg tgggctcgga gatg 54

<210> SEQ ID NO 309
<211> LENGTH: 54
<212> TYPE: DNA
<213> ORGANISM: Artificial Sequence
<220> FEATURE:
<223> OTHER INFORMATION: Synthetic Construct

<400> SEQUENCE: 309
caagcagaag acggcatacg agatctccta ctgagtctcg tgggctcgga gatg 54

<210> SEQ ID NO 310
<211> LENGTH: 54
<212> TYPE: DNA
<213> ORGANISM: Artificial Sequence
<220> FEATURE:
<223> OTHER INFORMATION: Synthetic Construct

<400> SEQUENCE: 310
caagcagaag acggcatacg agatctgcat acaggtctcg tgggctcgga gatg 54

<210> SEQ ID NO 311
<211> LENGTH: 54
<212> TYPE: DNA
<213> ORGANISM: Artificial Sequence
<220> FEATURE:
<223> OTHER INFORMATION: Synthetic Construct

<400> SEQUENCE: 311
caagcagaag acggcatacg agatctgtta aggcgtctcg tgggctcgga gatg 54

<210> SEQ ID NO 312
<211> LENGTH: 54
<212> TYPE: DNA
<213> ORGANISM: Artificial Sequence
<220> FEATURE:
<223> OTHER INFORMATION: Synthetic Construct

<400> SEQUENCE: 312
caagcagaag acggcatacg agatctttgc gaaggtctcg tgggctcgga gatg 54

<210> SEQ ID NO 313
<211> LENGTH: 54
<212> TYPE: DNA
<213> ORGANISM: Artificial Sequence
<220> FEATURE:
<223> OTHER INFORMATION: Synthetic Construct

<400> SEQUENCE: 313
caagcagaag acggcatacg agattgttgg cttggtctcg tgggctcgga gatg 54

<210> SEQ ID NO 314
<211> LENGTH: 54
<212> TYPE: DNA
<213> ORGANISM: Artificial Sequence
<220> FEATURE:
<223> OTHER INFORMATION: Synthetic Construct

<400> SEQUENCE: 314
caagcagaag acggcatacg agattgatgc acgagtctcg tgggctcgga gatg 54

<210> SEQ ID NO 315
<211> LENGTH: 54
<212> TYPE: DNA
<213> ORGANISM: Artificial Sequence
<220> FEATURE:
<223> OTHER INFORMATION: Synthetic Construct

<400> SEQUENCE: 315
caagcagaag acggcatacg agattgggca agttgtctcg tgggctcgga gatg 54

<210> SEQ ID NO 316
<211> LENGTH: 54
<212> TYPE: DNA
<213> ORGANISM: Artificial Sequence
<220> FEATURE:
<223> OTHER INFORMATION: Synthetic Construct

<400> SEQUENCE: 316
caagcagaag acggcatacg agattgggac tgttgtctcg tgggctcgga gatg 54

<210> SEQ ID NO 317
<211> LENGTH: 54
<212> TYPE: DNA
<213> ORGANISM: Artificial Sequence
<220> FEATURE:
<223> OTHER INFORMATION: Synthetic Construct

<400> SEQUENCE: 317
caagcagaag acggcatacg agattgtgtt gtgggtctcg tgggctcgga gatg 54

<210> SEQ ID NO 318
<211> LENGTH: 54
<212> TYPE: DNA
<213> ORGANISM: Artificial Sequence
<220> FEATURE:
<223> OTHER INFORMATION: Synthetic Construct

<400> SEQUENCE: 318
caagcagaag acggcatacg agattgtcca atcggtctcg tgggctcgga gatg 54

<210> SEQ ID NO 319
<211> LENGTH: 54
<212> TYPE: DNA
<213> ORGANISM: Artificial Sequence
<220> FEATURE:
<223> OTHER INFORMATION: Synthetic Construct

<400> SEQUENCE: 319
caagcagaag acggcatacg agattgctgc gtatgtctcg tgggctcgga gatg 54

<210> SEQ ID NO 320
<211> LENGTH: 54
<212> TYPE: DNA
<213> ORGANISM: Artificial Sequence
<220> FEATURE:
<223> OTHER INFORMATION: Synthetic Construct

<400> SEQUENCE: 320
caagcagaag acggcatacg agattggaag gaaggtctcg tgggctcgga gatg 54

<210> SEQ ID NO 321
<211> LENGTH: 54
<212> TYPE: DNA
<213> ORGANISM: Artificial Sequence
<220> FEATURE:
<223> OTHER INFORMATION: Synthetic Construct

<400> SEQUENCE: 321
caagcagaag acggcatacg agattgctgg agtagtctcg tgggctcgga gatg 54

<210> SEQ ID NO 322
<211> LENGTH: 54
<212> TYPE: DNA
<213> ORGANISM: Artificial Sequence
<220> FEATURE:
<223> OTHER INFORMATION: Synthetic Construct

<400> SEQUENCE: 322
caagcagaag acggcatacg agattgtcct gctagtctcg tgggctcgga gatg 54

<210> SEQ ID NO 323
<211> LENGTH: 54
<212> TYPE: DNA
<213> ORGANISM: Artificial Sequence
<220> FEATURE:
<223> OTHER INFORMATION: Synthetic Construct

<400> SEQUENCE: 323
caagcagaag acggcatacg agattgcgtt atgcgtctcg tgggctcgga gatg 54

<210> SEQ ID NO 324
<211> LENGTH: 54
<212> TYPE: DNA
<213> ORGANISM: Artificial Sequence
<220> FEATURE:
<223> OTHER INFORMATION: Synthetic Construct

<400> SEQUENCE: 324
caagcagaag acggcatacg agattgctac ttgggtctcg tgggctcgga gatg 54

<210> SEQ ID NO 325
<211> LENGTH: 54
<212> TYPE: DNA
<213> ORGANISM: Artificial Sequence
<220> FEATURE:
<223> OTHER INFORMATION: Synthetic Construct

<400> SEQUENCE: 325
caagcagaag acggcatacg agatagagtt ggctgtctcg tgggctcgga gatg 54

<210> SEQ ID NO 326
<211> LENGTH: 54
<212> TYPE: DNA
<213> ORGANISM: Artificial Sequence
<220> FEATURE:
<223> OTHER INFORMATION: Synthetic Construct

<400> SEQUENCE: 326
caagcagaag acggcatacg agatagaggt gtacgtctcg tgggctcgga gatg 54

<210> SEQ ID NO 327
<211> LENGTH: 54
<212> TYPE: DNA
<213> ORGANISM: Artificial Sequence
<220> FEATURE:
<223> OTHER INFORMATION: Synthetic Construct

<400> SEQUENCE: 327
caagcagaag acggcatacg agatagcgat agaggtctcg tgggctcgga gatg 54

<210> SEQ ID NO 328
<211> LENGTH: 54
<212> TYPE: DNA
<213> ORGANISM: Artificial Sequence
<220> FEATURE:
<223> OTHER INFORMATION: Synthetic Construct

<400> SEQUENCE: 328
caagcagaag acggcatacg agatagataa ggcggtctcg tgggctcgga gatg 54

<210> SEQ ID NO 329
<211> LENGTH: 54
<212> TYPE: DNA
<213> ORGANISM: Artificial Sequence
<220> FEATURE:
<223> OTHER INFORMATION: Synthetic Construct

<400> SEQUENCE: 329
caagcagaag acggcatacg agataggtag tcaggtctcg tgggctcgga gatg 54

<210> SEQ ID NO 330
<211> LENGTH: 54
<212> TYPE: DNA
<213> ORGANISM: Artificial Sequence
<220> FEATURE:
<223> OTHER INFORMATION: Synthetic Construct

<400> SEQUENCE: 330
caagcagaag acggcatacg agatagcaag cagtgtctcg tgggctcgga gatg 54

<210> SEQ ID NO 331
<211> LENGTH: 54
<212> TYPE: DNA
<213> ORGANISM: Artificial Sequence
<220> FEATURE:
<223> OTHER INFORMATION: Synthetic Construct

<400> SEQUENCE: 331
caagcagaag acggcatacg agatagtgtc cagagtctcg tgggctcgga gatg 54

<210> SEQ ID NO 332
<211> LENGTH: 54
<212> TYPE: DNA
<213> ORGANISM: Artificial Sequence
<220> FEATURE:
<223> OTHER INFORMATION: Synthetic Construct

<400> SEQUENCE: 332
caagcagaag acggcatacg agatagtcgt tcgtgtctcg tgggctcgga gatg 54

<210> SEQ ID NO 333
<211> LENGTH: 54
<212> TYPE: DNA
<213> ORGANISM: Artificial Sequence
<220> FEATURE:
<223> OTHER INFORMATION: Synthetic Construct

<400> SEQUENCE: 333
caagcagaag acggcatacg agatagtctt ctgcgtctcg tgggctcgga gatg 54

<210> SEQ ID NO 334
<211> LENGTH: 54
<212> TYPE: DNA
<213> ORGANISM: Artificial Sequence
<220> FEATURE:
<223> OTHER INFORMATION: Synthetic Construct

<400> SEQUENCE: 334
caagcagaag acggcatacg agatagctga agctgtctcg tgggctcgga gatg 54

<210> SEQ ID NO 335
<211> LENGTH: 54
<212> TYPE: DNA
<213> ORGANISM: Artificial Sequence
<220> FEATURE:
<223> OTHER INFORMATION: Synthetic Construct

<400> SEQUENCE: 335
caagcagaag acggcatacg agatagcatg aggagtctcg tgggctcgga gatg 54

<210> SEQ ID NO 336
<211> LENGTH: 54
<212> TYPE: DNA
<213> ORGANISM: Artificial Sequence
<220> FEATURE:
<223> OTHER INFORMATION: Synthetic Construct

<400> SEQUENCE: 336
caagcagaag acggcatacg agatagactg tgtcgtctcg tgggctcgga gatg 54

<210> SEQ ID NO 337
<211> LENGTH: 54
<212> TYPE: DNA
<213> ORGANISM: Artificial Sequence
<220> FEATURE:
<223> OTHER INFORMATION: Synthetic Construct

<400> SEQUENCE: 337
caagcagaag acggcatacg agattcggcg ttatgtctcg tgggctcgga gatg 54

<210> SEQ ID NO 338

<211> LENGTH: 54
<212> TYPE: DNA
<213> ORGANISM: Artificial Sequence
<220> FEATURE:
<223> OTHER INFORMATION: Synthetic Construct

<400> SEQUENCE: 338
caagcagaag acggcatacg agattctgta gccagtctcg tgggctcgga gatg 54

<210> SEQ ID NO 339
<211> LENGTH: 54
<212> TYPE: DNA
<213> ORGANISM: Artificial Sequence
<220> FEATURE:
<223> OTHER INFORMATION: Synthetic Construct

<400> SEQUENCE: 339
caagcagaag acggcatacg agattccgac cattgtctcg tgggctcgga gatg 54

<210> SEQ ID NO 340
<211> LENGTH: 54
<212> TYPE: DNA
<213> ORGANISM: Artificial Sequence
<220> FEATURE:
<223> OTHER INFORMATION: Synthetic Construct

<400> SEQUENCE: 340
caagcagaag acggcatacg agattcatga cgtcgtctcg tgggctcgga gatg 54

<210> SEQ ID NO 341
<211> LENGTH: 54
<212> TYPE: DNA
<213> ORGANISM: Artificial Sequence
<220> FEATURE:
<223> OTHER INFORMATION: Synthetic Construct

<400> SEQUENCE: 341
caagcagaag acggcatacg agattctaca tcgggtctcg tgggctcgga gatg 54

<210> SEQ ID NO 342
<211> LENGTH: 54
<212> TYPE: DNA
<213> ORGANISM: Artificial Sequence
<220> FEATURE:
<223> OTHER INFORMATION: Synthetic Construct

<400> SEQUENCE: 342
caagcagaag acggcatacg agattcgtca ctgtgtctcg tgggctcgga gatg 54

<210> SEQ ID NO 343
<211> LENGTH: 54
<212> TYPE: DNA
<213> ORGANISM: Artificial Sequence
<220> FEATURE:
<223> OTHER INFORMATION: Synthetic Construct

<400> SEQUENCE: 343
caagcagaag acggcatacg agattcgata ggctgtctcg tgggctcgga gatg 54

<210> SEQ ID NO 344
<211> LENGTH: 54
<212> TYPE: DNA
<213> ORGANISM: Artificial Sequence
<220> FEATURE:
<223> OTHER INFORMATION: Synthetic Construct

<400> SEQUENCE: 344
caagcagaag acggcatacg agattcttgt cggtgtctcg tgggctcgga gatg 54

<210> SEQ ID NO 345
<211> LENGTH: 54
<212> TYPE: DNA
<213> ORGANISM: Artificial Sequence
<220> FEATURE:
<223> OTHER INFORMATION: Synthetic Construct

<400> SEQUENCE: 345
caagcagaag acggcatacg agattcagac cgtagtctcg tgggctcgga gatg 54

<210> SEQ ID NO 346
<211> LENGTH: 54
<212> TYPE: DNA
<213> ORGANISM: Artificial Sequence
<220> FEATURE:
<223> OTHER INFORMATION: Synthetic Construct

<400> SEQUENCE: 346
caagcagaag acggcatacg agattccgaa ctgtgtctcg tgggctcgga gatg 54

<210> SEQ ID NO 347
<211> LENGTH: 54
<212> TYPE: DNA
<213> ORGANISM: Artificial Sequence
<220> FEATURE:
<223> OTHER INFORMATION: Synthetic Construct

<400> SEQUENCE: 347
caagcagaag acggcatacg agattccact agctgtctcg tgggctcgga gatg 54

<210> SEQ ID NO 348
<211> LENGTH: 54
<212> TYPE: DNA
<213> ORGANISM: Artificial Sequence
<220> FEATURE:
<223> OTHER INFORMATION: Synthetic Construct

<400> SEQUENCE: 348
caagcagaag acggcatacg agattccact agctgtctcg tgggctcgga gatg 54

<210> SEQ ID NO 349
<211> LENGTH: 54
<212> TYPE: DNA
<213> ORGANISM: Artificial Sequence
<220> FEATURE:
<223> OTHER INFORMATION: Synthetic Construct

<400> SEQUENCE: 349
caagcagaag acggcatacg agatacgcct atcagtctcg tgggctcgga gatg 54

<210> SEQ ID NO 350
<211> LENGTH: 54
<212> TYPE: DNA
<213> ORGANISM: Artificial Sequence
<220> FEATURE:
<223> OTHER INFORMATION: Synthetic Construct

<400> SEQUENCE: 350
caagcagaag acggcatacg agatacgata gcgagtctcg tgggctcgga gatg 54

<210> SEQ ID NO 351
<211> LENGTH: 54
<212> TYPE: DNA

<213> ORGANISM: Artificial Sequence
<220> FEATURE:
<223> OTHER INFORMATION: Synthetic Construct

<400> SEQUENCE: 351
caagcagaag acggcatacg agatactcga accagtctcg tgggctcgga gatg 54

<210> SEQ ID NO 352
<211> LENGTH: 54
<212> TYPE: DNA
<213> ORGANISM: Artificial Sequence
<220> FEATURE:
<223> OTHER INFORMATION: Synthetic Construct

<400> SEQUENCE: 352
caagcagaag acggcatacg agatacagtg cagtgtctcg tgggctcgga gatg 54

<210> SEQ ID NO 353
<211> LENGTH: 54
<212> TYPE: DNA
<213> ORGANISM: Artificial Sequence
<220> FEATURE:
<223> OTHER INFORMATION: Synthetic Construct

<400> SEQUENCE: 353
caagcagaag acggcatacg agatactgtg actggtctcg tgggctcgga gatg 54

<210> SEQ ID NO 354
<211> LENGTH: 54
<212> TYPE: DNA
<213> ORGANISM: Artificial Sequence
<220> FEATURE:
<223> OTHER INFORMATION: Synthetic Construct

<400> SEQUENCE: 354
caagcagaag acggcatacg agatacggtt gatggtctcg tgggctcgga gatg 54

<210> SEQ ID NO 355
<211> LENGTH: 54
<212> TYPE: DNA
<213> ORGANISM: Artificial Sequence
<220> FEATURE:
<223> OTHER INFORMATION: Synthetic Construct

<400> SEQUENCE: 355
caagcagaag acggcatacg agatactaga cgtggtctcg tgggctcgga gatg 54

<210> SEQ ID NO 356
<211> LENGTH: 54
<212> TYPE: DNA
<213> ORGANISM: Artificial Sequence
<220> FEATURE:
<223> OTHER INFORMATION: Synthetic Construct

<400> SEQUENCE: 356
caagcagaag acggcatacg agatacagaa gcgtgtctcg tgggctcgga gatg 54

<210> SEQ ID NO 357
<211> LENGTH: 54
<212> TYPE: DNA
<213> ORGANISM: Artificial Sequence
<220> FEATURE:
<223> OTHER INFORMATION: Synthetic Construct

<400> SEQUENCE: 357
caagcagaag acggcatacg agataccgta ggttgtctcg tgggctcgga gatg 54

<210> SEQ ID NO 358
<211> LENGTH: 54
<212> TYPE: DNA
<213> ORGANISM: Artificial Sequence
<220> FEATURE:
<223> OTHER INFORMATION: Synthetic Construct

<400> SEQUENCE: 358
caagcagaag acggcatacg agataccaga gtgtgtctcg tgggctcgga gatg 54

<210> SEQ ID NO 359
<211> LENGTH: 54
<212> TYPE: DNA
<213> ORGANISM: Artificial Sequence
<220> FEATURE:
<223> OTHER INFORMATION: Synthetic Construct

<400> SEQUENCE: 359
caagcagaag acggcatacg agatactgct catggtctcg tgggctcgga gatg 54

<210> SEQ ID NO 360
<211> LENGTH: 54
<212> TYPE: DNA
<213> ORGANISM: Artificial Sequence
<220> FEATURE:
<223> OTHER INFORMATION: Synthetic Construct

<400> SEQUENCE: 360
caagcagaag acggcatacg agatactcat ggtggtctcg tgggctcgga gatg 54

<210> SEQ ID NO 361
<211> LENGTH: 54
<212> TYPE: DNA
<213> ORGANISM: Artificial Sequence
<220> FEATURE:
<223> OTHER INFORMATION: Synthetic Construct

<400> SEQUENCE: 361
caagcagaag acggcatacg agatcacgta cgaagtctcg tgggctcgga gatg 54

<210> SEQ ID NO 362
<211> LENGTH: 54
<212> TYPE: DNA
<213> ORGANISM: Artificial Sequence
<220> FEATURE:
<223> OTHER INFORMATION: Synthetic Construct

<400> SEQUENCE: 362
caagcagaag acggcatacg agatcactta gtgggtctcg tgggctcgga gatg 54

<210> SEQ ID NO 363
<211> LENGTH: 54
<212> TYPE: DNA
<213> ORGANISM: Artificial Sequence
<220> FEATURE:
<223> OTHER INFORMATION: Synthetic Construct

<400> SEQUENCE: 363
caagcagaag acggcatacg agatcaccaa gactgtctcg tgggctcgga gatg 54

<210> SEQ ID NO 364
<211> LENGTH: 54
<212> TYPE: DNA
<213> ORGANISM: Artificial Sequence
<220> FEATURE:

<223> OTHER INFORMATION: Synthetic Construct

<400> SEQUENCE: 364
caagcagaag acggcatacg agatcacgtg atcagtctcg tgggctcgga gatg 54

<210> SEQ ID NO 365
<211> LENGTH: 54
<212> TYPE: DNA
<213> ORGANISM: Artificial Sequence
<220> FEATURE:
<223> OTHER INFORMATION: Synthetic Construct

<400> SEQUENCE: 365
caagcagaag acggcatacg agatcaggaa ggatgtctcg tgggctcgga gatg 54

<210> SEQ ID NO 366
<211> LENGTH: 54
<212> TYPE: DNA
<213> ORGANISM: Artificial Sequence
<220> FEATURE:
<223> OTHER INFORMATION: Synthetic Construct

<400> SEQUENCE: 366
caagcagaag acggcatacg agatcaacct ctgtgtctcg tgggctcgga gatg 54

<210> SEQ ID NO 367
<211> LENGTH: 54
<212> TYPE: DNA
<213> ORGANISM: Artificial Sequence
<220> FEATURE:
<223> OTHER INFORMATION: Synthetic Construct

<400> SEQUENCE: 367
caagcagaag acggcatacg agatcaaaga aggcgtctcg tgggctcgga gatg 54

<210> SEQ ID NO 368
<211> LENGTH: 54
<212> TYPE: DNA
<213> ORGANISM: Artificial Sequence
<220> FEATURE:
<223> OTHER INFORMATION: Synthetic Construct

<400> SEQUENCE: 368
caagcagaag acggcatacg agatcagttg acctgtctcg tgggctcgga gatg 54

<210> SEQ ID NO 369
<211> LENGTH: 54
<212> TYPE: DNA
<213> ORGANISM: Artificial Sequence
<220> FEATURE:
<223> OTHER INFORMATION: Synthetic Construct

<400> SEQUENCE: 369
caagcagaag acggcatacg agatcacaag gtctgtctcg tgggctcgga gatg 54

<210> SEQ ID NO 370
<211> LENGTH: 54
<212> TYPE: DNA
<213> ORGANISM: Artificial Sequence
<220> FEATURE:
<223> OTHER INFORMATION: Synthetic Construct

<400> SEQUENCE: 370
caagcagaag acggcatacg agatcagtca tcgagtctcg tgggctcgga gatg 54

<210> SEQ ID NO 371
<211> LENGTH: 54
<212> TYPE: DNA
<213> ORGANISM: Artificial Sequence
<220> FEATURE:
<223> OTHER INFORMATION: Synthetic Construct

<400> SEQUENCE: 371
caagcagaag acggcatacg agatcaacat cctggtctcg tgggctcgga gatg 54

<210> SEQ ID NO 372
<211> LENGTH: 54
<212> TYPE: DNA
<213> ORGANISM: Artificial Sequence
<220> FEATURE:
<223> OTHER INFORMATION: Synthetic Construct

<400> SEQUENCE: 372
caagcagaag acggcatacg agatcaccaa gttggtctcg tgggctcgga gatg 54

<210> SEQ ID NO 373
<211> LENGTH: 54
<212> TYPE: DNA
<213> ORGANISM: Artificial Sequence
<220> FEATURE:
<223> OTHER INFORMATION: Synthetic Construct

<400> SEQUENCE: 373
caagcagaag acggcatacg agatgactca ttgcgtctcg tgggctcgga gatg 54

<210> SEQ ID NO 374
<211> LENGTH: 54
<212> TYPE: DNA
<213> ORGANISM: Artificial Sequence
<220> FEATURE:
<223> OTHER INFORMATION: Synthetic Construct

<400> SEQUENCE: 374
caagcagaag acggcatacg agatgatgat cggagtctcg tgggctcgga gatg 54

<210> SEQ ID NO 375
<211> LENGTH: 54
<212> TYPE: DNA
<213> ORGANISM: Artificial Sequence
<220> FEATURE:
<223> OTHER INFORMATION: Synthetic Construct

<400> SEQUENCE: 375
caagcagaag acggcatacg agatgatgcg cttagtctcg tgggctcgga gatg 54

<210> SEQ ID NO 376
<211> LENGTH: 54
<212> TYPE: DNA
<213> ORGANISM: Artificial Sequence
<220> FEATURE:
<223> OTHER INFORMATION: Synthetic Construct

<400> SEQUENCE: 376
caagcagaag acggcatacg agatgagtgt tcctgtctcg tgggctcgga gatg 54

<210> SEQ ID NO 377
<211> LENGTH: 54
<212> TYPE: DNA
<213> ORGANISM: Artificial Sequence
<220> FEATURE:
<223> OTHER INFORMATION: Synthetic Construct

<400> SEQUENCE: 377
caagcagaag acggcatacg agatgacttg tcgagtctcg tgggctcgga gatg 54

<210> SEQ ID NO 378
<211> LENGTH: 54
<212> TYPE: DNA
<213> ORGANISM: Artificial Sequence
<220> FEATURE:
<223> OTHER INFORMATION: Synthetic Construct

<400> SEQUENCE: 378
caagcagaag acggcatacg agatgactcg tcttgtctcg tgggctcgga gatg 54

<210> SEQ ID NO 379
<211> LENGTH: 54
<212> TYPE: DNA
<213> ORGANISM: Artificial Sequence
<220> FEATURE:
<223> OTHER INFORMATION: Synthetic Construct

<400> SEQUENCE: 379
caagcagaag acggcatacg agatgagtgt gacagtctcg tgggctcgga gatg 54

<210> SEQ ID NO 380
<211> LENGTH: 54
<212> TYPE: DNA
<213> ORGANISM: Artificial Sequence
<220> FEATURE:
<223> OTHER INFORMATION: Synthetic Construct

<400> SEQUENCE: 380
caagcagaag acggcatacg agatgactgg ttctgtctcg tgggctcgga gatg 54

<210> SEQ ID NO 381
<211> LENGTH: 54
<212> TYPE: DNA
<213> ORGANISM: Artificial Sequence
<220> FEATURE:
<223> OTHER INFORMATION: Synthetic Construct

<400> SEQUENCE: 381
caagcagaag acggcatacg agatgagcac aactgtctcg tgggctcgga gatg 54

<210> SEQ ID NO 382
<211> LENGTH: 54
<212> TYPE: DNA
<213> ORGANISM: Artificial Sequence
<220> FEATURE:
<223> OTHER INFORMATION: Synthetic Construct

<400> SEQUENCE: 382
caagcagaag acggcatacg agatgacatg gctagtctcg tgggctcgga gatg 54

<210> SEQ ID NO 383
<211> LENGTH: 54
<212> TYPE: DNA
<213> ORGANISM: Artificial Sequence
<220> FEATURE:
<223> OTHER INFORMATION: Synthetic Construct

<400> SEQUENCE: 383
caagcagaag acggcatacg agatgactca tcaggtctcg tgggctcgga gatg 54

<210> SEQ ID NO 384
<211> LENGTH: 54

<212> TYPE: DNA
<213> ORGANISM: Artificial Sequence
<220> FEATURE:
<223> OTHER INFORMATION: Synthetic Construct

<400> SEQUENCE: 384
caagcagaag acggcatacg agatgatgat acgcgtctcg tgggctcgga gatg 54

<210> SEQ ID NO 385
<211> LENGTH: 54
<212> TYPE: DNA
<213> ORGANISM: Artificial Sequence
<220> FEATURE:
<223> OTHER INFORMATION: Synthetic Construct

<400> SEQUENCE: 385
caagcagaag acggcatacg agatgtgatc catggtctcg tgggctcgga gatg 54

<210> SEQ ID NO 386
<211> LENGTH: 54
<212> TYPE: DNA
<213> ORGANISM: Artificial Sequence
<220> FEATURE:
<223> OTHER INFORMATION: Synthetic Construct

<400> SEQUENCE: 386
caagcagaag acggcatacg agatgtccga ctatgtctcg tgggctcgga gatg 54

<210> SEQ ID NO 387
<211> LENGTH: 54
<212> TYPE: DNA
<213> ORGANISM: Artificial Sequence
<220> FEATURE:
<223> OTHER INFORMATION: Synthetic Construct

<400> SEQUENCE: 387
caagcagaag acggcatacg agatgtttca ggaggtctcg tgggctcgga gatg 54

<210> SEQ ID NO 388
<211> LENGTH: 54
<212> TYPE: DNA
<213> ORGANISM: Artificial Sequence
<220> FEATURE:
<223> OTHER INFORMATION: Synthetic Construct

<400> SEQUENCE: 388
caagcagaag acggcatacg agatgtttca ggaggtctcg tgggctcgga gatg 54

<210> SEQ ID NO 389
<211> LENGTH: 54
<212> TYPE: DNA
<213> ORGANISM: Artificial Sequence
<220> FEATURE:
<223> OTHER INFORMATION: Synthetic Construct

<400> SEQUENCE: 389
caagcagaag acggcatacg agatgtagct cctagtctcg tgggctcgga gatg 54

<210> SEQ ID NO 390
<211> LENGTH: 54
<212> TYPE: DNA
<213> ORGANISM: Artificial Sequence
<220> FEATURE:
<223> OTHER INFORMATION: Synthetic Construct

<400> SEQUENCE: 390
caagcagaag acggcatacg agatgtcgct ctatgtctcg tgggctcgga gatg 54

<210> SEQ ID NO 391
<211> LENGTH: 54
<212> TYPE: DNA
<213> ORGANISM: Artificial Sequence
<220> FEATURE:
<223> OTHER INFORMATION: Synthetic Construct

<400> SEQUENCE: 391
caagcagaag acggcatacg agatgtggat tcgtgtctcg tgggctcgga gatg 54

<210> SEQ ID NO 392
<211> LENGTH: 54
<212> TYPE: DNA
<213> ORGANISM: Artificial Sequence
<220> FEATURE:
<223> OTHER INFORMATION: Synthetic Construct

<400> SEQUENCE: 392
caagcagaag acggcatacg agatgtatgc caacgtctcg tgggctcgga gatg 54

<210> SEQ ID NO 393
<211> LENGTH: 54
<212> TYPE: DNA
<213> ORGANISM: Artificial Sequence
<220> FEATURE:
<223> OTHER INFORMATION: Synthetic Construct

<400> SEQUENCE: 393
caagcagaag acggcatacg agatgtgact atgcgtctcg tgggctcgga gatg 54

<210> SEQ ID NO 394
<211> LENGTH: 54
<212> TYPE: DNA
<213> ORGANISM: Artificial Sequence
<220> FEATURE:
<223> OTHER INFORMATION: Synthetic Construct

<400> SEQUENCE: 394
caagcagaag acggcatacg agatgtatat gcgcgtctcg tgggctcgga gatg 54

<210> SEQ ID NO 395
<211> LENGTH: 54
<212> TYPE: DNA
<213> ORGANISM: Artificial Sequence
<220> FEATURE:
<223> OTHER INFORMATION: Synthetic Construct

<400> SEQUENCE: 395
caagcagaag acggcatacg agatgtagga ggaagtctcg tgggctcgga gatg 54

<210> SEQ ID NO 396
<211> LENGTH: 54
<212> TYPE: DNA
<213> ORGANISM: Artificial Sequence
<220> FEATURE:
<223> OTHER INFORMATION: Synthetic Construct

<400> SEQUENCE: 396
caagcagaag acggcatacg agatgtatgg aagggtctcg tgggctcgga gatg 54

<210> SEQ ID NO 397
<211> LENGTH: 54
<212> TYPE: DNA
<213> ORGANISM: Artificial Sequence
<220> FEATURE:
<223> OTHER INFORMATION: Synthetic Construct

<400> SEQUENCE: 397
caagcagaag acggcatacg agatctggtt gtcagtctcg tgggctcgga gatg 54

<210> SEQ ID NO 398
<211> LENGTH: 54
<212> TYPE: DNA
<213> ORGANISM: Artificial Sequence
<220> FEATURE:
<223> OTHER INFORMATION: Synthetic Construct

<400> SEQUENCE: 398
caagcagaag acggcatacg agatctgatg agacgtctcg tgggctcgga gatg 54

<210> SEQ ID NO 399
<211> LENGTH: 54
<212> TYPE: DNA
<213> ORGANISM: Artificial Sequence
<220> FEATURE:
<223> OTHER INFORMATION: Synthetic Construct

<400> SEQUENCE: 399
caagcagaag acggcatacg agatcttcgt ggatgtctcg tgggctcgga gatg 54

<210> SEQ ID NO 400
<211> LENGTH: 54
<212> TYPE: DNA
<213> ORGANISM: Artificial Sequence
<220> FEATURE:
<223> OTHER INFORMATION: Synthetic Construct

<400> SEQUENCE: 400
caagcagaag acggcatacg agatctggac tagagtctcg tgggctcgga gatg 54

<210> SEQ ID NO 401
<211> LENGTH: 54
<212> TYPE: DNA
<213> ORGANISM: Artificial Sequence
<220> FEATURE:
<223> OTHER INFORMATION: Synthetic Construct

<400> SEQUENCE: 401
caagcagaag acggcatacg agatctaatg gacggtctcg tgggctcgga gatg 54

<210> SEQ ID NO 402
<211> LENGTH: 54
<212> TYPE: DNA
<213> ORGANISM: Artificial Sequence
<220> FEATURE:
<223> OTHER INFORMATION: Synthetic Construct

<400> SEQUENCE: 402
caagcagaag acggcatacg agatctctca gagtgtctcg tgggctcgga gatg 54

<210> SEQ ID NO 403
<211> LENGTH: 54
<212> TYPE: DNA
<213> ORGANISM: Artificial Sequence
<220> FEATURE:
<223> OTHER INFORMATION: Synthetic Construct

<400> SEQUENCE: 403
caagcagaag acggcatacg agatctggat gtaggtctcg tgggctcgga gatg 54

<210> SEQ ID NO 404
<211> LENGTH: 54
<212> TYPE: DNA
<213> ORGANISM: Artificial Sequence
<220> FEATURE:
<223> OTHER INFORMATION: Synthetic Construct

<400> SEQUENCE: 404
caagcagaag acggcatacg agatctcaag tgcagtctcg tgggctcgga gatg 54

<210> SEQ ID NO 405
<211> LENGTH: 54
<212> TYPE: DNA
<213> ORGANISM: Artificial Sequence
<220> FEATURE:
<223> OTHER INFORMATION: Synthetic Construct

<400> SEQUENCE: 405
caagcagaag acggcatacg agatctttag gtcggtctcg tgggctcgga gatg 54

<210> SEQ ID NO 406
<211> LENGTH: 54
<212> TYPE: DNA
<213> ORGANISM: Artificial Sequence
<220> FEATURE:
<223> OTHER INFORMATION: Synthetic Construct

<400> SEQUENCE: 406
caagcagaag acggcatacg agatcttcta gctggtctcg tgggctcgga gatg 54

<210> SEQ ID NO 407
<211> LENGTH: 54
<212> TYPE: DNA
<213> ORGANISM: Artificial Sequence
<220> FEATURE:
<223> OTHER INFORMATION: Synthetic Construct

<400> SEQUENCE: 407
caagcagaag acggcatacg agatctggtc agatgtctcg tgggctcgga gatg 54

<210> SEQ ID NO 408
<211> LENGTH: 54
<212> TYPE: DNA
<213> ORGANISM: Artificial Sequence
<220> FEATURE:
<223> OTHER INFORMATION: Synthetic Construct

<400> SEQUENCE: 408
caagcagaag acggcatacg agatctgtag catcgtctcg tgggctcgga gatg 54

<210> SEQ ID NO 409
<211> LENGTH: 54
<212> TYPE: DNA
<213> ORGANISM: Artificial Sequence
<220> FEATURE:
<223> OTHER INFORMATION: Synthetic Construct

<400> SEQUENCE: 409
caagcagaag acggcatacg agattgtcgg ttacgtctcg tgggctcgga gatg 54

<210> SEQ ID NO 410
<211> LENGTH: 54
<212> TYPE: DNA
<213> ORGANISM: Artificial Sequence
<220> FEATURE:
<223> OTHER INFORMATION: Synthetic Construct

<400> SEQUENCE: 410
caagcagaag acggcatacg agattgcgga ttgagtctcg tgggctcgga gatg 54

<210> SEQ ID NO 411
<211> LENGTH: 54
<212> TYPE: DNA
<213> ORGANISM: Artificial Sequence
<220> FEATURE:
<223> OTHER INFORMATION: Synthetic Construct

<400> SEQUENCE: 411
caagcagaag acggcatacg agattgaata cgcggtctcg tgggctcgga gatg 54

<210> SEQ ID NO 412
<211> LENGTH: 54
<212> TYPE: DNA
<213> ORGANISM: Artificial Sequence
<220> FEATURE:
<223> OTHER INFORMATION: Synthetic Construct

<400> SEQUENCE: 412
caagcagaag acggcatacg agattgacca gcttgtctcg tgggctcgga gatg 54

<210> SEQ ID NO 413
<211> LENGTH: 54
<212> TYPE: DNA
<213> ORGANISM: Artificial Sequence
<220> FEATURE:
<223> OTHER INFORMATION: Synthetic Construct

<400> SEQUENCE: 413
caagcagaag acggcatacg agattgctcg atacgtctcg tgggctcgga gatg 54

<210> SEQ ID NO 414
<211> LENGTH: 54
<212> TYPE: DNA
<213> ORGANISM: Artificial Sequence
<220> FEATURE:
<223> OTHER INFORMATION: Synthetic Construct

<400> SEQUENCE: 414
caagcagaag acggcatacg agattgtcaa ctgggtctcg tgggctcgga gatg 54

<210> SEQ ID NO 415
<211> LENGTH: 54
<212> TYPE: DNA
<213> ORGANISM: Artificial Sequence
<220> FEATURE:
<223> OTHER INFORMATION: Synthetic Construct

<400> SEQUENCE: 415
caagcagaag acggcatacg agattgaccg tagtgtctcg tgggctcgga gatg 54

<210> SEQ ID NO 416
<211> LENGTH: 54
<212> TYPE: DNA
<213> ORGANISM: Artificial Sequence
<220> FEATURE:
<223> OTHER INFORMATION: Synthetic Construct

<400> SEQUENCE: 416
caagcagaag acggcatacg agattgccgg aattgtctcg tgggctcgga gatg 54

<210> SEQ ID NO 417

<211> LENGTH: 54
<212> TYPE: DNA
<213> ORGANISM: Artificial Sequence
<220> FEATURE:
<223> OTHER INFORMATION: Synthetic Construct

<400> SEQUENCE: 417
caagcagaag acggcatacg agattgcgtc ttgtgtctcg tgggctcgga gatg 54

<210> SEQ ID NO 418
<211> LENGTH: 54
<212> TYPE: DNA
<213> ORGANISM: Artificial Sequence
<220> FEATURE:
<223> OTHER INFORMATION: Synthetic Construct

<400> SEQUENCE: 418
caagcagaag acggcatacg agattggaat ccgagtctcg tgggctcgga gatg 54

<210> SEQ ID NO 419
<211> LENGTH: 54
<212> TYPE: DNA
<213> ORGANISM: Artificial Sequence
<220> FEATURE:
<223> OTHER INFORMATION: Synthetic Construct

<400> SEQUENCE: 419
caagcagaag acggcatacg agattgacga tgacgtctcg tgggctcgga gatg 54

<210> SEQ ID NO 420
<211> LENGTH: 54
<212> TYPE: DNA
<213> ORGANISM: Artificial Sequence
<220> FEATURE:
<223> OTHER INFORMATION: Synthetic Construct

<400> SEQUENCE: 420
caagcagaag acggcatacg agattgcgta ttcggtctcg tgggctcgga gatg 54

<210> SEQ ID NO 421
<211> LENGTH: 54
<212> TYPE: DNA
<213> ORGANISM: Artificial Sequence
<220> FEATURE:
<223> OTHER INFORMATION: Synthetic Construct

<400> SEQUENCE: 421
caagcagaag acggcatacg agatagaagt cgaggtctcg tgggctcgga gatg 54

<210> SEQ ID NO 422
<211> LENGTH: 54
<212> TYPE: DNA
<213> ORGANISM: Artificial Sequence
<220> FEATURE:
<223> OTHER INFORMATION: Synthetic Construct

<400> SEQUENCE: 422
caagcagaag acggcatacg agatagagtg ttgggtctcg tgggctcgga gatg 54

<210> SEQ ID NO 423
<211> LENGTH: 54
<212> TYPE: DNA
<213> ORGANISM: Artificial Sequence
<220> FEATURE:
<223> OTHER INFORMATION: Synthetic Construct

<400> SEQUENCE: 423
caagcagaag acggcatacg agatagcagg tatcgtctcg tgggctcgga gatg 54

<210> SEQ ID NO 424
<211> LENGTH: 54
<212> TYPE: DNA
<213> ORGANISM: Artificial Sequence
<220> FEATURE:
<223> OTHER INFORMATION: Synthetic Construct

<400> SEQUENCE: 424
caagcagaag acggcatacg agatagtatc ggtcgtctcg tgggctcgga gatg 54

<210> SEQ ID NO 425
<211> LENGTH: 54
<212> TYPE: DNA
<213> ORGANISM: Artificial Sequence
<220> FEATURE:
<223> OTHER INFORMATION: Synthetic Construct

<400> SEQUENCE: 425
caagcagaag acggcatacg agatagtctc cgatgtctcg tgggctcgga gatg 54

<210> SEQ ID NO 426
<211> LENGTH: 54
<212> TYPE: DNA
<213> ORGANISM: Artificial Sequence
<220> FEATURE:
<223> OTHER INFORMATION: Synthetic Construct

<400> SEQUENCE: 426
caagcagaag acggcatacg agatagcaca catggtctcg tgggctcgga gatg 54

<210> SEQ ID NO 427
<211> LENGTH: 54
<212> TYPE: DNA
<213> ORGANISM: Artificial Sequence
<220> FEATURE:
<223> OTHER INFORMATION: Synthetic Construct

<400> SEQUENCE: 427
caagcagaag acggcatacg agatagccac ttctgtctcg tgggctcgga gatg 54

<210> SEQ ID NO 428
<211> LENGTH: 54
<212> TYPE: DNA
<213> ORGANISM: Artificial Sequence
<220> FEATURE:
<223> OTHER INFORMATION: Synthetic Construct

<400> SEQUENCE: 428
caagcagaag acggcatacg agataggagt ctctgtctcg tgggctcgga gatg 54

<210> SEQ ID NO 429
<211> LENGTH: 54
<212> TYPE: DNA
<213> ORGANISM: Artificial Sequence
<220> FEATURE:
<223> OTHER INFORMATION: Synthetic Construct

<400> SEQUENCE: 429
caagcagaag acggcatacg agatagcata ccacgtctcg tgggctcgga gatg 54

<210> SEQ ID NO 430
<211> LENGTH: 54
<212> TYPE: DNA

<213> ORGANISM: Artificial Sequence
<220> FEATURE:
<223> OTHER INFORMATION: Synthetic Construct

<400> SEQUENCE: 430
caagcagaag acggcatacg agatagaagg acacgtctcg tgggctcgga gatg 54

<210> SEQ ID NO 431
<211> LENGTH: 54
<212> TYPE: DNA
<213> ORGANISM: Artificial Sequence
<220> FEATURE:
<223> OTHER INFORMATION: Synthetic Construct

<400> SEQUENCE: 431
caagcagaag acggcatacg agataggaat cgtggtctcg tgggctcgga gatg 54

<210> SEQ ID NO 432
<211> LENGTH: 54
<212> TYPE: DNA
<213> ORGANISM: Artificial Sequence
<220> FEATURE:
<223> OTHER INFORMATION: Synthetic Construct

<400> SEQUENCE: 432
caagcagaag acggcatacg agatagtcag gcttgtctcg tgggctcgga gatg 54

<210> SEQ ID NO 433
<211> LENGTH: 54
<212> TYPE: DNA
<213> ORGANISM: Artificial Sequence
<220> FEATURE:
<223> OTHER INFORMATION: Synthetic Construct

<400> SEQUENCE: 433
caagcagaag acggcatacg agattctaga gctcgtctcg tgggctcgga gatg 54

<210> SEQ ID NO 434
<211> LENGTH: 54
<212> TYPE: DNA
<213> ORGANISM: Artificial Sequence
<220> FEATURE:
<223> OTHER INFORMATION: Synthetic Construct

<400> SEQUENCE: 434
caagcagaag acggcatacg agattcgtgt ctgagtctcg tgggctcgga gatg 54

<210> SEQ ID NO 435
<211> LENGTH: 54
<212> TYPE: DNA
<213> ORGANISM: Artificial Sequence
<220> FEATURE:
<223> OTHER INFORMATION: Synthetic Construct

<400> SEQUENCE: 435
caagcagaag acggcatacg agattcgcat gtctgtctcg tgggctcgga gatg 54

<210> SEQ ID NO 436
<211> LENGTH: 54
<212> TYPE: DNA
<213> ORGANISM: Artificial Sequence
<220> FEATURE:
<223> OTHER INFORMATION: Synthetic Construct

<400> SEQUENCE: 436
caagcagaag acggcatacg agattcaatg cctcgtctcg tgggctcgga gatg 54

<210> SEQ ID NO 437
<211> LENGTH: 54
<212> TYPE: DNA
<213> ORGANISM: Artificial Sequence
<220> FEATURE:
<223> OTHER INFORMATION: Synthetic Construct

<400> SEQUENCE: 437
caagcagaag acggcatacg agattcgatc gtacgtctcg tgggctcgga gatg 54

<210> SEQ ID NO 438
<211> LENGTH: 54
<212> TYPE: DNA
<213> ORGANISM: Artificial Sequence
<220> FEATURE:
<223> OTHER INFORMATION: Synthetic Construct

<400> SEQUENCE: 438
caagcagaag acggcatacg agattcacca atgcgtctcg tgggctcgga gatg 54

<210> SEQ ID NO 439
<211> LENGTH: 54
<212> TYPE: DNA
<213> ORGANISM: Artificial Sequence
<220> FEATURE:
<223> OTHER INFORMATION: Synthetic Construct

<400> SEQUENCE: 439
caagcagaag acggcatacg agattcgctg gattgtctcg tgggctcgga gatg 54

<210> SEQ ID NO 440
<211> LENGTH: 54
<212> TYPE: DNA
<213> ORGANISM: Artificial Sequence
<220> FEATURE:
<223> OTHER INFORMATION: Synthetic Construct

<400> SEQUENCE: 440
caagcagaag acggcatacg agattctggc tatcgtctcg tgggctcgga gatg 54

<210> SEQ ID NO 441
<211> LENGTH: 54
<212> TYPE: DNA
<213> ORGANISM: Artificial Sequence
<220> FEATURE:
<223> OTHER INFORMATION: Synthetic Construct

<400> SEQUENCE: 441
caagcagaag acggcatacg agattcaacg gtcagtctcg tgggctcgga gatg 54

<210> SEQ ID NO 442
<211> LENGTH: 54
<212> TYPE: DNA
<213> ORGANISM: Artificial Sequence
<220> FEATURE:
<223> OTHER INFORMATION: Synthetic Construct

<400> SEQUENCE: 442
caagcagaag acggcatacg agattcgtac tctcgtctcg tgggctcgga gatg 54

<210> SEQ ID NO 443
<211> LENGTH: 54
<212> TYPE: DNA
<213> ORGANISM: Artificial Sequence
<220> FEATURE:

<223> OTHER INFORMATION: Synthetic Construct

<400> SEQUENCE: 443
caagcagaag acggcatacg agattccgtg tactgtctcg tgggctcgga gatg 54

<210> SEQ ID NO 444
<211> LENGTH: 54
<212> TYPE: DNA
<213> ORGANISM: Artificial Sequence
<220> FEATURE:
<223> OTHER INFORMATION: Synthetic Construct

<400> SEQUENCE: 444
caagcagaag acggcatacg agattctgaa gacggtctcg tgggctcgga gatg 54

<210> SEQ ID NO 445
<211> LENGTH: 54
<212> TYPE: DNA
<213> ORGANISM: Artificial Sequence
<220> FEATURE:
<223> OTHER INFORMATION: Synthetic Construct

<400> SEQUENCE: 445
caagcagaag acggcatacg agataccttc cgtagtctcg tgggctcgga gatg 54

<210> SEQ ID NO 446
<211> LENGTH: 54
<212> TYPE: DNA
<213> ORGANISM: Artificial Sequence
<220> FEATURE:
<223> OTHER INFORMATION: Synthetic Construct

<400> SEQUENCE: 446
caagcagaag acggcatacg agataccaca agtcgtctcg tgggctcgga gatg 54

<210> SEQ ID NO 447
<211> LENGTH: 54
<212> TYPE: DNA
<213> ORGANISM: Artificial Sequence
<220> FEATURE:
<223> OTHER INFORMATION: Synthetic Construct

<400> SEQUENCE: 447
caagcagaag acggcatacg agataccggt catagtctcg tgggctcgga gatg 54

<210> SEQ ID NO 448
<211> LENGTH: 54
<212> TYPE: DNA
<213> ORGANISM: Artificial Sequence
<220> FEATURE:
<223> OTHER INFORMATION: Synthetic Construct

<400> SEQUENCE: 448
caagcagaag acggcatacg agatacacgc ctaagtctcg tgggctcgga gatg 54

<210> SEQ ID NO 449
<211> LENGTH: 54
<212> TYPE: DNA
<213> ORGANISM: Artificial Sequence
<220> FEATURE:
<223> OTHER INFORMATION: Synthetic Construct

<400> SEQUENCE: 449
caagcagaag acggcatacg agatactgag ctaggtctcg tgggctcgga gatg 54

<210> SEQ ID NO 450
<211> LENGTH: 54
<212> TYPE: DNA
<213> ORGANISM: Artificial Sequence
<220> FEATURE:
<223> OTHER INFORMATION: Synthetic Construct

<400> SEQUENCE: 450
caagcagaag acggcatacg agatactaat gccggtctcg tgggctcgga gatg 54

<210> SEQ ID NO 451
<211> LENGTH: 54
<212> TYPE: DNA
<213> ORGANISM: Artificial Sequence
<220> FEATURE:
<223> OTHER INFORMATION: Synthetic Construct

<400> SEQUENCE: 451
caagcagaag acggcatacg agatacgata ctgggtctcg tgggctcgga gatg 54

<210> SEQ ID NO 452
<211> LENGTH: 54
<212> TYPE: DNA
<213> ORGANISM: Artificial Sequence
<220> FEATURE:
<223> OTHER INFORMATION: Synthetic Construct

<400> SEQUENCE: 452
caagcagaag acggcatacg agatacaaca ggacgtctcg tgggctcgga gatg 54

<210> SEQ ID NO 453
<211> LENGTH: 54
<212> TYPE: DNA
<213> ORGANISM: Artificial Sequence
<220> FEATURE:
<223> OTHER INFORMATION: Synthetic Construct

<400> SEQUENCE: 453
caagcagaag acggcatacg agatacatcc ggtagtctcg tgggctcgga gatg 54

<210> SEQ ID NO 454
<211> LENGTH: 54
<212> TYPE: DNA
<213> ORGANISM: Artificial Sequence
<220> FEATURE:
<223> OTHER INFORMATION: Synthetic Construct

<400> SEQUENCE: 454
caagcagaag acggcatacg agatacaagc gcatgtctcg tgggctcgga gatg 54

<210> SEQ ID NO 455
<211> LENGTH: 54
<212> TYPE: DNA
<213> ORGANISM: Artificial Sequence
<220> FEATURE:
<223> OTHER INFORMATION: Synthetic Construct

<400> SEQUENCE: 455
caagcagaag acggcatacg agatacactg aggtgtctcg tgggctcgga gatg 54

<210> SEQ ID NO 456
<211> LENGTH: 54
<212> TYPE: DNA
<213> ORGANISM: Artificial Sequence
<220> FEATURE:
<223> OTHER INFORMATION: Synthetic Construct

<400> SEQUENCE: 456
caagcagaag acggcatacg agatacgtag agcagtctcg tgggctcgga gatg 54

<210> SEQ ID NO 457
<211> LENGTH: 54
<212> TYPE: DNA
<213> ORGANISM: Artificial Sequence
<220> FEATURE:
<223> OTHER INFORMATION: Synthetic Construct

<400> SEQUENCE: 457
caagcagaag acggcatacg agatcattcc aagggtctcg tgggctcgga gatg 54

<210> SEQ ID NO 458
<211> LENGTH: 54
<212> TYPE: DNA
<213> ORGANISM: Artificial Sequence
<220> FEATURE:
<223> OTHER INFORMATION: Synthetic Construct

<400> SEQUENCE: 458
caagcagaag acggcatacg agatcacctt ccttgtctcg tgggctcgga gatg 54

<210> SEQ ID NO 459
<211> LENGTH: 54
<212> TYPE: DNA
<213> ORGANISM: Artificial Sequence
<220> FEATURE:
<223> OTHER INFORMATION: Synthetic Construct

<400> SEQUENCE: 459
caagcagaag acggcatacg agatcagcaa ttcggtctcg tgggctcgga gatg 54

<210> SEQ ID NO 460
<211> LENGTH: 54
<212> TYPE: DNA
<213> ORGANISM: Artificial Sequence
<220> FEATURE:
<223> OTHER INFORMATION: Synthetic Construct

<400> SEQUENCE: 460
caagcagaag acggcatacg agatcatcgt agtcgtctcg tgggctcgga gatg 54

<210> SEQ ID NO 461
<211> LENGTH: 54
<212> TYPE: DNA
<213> ORGANISM: Artificial Sequence
<220> FEATURE:
<223> OTHER INFORMATION: Synthetic Construct

<400> SEQUENCE: 461
caagcagaag acggcatacg agatcattca gcctgtctcg tgggctcgga gatg 54

<210> SEQ ID NO 462
<211> LENGTH: 54
<212> TYPE: DNA
<213> ORGANISM: Artificial Sequence
<220> FEATURE:
<223> OTHER INFORMATION: Synthetic Construct

<400> SEQUENCE: 462
caagcagaag acggcatacg agatcaagga acctgtctcg tgggctcgga gatg 54

<210> SEQ ID NO 463
<211> LENGTH: 54

<212> TYPE: DNA
<213> ORGANISM: Artificial Sequence
<220> FEATURE:
<223> OTHER INFORMATION: Synthetic Construct

<400> SEQUENCE: 463
caagcagaag acggcatacg agatcaagtt cgtcgtctcg tgggctcgga gatg 54

<210> SEQ ID NO 464
<211> LENGTH: 54
<212> TYPE: DNA
<213> ORGANISM: Artificial Sequence
<220> FEATURE:
<223> OTHER INFORMATION: Synthetic Construct

<400> SEQUENCE: 464
caagcagaag acggcatacg agatcagtca gttggtctcg tgggctcgga gatg 54

<210> SEQ ID NO 465
<211> LENGTH: 54
<212> TYPE: DNA
<213> ORGANISM: Artificial Sequence
<220> FEATURE:
<223> OTHER INFORMATION: Synthetic Construct

<400> SEQUENCE: 465
caagcagaag acggcatacg agatcaagga tctggtctcg tgggctcgga gatg 54

<210> SEQ ID NO 466
<211> LENGTH: 54
<212> TYPE: DNA
<213> ORGANISM: Artificial Sequence
<220> FEATURE:
<223> OTHER INFORMATION: Synthetic Construct

<400> SEQUENCE: 466
caagcagaag acggcatacg agatcaaagc actggtctcg tgggctcgga gatg 54

<210> SEQ ID NO 467
<211> LENGTH: 54
<212> TYPE: DNA
<213> ORGANISM: Artificial Sequence
<220> FEATURE:
<223> OTHER INFORMATION: Synthetic Construct

<400> SEQUENCE: 467
caagcagaag acggcatacg agatcatccg agttgtctcg tgggctcgga gatg 54

<210> SEQ ID NO 468
<211> LENGTH: 54
<212> TYPE: DNA
<213> ORGANISM: Artificial Sequence
<220> FEATURE:
<223> OTHER INFORMATION: Synthetic Construct

<400> SEQUENCE: 468
caagcagaag acggcatacg agatcatgaa cctggtctcg tgggctcgga gatg 54

<210> SEQ ID NO 469
<211> LENGTH: 54
<212> TYPE: DNA
<213> ORGANISM: Artificial Sequence
<220> FEATURE:
<223> OTHER INFORMATION: Synthetic Construct

<400> SEQUENCE: 469
caagcagaag acggcatacg agatgagcca taacgtctcg tgggctcgga gatg 54

<210> SEQ ID NO 470
<211> LENGTH: 54
<212> TYPE: DNA
<213> ORGANISM: Artificial Sequence
<220> FEATURE:
<223> OTHER INFORMATION: Synthetic Construct

<400> SEQUENCE: 470
caagcagaag acggcatacg agatgattgg acgtgtctcg tgggctcgga gatg 54

<210> SEQ ID NO 471
<211> LENGTH: 54
<212> TYPE: DNA
<213> ORGANISM: Artificial Sequence
<220> FEATURE:
<223> OTHER INFORMATION: Synthetic Construct

<400> SEQUENCE: 471
caagcagaag acggcatacg agatgattcc tgtggtctcg tgggctcgga gatg 54

<210> SEQ ID NO 472
<211> LENGTH: 54
<212> TYPE: DNA
<213> ORGANISM: Artificial Sequence
<220> FEATURE:
<223> OTHER INFORMATION: Synthetic Construct

<400> SEQUENCE: 472
caagcagaag acggcatacg agatgagcac gtaagtctcg tgggctcgga gatg 54

<210> SEQ ID NO 473
<211> LENGTH: 54
<212> TYPE: DNA
<213> ORGANISM: Artificial Sequence
<220> FEATURE:
<223> OTHER INFORMATION: Synthetic Construct

<400> SEQUENCE: 473
caagcagaag acggcatacg agatgacatc tacggtctcg tgggctcgga gatg 54

<210> SEQ ID NO 474
<211> LENGTH: 54
<212> TYPE: DNA
<213> ORGANISM: Artificial Sequence
<220> FEATURE:
<223> OTHER INFORMATION: Synthetic Construct

<400> SEQUENCE: 474
caagcagaag acggcatacg agatgatact gcgtgtctcg tgggctcgga gatg 54

<210> SEQ ID NO 475
<211> LENGTH: 54
<212> TYPE: DNA
<213> ORGANISM: Artificial Sequence
<220> FEATURE:
<223> OTHER INFORMATION: Synthetic Construct

<400> SEQUENCE: 475
caagcagaag acggcatacg agatgatatg gcaggtctcg tgggctcgga gatg 54

<210> SEQ ID NO 476
<211> LENGTH: 54
<212> TYPE: DNA
<213> ORGANISM: Artificial Sequence
<220> FEATURE:
<223> OTHER INFORMATION: Synthetic Construct

<400> SEQUENCE: 476
caagcagaag acggcatacg agatgaacag caacgtctcg tgggctcgga gatg 54

<210> SEQ ID NO 477
<211> LENGTH: 54
<212> TYPE: DNA
<213> ORGANISM: Artificial Sequence
<220> FEATURE:
<223> OTHER INFORMATION: Synthetic Construct

<400> SEQUENCE: 477
caagcagaag acggcatacg agatgagtta gacggtctcg tgggctcgga gatg 54

<210> SEQ ID NO 478
<211> LENGTH: 54
<212> TYPE: DNA
<213> ORGANISM: Artificial Sequence
<220> FEATURE:
<223> OTHER INFORMATION: Synthetic Construct

<400> SEQUENCE: 478
caagcagaag acggcatacg agatgattgc cactgtctcg tgggctcgga gatg 54

<210> SEQ ID NO 479
<211> LENGTH: 54
<212> TYPE: DNA
<213> ORGANISM: Artificial Sequence
<220> FEATURE:
<223> OTHER INFORMATION: Synthetic Construct

<400> SEQUENCE: 479
caagcagaag acggcatacg agatgattcg ttgggtctcg tgggctcgga gatg 54

<210> SEQ ID NO 480
<211> LENGTH: 54
<212> TYPE: DNA
<213> ORGANISM: Artificial Sequence
<220> FEATURE:
<223> OTHER INFORMATION: Synthetic Construct

<400> SEQUENCE: 480
caagcagaag acggcatacg agatgaagct tgaggtctcg tgggctcgga gatg 54

<210> SEQ ID NO 481
<211> LENGTH: 308
<212> TYPE: DNA
<213> ORGANISM: Artificial Sequence
<220> FEATURE:
<223> OTHER INFORMATION: Synthetic Construct

<400> SEQUENCE: 481
ctggcggcta tccagtacag cgccgtacca agataacgcg tgctggtttc aacctgtctg 60
atatccgcaa tctgcttttc cgagaaccag aactcaaact gtaccgtcgg gtcataaacg 120
gcaagatgcg gcgtggcggt tatctgaaaa tagcccggcg tcagctcaat cctcgacggt 180
gctgccggtg cggcaatccg gaacgatacc gacgccggat cgccctgctg cccccacgca 240
tttaccgccc ggactgtcag cctgtagttc cccagcgcca gttgcgtgaa gcggtatgtg 300
gtttccgt 308

<210> SEQ ID NO 482

<211> LENGTH: 20
<212> TYPE: DNA
<213> ORGANISM: Artificial Sequence
<220> FEATURE:
<223> OTHER INFORMATION: Synthetic Construct

<400> SEQUENCE: 482
ctggcggcta tccagtacag 20

<210> SEQ ID NO 483
<211> LENGTH: 20
<212> TYPE: DNA
<213> ORGANISM: Artificial Sequence
<220> FEATURE:
<223> OTHER INFORMATION: Synthetic Construct

<400> SEQUENCE: 483
acggaaacca cataccgctt 20

<210> SEQ ID NO 484
<211> LENGTH: 36
<212> TYPE: DNA
<213> ORGANISM: Artificial Sequence
<220> FEATURE:
<223> OTHER INFORMATION: Synthetic Construct

<400> SEQUENCE: 484
tttttttttt ttcaagcaga agacggcata cgagat 36

<210> SEQ ID NO 485
<211> LENGTH: 34
<212> TYPE: DNA
<213> ORGANISM: Artificial Sequence
<220> FEATURE:
<223> OTHER INFORMATION: Synthetic Construct

<400> SEQUENCE: 485
ctgtctctta tacacatctc cgagcccacg agac 34

<210> SEQ ID NO 486
<211> LENGTH: 80
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (37)..(46)
<223> OTHER INFORMATION: n is a, c, g, or t

<400> SEQUENCE: 486
tttttttttt ttcaagcaga agacggcata cgagatnnnn nnnnnngtct cgtgggctcg 60
gagatgtgta taagagacag 80

<210> SEQ ID NO 487
<211> LENGTH: 22
<212> TYPE: DNA
<213> ORGANISM: Artificial Sequence
<220> FEATURE:
<223> OTHER INFORMATION: Synthetic Construct

<400> SEQUENCE: 487
caagcagaag acggcatacg ag 22

<210> SEQ ID NO 488
<211> LENGTH: 19

<212> TYPE: DNA
<213> ORGANISM: Artificial Sequence
<220> FEATURE:
<223> OTHER INFORMATION: Synthetic Construct

<400> SEQUENCE: 488
ctgtctctta tacacatct 19

<210> SEQ ID NO 489
<211> LENGTH: 21
<212> TYPE: DNA
<213> ORGANISM: Artificial Sequence
<220> FEATURE:
<223> OTHER INFORMATION: Synthetic Construct

<400> SEQUENCE: 489
aatgatacgg cgaccaccga g 21

<210> SEQ ID NO 490
<211> LENGTH: 70
<212> TYPE: DNA
<213> ORGANISM: Artificial Sequence
<220> FEATURE:
<223> OTHER INFORMATION: Synthetic Construct

<400> SEQUENCE: 490
aatgatacgg cgaccaccga gatctacaca cacagcttcg tcggcagcgt cagatgtgta 60
taagagacag 70

<210> SEQ ID NO 491
<211> LENGTH: 19
<212> TYPE: DNA
<213> ORGANISM: Artificial Sequence
<220> FEATURE:
<223> OTHER INFORMATION: Synthetic Construct

<400> SEQUENCE: 491
ctgtctctta tacacatct 19

<210> SEQ ID NO 492
<211> LENGTH: 21
<212> TYPE: DNA
<213> ORGANISM: Artificial Sequence
<220> FEATURE:
<223> OTHER INFORMATION: Synthetic Construct

<400> SEQUENCE: 492
aatgatacgg cgaccaccga g 21

<210> SEQ ID NO 493
<211> LENGTH: 22
<212> TYPE: DNA
<213> ORGANISM: Artificial Sequence
<220> FEATURE:
<223> OTHER INFORMATION: Synthetic Construct

<400> SEQUENCE: 493
caagcagaag acggcatacg ag 22

<210> SEQ ID NO 494
<211> LENGTH: 476
<212> TYPE: PRT
<213> ORGANISM: Artificial Sequence
<220> FEATURE:
<223> OTHER INFORMATION: Synthetic Construct

<400> SEQUENCE: 494

Met Ile Thr Ser Ala Leu His Arg Ala Ala Asp Trp Ala Lys Ser Val
1 5 10 15

Phe Ser Ser Ala Ala Leu Gly Asp Pro Arg Arg Thr Ala Arg Leu Val
20 25 30

Asn Val Ala Ala Gln Leu Ala Lys Tyr Ser Gly Lys Ser Ile Thr Ile
35 40 45

Ser Ser Glu Gly Ser Glu Ala Met Gln Glu Gly Ala Tyr Arg Phe Ile
50 55 60

Arg Asn Pro Asn Val Ser Ala Glu Ala Ile Arg Lys Ala Gly Ala Met
65 70 75 80

Gln Thr Val Lys Leu Ala Gln Glu Phe Pro Glu Leu Leu Ala Ile Glu
85 90 95

Asp Thr Thr Ser Leu Ser Tyr Arg His Gln Val Ala Glu Glu Leu Gly
100 105 110

Lys Leu Gly Ser Ile Gln Asp Lys Ser Arg Gly Trp Trp Val His Ser
115 120 125

Val Leu Leu Leu Glu Ala Thr Thr Phe Arg Thr Val Gly Leu Leu His
130 135 140

Gln Glu Trp Trp Met Arg Pro Asp Asp Pro Ala Asp Ala Asp Glu Lys
145 150 155 160

Glu Ser Gly Lys Trp Leu Ala Ala Ala Ala Thr Ser Arg Leu Arg Met
165 170 175

Gly Ser Met Met Ser Asn Val Ile Ala Val Cys Asp Arg Glu Ala Asp
180 185 190

Ile His Ala Tyr Leu Gln Asp Lys Leu Ala His Asn Glu Arg Phe Val
195 200 205

Val Arg Ser Lys His Pro Arg Lys Asp Val Glu Ser Gly Leu Tyr Leu
210 215 220

Tyr Asp His Leu Lys Asn Gln Pro Glu Leu Gly Gly Tyr Gln Ile Ser
225 230 235 240

Ile Pro Gln Lys Gly Val Val Asp Lys Arg Gly Lys Arg Lys Asn Arg
245 250 255

Pro Ala Arg Lys Ala Ser Leu Ser Leu Arg Ser Gly Arg Ile Thr Leu
260 265 270

Lys Gln Gly Asn Ile Thr Leu Asn Ala Val Leu Ala Glu Glu Ile Asn
275 280 285

Pro Pro Lys Gly Glu Thr Pro Leu Lys Trp Leu Leu Leu Thr Ser Glu
290 295 300

Pro Val Glu Ser Leu Ala Gln Ala Leu Arg Val Ile Asp Ile Tyr Thr
305 310 315 320

His Arg Trp Arg Ile Glu Glu Phe His Lys Ala Trp Lys Thr Gly Ala
325 330 335

Gly Ala Glu Arg Gln Arg Met Glu Glu Pro Asp Asn Leu Glu Arg Met
340 345 350

Val Ser Ile Leu Ser Phe Val Ala Val Arg Leu Leu Gln Leu Arg Glu
355 360 365

Ser Phe Thr Leu Pro Gln Ala Leu Arg Ala Gln Gly Leu Leu Lys Glu
370 375 380

Ala Glu His Val Glu Ser Gln Ser Ala Glu Thr Val Leu Thr Pro Asp
385 390 395 400

Glu Cys Gln Leu Leu Gly Tyr Leu Asp Lys Gly Lys Arg Lys Arg Lys
405 410 415

Glu Lys Ala Gly Ser Leu Gln Trp Ala Tyr Met Ala Ile Ala Arg Leu
420 425 430

Gly Gly Phe Met Asp Ser Lys Arg Thr Gly Ile Ala Ser Trp Gly Ala
435 440 445

Leu Trp Glu Gly Trp Glu Ala Leu Gln Ser Lys Leu Asp Gly Phe Leu
450 455 460

Ala Ala Lys Asp Leu Met Ala Gln Gly Ile Lys Ile
465 470 475

<210> SEQ ID NO 495
<211> LENGTH: 19
<212> TYPE: DNA
<213> ORGANISM: Artificial Sequence
<220> FEATURE:
<223> OTHER INFORMATION: Synthetic Construct

<400> SEQUENCE: 495
ctgactctta tacacaagt 19

<210> SEQ ID NO 496
<211> LENGTH: 19
<212> TYPE: DNA
<213> ORGANISM: Artificial Sequence
<220> FEATURE:
<223> OTHER INFORMATION: Synthetic Construct

<400> SEQUENCE: 496
ctgtctcttg atcagatct 19

<210> SEQ ID NO 497
<211> LENGTH: 19
<212> TYPE: DNA
<213> ORGANISM: Artificial Sequence
<220> FEATURE:
<223> OTHER INFORMATION: Synthetic Construct

<400> SEQUENCE: 497
ctgtctctta tacacatct 19

<210> SEQ ID NO 498
<211> LENGTH: 19
<212> TYPE: DNA
<213> ORGANISM: Artificial Sequence
<220> FEATURE:
<223> OTHER INFORMATION: Synthetic Construct

<400> SEQUENCE: 498
ctgtctctta tacagatct 19

<210> SEQ ID NO 499
<211> LENGTH: 663
<212> TYPE: PRT
<213> ORGANISM: Artificial Sequence
<220> FEATURE:
<223> OTHER INFORMATION: Synthetic Construct

<400> SEQUENCE: 499

Met Glu Leu Trp Val Ser Pro Lys Glu Cys Ala Asn Leu Pro Gly Leu
1 5 10 15

Pro Lys Thr Ser Ala Gly Val Ile Tyr Val Ala Lys Lys Gln Gly Trp
20 25 30

Gln Asn Arg Thr Arg Ala Gly Val Lys Gly Gly Lys Ala Ile Glu Tyr
35 40 45

```
Asn Ala Asn Ser Leu Pro Val Glu Ala Lys Ala Ala Leu Leu Leu Arg
    50                  55                  60

Gln Gly Glu Ile Glu Thr Ser Leu Gly Tyr Phe Glu Ile Ala Arg Pro
65                  70                  75                  80

Thr Leu Glu Ala His Asp Tyr Asp Arg Glu Ala Leu Trp Ser Lys Trp
                85                  90                  95

Asp Asn Ala Ser Asp Ser Gln Arg Arg Leu Ala Glu Lys Trp Leu Pro
            100                 105                 110

Ala Val Gln Ala Ala Asp Glu Met Leu Asn Gln Gly Ile Ser Thr Lys
        115                 120                 125

Thr Ala Phe Ala Thr Val Ala Gly His Tyr Gln Val Ser Ala Ser Thr
    130                 135                 140

Leu Arg Asp Lys Tyr Tyr Gln Val Gln Lys Phe Ala Lys Pro Asp Trp
145                 150                 155                 160

Ala Ala Ala Leu Val Asp Gly Arg Gly Ala Ser Arg Arg Asn Val His
                165                 170                 175

Lys Ser Glu Phe Asp Glu Asp Ala Trp Gln Phe Leu Ile Ala Asp Tyr
            180                 185                 190

Leu Arg Pro Glu Lys Pro Ala Phe Arg Lys Cys Tyr Glu Arg Leu Glu
        195                 200                 205

Leu Ala Ala Arg Glu His Gly Trp Ser Ile Pro Ser Arg Ala Thr Ala
    210                 215                 220

Phe Arg Arg Ile Gln Gln Leu Asp Glu Ala Met Val Val Ala Cys Arg
225                 230                 235                 240

Glu Gly Glu His Ala Leu Met His Leu Ile Pro Ala Gln Gln Arg Thr
                245                 250                 255

Val Glu His Leu Asp Ala Met Gln Trp Ile Asn Gly Asp Gly Tyr Leu
            260                 265                 270

His Asn Val Phe Val Arg Trp Phe Asn Gly Asp Val Ile Arg Pro Lys
        275                 280                 285

Thr Trp Phe Trp Gln Asp Val Lys Thr Arg Lys Ile Leu Gly Trp Arg
    290                 295                 300

Cys Asp Val Ser Glu Asn Ile Asp Ser Ile Arg Leu Ser Phe Met Asp
305                 310                 315                 320

Val Val Thr Arg Tyr Gly Ile Pro Glu Asp Phe His Ile Thr Ile Asp
                325                 330                 335

Asn Thr Arg Gly Ala Ala Asn Lys Trp Leu Thr Gly Gly Ala Pro Asn
            340                 345                 350

Arg Tyr Arg Phe Lys Val Lys Glu Asp Asp Pro Lys Gly Leu Phe Leu
        355                 360                 365

Leu Met Gly Ala Lys Met His Trp Thr Ser Val Val Ala Gly Lys Gly
    370                 375                 380

Trp Gly Gln Ala Lys Pro Val Glu Arg Ala Phe Gly Val Gly Gly Leu
385                 390                 395                 400

Glu Glu Tyr Val Asp Lys His Pro Ala Leu Ala Gly Ala Tyr Thr Gly
                405                 410                 415

Pro Asn Pro Gln Ala Lys Pro Asp Asn Tyr Gly Asp Arg Ala Val Asp
            420                 425                 430

Ala Glu Leu Phe Leu Lys Thr Leu Ala Glu Gly Val Ala Met Phe Asn
        435                 440                 445

Ala Arg Thr Gly Arg Glu Thr Glu Met Cys Gly Gly Lys Leu Ser Phe
    450                 455                 460
```

```
Asp Asp Val Phe Glu Arg Glu Tyr Ala Arg Thr Ile Val Arg Lys Pro
465                 470                 475                 480

Thr Glu Glu Gln Lys Arg Met Leu Leu Leu Pro Ala Glu Ala Val Asn
                485                 490                 495

Val Ser Arg Lys Gly Glu Phe Thr Leu Lys Val Gly Gly Ser Leu Lys
            500                 505                 510

Gly Ala Lys Asn Val Tyr Tyr Asn Met Ala Leu Met Asn Ala Gly Val
        515                 520                 525

Lys Lys Val Val Val Arg Phe Asp Pro Gln Gln Leu His Ser Thr Val
    530                 535                 540

Tyr Cys Tyr Thr Leu Asp Gly Arg Phe Ile Cys Glu Ala Glu Cys Leu
545                 550                 555                 560

Ala Pro Val Ala Phe Asn Asp Ala Ala Ala Gly Arg Glu Tyr Arg Arg
                565                 570                 575

Arg Gln Lys Gln Leu Lys Ser Ala Thr Lys Ala Ala Ile Lys Ala Gln
            580                 585                 590

Lys Gln Met Asp Ala Leu Glu Val Ala Glu Leu Leu Pro Gln Ile Ala
        595                 600                 605

Glu Pro Ala Ala Pro Glu Ser Arg Ile Val Gly Ile Phe Arg Pro Ser
    610                 615                 620

Gly Asn Thr Glu Arg Val Lys Asn Gln Glu Arg Asp Asp Glu Tyr Glu
625                 630                 635                 640

Thr Glu Arg Asp Glu Tyr Leu Asn His Ser Leu Asp Ile Leu Glu Gln
                645                 650                 655

Asn Arg Arg Lys Lys Ala Ile
            660


<210> SEQ ID NO 500
<211> LENGTH: 26
<212> TYPE: DNA
<213> ORGANISM: Artificial Sequence
<220> FEATURE:
<223> OTHER INFORMATION: Synthetic Construct

<400> SEQUENCE: 500

tgtattgatt cactgaagta cgaaaa                                          26


<210> SEQ ID NO 501
<211> LENGTH: 23
<212> TYPE: DNA
<213> ORGANISM: Artificial Sequence
<220> FEATURE:
<223> OTHER INFORMATION: Synthetic Construct

<400> SEQUENCE: 501

ccttaatcaa tgaaacgcga aag                                             23


<210> SEQ ID NO 502
<211> LENGTH: 23
<212> TYPE: DNA
<213> ORGANISM: Artificial Sequence
<220> FEATURE:
<223> OTHER INFORMATION: Synthetic Construct

<400> SEQUENCE: 502

ttgtttcatt gaaaatacga aaa                                             23


<210> SEQ ID NO 503
<211> LENGTH: 27
<212> TYPE: DNA
```

<213> ORGANISM: Artificial Sequence
<220> FEATURE:
<223> OTHER INFORMATION: Synthetic Construct

<400> SEQUENCE: 503
tgaagcggcg cacgaaaaat gcgaaaa 27

<210> SEQ ID NO 504
<211> LENGTH: 23
<212> TYPE: DNA
<213> ORGANISM: Artificial Sequence
<220> FEATURE:
<223> OTHER INFORMATION: Synthetic Construct

<400> SEQUENCE: 504
gcgtttcacg ataaatgcga aaa 23

<210> SEQ ID NO 505
<211> LENGTH: 23
<212> TYPE: DNA
<213> ORGANISM: Artificial Sequence
<220> FEATURE:
<223> OTHER INFORMATION: Synthetic Construct

<400> SEQUENCE: 505
ccgtttcatt tgaagcgcga aaa 23

<210> SEQ ID NO 506
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (9)..(10)
<223> OTHER INFORMATION: n is a, c, g, or t

<400> SEQUENCE: 506
ygtttcaynn raaryrcgaa ar 22

<210> SEQ ID NO 507
<211> LENGTH: 402
<212> TYPE: PRT
<213> ORGANISM: Artificial Sequence
<220> FEATURE:
<223> OTHER INFORMATION: Synthetic Construct

<400> SEQUENCE: 507

```
Met Cys Glu Leu Asp Ile Leu His Asp Ser Leu Tyr Gln Phe Cys Pro
1               5                   10                  15

Glu Leu His Leu Lys Arg Leu Asn Ser Leu Thr Leu Ala Cys His Ala
            20                  25                  30

Leu Leu Asp Cys Lys Thr Leu Thr Leu Thr Glu Leu Gly Arg Asn Leu
        35                  40                  45

Pro Thr Lys Ala Arg Thr Lys His Asn Ile Lys Arg Ile Asp Arg Leu
    50                  55                  60

Leu Gly Asn Arg His Leu His Lys Glu Arg Leu Ala Val Tyr Arg Trp
65                  70                  75                  80

His Ala Ser Phe Ile Cys Ser Gly Asn Thr Met Pro Ile Val Leu Val
                85                  90                  95

Asp Trp Ser Asp Ile Arg Glu Gln Lys Arg Leu Met Val Leu Arg Ala
            100                 105                 110
```

```
Ser Val Ala Leu His Gly Arg Ser Val Thr Leu Tyr Glu Lys Ala Phe
        115                 120                 125

Pro Leu Ser Glu Gln Cys Ser Lys Lys Ala His Asp Gln Phe Leu Ala
    130                 135                 140

Asp Leu Ala Ser Ile Leu Pro Ser Asn Thr Thr Pro Leu Ile Val Ser
145                 150                 155                 160

Asp Ala Gly Phe Lys Val Pro Trp Tyr Lys Ser Val Glu Lys Leu Gly
                165                 170                 175

Trp Tyr Trp Leu Ser Arg Val Arg Gly Lys Val Gln Tyr Ala Asp Leu
            180                 185                 190

Gly Ala Glu Asn Trp Lys Pro Ile Ser Asn Leu His Asp Met Ser Ser
        195                 200                 205

Ser His Ser Lys Thr Leu Gly Tyr Lys Arg Leu Thr Lys Ser Asn Pro
    210                 215                 220

Ile Ser Cys Gln Ile Leu Leu Tyr Lys Ser Arg Ser Lys Gly Arg Lys
225                 230                 235                 240

Asn Gln Arg Ser Thr Arg Thr His Cys His His Pro Ser Pro Lys Ile
                245                 250                 255

Tyr Ser Ala Ser Ala Lys Glu Pro Trp Val Leu Ala Thr Asn Leu Pro
            260                 265                 270

Val Glu Ile Arg Thr Pro Lys Gln Leu Val Asn Ile Tyr Ser Lys Arg
        275                 280                 285

Met Gln Ile Glu Glu Thr Phe Arg Asp Leu Lys Ser Pro Ala Tyr Gly
    290                 295                 300

Leu Gly Leu Arg His Ser Arg Thr Ser Ser Ser Glu Arg Phe Asp Ile
305                 310                 315                 320

Met Leu Leu Ile Ala Leu Met Leu Gln Leu Thr Cys Trp Leu Ala Gly
                325                 330                 335

Val His Ala Gln Lys Gln Gly Trp Asp Lys His Phe Gln Ala Asn Thr
            340                 345                 350

Val Arg Asn Arg Asn Val Leu Ser Thr Val Arg Leu Gly Met Glu Val
        355                 360                 365

Leu Arg His Ser Gly Tyr Thr Ile Thr Arg Glu Asp Leu Leu Val Ala
    370                 375                 380

Ala Thr Leu Leu Ala Gln Asn Leu Phe Thr His Gly Tyr Ala Leu Gly
385                 390                 395                 400

Lys Leu
```

<210> SEQ ID NO 508
<211> LENGTH: 23
<212> TYPE: DNA
<213> ORGANISM: Artificial Sequence
<220> FEATURE:
<223> OTHER INFORMATION: Synthetic Construct

<400> SEQUENCE: 508
ctgakrratc ccctmatrat tty 23

<210> SEQ ID NO 509
<211> LENGTH: 273
<212> TYPE: PRT
<213> ORGANISM: Artificial Sequence
<220> FEATURE:
<223> OTHER INFORMATION: Synthetic Construct

<400> SEQUENCE: 509

Met Ala Lys Ala Asn Ser Ser Phe Ser Glu Val Gln Ile Ala Arg Arg

```
1               5                   10                  15

Ile Lys Glu Gly Arg Gly Gln Gly His Gly Lys Asp Tyr Ile Pro Trp
            20                  25                  30

Leu Thr Val Gln Glu Val Pro Ser Ser Gly Arg Ser His Arg Ile Tyr
        35                  40                  45

Ser His Lys Thr Gly Arg Val His His Leu Leu Ser Asp Leu Glu Leu
    50                  55                  60

Ala Val Phe Leu Ser Leu Glu Trp Glu Ser Ser Val Leu Asp Ile Arg
65                  70                  75                  80

Glu Gln Phe Pro Leu Leu Pro Ser Asp Thr Arg Gln Ile Ala Ile Asp
                85                  90                  95

Ser Gly Ile Lys His Pro Val Ile Arg Gly Val Asp Gln Val Met Ser
            100                 105                 110

Thr Asp Phe Leu Val Asp Cys Lys Asp Gly Pro Phe Glu Gln Phe Ala
        115                 120                 125

Ile Gln Val Lys Pro Ala Ala Ala Leu Gln Asp Glu Arg Thr Leu Glu
    130                 135                 140

Lys Leu Glu Leu Glu Arg Arg Tyr Trp Gln Gln Lys Gln Ile Pro Trp
145                 150                 155                 160

Phe Ile Phe Thr Asp Lys Glu Ile Asn Pro Val Val Lys Glu Asn Ile
                165                 170                 175

Glu Trp Leu Tyr Ser Val Lys Thr Glu Glu Val Ser Ala Glu Leu Leu
            180                 185                 190

Ala Gln Leu Ser Pro Leu Ala His Ile Leu Gln Glu Lys Gly Asp Glu
        195                 200                 205

Asn Ile Ile Asn Val Cys Lys Gln Val Asp Ile Ala Tyr Asp Leu Glu
    210                 215                 220

Leu Gly Lys Thr Leu Ser Glu Ile Arg Ala Leu Thr Ala Asn Gly Phe
225                 230                 235                 240

Ile Lys Phe Asn Ile Tyr Lys Ser Phe Arg Ala Asn Lys Cys Ala Asp
                245                 250                 255

Leu Cys Ile Ser Gln Val Val Asn Met Glu Glu Leu Arg Tyr Val Ala
            260                 265                 270

Asn
```

<210> SEQ ID NO 510
<211> LENGTH: 702
<212> TYPE: PRT
<213> ORGANISM: Artificial Sequence
<220> FEATURE:
<223> OTHER INFORMATION: Synthetic Construct

<400> SEQUENCE: 510

```
Met Trp Gln Ile Asn Glu Val Val Leu Phe Asp Asn Asp Pro Tyr Arg
1               5                   10                  15

Ile Leu Ala Ile Glu Asp Gly Gln Val Val Trp Met Gln Ile Ser Ala
            20                  25                  30

Asp Lys Gly Val Pro Gln Ala Arg Ala Glu Leu Leu Leu Met Gln Tyr
        35                  40                  45

Leu Asp Glu Gly Arg Leu Val Arg Thr Asp Asp Pro Tyr Val His Leu
    50                  55                  60

Asp Leu Glu Glu Pro Ser Val Asp Ser Val Ser Phe Gln Lys Arg Glu
65                  70                  75                  80

Glu Asp Tyr Arg Lys Ile Leu Pro Ile Ile Asn Ser Lys Asp Arg Phe
                85                  90                  95
```

Asp Pro Lys Val Arg Ser Glu Leu Val Glu His Val Val Gln Glu His
100 105 110

Lys Val Thr Lys Ala Thr Val Tyr Lys Leu Leu Arg Arg Tyr Trp Gln
115 120 125

Arg Gly Gln Thr Pro Asn Ala Leu Ile Pro Asp Tyr Lys Asn Ser Gly
130 135 140

Ala Pro Gly Glu Arg Arg Ser Ala Thr Gly Thr Ala Lys Ile Gly Arg
145 150 155 160

Ala Arg Glu Tyr Gly Lys Gly Glu Gly Thr Lys Val Thr Pro Glu Ile
165 170 175

Glu Arg Leu Phe Arg Leu Thr Ile Glu Lys His Leu Leu Asn Gln Lys
180 185 190

Gly Thr Lys Thr Thr Val Ala Tyr Arg Arg Phe Val Asp Leu Phe Ala
195 200 205

Gln Tyr Phe Pro Arg Ile Pro Gln Glu Asp Tyr Pro Thr Leu Arg Gln
210 215 220

Phe Arg Tyr Phe Tyr Asp Arg Glu Tyr Pro Lys Ala Gln Arg Leu Lys
225 230 235 240

Ser Arg Val Lys Ala Gly Val Tyr Lys Lys Asp Val Arg Pro Leu Ser
245 250 255

Ser Thr Ala Thr Ser Gln Ala Leu Gly Pro Gly Ser Arg Tyr Glu Ile
260 265 270

Asp Ala Thr Ile Ala Asp Ile Tyr Leu Val Asp His His Asp Arg Gln
275 280 285

Lys Ile Ile Gly Arg Pro Thr Leu Tyr Ile Val Ile Asp Val Phe Ser
290 295 300

Arg Met Ile Thr Gly Phe Tyr Ile Gly Phe Glu Asn Pro Ser Tyr Val
305 310 315 320

Val Ala Met Gln Ala Phe Val Asn Ala Cys Ser Asp Lys Thr Ala Ile
325 330 335

Cys Ala Gln His Asp Ile Glu Ile Ser Ser Ser Asp Trp Pro Cys Val
340 345 350

Gly Leu Pro Asp Val Leu Leu Ala Asp Arg Gly Glu Leu Met Ser His
355 360 365

Gln Val Glu Ala Leu Val Ser Ser Phe Asn Val Arg Val Glu Ser Ala
370 375 380

Pro Pro Arg Arg Gly Asp Ala Lys Gly Ile Val Glu Ser Thr Phe Arg
385 390 395 400

Thr Leu Gln Ala Glu Phe Lys Ser Phe Ala Pro Gly Ile Val Glu Gly
405 410 415

Ser Arg Ile Lys Ser His Gly Glu Thr Asp Tyr Arg Leu Asp Ala Ser
420 425 430

Leu Ser Val Phe Glu Phe Thr Gln Ile Ile Leu Arg Thr Ile Leu Phe
435 440 445

Arg Asn Asn His Leu Val Met Asp Lys Tyr Asp Arg Asp Ala Asp Phe
450 455 460

Pro Thr Asp Leu Pro Ser Ile Pro Val Gln Leu Trp Gln Trp Gly Met
465 470 475 480

Gln His Arg Thr Gly Ser Leu Arg Ala Val Glu Gln Glu Gln Leu Arg
485 490 495

Val Ala Leu Leu Pro Arg Arg Lys Val Ser Ile Ser Ser Phe Gly Val
500 505 510

```
Asn Leu Trp Gly Leu Tyr Tyr Ser Gly Ser Glu Ile Leu Arg Glu Gly
        515                 520                 525

Trp Leu Gln Arg Ser Thr Asp Ile Ala Arg Pro Gln His Leu Glu Ala
    530                 535                 540

Ala Tyr Asp Pro Val Leu Val Asp Thr Ile Tyr Leu Phe Pro Gln Val
545                 550                 555                 560

Gly Ser Arg Val Phe Trp Arg Cys Asn Leu Thr Glu Arg Ser Arg Gln
                565                 570                 575

Phe Lys Gly Leu Ser Phe Trp Glu Val Trp Asp Ile Gln Ala Gln Glu
            580                 585                 590

Lys His Asn Lys Ala Asn Ala Lys Gln Asp Glu Leu Thr Lys Arg Arg
        595                 600                 605

Glu Leu Glu Ala Phe Ile Gln Gln Thr Ile Gln Lys Ala Asn Lys Leu
    610                 615                 620

Thr Pro Ser Thr Thr Glu Pro Lys Ser Thr Arg Ile Lys Gln Ile Lys
625                 630                 635                 640

Thr Asn Lys Lys Glu Ala Val Thr Ser Glu Arg Lys Lys Arg Ala Glu
                645                 650                 655

His Leu Lys Pro Ser Ser Ser Gly Asp Glu Ala Lys Val Ile Pro Phe
            660                 665                 670

Asn Ala Val Glu Ala Asp Asp Gln Glu Asp Tyr Ser Leu Pro Thr Tyr
        675                 680                 685

Val Pro Glu Leu Phe Gln Asp Pro Pro Glu Lys Asp Glu Ser
    690                 695                 700
```

<210> SEQ ID NO 511
<211> LENGTH: 22
<212> TYPE: DNA
<213> ORGANISM: Artificial Sequence
<220> FEATURE:
<223> OTHER INFORMATION: Synthetic Construct

<400> SEQUENCE: 511
tgayaataaa gttgattata ct 22

<210> SEQ ID NO 512
<211> LENGTH: 38
<212> TYPE: DNA
<213> ORGANISM: Artificial Sequence
<220> FEATURE:
<223> OTHER INFORMATION: Synthetic Construct

<400> SEQUENCE: 512
ggggtctgac gctcagtgga acgaaaactc acgttaag 38

<210> SEQ ID NO 513
<211> LENGTH: 38
<212> TYPE: DNA
<213> ORGANISM: Artificial Sequence
<220> FEATURE:
<223> OTHER INFORMATION: Synthetic Construct

<400> SEQUENCE: 513
cttaacgtga gttttcgttc cactgagcgt cagacccc 38

<210> SEQ ID NO 514
<211> LENGTH: 38
<212> TYPE: DNA
<213> ORGANISM: Artificial Sequence
<220> FEATURE:
<223> OTHER INFORMATION: Synthetic Construct

<400> SEQUENCE: 514
ggggtttgag ggccaatgga acgaaaacgt acgttaag 38

<210> SEQ ID NO 515
<211> LENGTH: 38
<212> TYPE: DNA
<213> ORGANISM: Artificial Sequence
<220> FEATURE:
<223> OTHER INFORMATION: Synthetic Construct

<400> SEQUENCE: 515
ataaacgtac gttttcgttc cattggccct caaacccc 38

<210> SEQ ID NO 516
<211> LENGTH: 255
<212> TYPE: DNA
<213> ORGANISM: Artificial Sequence
<220> FEATURE:
<223> OTHER INFORMATION: Synthetic Construct

<400> SEQUENCE: 516
cgcttaactt aatacgagcc ccaaccacta ttaattcgaa cagcatgttt tttttgcagt 60
gcgcaatgtt taacacacta tattatcaat actactaaag ataacacata ccaatgcatt 120
tcgtctcaaa gagaatttta ttctcttcac gacgaaaaaa aaagttttgc tctatttcca 180
acaacaacaa aaatatgagt aatttattca aacggtttgc ttaagagata agaaaaaagt 240
gaccactatt aattc 255

<210> SEQ ID NO 517
<211> LENGTH: 255
<212> TYPE: DNA
<213> ORGANISM: Artificial Sequence
<220> FEATURE:
<223> OTHER INFORMATION: Synthetic Construct

<400> SEQUENCE: 517
atagtaaatc acattacgcc gcgttcgaat taatagtggt cacttttttc ttatctctta 60
agcaaaccgt ttgaataaat tactcatatt tttgttgttg ttggaaatag agcaaaactt 120 ttttttttcgt cgtgaagaga ataaaattct ctttgagacg aaatgcattg gtatgtgtta 180
tctttagtag tattgataat atagtgtgtt aaacattgcg cactgcaaaa aaaacatgct 240
gttcgaatta atagt 255

<210> SEQ ID NO 518
<211> LENGTH: 340
<212> TYPE: PRT
<213> ORGANISM: Artificial Sequence
<220> FEATURE:
<223> OTHER INFORMATION: Synthetic Construct

<400> SEQUENCE: 518

Met Gly Lys Ser Lys Glu Ile Ser Gln Asp Leu Arg Lys Lys Ile Val
1               5                   10                  15

Asp Leu His Lys Ser Gly Ser Ser Leu Gly Ala Ile Ser Lys Arg Leu
            20                  25                  30

Lys Val Pro Arg Ser Ser Val Gln Thr Ile Val Arg Lys Tyr Lys His
        35                  40                  45

His Gly Thr Thr Gln Pro Ser Tyr Arg Ser Gly Arg Arg Arg Val Leu
    50                  55                  60

-continued

| | | | | | | | | | | | | | | | |
|---|---|---|---|---|---|---|---|---|---|---|---|---|---|---|---|
| Ser | Pro | Arg | Asp | Glu | Arg | Thr | Leu | Val | Arg | Lys | Val | Gln | Ile | Asn | Pro |
| 65 | | | | | 70 | | | | | 75 | | | | | 80 |
| Arg | Thr | Thr | Ala | Lys | Asp | Leu | Val | Lys | Met | Leu | Glu | Glu | Thr | Gly | Thr |
| | | | | 85 | | | | | 90 | | | | | 95 | |
| Lys | Val | Ser | Ile | Ser | Thr | Val | Lys | Arg | Val | Leu | Tyr | Arg | His | Asn | Leu |
| | | | 100 | | | | | 105 | | | | | 110 | | |
| Lys | Gly | Arg | Ser | Ala | Arg | Lys | Lys | Pro | Leu | Leu | Gln | Asn | Arg | His | Lys |
| | | 115 | | | | | 120 | | | | | 125 | | | |
| Lys | Ala | Arg | Leu | Arg | Phe | Ala | Thr | Ala | His | Gly | Asp | Lys | Asp | Arg | Thr |
| | 130 | | | | | 135 | | | | | 140 | | | | |
| Phe | Trp | Arg | Asn | Val | Leu | Trp | Ser | Asp | Glu | Thr | Lys | Ile | Glu | Leu | Phe |
| 145 | | | | | 150 | | | | | 155 | | | | | 160 |
| Gly | His | Asn | Asp | His | Arg | Tyr | Val | Trp | Arg | Lys | Lys | Gly | Glu | Ala | Cys |
| | | | | 165 | | | | | 170 | | | | | 175 | |
| Lys | Pro | Lys | Asn | Thr | Ile | Pro | Thr | Val | Lys | His | Gly | Gly | Gly | Ser | Ile |
| | | | 180 | | | | | 185 | | | | | 190 | | |
| Met | Leu | Trp | Cys | Gly | Phe | Ala | Ala | Gly | Gly | Thr | Gly | Ala | Leu | His | Lys |
| | | 195 | | | | | 200 | | | | | 205 | | | |
| Ile | Asp | Gly | Ile | Met | Arg | Lys | Glu | Asn | Tyr | Val | Asp | Ile | Leu | Lys | Gln |
| | 210 | | | | | 215 | | | | | 220 | | | | |
| His | Leu | Lys | Thr | Ser | Val | Arg | Lys | Leu | Lys | Leu | Gly | Arg | Lys | Trp | Val |
| 225 | | | | | 230 | | | | | 235 | | | | | 240 |
| Phe | Gln | Met | Asp | Asn | Asp | Pro | Lys | His | Thr | Ser | Lys | Val | Val | Ala | Lys |
| | | | | 245 | | | | | 250 | | | | | 255 | |
| Trp | Leu | Lys | Asp | Asn | Lys | Val | Lys | Val | Leu | Glu | Trp | Pro | Ser | Gln | Ser |
| | | | 260 | | | | | 265 | | | | | 270 | | |
| Pro | Asp | Leu | Asn | Pro | Ile | Glu | Asn | Leu | Trp | Ala | Glu | Leu | Lys | Lys | Arg |
| | | 275 | | | | | 280 | | | | | 285 | | | |
| Val | Arg | Ala | Arg | Arg | Pro | Thr | Asn | Leu | Thr | Gln | Leu | His | Gln | Leu | Cys |
| | 290 | | | | | 295 | | | | | 300 | | | | |
| Gln | Glu | Glu | Trp | Ala | Lys | Ile | His | Pro | Thr | Tyr | Cys | Gly | Lys | Leu | Val |
| 305 | | | | | 310 | | | | | 315 | | | | | 320 |
| Glu | Gly | Tyr | Pro | Lys | Arg | Leu | Thr | Gln | Val | Lys | Gln | Phe | Lys | Gly | Asn |
| | | | | 325 | | | | | 330 | | | | | 335 | |
| Ala | Thr | Lys | Tyr | | | | | | | | | | | | |
| | | | 340 | | | | | | | | | | | | |

COMPOSITIONS AND METHODS FOR SEQUENCING NUCLEIC ACIDS

SEQUENCE LISTING

The instant application contains a Sequence Listing which has been submitted electronically in ASCII format and is hereby incorporated by reference in its entirety. Said ASCII copy, created on Feb. 14, 2018, is named 51178-003WO2_Sequence_Listing_2.14.18_ST25 and is 125,690 bytes in size.

FIELD OF THE INVENTION

The present invention relates generally to nucleic acid (e.g., DNA) sequencing and, more specifically, to artificial nucleic acids, compositions that include artificial nucleic acids and transposases, and methods of use thereof, e.g., for library preparation and sequencing.

BACKGROUND

Nucleic acid (e.g., DNA) sequencing has become an indispensable part of modern biology, and has wide uses, for example, identification and classification of species (e.g., pathogens), identification of genetic abnormalities such as disease-associated mutations, measuring RNA transcripts present in a cell, among many others. Current approaches include massively parallel or "next-generation" sequencing (NGS), which allow for parallel processing of many nucleic acids in a single sequencing run. NGS has revolutionized genomics and molecular biology by greatly increasing the speed of sequencing while reducing costs. In general, NGS approaches involve preparing a library of template nucleic acids from a target nucleic acid to be sequenced, obtaining sequence data from the library, and assembling the sequence data to infer the sequence of the target nucleic acid. Most NGS approaches utilize sequencing libraries having small fragments (typically on the order of hundreds of base pairs), in part due to technical limitations of the approaches. The resulting short reads are assembled computationally, often by alignment to a reference sequence, to infer the sequence of the target nucleic acid.

One of the limitations of current library preparation approaches for NGS is that each of the fragments in the library typically represents only a very small piece of a much larger original source target nucleic acid. For example, the fragments in the library may be only a few hundred nucleotides long whereas the source target nucleic acid(s) may have been a chromosome or an entire genome. This makes it difficult to use current library preparation methods to sequence DNA, and particularly whole genomes, because the contiguity of bases over longer distances (e.g., thousands or millions of bases) can only be inferred computationally by attempting to overlap smaller fragments (in a computational process called de novo sequence assembly). The inherent "short range" limitation of conventional NGS library preparation methods limits the use of current DNA sequencing methods to those that can be carried out using relatively homogeneous, high purity samples. Additionally, the small size of library fragments makes it highly unlikely that library fragments originate from the same target nucleic acid molecule.

Therefore, there remains a need for compositions and methods useful for library preparation and sequencing that can obtain long distance linkage and sequence information, as well as for preparing libraries having a high proportion of fragments originating from the same target nucleic acid molecule.

SUMMARY OF THE INVENTION

In general, the invention relates to multivalent tethered synaptic complexes (TSCs), reagents employed in the synthesis of such TSCs, and methods of use thereof.

In one aspect, the invention provides a multivalent transposase reagent having a water soluble multivalent core and a first artificial nucleic acid with a first end having a transposase binding site (TBS); a second artificial nucleic acid with a first end having a TBS; and a third artificial nucleic acid with a first end having a TBS linked to the water-soluble multivalent core.

In certain embodiments, the first, second, or third artificial nucleic acid is linked to the soluble multivalent core by a covalent bond resulting from a conjugation reaction, e.g., an azide-alkyne Huisgen cycloaddition, amide or thioamide bond formation, a pericyclic reaction, a Diels-Alder reaction, sulfonamide bond formation, alcohol or phenol alkylation, a condensation reaction, disulfide bond formation, or a nucleophilic substitution. For example, the conjugation reaction is an azide-alkyne Huisgen cycloaddition, e.g., a copper(I)-catalyzed azide-alkyne cycloaddition (CuAAC) or a strain-promoted azide-alkyne cycloaddition (SPAAC).

In other embodiments, the first, second, or third artificial nucleic acid is linked non-covalently to the soluble multivalent core. For example, the first, second, or third artificial nucleic acid is linked to the soluble multivalent core by an affinity binding pair, such as biotin-streptavidin, biotin-avidin, ligand-receptor, antigen-antibody or antigen binding fragment, or Ig binding protein-Ig. In certain embodiments, the affinity binding pair includes biotin-streptavidin or biotin-avidin. The affinity binding pair can include a first affinity component that binds a second affinity component, where the first affinity component is linked to the soluble multivalent core, and the second affinity component is linked to the first, second, or third artificial nucleic acid.

In further embodiments, the reagent further includes first, second, and third transposases bound to the TBS of the first, second, and third artificial nucleic acids. The reagent may also include a fourth artificial nucleic acid with a first end having a TBS and being linked to the soluble multivalent core, and a fourth transposase may be bound to the TBS of the fourth artificial nucleic acid. When two or more transposases are bound to the reagent, they may form an oligomerized pair, e.g., at least two of the first, second, third, and fourth transposases may form an oligomerized pair. In other embodiments, the first and second transposase form a first synaptic complex, and the third and fourth transposase form a second synaptic complex.

The reagent may further include a fifth and a sixth transposase, wherein the first and fifth transposase are oligomerized to form a first synaptic complex and the second and sixth transposase are oligomerized to form a second synaptic complex, wherein the fifth and sixth transposase are bound to adapter nucleic acids, each with a first end having a TBS.

In some embodiments, the reagent further includes a plurality of additional artificial nucleic acids, each additional artificial nucleic acid with a first end having a TBS, and each additional artificial acid being linked to the multivalent core. A plurality of additional transposases may also be bound to the TBSs of the plurality of additional artificial nucleic acids, wherein pairs of the plurality of additional transposases oligomerize to form synaptic complexes. For example, the reagent includes between 3 and 1000 synaptic complexes, e.g., between 3 and 12 synaptic complexes.

In another aspect, the invention provides a multivalent transposase reagent including a water soluble multivalent core; three or more synaptic complexes being linked to the soluble multivalent core, each of said synaptic complexes including a first transposase and a second transposase. The first transposase is bound to a first artificial nucleic acid having a TBS, the second transposase is bound to a second artificial nucleic acid having a TBS, and the first transposase and the second transposase are oligomerized. In certain embodiments, the first artificial nucleic acid and the second artificial nucleic acid of each synaptic complex is linked to the soluble multivalent core. In alternative embodiments, the first or second artificial nucleic acid of at least one synaptic complex is not linked to the soluble multivalent core. For any of the reagents of the invention, the soluble multivalent core may be a polymer, a nucleic acid, a peptide, a polypeptide, a protein, or a micelle. In certain embodiments, the soluble multivalent core is a polymer, such as a branched polymer, e.g., a star-shaped polymer, a comb polymer, a brush polymer, a hyperbranched polymer, or a dendrimer. An exemplary polymer is a polyethylene glycol (PEG)-based polymer, e.g., a PEG dendrimer or a multi-arm PEG (such as a 3-arm PEG, a 4-arm PEG, a 6-arm PEG, or an 8-arm PEG). In other embodiments, the soluble multivalent core is a nucleic acid, e.g., having between about 20 and about 1000 bp, e.g., between about 250 and about 500 bp. For example, the soluble multivalent core is DNA, such as double-stranded DNA. In further embodiments, the soluble multivalent core is a protein, e.g., a multimeric protein, such as avidin or streptavidin.

In further embodiments of any of the reagents of the invention, a plurality of the artificial nucleic acids of the reagent include an identifiable sequence tag (1ST). Each IST may be identical, or at least two ISTs are not identical.

In yet another aspect, the invention features a method of sequencing a target nucleic acid by combining any one of the reagents described herein with a target nucleic acid under conditions and for a time sufficient for the reagent to carry out a transposition event; fragmenting the target nucleic acid and optionally adding a polynucleotide to the resulting ends of the nucleic acid fragments; selecting DNA fragments including a nucleic acid sequence resulting from the transposition event; amplifying the selected fragments; and sequencing the amplified fragments. In some embodiments, the fragmenting may include tagmentation (e.g., by combining the target nucleic acid with soluble transposome complexes) or random shearing and adapter ligation. In some embodiments, the selecting includes selecting nucleic acid fragments including an 1ST. In some embodiments, the amplifying includes polymerase chain reaction (PCR), multiple displacement amplification (MDA), ligase chain reaction (LCR), loop mediated isothermal amplification (LAMP), rolling circle amplification (RCA), or strand displacement amplification (SDA). In some embodiments, the sequencing includes sequencing by synthesis, sequencing by ligation, or nanopore sequencing. In some embodiments, the sequencing by synthesis includes Illumina™ dye sequencing, single-molecule real-time (SMRT™) sequencing, or pyrosequencing. In some embodiments, the sequencing by ligation includes polony-based sequencing or SOLiD™ sequencing. In certain embodiments, the method further includes analyzing the sequenced fragments to identify fragments of the target nucleic acid that can be linked by the presence of a nucleic acid sequence resulting from the transposition event.

In some embodiments of any of the preceding methods, the target nucleic acid includes genomic DNA or cDNAs from a single cell. In other embodiments, the target nucleic acid includes nucleic acids from a plurality of haplotypes. In some embodiments, the sequence of the amplified fragments is used to perform de novo sequence assembly. In some embodiments, the target nucleic acid is crosslinked via histones or chromatin from single or multiple cells. In some embodiments, the target nucleic acid has been condensed or optionally treated with one or more condensing agents.

In another aspect, the invention provides a kit including any one of the reagents described herein and one or more additional reagents. The one or more additional reagents can include one or more of a soluble transposome (e.g., a tagmentation reagent), a cofactor, a buffered solution, or a reference nucleic acid. In some embodiments, the cofactor is a divalent metal cation (e.g., a magnesium cation).

Any of the kits described herein can further include a reagent for nucleic acid sequencing. In some embodiments, the reagent is selected from the group consisting of an oligonucleotide primer, a substrate, an enzyme, and a mixture of nucleotides. In yet another aspect, the invention provides a nucleic acid comprising or consisting of the nucleic acid sequence set forth in any one of SEQ ID NOs: 1-480, a fragment thereof, or a sequence having about 80%, about 85%, about 90%, about 95%, about 96%, about 97%, about 98%, or about 99% sequence identity to the nucleic acid sequence set forth in any one of SEQ ID NOs: 1-480 or a complement thereof.

In another aspect, the invention provides a mixture of a plurality of any of the reagents described herein. In some embodiments, at least two members of the plurality include different ISTs. The mixture may include at least 10, 100, 500, 1000, 10,000, or 100,000 distinct reagents, e.g., different by 1ST.

In a further aspect, the invention provides a library produced by combining any of the reagents described herein with a target nucleic acid under conditions and for a time sufficient for the reagent to carry out a transposition event. In some embodiments, the library includes a nucleic acid comprising or consisting of the nucleic acid sequence set forth in any one of SEQ ID NOs: 1-480, a fragment thereof, or a sequence having about 80%, about 85%, about 90%, about 95%, about 96%, about 97%, about 98%, or about 99% sequence identity to the nucleic acid sequence set forth in any one of SEQ ID NOs: 1-480 or a complement thereof.

Definitions

The term "about" is used herein to indicate that a value includes an inherent variation of error for the device or the method being employed to determine the value or to indicate plus-or-minus 10% of the stated value, whichever is greater.

The term "affinity binding pair" refers to a pair of moieties that bind and form a complex. In general, the affinity binding pairs used in the invention interact non-covalently. Exemplary affinity binding pairs include, without limitation, biotin-biotin binding protein (e.g., biotin-streptavidin and biotin-avidin), ligand-receptor, antigen-antibody or antigen binding fragment, hapten-anti-hapten, and immunoglobulin (Ig) binding protein-Ig. The members of an affinity binding pair may have any suitable binding affinity. For example, the members of an affinity binding pair may bind with an equilibrium binding constant ($K_D$) of about $10^{-5}$M, $10^{-6}$M, $10^{-7}$M, $10^{-8}$M, $10^{-9}$M, $10^{-10}$M, $10^{-11}$M, $10^{-12}$M, $10^{-13}$ M, $10^{-14}$ M, $10^{-15}$M, or lower.

"Amino acid sequence," as used herein, refers to a peptide, polypeptide, or protein sequence, and fragments or portions thereof, and to naturally occurring or synthetic molecules. The terms "protein" and "polypeptide" are used interchangeably herein.

The term "biologically active variant" refers to a moiety that is similar to, but not identical to, a reference moiety (e.g., a "parent" molecule or template) and that exhibits sufficient activity to be useful in one or more of the compositions or methods described herein (e.g., in place of the reference moiety). In some instances, the reference moiety is naturally occurring, and the biologically active variant thereof is not. For example, where the reference moiety is a naturally occurring nucleic acid sequence, a biologically active variant thereof can include a limited number of non-naturally occurring nucleotides; can have a nucleic acid sequence that differs from its naturally occurring counterpart (e.g., by one or more insertions, deletions, and/or substitutions); or can otherwise vary from its naturally occurring counterpart. For example, the nucleic acids described herein (and the multivalent transposase reagents and tethered synaptic complexes which contain them) can include a transposase binding site (TBS) that differs from a naturally occurring TBS but nevertheless retains the ability to bind a transposase and to function in the present compositions and methods. Where the reference moiety is a naturally occurring protein, a biologically active variant thereof can include a limited number of non-naturally occurring amino acids; can have a peptide sequence that differs from its naturally occurring counterpart; or can otherwise vary from its naturally occurring counterpart (e.g., by virtue of being modified post-translationally (e.g., its glycosylation pattern may differ)). The reference moiety may also be non-naturally occurring.

A "conjugation reaction" is a reaction that results in the formation of a covalent bond. For the purposes of the present disclosure, a conjugation reaction excludes formation of a phosphodiester bond. Non-limiting examples of conjugation reactions include cycloaddition (e.g., an azide-alkyne Huisgen cycloaddition (e.g., a copper(I)-catalyzed azide-alkyne cycloaddition (CuAAC) or a strain-promoted azide-alkyne cycloaddition (SPAAC))), amide or thioamide bond formation, a pericyclic reaction, a Diels-Alder reaction, sulfonamide bond formation, alcohol or phenol alkylation, a condensation reaction, disulfide bond formation, and a nucleophilic substitution.

A "distal site" is a location on a target DNA that is situated between about 100 base pairs (bp) and about 20 million bp from a reference point. For example, a distal site may be about 100 bp, about 200 bp, about 500 bp, about 1000 bp, about 5000 bp, about 10,000 bp, about 20,000 bp, about 50,000 bp, about 100,000 bp, about 250,000 bp, about 500,000 bp, about 750,000 bp, about 1 million bp, about 5 million bp, about 10 million bp, about 15 million bp, or about 20 million bp from a reference point. Two sites (e.g., "A" and "B") may be referred to as distal sites when A is situated between about 100 bp and 20 million bp away from B.

An "identifiable sequence tag" (IST) refers to any nucleic acid sequence that can be identified and used as a marker that a transposable nucleic acid has transposed into a target nucleic acid. The IST may be random, semi-random, or non-random. In some embodiments, an IST may be a nucleic acid barcode. An IST can include, for example, about 1, 2, 3, 4, 5, 6, 7, 8, 9, 10, 11, 12, 13, 14, 15, 16, 17, 18, 19, 20, 25, 30, 35, 40, 50, 60, 70, 80, 90, 100, or more consecutive nucleotides. A transposable nucleic acid may include, for example, 1, 2, 3, 4, 5, 6, 7, 8, 9, 10, or more ISTs.

As used herein, the term "fusion protein" refers to a composition containing all or a portion of the amino acid sequences of two or more proteins. For example, a fusion protein may include a transposase and a polypeptide targeting moiety. A fusion protein may include one or more linkers between the amino acid sequences of the proteins. The term "portion" includes any region of a polypeptide, such as a fragment (e.g., a cleavage product or a recombinantly-produced fragment) or an element or domain (e.g., a region of a polypeptide having an activity, for example, nucleic acid (e.g., DNA) binding), that contains fewer amino acids than the full-length or reference polypeptide (e.g., about 5%, 10%, 15%, 20%, 30%, 40%, 50%, 60%, 70%, 80%, 90%, 95%, or 99% fewer amino acids).

A "linking segment" or "linker," as used interchangeably herein, refers to an element that is disposed between two sequences (e.g., nucleic acid or polypeptide sequences) and which links the two sequences. The linkage can be covalent or non-covalent. A linking segment can include, for example, a nucleotide, a nucleic acid, a non-nucleotide chemical moiety (e.g., (poly)-ethyl chains), an amino acid, peptide, or polypeptide. A nucleic acid linking segment can include, for example, about 1, 2, 3, 4, 5, 10, 15, 20, 25, 30, 35, 40, 45, 50, 55, 60, 65, 70, 75, 80, 85, 90, 100, 120, 140, 160, 180, 200, 225, 250, 275, 300, 400, 500, 1000, 2000, 5000, or more nucleotides. A polypeptide linking segment can include, for example, about 1, 2, 3, 4, 5, 10, 15, 20, 25, 30, 35, 40, 45, 50, 55, 60, 65, 70, 75, 80, 85, 90, 100, 120, 140, 160, 180, 200, 225, 250, 275, 300, 400, 500, 1000, or more amino acids.

By "multivalent core" is meant a moiety that contains more than two linkage sites that are capable of being linked to a nucleic acid that includes a TBS. The linkage site may be linked covalently (i.e., by a covalent bond) or non-covalently (e.g., by an affinity binding pair) to the nucleic acid that includes a TBS. A multivalent core may have, for example, 3, 4, 5, 6, 7, 8, 9, 10, 15, 20, 25, 30, 35, 40, 45, 50, 100, 200, 500, 1000, or more linkage sites. The term "water soluble multivalent core" specifically excludes solid substrates (e.g., the surface of a well or a bead). Non-limiting examples of multivalent cores include polymers, including branched polymers (e.g., star-shaped polymers, comb polymers, brush polymers, hyperbranched polymers, and dendrimers (e.g., poly(amidoamine) (PAMAM) dendrimers)); nucleic acids (e.g., oligonucleotides or longer nucleic acid molecules); peptides, polypeptides, or proteins (e.g., streptavidin and antibodies or antigen-binding fragments thereof); and micelles. A multivalent core (e.g., a water soluble multivalent core) can have a mass of about 15 fg or less, about 14 fg or less, about 13 fg or less, about 12 fg or less, about 11 fg or less, about 10 fg or less, about 9 fg or less, about 8 fg or less, about 7 fg or less, about 6 fg or less, about 5 fg or less, about 4 fg or less, about 3 fg or less, about 2 fg or less, about 1 fg or less, about $1\times10^{-16}$ g or less, about $1\times10^{-17}$ grams or less, about $1\times10^{-18}$ grams or less, about $1\times10^{-19}$ grams or less, or about $1\times10^{-20}$ grams or less. For example, in some instances, the multivalent core (e.g., a water soluble multivalent core) has a mass of about $1\times10^{-20}$ grams to about 15 fg (e.g., about $1\times10^{-20}$ grams to about 15 fg, about $1\times10^{-20}$ grams to about 10 fg, about $1\times10^{-20}$ grams to about 5 fg, about $1\times10^{-2o}$ grams to about 1 fg, about $1\times10^{-2o}$ grams to about $1\times10^{-16}$ g, about $1\times10^{-2o}$ grams to about $1\times10^{-17}$ g, about $1\times10^{-20}$ grams to about $1\times10^{-18}$ g, or about $1\times10^{-20}$ grams to about $1\times10^{-19}$ g).

The terms "nucleic acid" and "polynucleotide," as used interchangeably herein, refer to at least two linked nucleotide monomers. The term encompasses, for example, deoxyribonucleic acid (DNA), ribonucleic acid (RNA), hybrids thereof, and mixtures thereof. Nucleotides are typically linked in a nucleic acid by phosphodiester bonds, although the term "nucleic acid" also encompasses nucleic acid analogs having other types of linkages or backbones (e.g., phosphoramide, phosphorothioate, phosphorodithioate, O-methylphosphoroamidate, morpholino, locked nucleic acid (LNA), glycerol nucleic acid (GNA), threose nucleic acid (TNA), and peptide nucleic acid (PNA) linkages or backbones, among others). The nucleic acids may be single-stranded, double-stranded, or contain portions of both single-stranded and double-stranded sequence. A nucleic acid can contain any combination of deoxyribonucleotides and ribonucleotides, as well as any combination of bases, including, for example, adenine, thymine, cytosine, guanine, uracil, and modified or non-canonical bases (including, e.g., hypoxanthine, xanthine, 7-methylguanine, 5,6-dihydrouracil, 5-methylcytosine, and 5-hydroxymethylcytosine).

An "artificial nucleic acid" refers to a non-naturally occurring nucleic acid. Such artificial nucleic acids differ in some respect from nucleic acids that occur in nature without human intervention, whether by sequence, chemical composition, and/or functional properties.

The terms "operable linkage" and "operably linked," as used herein, refer to a physical or functional juxtaposition of the components so described as to permit them to function in their intended manner. For example, a targeting moiety may be operably linked with a transposase (e.g., by being fusion partners in a fusion protein or by being otherwise covalently or non-covalently conjugated) in order to promote transposition at a specific sequences in a target nucleic acid (e.g., DNA).

By "synaptic complex" is meant a structure that includes a pair of oligomerized transposases (e.g., dimerized transposases or a tetramer (e.g., dimer of dimers) of transposases) in which each transposase of the pair is bound to a TBS. In nature, a nucleic acid that includes two TBSs may form a synaptic complex by oligomerization of the transposases that bind to each TBS, which results in looping of the nucleic acid. In the context of the present invention, a synaptic complex includes a pair of oligomerized transposases in which each transposase is bound to a TBS present on a different nucleic acid molecule. Accordingly, a synaptic complex constitutes a part of a larger molecular complex as described herein. For example, two synaptic complexes can be tethered by a nucleic acid having a TBS at each terminus to generate a TSC as described below such that, when combined with a target nucleic acid (e.g., DNA), the TSC exhibits transposase activity, cleaving the target nucleic acid, and ligating the tethering nucleic acid (which may include, for example, identifiable sequence tags) to distal sites within the target nucleic acid (e.g., DNA).

A "targeting moiety" refers to any compound (e.g., nucleic acid or polypeptide) that can promote preferential or specific binding to a nucleic acid sequence. For example, a targeting moiety may be a polypeptide that includes a DNA binding domain (DBD), for example, a zinc finger motif or a transcription activator-like (TAL) effector protein; an RNA-guided endonuclease (e.g., Cas9, Cpf1, and C2c2), DNA-guided endonuclease (e.g., Argonaute), or biologically active variants thereof, including nuclease-deficient or nuclease-null variants; or an oligonucleotide (e.g., RNA or DNA) that hybridizes to a nucleic acid sequence.

A "target nucleic acid" refers to any nucleic acid (e.g., DNA) of interest that is selected for modification or analysis (e.g., sequence analysis) using a composition of the invention (e.g., a TSC) as described herein. The present methods can be carried out using target nucleic acids (e.g., DNAs) pooled from more than one source. It is to be understood that the target nucleic acid may be DNA or RNA, for example. In some instances, RNA may be converted to cDNA prior to being treated with a composition of the invention (e.g., a TSC).

A "tethered synaptic complex" (TSC) is a molecular complex that includes a plurality of synaptic complexes that are tethered by a multivalent core (e.g., a water soluble multivalent core). In some embodiments, a subunit of the TSC includes a subsequence that includes an identifiable sequence tag. These tags can be used to identify or differentiate one subunit of a TSC from another or, similarly, to identify or differentiate one TSC from another. Further, in certain embodiments, because the identifiable sequence tag in a subunit of the TSC is incorporated into a first site on the target nucleic acid (e.g., DNA), while an identical or related identifiable sequence tag is incorporated into a second site on the target nucleic acid (the first and second sites being distal from one another), one can conclude, by virtue of the presence of the identical and/or related sequence tags attached to the same TSC, that two sequenced fragments originated from distal sites on the same target nucleic acid molecule. The subsequence can also include a sequence to which a defined oligonucleotide can hybridize in order to serve as, for example, a primer binding site for amplification or sequencing.

"Transferred" or "transposed" nucleic acid is any nucleic acid that is ligated to a target nucleic acid (e.g., DNA) in a transposition event (e.g., in the context of a sequencing method described herein).

A "transposable nucleic acid" is any nucleic acid that can participate in the formation of a functionally active TSC and attach to a target nucleic acid (e.g., DNA) by virtue of including a transposase binding site (TBS) at one or both termini.

The term "transposase" refers to a moiety that binds to a transposase binding site (TBS) and that can catalyze movement of the TBS as well as associated transposable nucleic acid sequence to a different nucleic acid (e.g., DNA) molecule. In nature, transposases bind to TBSs at the ends of a transposon (also known as a transposable element) prior to catalyzing movement the transposon to a different location of the host genome. Transposases typically effect transposition of nucleic acid (e.g., DNA) sequences using a cut and paste mechanism or a replicative transposition mechanism. Transposases typically catalyze nucleic acid transposition as oligomers. For example, Tn5 transposases catalyze transposition as a dimer, with a monomer binding each TBS. Other transposases, such as Mu (also referred to as MuA), catalyze transposition as a tetramer (dimer of dimers), with a dimer binding each TBS. The term "transposase," as used herein, refers to the minimal unit that binds to a TBS, and may include, for example, one transposase protein (e.g., a monomer) or more than one transposase protein (e.g., a dimer). Transposases are members of the RnaseH superfamily of proteins, which is characterized by an active site that includes DDE residues that chelate two $Mg^{++}$ ions, which are critical for catalysis, and the overall architecture and active site DDE are considered to be nearly identical to that of retroviral integrases, RuvC, and RnaseH (see, e.g., Reznikoff, *Mol. Microbiol.* 47(5):1199-1206, 2003). Given that transposases and retroviral integrases share common active site architecture (including the DDE active site) as well as catalytic mechanisms (e.g., transposon-donor backbone DNA nicking and strand transfer), it is expressly contemplated that retroviral integrases (e.g., human immunodeficiency virus (HIV)-1, HIV-2, simian immunodeficiency virus (SIV), and Rous sarcoma virus integrases) and other related integrases (e.g., integrases of retrotransposons, for example, yeast Ty integrases (e.g., Ty1, Ty2, Ty3, Ty4, and Ty5 integrase)) may also be used in the context of the invention as falling within the scope of "transposase."

A "transposase binding site" (TBS) is a nucleic acid (e.g., DNA) sequence that can be selectively bound by a transposase. In particular embodiments, the sequence is a DNA sequence. Under at least a condition specified herein and/or in the context of a sequencing method of the invention, transposase binding sites attached to the target nucleic acid (e.g., DNA) by transposase activity remain selectively bound by transposases within the TSC.

A "transposition event" is a reaction in which a synaptic complex cleaves a target nucleic acid (e.g., DNA) and ligates a transposable nucleic acid (e.g., all or a part of the transposable nucleic acid, which may include an identifiable sequence tag) to a cleaved target nucleic acid. In particular embodiments, the target nucleic acid is DNA.

DETAILED DESCRIPTION

The invention provides nucleic acids, multivalent transposase reagents, multivalent tethered synaptic complexes (TSCs), TSC-modified libraries, and methods of use thereof. Below, specific compositions and methods encompassed by the present invention are described, examples and representative embodiments of which are shown in FIG. 1 to FIG. 19. These examples and embodiments should not be interpreted or construed as representing all possible embodiments or modifications of the claimed methods and compositions.

In one aspect, the compositions of the invention include the TSCs described herein, which we developed to allow multiple, distinct transposition events resulting in the insertion of known nucleic acid (e.g., DNA) cargo molecules (e.g., identifiable sequence tags) into sites within a target nucleic acid (e.g., DNA) that are separated by hundreds, thousands, or even millions of base pairs. In another aspect, the invention features methods of using the compositions described herein (e.g., TSCs) to obtain a library of nucleic acid (e.g., DNA) molecules from an original nucleic acid source. Such libraries can be used to determine the sequence of a template nucleic acid of interest (e.g., a genome). The methods can preserve and make readable information from two or more shorter subsequences on each library molecule originating from two potentially distal regions on the same original nucleic acid (e.g., DNA) molecule.

The compositions (e.g., TSCs) and methods described herein can be used in a wide variety of sequencing applications, particularly those in which incorporation of defined nucleic acid sequences (e.g., identifiable sequence tag(s)) into a target nucleic acid (e.g., DNA) is desired. The inventive approach creates a more accurate and valuable view of full sequence information of long segments of nucleic acids (e.g., DNA) by connecting regions present on the same original DNA molecule. The compositions and methods can be used, for example, to obtain fully phased resolved sequence information and can overcome the length limitation imposed by most NGS instruments. The compositions and methods also improve the ability to assemble longer regions, resolve difficult repeat regions, phase complex heterozygotes, and accurately identify RNA splice isoforms, as detailed further below.

Methods for Manufacturing Multivalent Core Molecules for Tethering Synaptic Complexes The invention provides TSCs that include one or more multivalent cores. Any suitable multivalent core can be used. For example, the template for producing DNA-based multivalent core molecules described in Example 1 was derived from a naturally-occurring DNA. A variety of methods known in the art can be used to derive a core molecule having particular desired or advantageous attributes; such modifications to the TSC core molecule can yield TSCs that are particularly adapted via their length, density of transposase binding sites, and other attributes, for different end uses.

Figure 9:
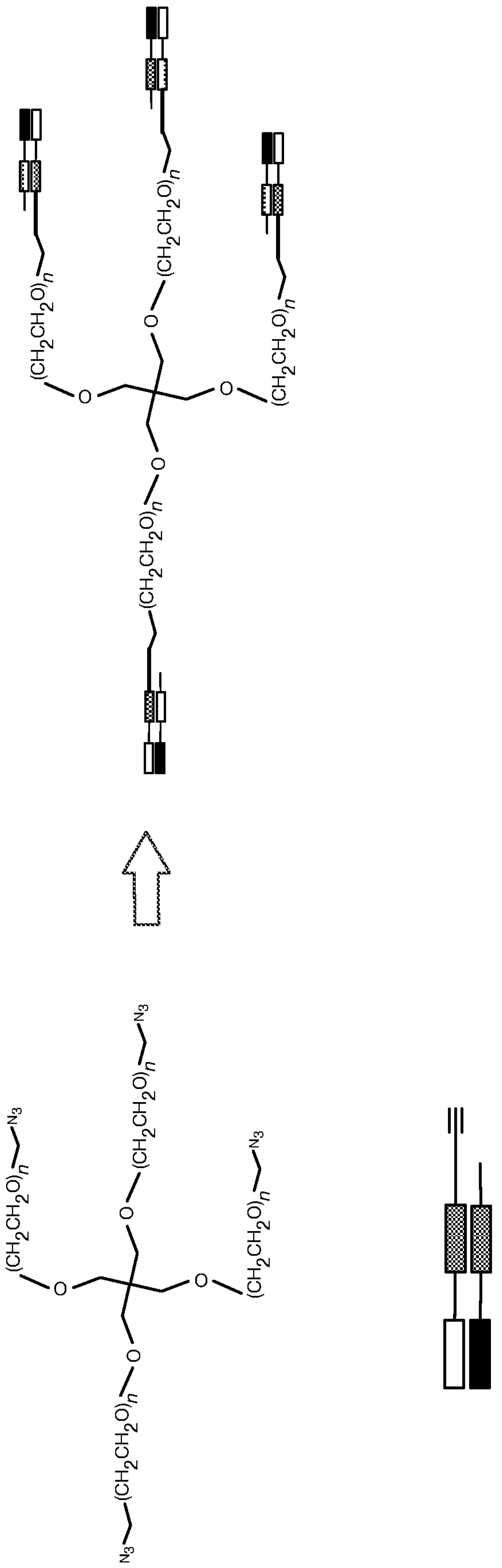
FIG. 9 illustrates a multi-arm PEG used as a TSC scaffold.
Figure 10:
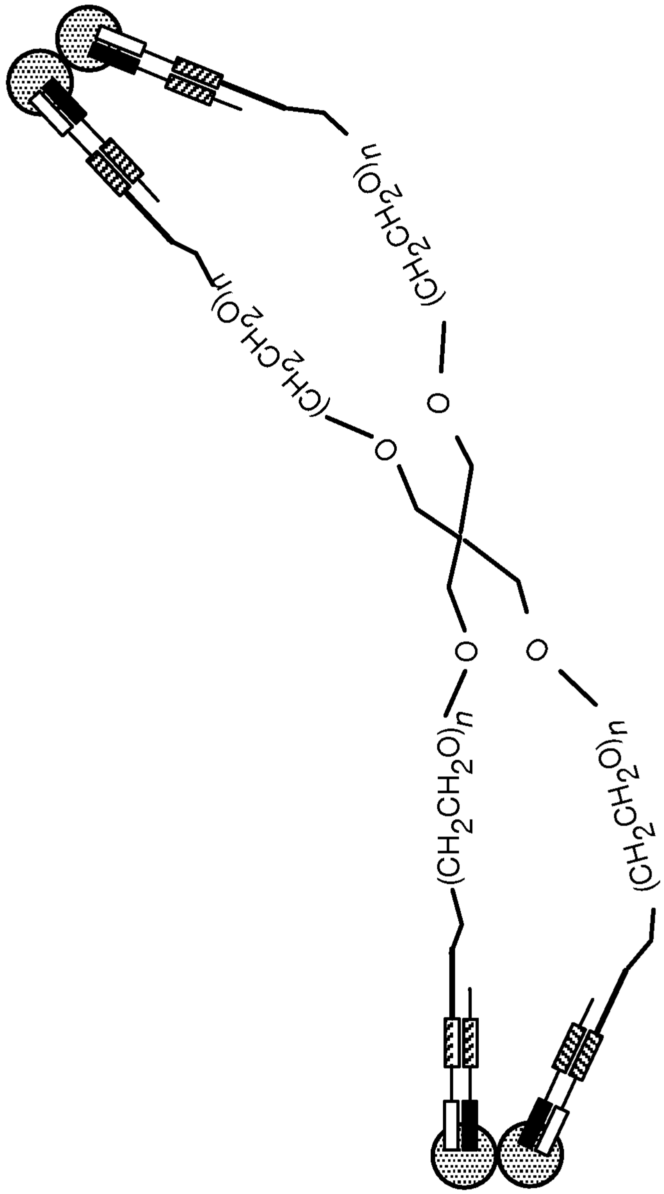
FIG. 10 illustrates the formation of tethered synaptic complexes via addition of transposase to a four-arm scaffolded TBS-containing PEG substrate.
Figure 11:
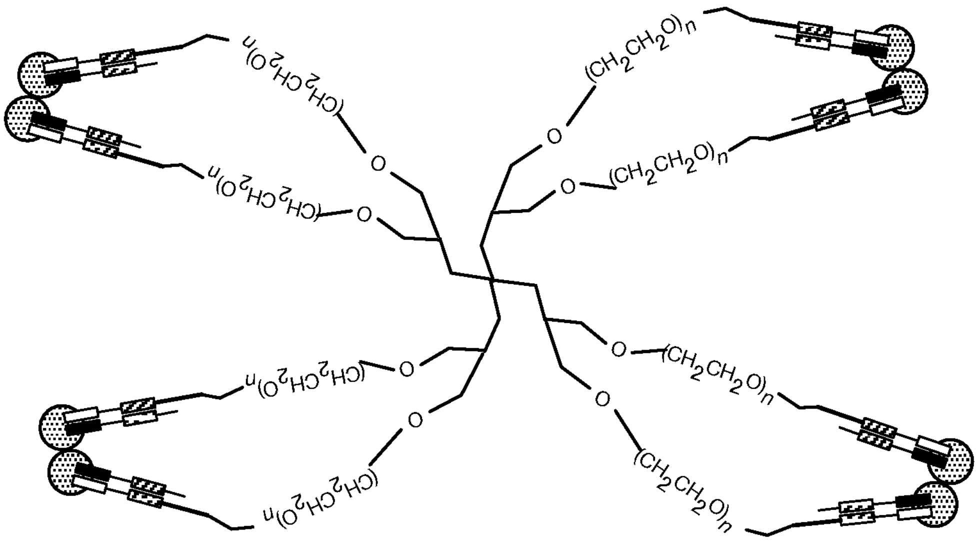
FIG. 11 illustrates the formation of tethered synaptic complexes via addition of transposase to an eight-arm scaffolded TBS-containing PEG substrate.
Figure 12:
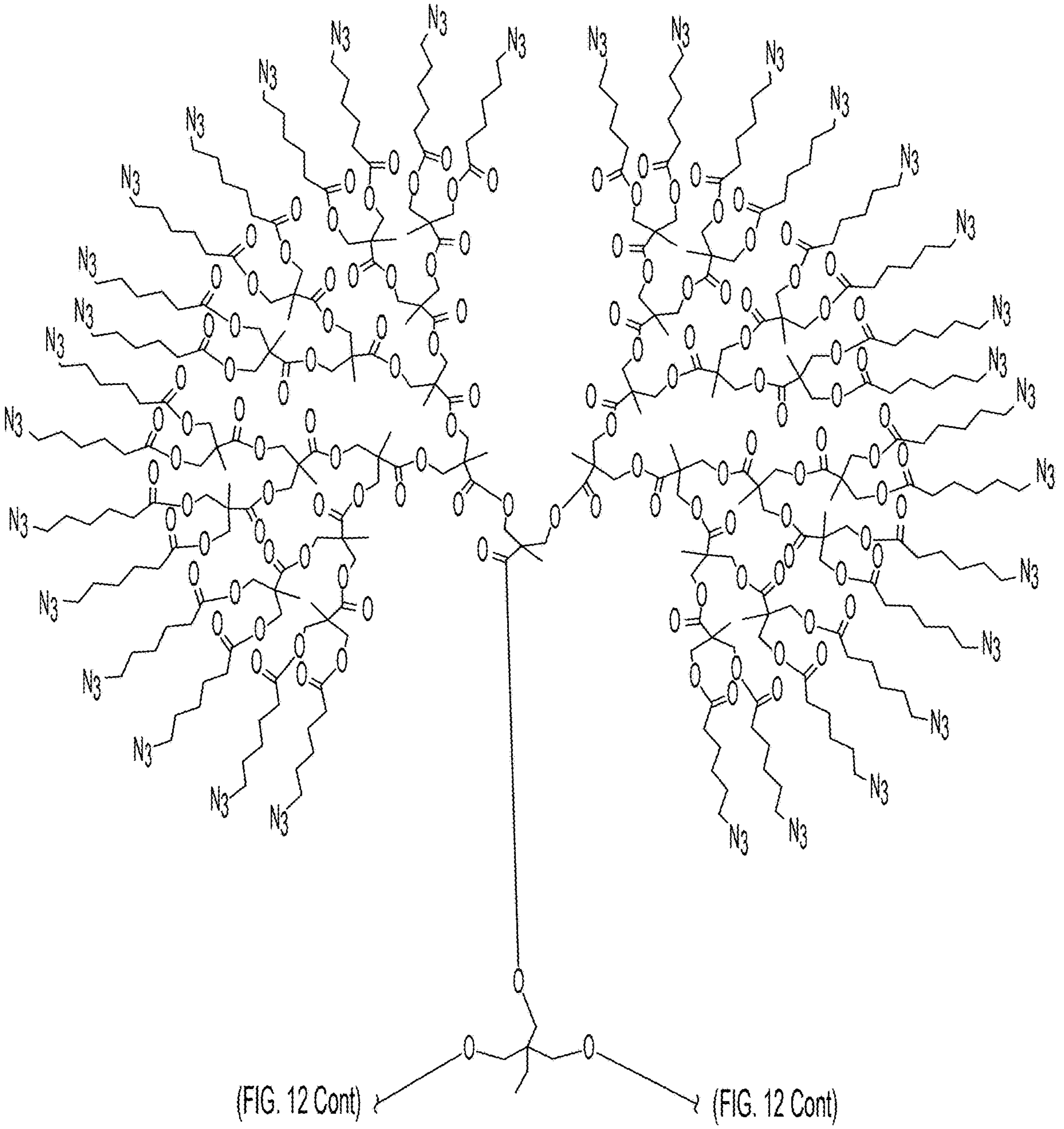
FIG. 12 illustrates the formation of tethered synaptic complexes via addition of transposase to a 96-arm scaffolded TBS-containing PEG substrate.
Figure 12:
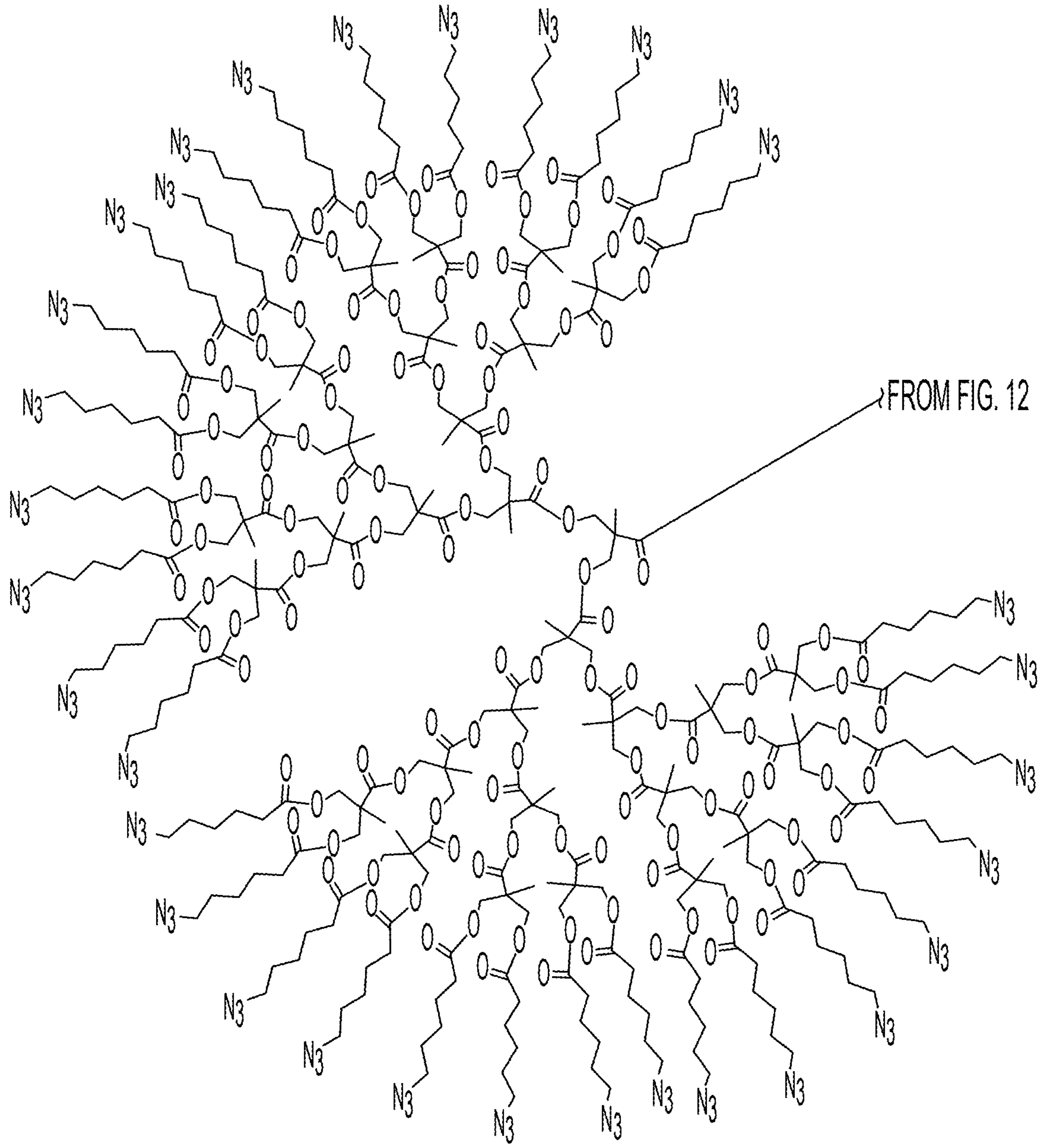
Figure 12:
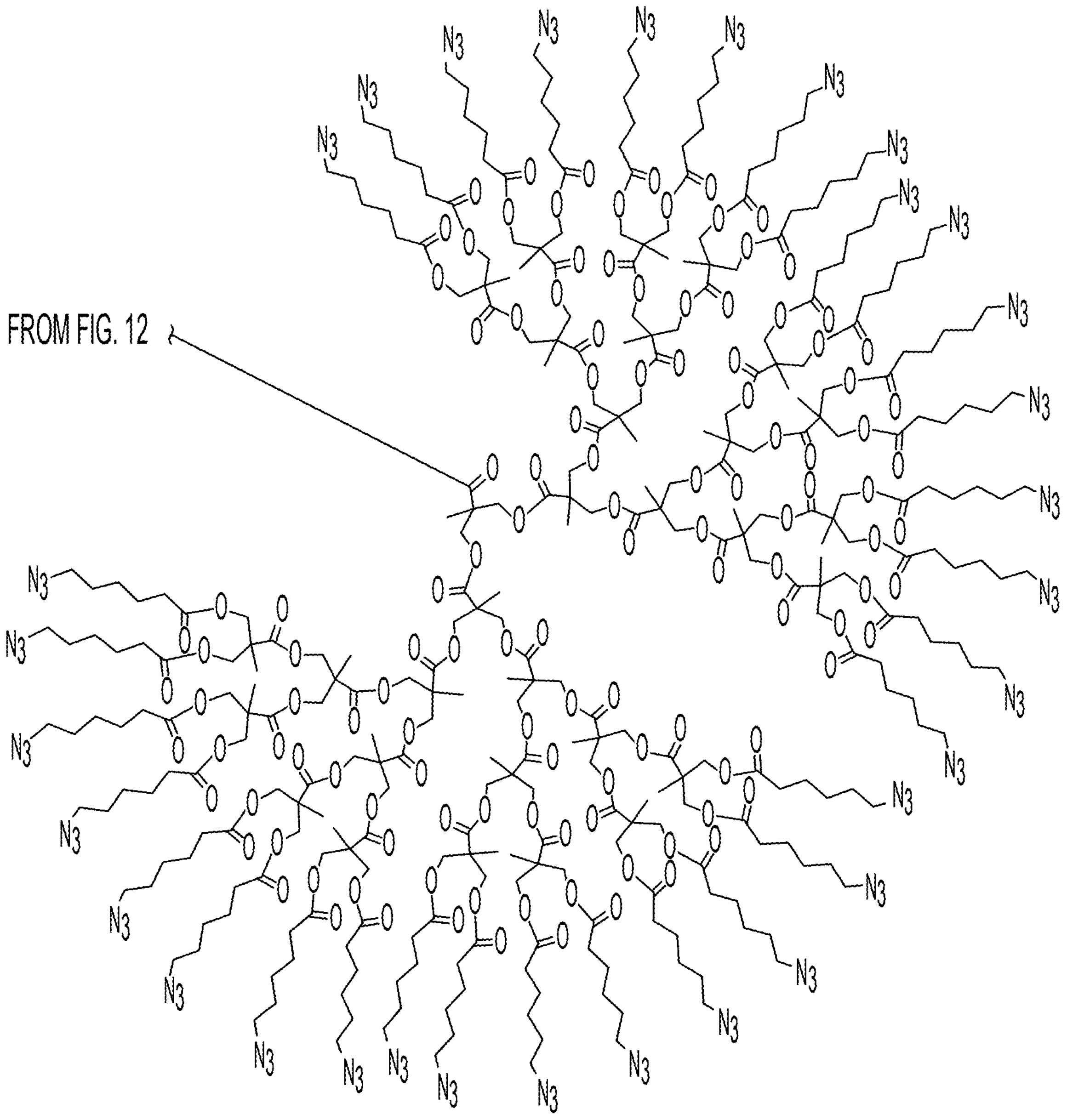

For example, the average spacing between sites for tethering synaptic complexes can be adjusted by modifying the ratio of modified nucleotides to natural nucleotides in a polymerase extension reaction. Another means of modifying the distance between sites for tethering is selecting naturally-occurring template with different G+C content. Alternatively, a non-natural nucleic acid template for producing multivalent core molecules can be manufactured by oligonucleotide synthesis. If a modified nucleotide, or an oligonucleotide containing a modified nucleotide that serves as a site for tethering is incorporated by template-dependent enzymatic activity (e.g., by polymerase, or by ligation), or if by sequence-specific hybridization, the spacing between points for tethering can be precisely controlled by designing a synthetic template molecule that produces a multivalent core with modified nucleotides at any prescribed spacing. The length of the multivalent core molecule can be modified by the length of the template used to produce it. Examples of templates for producing multivalent cores can be DNA, RNA, or any polymer that supports hybridization of nucleic acids in a template-dependent manner, for example, PNA (peptide nucleic acid). An RNA multivalent core can be produced from a natural or synthetic DNA template using a DNA-dependent RNA polymerase and a modified nucleotide such as 5-Azido-PEG4-CTP (5-Azido-PEG4-cytidine-5'-triphosphate), or, by ligating modified RNA after hybridizing to a DNA template. Given the above description of assembly of a RNA-based multivalent core on a DNA template, it would be readily apparent to one skilled in the art that a DNA-based multivalent core could be assembled on an RNA template, or that an RNA-based multivalent core could be assembled on an RNA template, and furthermore, that after hybridization to the template molecule, some embodiments of the template can be used to attach multivalent core components by employing enzymatic amplification, ligation, affinity, or chemical reactions (e.g., azide alkyne Huisgen cycloaddition reaction, also more commonly known as click chemistry). In some embodiments the template can be used once to guide the multivalent core assembly, while in other embodiments, the template can be reused to assemble many multivalent core molecules from a single template. Nucleic acids can be suitably modified for attachment to a multivalent core molecule as described in Example 1 (see FIG. 3 and FIG. 4), wherein oligonucleotides modified with 5'-DBCO (Dibenzocyclooctyl) were attached to the azide groups present on the multivalent core molecule via a click chemistry reaction (SPAAC). Also, for immobilization via click chemistry reaction, DBCO could be provided on the multivalent core molecule, while the azide group could be provided as a modified base on the nucleic acid to be attached. There are various soluble polymeric materials with reactive groups that can serve as multivalent cores for attaching nucleic acids. These soluble polymeric materials include, but are not limited to, azide-containing polyethylene glycols that are commercially available in a variety of molecular weights from Creative PEGworks, such as: Azide-PEG-Azide, 4-arm PEG-Azide (click chemistry attachment of nucleic acid adapters to 4-arm PEG-Azide, and subsequently, formation of two TSCs with Tn5 transposase is shown in FIG. 9 and FIG. 10, respectively), and 8-arm PEG-Azide (formation of four TSCs with Tn5 transposase after click chemistry attachment of nucleic acid adapters is shown in FIG. 11). Also, branched dendrimeric polymers from Polymer Factory carry 6-96 azide end-groups linked to a trimethylol propane core (shown in FIG. 12), and can also react with suitably modified nucleic acids using the click chemistry reaction. These examples should not be interpreted as limiting, almost any method known for stably linking nucleic acids to other molecules could be employed to attach nucleic acids to a multivalent core molecule, which ultimately could be used to form TSCs using the compositions and methods described herein.

Figure 13:
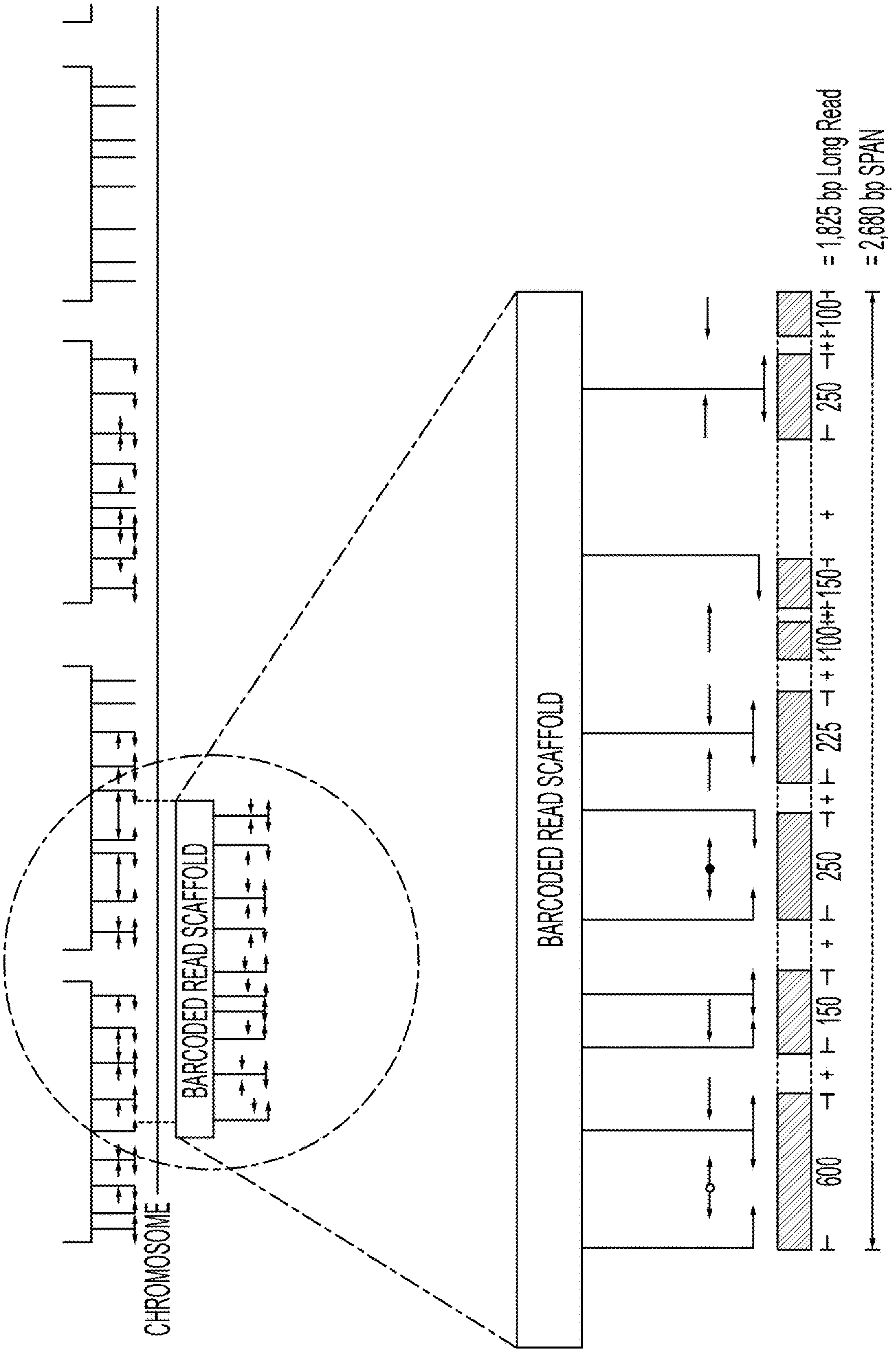
FIG. 13 illustrates the generation of linked read sets derived by the scaffolded transposition of multiple sites of a target DNA by multiple SCs on a single TSC scaffold. The library preparation reagent described in Example 1 contained 480 distinct types of multivalent TSCs in a single tube, and each individual TSC carried hundreds of identical barcoded adapters. The library preparation reagent inserted sequences containing the same barcode into discrete regions of individual target DNA molecules. The library preparation reagent inserted many barcoded sequences from a single TSC into a single target DNA molecule (multiple proximal cis transposition events). The shaded portions indicate areas with phased sequencing coverage from the same TSC after mapping of dual index reads (where the arrows indicate directionality of the sequencing reads), whereas, the unshaded portions indicate areas without phased sequencing coverage from the same TSC.

FIG. 13 illustrates how linked barcoded reads originating from a single target DNA molecule can be assembled into long reads.

Figure 14:
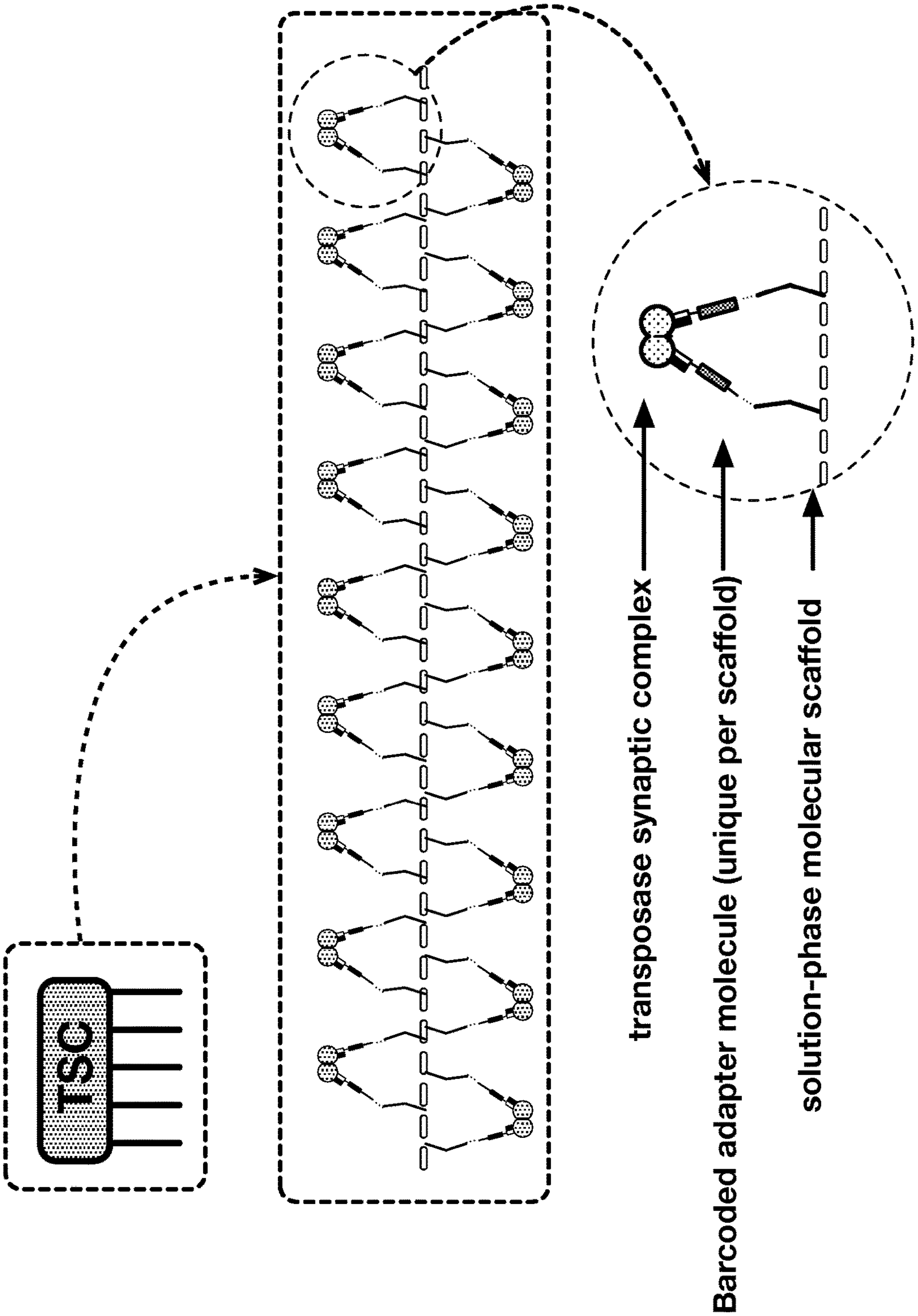
FIG. 14 illustrates the molecular structure of a tethered synaptic complex polymer. Barcoded oligonucleotide adapter molecules are covalently attached to a synthetic scaffold, and transposase proteins are then loaded onto this synthetic structure to create multiple co-bound synaptic complexes.
Figure 15:
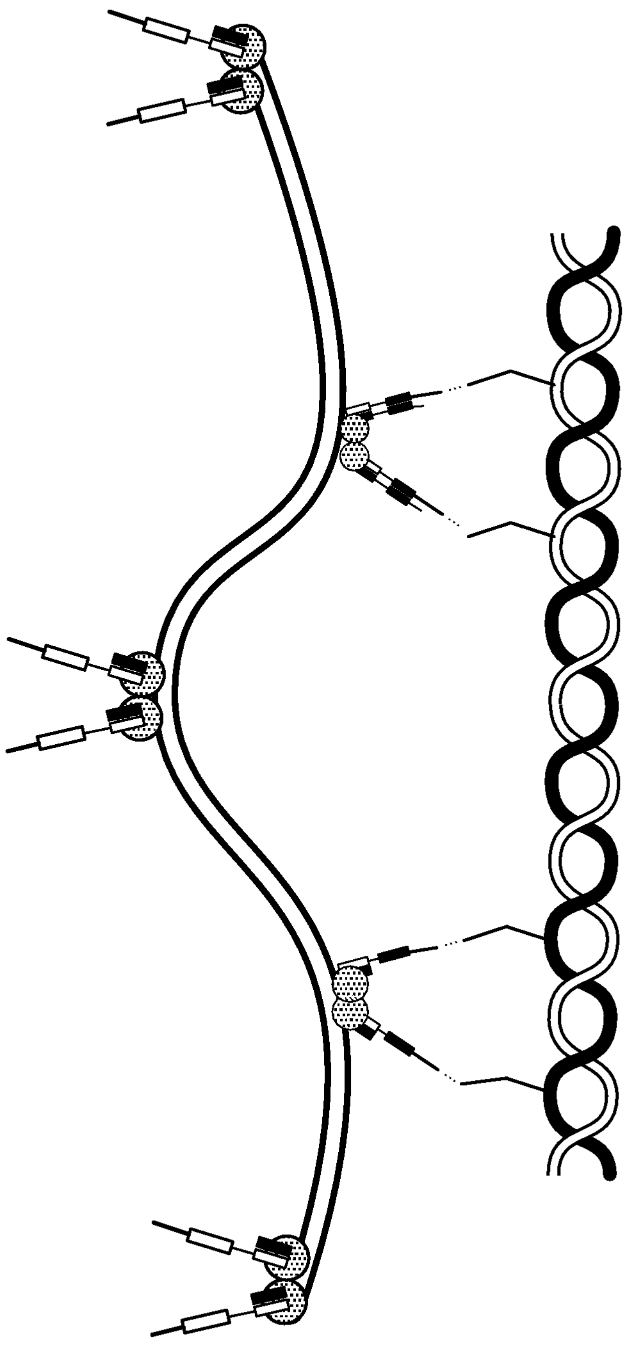
FIG. 15 illustrates a method for generating library molecules (e.g., for sequencing) from a TSC. A DNA molecule is tagged with P7-containing adapters at multiple tandem sites by two or more synaptic complexes that are attached to a scaffold backbone. Next, a solution-phase transposome is used to generate amplifiable library fragments by transposing P5-containing adapters at sites flanking the sites of P7 adapter addition.

FIG. 14 illustrates an exemplary tethered synaptic complex polymer in which the barcoded adapter molecule is unique per scaffold.

Figure 17:
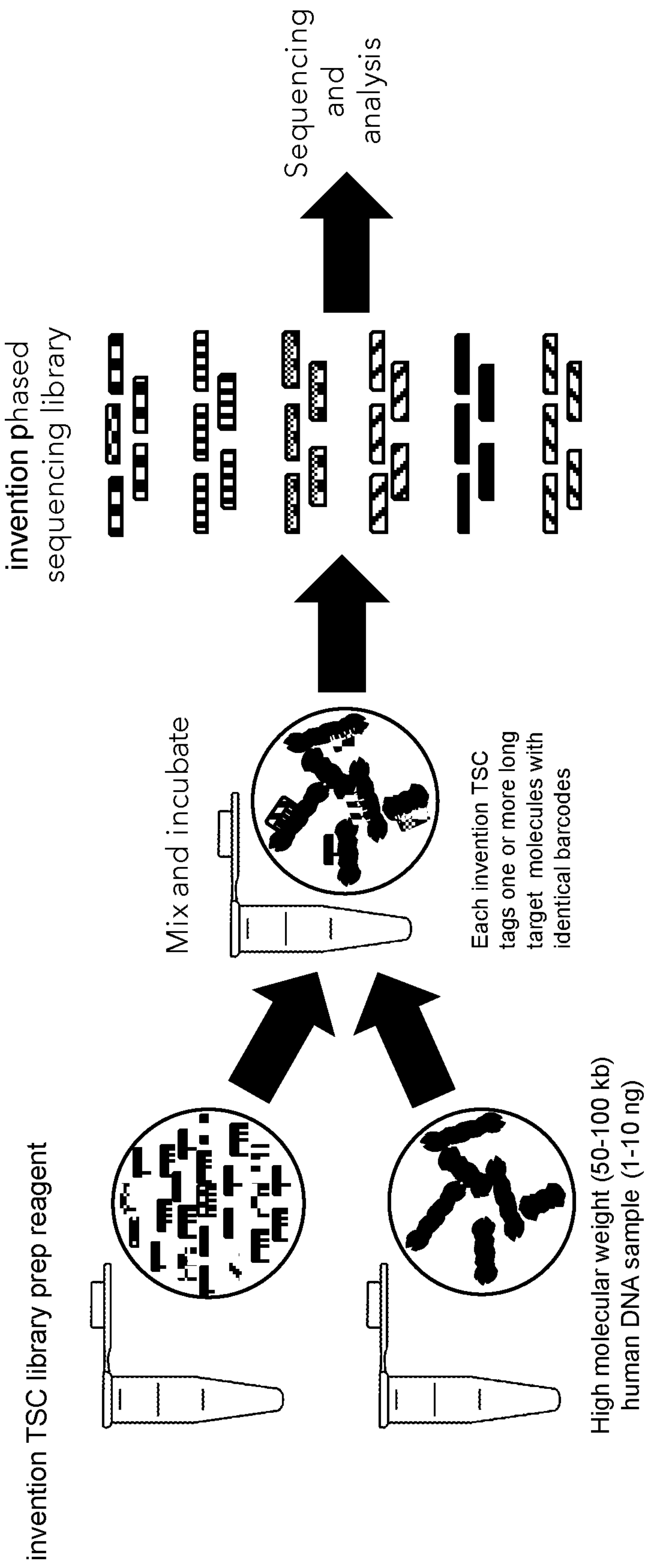
FIG. 17 illustrates a schematic view of the workflow of using a mixture of barcoded TSCs to treat a sample of human genomic DNA. The TSC mixture allows individual DNA molecules in a complex mixture to be statistically partitioned onto TSC complexes having any one of a large number of barcodes. The barcode information is then used to assign the obtained sequencing reads to an original long DNA molecule of interest.

FIG. 17 illustrates an exemplary workflow for preparing and sequencing a target DNA using TSCs.

Compositions of the Invention

The invention provides compositions that include artificial nucleic acids, as well as multivalent transposase reagents and TSCs that contain them. In general, the artificial nucleic acids of the invention include one or more TBSs. The invention further provides compositions (e.g., TSCs) that include one or more multivalent cores (e.g., water soluble multivalent cores), which may be linked to one or more of the artificial nucleic acids described herein. The compositions can further include one or more transposases bound to the TBSs of the composition. The transposases can oligomerize to form synaptic complexes. In some embodiments, the artificial nucleic acids include a TBS at each terminus separated by one or more intervening linker segments. In some embodiments, such artificial nucleic acids can be linked to a multivalent core (e.g., a water soluble multivalent core), for example, by linking the linking segment to the multivalent core. Multivalent transposase reagents of the invention include artificial nucleic acids that are linked to multivalent cores (e.g., water soluble multivalent cores). These multivalent transposase reagents can be subunits of TSCs.

The invention provides multivalent transposase reagents and TSCs that include a multivalent core (e.g., a water soluble multivalent core) and three or more artificial nucleic acids (e.g., 3, 4, 5, 6, 7, 8, 9, about 10, about 20, about 25, about 30, about 40, about 50, about 60, about 70, about 80, about 90, about 100, about 125, about 150, about 175, about 200, about 225, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 3000, about 4000, about 5000, or more artificial nucleic acids) linked to the multivalent core (e.g., water soluble multivalent core), in which the artificial nucleic acids each include a first end including a TBS.

For example, the invention provides multivalent transposase reagents and TSCs that include a multivalent core (e.g., a water soluble multivalent core); a first artificial nucleic acid that includes a first end that includes a TBS; a second artificial nucleic acid that includes a first end that includes a TBS; and a third artificial nucleic acid that includes a first end that includes a TBS, in which the first, second, and third artificial nucleic acids are linked to the soluble multivalent core.

The artificial nucleic acids can be covalently linked to the multivalent core (e.g., water soluble multivalent core). In some instances, the artificial nucleic acids are linked to the soluble multivalent core by a covalent bond resulting from a conjugation reaction (e.g., an azide-alkyne Huisgen cycloaddition (e.g., a copper(I)-catalyzed azide-alkyne cycloaddition (CuAAC) or a strain-promoted azide-alkyne cycloaddition (SPAAC)), amide or thioamide bond formation, a pericyclic reaction, a Diels-Alder reaction, sulfonamide bond formation, alcohol or phenol alkylation, a condensation reaction, disulfide bond formation, and a nucleophilic substitution).

In other instances, the artificial nucleic acids can be non-covalently linked to the multivalent core (e.g., the water soluble multivalent core), for example, by affinity binding pairs (e.g., biotin-streptavidin, biotin-avidin, ligand-receptor, antigen-antibody or antigen binding fragment, or Ig binding protein-Ig). In some instances, the affinity binding pair comprises a first affinity component that binds a second affinity component, where the first affinity component is linked to the soluble multivalent core, and the second affinity component is linked to the artificial nucleic acid.

In some instances, a first population of artificial nucleic acids each containing TBSs can be covalently linked to the multivalent core (e.g., water soluble multivalent core), and a second population of artificial nucleic acids each containing TBSs can be non-covalently linked to the multivalent core.

The multivalent transposase reagents and TSCs can include transposases bound to the TBSs of the artificial nucleic acids (e.g., 3, 4, 5, 6, 7, 8, 9, about 10, about 20, about 25, about 30, about 40, about 50, about 60, about 70, about 80, about 90, about 100, about 125, about 150, about 175, about 200, about 225, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 3000, about 4000, about 5000, or more transposases). The transposases can oligomerize to form synaptic complexes.

In some instances, the multivalent transposase reagents and TSCs can include 3 or more synaptic complexes (e.g., 3, 4, 5, 6, 7, 8, 9, about 10, about 20, about 25, about 30, about 40, about 50, about 60, about 70, about 80, about 90, about 100, about 125, about 150, about 175, about 200, about 225, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2500, or more synaptic complexes). For example, in some instances, the reagent includes between 3 and 12 synaptic complexes, between 3 and 25 synaptic complexes, between 3 and 50 synaptic complexes, between 3 and 75 synaptic complexes, between 3 and 100 synaptic complexes, between 3 and 125 synaptic complexes, between 3 and 150 synaptic complexes, between 3 and 175 synaptic complexes, between 3 and 200 synaptic complexes, or between 3 and 250 synaptic complexes.

For example, the invention provides multivalent transposase reagents and TSCs that include a multivalent core (e.g., a water soluble multivalent core) and three or more synaptic complexes being linked to the multivalent core, where each of the synaptic complexes includes a first transposase and a second transposase, and where the first transposase is bound to a first artificial nucleic acid including a TBS and the second transposase is bound to a second artificial nucleic acid including a TBS, and wherein the first transposase and the second transposase are oligomerized. In some instances, the first artificial nucleic acid and the second artificial nucleic acid of each synaptic complex is linked to the soluble multivalent core. In other instances, the first or second artificial nucleic acid of at least one synaptic complex is not linked to the soluble multivalent core.

Any suitable water soluble multivalent core can be used in the context of the invention. For example, the water soluble multivalent core can be a nucleic acid (e.g., DNA, RNA, PNA, and combinations thereof), a polymer (e.g., a branched polymer, such as a star-shaped polymer, a comb polymer, a brush polymer, a hyperbranched polymer, or a dendrimer), a peptide, a polypeptide, a protein, or a micelle. The nucleic acid can be single-stranded, double-stranded, or combinations thereof. In some instances, the nucleic acid includes between about 10 and about 10,000 bp (e.g., about 10 bp, about 20 bp, about 30 bp, about 40 bp, about 50 bp, about 60 bp, about 70 bp, about 80 bp, about 90 bp, about 100 bp, about 200 bp, about 300 bp, about 400 bp, about 500 bp, about 600 bp, about 700 bp, about 800 bp, about 900 bp, about 1000 bp, about 1250 bp, about 1500 bp, about 1750 bp, about 2000 bp, about 3000 bp, about 4000 bp, about 5000 bp, about 6000 bp, about 7000 bp, about 8000 bp, about 9000 bp, about 10,000 bp, or more). The polymer can be a polyethylene glycol (PEG)-based polymer, such as a PEG dendrimer or a multi-arm PEG (e.g., a 3-arm PEG, a 4-arm PEG, a 6-arm PEG, or an 8-arm PEG). The protein can be a multimeric protein (e.g., avidin or streptavidin).

In any of the multivalent reagents and TSCs described herein, a plurality of the artificial nucleic acids can include an IST (e.g., a random, semi-random, or non-random 1ST). Each IST can be identical or non-identical.

The invention provides artificial nucleic acids that include a first end that includes a TBS and a second end that includes a conjugating moiety or a component of an affinity binding pair. Such artificial nucleic acids can be linked to a multivalent core (e.g., a water soluble multivalent core).

The artificial nucleic acids may further include one or more additional elements. For example, the linking segment may include an identifiable sequence tag (1ST), a primer binding site, or a cleavage site. The IST may be, for example, a random 1ST, a semi-random 1ST, or a non-random 1ST. Approaches for generating ISTs, such as barcodes, are known in the art. The cleavage site may be, for example, a restriction endonuclease recognition site or a nickase site. The linking segment may be any suitable length, for example about 20 bp to about 1000 bp or more in length, which may vary depending on the nature of the transposases intended for use with the artificial nucleic acid, as described herein. For example, the artificial nucleic acids may be about 20, about 25, about 30, about 35, about 40, about 45, about 50, about 55, about 60, about 65, about 70, about 75, about 80, about 85, about 90, about 100, about 120, about 140, about 160, about 180, about 200, about 225, about 250, about 275, about 300, about 400, about 500, about 1000, about 2000, about 5000, or about 10,000 bp in length.

In some instances, the artificial nucleic acids can have a length in the range of between about 20 and about 5,000 bp, about 20 and about 2,000 bp, about 20 and about 1,000 bp, about 20 and about 900 bp, about 20 and about 800 bp, about 20 and about 700 bp, about 20 and about 700 bp, about 20 and about 600 bp, about 20 and about 500 bp, about 20 and about 400 bp, about 20 and about 300 bp, about 20 and about 200 bp, about 20 and 100 bp, about 20 and about 65 bp, about 50 and about 5,000 bp, about 50 and about 2,000 bp, about 50 and about 1,000 bp, about 50 and about 900 bp, about 50 and about 800 bp, about 50 and about 700 bp, about 50 and about 700 bp, about 50 and about 600 bp, about 50 and about 500 bp, about 50 and about 400 bp, about 50 and about 300 bp, about 50 and about 200 bp, about 50 and about 100 bp, about 50 and about 65 bp, about 100 and about 5,000 bp, about 100 and about 2,000 bp, about 100 and about 1,000 bp, about 100 and about 900 bp, about 100 and about 800 bp, about 100 and about 700 bp, about 100 and about 700 bp, about 100 and about 600 bp, about 100 and about 500 bp, about 100 and about 400 bp, about 100 and about 300 bp, about 100 and about 200 bp, about 200 and about 5,000 bp, about 200 and about 2,000 bp, about 200 and about 1,000 bp, about 200 and about 900 bp, about 200 and about 800 bp, about 200 and about 700 bp, about 200 and about 700 bp, about 200 and about 600 bp, about 200 and about 500 bp, about 200 and about 400 bp, about 200 and about 300 bp, about 500 and about 5,000 bp, about 500 and about 2,000 bp, about 500 and about 1,000 bp, about 500 and about 900 bp, about 500 and about 800 bp, about 500 and about 700 bp, about 500 and about 700 bp, or about 500 and about 600 bp.

In any of the preceding artificial nucleic acids, a TBS may be at least partially single-stranded or double-stranded. A transposase protein typically binds to a double-stranded TBS.

A TSC may include, for example, between 2 and 1000 or more synaptic complexes. For example, a TSC may include 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 90, 100, 200, 300, 400, 500, 600, 700, 800, 900, 1000, or more synaptic complexes.

In some instances, one or more, or all, of the artificial nucleic acids in a TSC includes an 1ST. The ISTs present in a TSC may be identical. In other instances, the TSC may include a plurality of different ISTs. For example, a TSC may include at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 90, 100, 200, 300, 400, 500, 600, 700, 800, 900, 1000, or more different ISTs.

Any of the transposases described herein may be used in the compositions of the invention, including those described further below. For example, the transposase may be Tn3, Tn5, Tn9, Tn10, gamma-delta, Mu, piggyBac, Minos, Tc1, or Sleeping Beauty transposase or a biologically active variant thereof. The biologically active variant may be a hyperactive variant. Other transposases are known in the art and may also be used in the invention. Likewise, any of the TBSs described herein may be used in the compositions of the invention. In some instances, a transposase may be operably linked to a targeting moiety. The targeting moiety may be any targeting moiety described herein or known in the art. For example, the targeting moiety may be a polypeptide comprising a DNA binding domain (DBD) or an RNA-guided endonuclease. The DBD may be a zinc finger domain or a transcription activator-like (TAL) effector. The RNA-guided effector may be Cas9, Cpf1, C2c2, or a biologically active variant thereof (e.g., a nuclease-deficient variant). The transposases in the composition can be of the same type (e.g., each transposase in the composition can be a Tn5 transposase), or the compositions can include more than one type of transposase (e.g., one or more Tn5 transposases and one or more Mu transposases).

Transposases and Transposase Binding Sites

The compositions of the invention may include transposase(s) and transposase binding sites (TBSs) from any suitable transposition system known in the art. The transposition system may be from a virus (e.g., a phage or a retrovirus), a prokaryote (e.g., a bacterium), or a eukaryote (e.g., a fungus (e.g., yeast) or a mammal). Exemplary transposases that may be used include, but are not limited to, transposases from the transposon systems Tn1, Tn2, Tn3, Tn5, Tn7, Tn9, Tn10, Tn903, Tn1000/Gamma-delta, Minos, Sleeping beauty, piggyBac, Tol2, Mos1, Himar1, Hermes, Tol2, Minos, P-element, Tc1/mariner, Tc3, or biologically active variants thereof. In some instances, the biologically active variant of a transposase, which may be naturally occurring or engineered, may include one or more modifications relative to a reference transposase (e.g., one or more (e.g., 1, 2, 3, 4, 5, 6, 7, 8, 9, 10, 11, 12, 13, 14, 15, 20, or more) amino acid substitutions, insertions, and/or deletions), which may affect the activity (e.g., transposition activity), binding (e.g., binding specificity or affinity), or other properties of the transposase. In particular embodiments, the biologically active variant may be a hyperactive variant, which may have increased transposition activity in vitro or in vivo.

Any suitable TBS may be used in the compositions of the invention. The TBS may be a TBS from the transposition systems Tn1, Tn2, Tn3, Tn5, Tn7, Tn9, Tn10, Tn903, Tn1000/Gamma-delta, Minos, Sleeping beauty, piggyBac, Tol2, Mos1, Himar1, Hermes, Tol2, Minos, P-element, Tc1/mariner, Tc3, or biologically active variants thereof. A TBS may be a naturally occurring TBS or a biologically active variant thereof. A biologically active variant may be naturally occurring or engineered, and may include insertions, deletions, and/or substitutions relative to a reference TBS. The biologically active variant TBS may affect the activity (e.g., transposition activity), binding (e.g., binding specificity or affinity), or other properties of the transposase(s) that bind to the TBS. The TBS may also include all or a minimal subset of a naturally occurring TBS. For example, the Tn7 transposon has 4 overlapping TnsB transposase binding sites on the right terminus and 3 widely spaced TnsB binding sites on the left terminus, but transposition can occur with a minimal subset of two TnsB binding sites on the right terminus (Parks et al., *Plasmid* 61(1):1-14, 2009). In some instances, the TBS may be or include a sequence that does not exist in nature (see, e.g., Goldhaber-Gordon et al., *J. Biol. Chem.* 277(10): 7703-7712, 2002), but still permits transposition by a transposase.

Many naturally occurring TBSs include inverted repeat nucleotide sequences at the termini of the transposable DNA fragment. These terminal inverted repeats are found in certain transposition systems, including those derived from Tn1, Tn2, Tn3, Tn5, Tn9, Tn10, and Tn903. In some instances, a TBS used in the invention may include terminal inverted repeats. In other instances, the TBS may lack inverted repeats, such as TBSs derived from the bacteriophage transposon Mu or the bacterial transposon Tn7.

Exemplary transposases and TBSs that may be used in the context of the invention are described further below.

Tn5

Tn5 is a well-studied transposition system derived from *E. coli* which can be used in the context of the invention (see, e.g., Reznikoff, *Mol. Microbiol.* 47(5):1199-206, 2003). NCBI Accession No. U00004 provides the nucleic acid sequence of the *E. coli* Tn5 transposon. Tn5 encodes the transposase TnpA (UniProt Accession No. Q46731), which is also referred to herein as Tn5 transposase. The amino acid sequence of wild-type Tn5 transposase is shown below:

(SEQ ID NO: 494)

```
MITSALHRAADWAKSVFSSAALGDPRRTARLVNVAAQLAKYSGKSITISS

EGSEAMQEGAYRFIRNPNVSAEAIRKAGAMQTVKLAQEFPELLAIEDTTS

LSYRHQVAEELGKLGSIQDKSRGWWVHSVLLLEATTFRTVGLLHQEWWMR

PDDPADADEKESGKWLAAAATSRLRMGSMMSNVIAVCDREADIHAYLQDK

LAHNERFVVRSKHPRKDVESGLYLYDHLKNQPELGGYQISIPQKGVVDKR

GKRKNRPARKASLSLRSGRITLKQGNITLNAVLAEEINPPKGETPLKWLL

LTSEPVESLAQALRVIDIYTHRWRIEEFHKAWKTGAGAERQRMEEPDNLE

RMVSILSFVAVRLLQLRESFTLPQALRAQGLLKEAEHVESQSAETVLTPD

ECQLLGYLDKGKRKRKEKAGSLQWAYMAIARLGGFMDSKRTGIASWGALW

EGWEALQSKLDGFLAAKDLMAQGIKI
```

Biologically active variants of Tn5 transposase, including variants with amino acid substitutions, insertions, and/or deletions, may be used in the compositions of the invention. Biologically active Tn5 transposase variants with amino acid substitutions are known in the art. In some instances, a biologically active variant has an enhanced transposition rate relative to wild-type Tn5, and is thus considered hyperactive (see, e.g., U.S. Pat. Nos. 5,965,443; 5,925,545; and 6,159,736). For example, substitution of a lysine residue at amino acid 54 in place of the glutamic acid found in wild-type Tn5 transposase (E54K) has been shown to improve the avidity of the modified transposase for OE termini and to increase the transposition rate approximately 10-fold. Other mutations that have been associated with Tn5 transposase hyperactivity include a substitution of amino acid 372 (leucine) with proline (L372P) and a substitution of amino acid 56 (methionine) with alanine (M56A). The substitution mutations may be relative to the exemplary wild-type sequence of Tn5 transposase shown in SEQ ID NO: 494. A biologically active variant may include any combination of the preceding substitution mutations. For example, in some instances, the Tn5 transposase includes the substitution mutations E54K, M56A, and L372P. In other instances, the Tn5 transposase includes the substitution mutations E54K and L372P. Hyperactive Tn5 tranposase proteins are commercially available, for example, Ez-Tn5™ transposase and Ez-Tn5™ Custom Transposome Construction Kits (Epicentre).

It is generally understood that to carry out transposition, Tn5 transposases bind a pair of inverted repeat nucleotide sequences that flank each side of the transposable DNA element. The inverted repeat sequences of the Tn5 transposase binding sites are referred to as the outside end (OE) (CTGACTCTTATACACAAGT (SEQ ID NO: 495)) and inside end (IE) (CTGTCTCTTGATCAGATCT (SEQ ID NO: 496)) (see, e.g., U.S. Pat. No. 5,965,443). Biologically active variants of a Tn5 TBS may be used, including end sequence variants that are associated with higher rates of transposition, for example, the hyperactive hybrid of the outside and inside ends (also referred to as "mosaic end" (ME)) CTGTCTCTTATACACATCT (SEQ ID NO: 497), which differs from the wild-type OE sequence at positions 4, 17, and 18, as well as CTGTCTCTTATACAGATCT (SEQ ID NO: 498), which differs from the wild-type OE sequence at positions 4, 15, 17, and 18 (see, e.g., U.S. Pat. No. 5,925,545). In some instances, a nucleic acid of the invention may include one or more Tn5 TBSs having a nucleic acid sequence selected from SEQ ID NOs:495-498 and/or a biologically active variant thereof.

Although the Tn5 inverted repeat sequences are often referred to as terminal repeat sequences, they need not be at the terminal ends of the donor DNA and need only to flank each side of the donor DNA to enable transposition (see, e.g., Johnson, et al., *Nature* 304:280, 1983 and U.S. Pat. No. 5,965,443). In some instances, the TBSs used in a nucleic acid of the invention may be any combination of two inverted sequences recognized by the Tn5 transposase, including the OE sequence, IE sequence and/or any other sequence variant (e.g., the ME sequence).

Mu

Another exemplary transposition system that can be harnessed by the present invention is from the Mu bacteriophage (see, e.g., Harshey, *Microbiol. Spectr.* 2(5), 2014). The complete nucleic acid sequence of the Mu genome is provided in NCBI Accession No. AF083977.1. Mu encodes the transposase MuA (UniProt Accession No. P07636), which is also referred to herein as Mu transposase. The amino acid sequence of wild-type Mu transposase is shown below:

(SEQ ID NO: 499)

```
MELWVSPKECANLPGLPKTSAGVIYVAKKQGWQNRTRAGVKGGKAIEYNA
NSLPVEAKAALLLRQGEIETSLGYFEIARPTLEAHDYDREALWSKWDNAS
DSQRRLAEKWLPAVQAADEMLNQGISTKTAFATVAGHYQVSASTLRDKYY
QVQKFAKPDWAAALVDGRGASRRNVHKSEFDEDAWQFLIADYLRPEKPAF
RKCYERLELAAREHGWSIPSRATAFRRIQQLDEAMVVACREGEHALMHLI
PAQQRTVEHLDAMQWINGDGYLHNVFVRWFNGDVIRPKTWFWQDVKTRKI
LGWRCDVSENIDSIRLSFMDVVTRYGIPEDFHITIDNTRGAANKWLTGGA
PNRYRFKVKEDDPKGLFLLMGAKMHWTSVVAGKGWGQAKPVERAFGVGGL
EEYVDKHPALAGAYTGPNPQAKPDNYGDRAVDAELFLKTLAEGVAMFNAR
TGRETEMCGGKLSFDDVFEREYARTIVRKPTEEQKRMLLLPAEAVNVSRK
GEFTLKVGGSLKGAKNVYYNMALMNAGVKKVVVRFDPQQLHSTVYCYTLD
GRFICEAECLAPVAFNDAAAGREYRRRQKQLKSATKAAIKAQKQMDALEV
AELLPQIAEPAAPESRIVGIFRPSGNTERVKNQERDDEYETERDEYLNHS
LDILEQNRRKKAI.
```

Biologically active variants of Mu transposase, including variants with deletions, insertions, or amino acid substitutions, are known in the art and can be used in the invention. For example, truncated Mu transposase variants, such as the truncation mutant Mu(77-663), which contains amino acids 77-663 of wild-type Mu transposase, has been described as a hyperactive variant (see Goldhaber-Gordon et al., *J. Biol. Chem.* 277(10):7694-702, 2002). Hyperactive Mu variants with amino acid substitution mutations are also known in the art (see, e.g., U.S. Pat. No. 9,234,190). For example, a hyperactive Mu transposase variant may include one or more (e.g., 1, 2, 3, 4, 5, 6, 7, 8, 9, 10, 11, 12, 13, 14, 15, 16, 17, 18, 19, 20, 21, 22, 23, 24, 25, 26, or 26) amino acid substitution mutations selected from the group consisting of A59V, D97G, W160R, E179V, E233K, E233V, Q254R, E258G, G302D, I335T, G340S, W345C, W345R, M374V, F447S, F464Y, R478H, R478C, E482K, E483G, E483V, M4871, V495A, V507A, Q539H, Q539R, and I617T. The mutations may be relative to the exemplary wild-type sequence of Mu transposase shown in SEQ ID NO: 499. For example, the substitution mutation may be E223V. In other instances, the Mu variant may include the substitution mutations W160R, E233K, and W345R.

Each end of the Mu transposon includes three Mu binding sites: L1, L2, and L3 on the left end and R1, R2, and R3 on the right end. The nucleic acids of these Mu TBSs are as follows: L1 (TGTATTGATTCACTGAAGTACGAAAA (SEQ ID NO: 500)), L2 (CCTTAATCAATGAAACGCGAAAG, SEQ ID NO: 501), L3 (TTGTTTCATTGAAAATACGAAAA, SEQ ID NO: 502), R1 (TGAAGCGGCGCACGAAAAATGCGAAAA, SEQ ID NO: 503), R2 (GCGTTTCACGATAAATGCGAAAA, SEQ ID NO: 504), and R3 (CCGTTTCATTTGAAGCGCGAAAA, SEQ ID NO: 505). The Mu binding sites have a 22-nucleotide consensus sequence, YGTTTCAYNNRAARYRCGAAAR (SEQ ID NO: 506), wherein Y denotes a pyrimidine (C or T), R denotes a purine (G or A), and N denotes any nucleotide. In some embodiments, a nucleic acid of the invention may include one or more Mu TBSs that include a nucleic acid sequence selected from SEQ ID NO: 500, SEQ ID NO: 501, SEQ ID NO: 502, SEQ ID NO: 503, SEQ ID NO: 504, SEQ ID NO: 505, SEQ ID NO: 506, and/or a biologically active variant thereof.

Previous studies indicate that under certain conditions, only a minimal number of elements are required for Mu transposition, namely a short Mu right-end donor DNA that includes the R1 (SEQ ID NO: 503) and R2 (SEQ ID NO: 504) binding sites, the Mu transposase, and a linear target DNA (see, e.g., Savilahti, *EMBO J.* 14(19):4893-4903, 1995). Therefore, in some instances, a nucleic acid of the invention may include a TBS that includes the nucleic acid sequences of SEQ ID NO:503 and SEQ ID NO: 504. Alternatively, the Mu TBS may include a sequence that does not occur in nature, but nonetheless permits transposition by the Mu transposase. For example, FIG. 2 of Goldhaber-Gordon et al. *J. Biol. Chem.* 277(10): 7703-7712, 2002 shows the nucleic acid sequences of 18 non-Mu sequences that function analogously to Mu TBSs.

Tn10

The transposase and TBSs of the Tn10 transposition system, or biologically active variants thereof, may be used in the context of the invention. NCBI Accession No. AY319289.1 provides the nucleic acid sequence of the *E. coli* Tn10 transposon. Tn10 encodes the transposase TnpA (UniProt Accession No. Q70BL4), also referred to herein as Tn10 transposase. The amino acid sequence of wild-type Tn10 transposase is shown below:

(SEQ ID NO: 507)

```
MCELDILHDSLYQFCPELHLKRLNSLTLACHALLDCKTLTLTELGRNLPT
KARTKHNIKRIDRLLGNRHLHKERLAVYRWHASFICSGNTMPIVLVDWSD
IREQKRLMVLRASVALHGRSVTLYEKAFPLSEQCSKKAHDQFLADLASIL
PSNTTPLIVSDAGFKVPWYKSVEKLGWYWLSRVRGKVQYADLGAENWKPI
SNLHDMSSSHSKTLGYKRLTKSNPISCQILLYKSRSKGRKNQRSTRTHCH
HPSPKIYSASAKEPWVLATNLPVEIRTPKQLVNIYSKRMQIEETFRDLKS
PAYGLGLRHSRTSSSERFDIMLLIALMLQLTCWLAGVHAQKQGWDKHFQA
NTVRNRNVLSTVRLGMEVLRHSGYTITREDLLVAATLLAQNLFTHGYALG
KL.
```

Hyperactive Tn10 transposase variants have been described (see, e.g., Way, Gene 32(3):369-79, 1984) and may be used in the invention.

Like Tn5 transposase, the Tn10 transposase typically binds a pair of inverted repeat nucleotide sequences that flank each side of the transposable DNA element. A Tn10 TBS may include Tn10 inverted repeat sequences, generally referred to as the outside ends (OE) and inside ends (IE), which have a consensus sequence of CTGAKRRATCCCCTMATRATTTY (SEQ ID NO: 508), wherein Y denotes a pyrimidine (C or T), R denotes a purine (G or A), M denotes A or G, and K denotes G or T (Mizuuchi, *Annu. Rev. Biochem.* 61:1011-51, 1992). In some instances, a nucleic acid of the invention may include one or more Tn10 TBSs having the nucleic acid sequence of SEQ ID NO: 508 and/or a biologically active variant thereof.

Tn7

In yet another example, the transposases and TBSs of the Tn7 transposition system may be used (see, e.g., Parks et al., *Plasmid.* 61(1):1-14, 2009). The Tn7 transposon encodes the transposases TnsA (Uniprot Accession No. P13988; also referred to as TnpA) and TnsB (Uniprot Accession No. P13989; also referred to as TnpB).

The amino acid sequence of wild-type Tn7 TnsA is shown below:

```
                                        (SEQ ID NO: 509)
MAKANSSFSEVQIARRIKEGRGQGHGKDYIPWLTVQEVPSSGRSHRIYSH
KTGRVHHLLSDLELAVFLSLEWESSVLDIREQFPLLPSDTRQIAIDSGIK
HPVIRGVDQVMSTDFLVDCKDGPFEQFAIQVKPAAALQDERTLEKLELER
RYWQQKQIPWFIFTDKEINPVVKENIEWLYSVKTEEVSAELLAQLSPLAH
ILQEKGDENIINVCKQVDIAYDLELGKTLSEIRALTANGFIKFNIYKSFR
ANKCADLCISQVVNMEELRYVAN
```

The amino acid sequence of wild-type Tn7 TnsB is shown below:

```
                                        (SEQ ID NO: 510)
MWQINEVVLFDNDPYRILAIEDGQVVWMQISADKGVPQARAELLLMQYLD
EGRLVRTDDPYVHLDLEEPSVDSVSFQKREEDYRKILPIINSKDRFDPKV
RSELVEHVVQEHKVTKATVYKLLRRYWQRGQTPNALIPDYKNSGAPGERR
SATGTAKIGRAREYGKGEGTKVTPEIERLFRLTIEKHLLNQKGTKTTVAY
RRFVDLFAQYFPRIPQEDYPTLRQFRYFYDREYPKAQRLKSRVKAGVYKK
DVRPLSSTATSQALGPGSRYEIDATIADIYLVDHHDRQKIIGRPTLYIVI
DVFSRMITGFYIGFENPSYVVAMQAFVNACSDKTAICAQHDIEISSSDWP
CVGLPDVLLADRGELMSHQVEALVSSFNVRVESAPPRRGDAKGIVESTFR
TLQAEFKSFAPGIVEGSRIKSHGETDYRLDASLSVFEFTQIILRTILFRN
NHLVMDKYDRDADFPTDLPSIPVQLWQWGMQHRTGSLRAVEQEQLRVALL
PRRKVSISSFGVNLWGLYYSGSEILREGWLQRSTDIARPQHLEAAYDPVL
VDTIYLFPQVGSRVFWRCNLTERSRQFKGLSFWEVWDIQAQEKHNKANAK
QDELTKRRELEAFIQQTIQKANKLTPSTTEPKSTRIKQIKTNKKEAVTSE
RKKRAEHLKPSSSGDEAKVIPFNAVEADDQEDYSLPTYVPELFQDPPEKD
ES
```

TnsA and TnsB are thought to form a heteromeric transposase. TnsB is a DDE-type transposase that catalyzes concerted breakage and rejoining reactions, joining the 3'-hydroxyl of the donor ends to the 5'-phosphate groups at the insertion site of the target DNA. TnsA structurally resembles a restriction endonuclease, and carries out the nicking reaction on the opposite strand of the donor DNA molecule. Accessory protein TnsC is thought to modulate the activity of the heteromeric TnsAB transposase, and activates transposition when complexed with target DNA and a target selection protein, TnsD or TnsE. TnsC variants have been isolated that can promote transposition in the absence of TnsD or TnsE. In some instances, biologically active variants of TnsA, TnsB, TnsC, TnsD, and/or TnsE may be used in the context of the invention, including variants with deletions, insertions, or amino acid substitutions. Hyperactive Tn7 transposase variants have previously been described. For example, Table 1 of Lu et al., (*EMBO J.* 19(13):3446-57, 2000) describes several TnsA and TnsB substitution mutants, including TnsA S69N, E73K, A65V, E185K, Q261Z, G239S, G239D, E185K, and Q261Z, as well as TnsB M3661, A325T, and A325V. In some instances, a biologically active Tn7 variant may include one or more of any of the preceding substitution mutations.

Seven Tn7 transposase binding sites are located on each end of the transposon, including four overlapping TnsB binding sites on the right end and three widely spaced TnsB binding sites on the left end. The consensus sequence of the seven Tn7 transposase binding sites is TGAYAATAAAGTTGATTATACT (SEQ ID NO: 511), wherein Y denotes a pyrimidine (C or T) (see, e.g., Parks et al., *Plasmid.* 61(1): 1-14, 2009). In some instances, a nucleic acid of the invention may include one or more Tn7 TBSs that include the nucleic acid sequence of SEQ ID NO: 511 and/or a biologically active variant thereof.

Tn3

The Tn3 transposon is another transposition system known in the art (see, e.g., Ichikawa et al., *Proc. Natl. Acad. Sci. USA* 84(23):8220-4, 1987). NCBI Accession No. V00613.1 provides the nucleic acid sequence of the *E. coli* Tn3 transposon. The Tn3 transposon encodes the transposase TnpA (UniProt Accession No. P03008), also referred to herein as Tn3 transposase, and the resolvase TnpR (Uniprot Accession No. POADI2). Tn3 utilizes a replicative transposition mechanism, with a first stage of replicative integration catalyzed by the Tn3 transposase that results in a "cointegrate" DNA molecule containing two copies of the transposon, followed by a resolution stage catalyzed by the resolvase that separates the donor and target DNA molecules.

The Tn3 transposase binds to terminal inverted repeat sequences comprising a left terminal inverted repeat, GGGGTCTGACGCTCAGTGGAACGAAAACTCACGTTAAG (SEQ ID NO: 512), and a right terminal inverted repeat, CTTAACGTGAGTTTTCGTTCCACTGAGCGTCAGACCCC (SEQ ID NO: 513). In some instances, a nucleic acid of the invention may include one or more Tn3 TBSs that includes the nucleic acid sequence of SEQ ID NO: 512, SEQ ID NO: 513, and/or a biologically active variant thereof.

Gamma-Delta

Some embodiments of the present invention may use the transposase and TBSs from the gamma-delta transposon, also referred to as Tn1000 (see, e.g., Broom, DNA Seq. 5(3):185-9, 1995). Gamma-delta is related to Tn3. NCBI Accession No. D16449.1 provides the nucleic acid sequence of the *E. coli* gamma delta transposon. The gamma delta transposon encodes the transposase TnpA (UniProt Accession No. Q00037), also referred to herein as gamma-delta transposase, and a resolvase TnpR (UniProt Accesion No. P03012).

The gamma-delta transposase binds to terminal inverted repeat sequences that include a "delta end" terminal inverted repeat, GGGGTTTGAGGGCCAATGGAACGAAAACGTACGTTAAG (SEQ ID NO: 514), and a "gamma end" terminal inverted repeat, ATAAACGTACGTTTTCGTTCCATTGGCCCTCAAACCCC (SEQ ID NO: 515). See, e.g., Maekawa et al., *Jpn. J. Genet.* 69(3):269-85, 1994. In some instances, a nucleic acid of the invention may include one or more gamma-delta TBSs that include the nucleic acid sequence of SEQ ID NO: 514, SEQ ID NO: 515, and/or a biologically active variant thereof.

piggyBac™

The piggyBac™ (pB) transposase, TBSs, and biologically active variants thereof may be used in the invention (see, e.g., Yusa, Microbiol. Spectr. 3(2), 2015). The pB transposon was isolated from the cabbage looper moth *Trichoplusia ni* genome. A number of pB-like transposons have also been identified in a variety of species. NCBI Accession No. J04364.2 provides the nucleic acid sequence of the *T. ni* pB transposon, which encodes the pB transposase (UniProt Accession No. Q27026). pB transposase typically integrates at TTAA sites in a target DNA. Biologically active variants of the pB transposase, including variants with deletions, insertions, or amino acid substitutions, may be used in the invention. Hyperactive pB variants with amino acid substitutions have previously been described (see, e.g., Yusa et al., *Proc. Natl. Acad. Sci. USA* 108(4):1531-6, 2011 and U.S. Pat. No. 8,399,643). pB transposon systems are commercially available (Transposagen).

pB TBSs are known in the art (see, e.g., Cary et al. *Virology* 172(1):156-169, 1989). The pB transposon includes 13-bp terminal inverted repeats and has additional inverted repeats of 19 bp in length located asymmetrically with respect to the element.

Minos

Minos transposase, TBSs, and biologically active variants thereof can be used in the invention. The Minos transposon was identified in the genome of the fruit fly *Drosophila hydei* (see, e.g., Pavlopoulos et al., *Genome Biol.* 8(Suppl 1), 2007). NCBI Accession No. X61695.1 provides the nucleic acid sequence of the Minos transposon, which encodes the Minos transposase (Uniprot Accession No. Q9U986).

The Minos transposase binds to a 5' inverted terminal repeat (ITR) that includes the following sequence:

(SEQ ID NO: 516)

```
CGCTTAACTTAATACGAGCCCCAACCACTATTAATTCGAACAGCATGTTT
TTTTTGCAGTGCGCAATGTTTAACACACTATATTATCAATACTACTAAAG
ATAACACATACCAATGCATTTCGTCTCAAAGAGAATTTTATTCTCTTCAC
GACGAAAAAAAAAGTTTTGCTCTATTTCCAACAACAACAAAAATATGAGT
AATTTATTCAAACGGTTTGCTTAAGAGATAAGAAAAAAGTGACCACTATT
AATTC
```

and a 3' ITR having the following sequence:

```
ATAGTAAATCACATTACGCCGCGTTCGAATTAATAGTGGTCACTTTTTTC
TTATCTCTTAAGCAAACCGTTTGAATAAATTACTCATATTTTTGTTGTTG
TTGGAAATAGAGCAAAACTTTTTTTTTCGTCGTGAAGAGAATAAAATTCT
CTTTGAGACGAAATGCATTGGTATGTGTTATCTTTAGTAGTATTGATAAT
ATAGTGTGTTAAACATTGCGCACTGCAAAAAAAACATGCTGTTCGAATTA
ATAGT
```

(SEQ. ID NO: 517). In some embodiments, a nucleic acid of the invention may include one or more Minos TBSs selected from SEQ ID NO: 516, SEQ ID NO: 517, and/or a biologically active variant thereof.

Sleeping Beauty

Sleeping Beauty (SB) transposase, TBSs, and biologically active variants thereof may be used in the invention. SB is a synthetic transposase Tc1/mariner-type transposase that was re-constructed from the genomes of salmonid fish (Ivics et al. *Cell* 91(4):501-510, 1997). SB transposases are known in the art (see, e.g., International Patent Application Publication No. WO99/25817 and U.S. Pat. No. 6,613,752). The amino acid sequence of a reference SB transposase is shown below:

(SEQ ID NO: 518)

```
MGKSKEISQDLRKKIVDLHKSGSSLGAISKRLKVPRSSVQTIVRKYKHHG
TTQPSYRSGRRRVLSPRDERTLVRKVQINPRTTAKDLVKMLEETGTKVSI
STVKRVLYRHNLKGRSARKKPLLQNRHKKARLRFATAHGDKDRTFWRNVL
WSDETKIELFGHNDHRYVWRKKGEACKPKNTIPTVKHGGGSIMLWCGFAA
GGTGALHKIDGIMRKENYVDILKQHLKTSVRKLKLGRKWVFQMDNDPKHT
SKVVAKWLKDNKVKVLEWPSQSPDLNPIENLWAELKKRVRARRPTNLTQL
HQLCQEEWAKIHPTYCGKLVEGYPKRLTQVKQFKGNATKY
```

Hyperactive SB variants that include amino acid substitutions are known in the art (see, e.g., U.S. Pat. Nos. 7,985,739 and 9,228,180). For example, a hyperactive SB variant may include one or more substitution mutations selected from the following: K13A, K14R, K13D, K30R, K33A, T83A, 1100L, R115H, R143L, R147E, A205K/H207V/K208R/D210E; H207V/K208R/D210E; R214D/K215A/E216V/N217Q; M243H; M243Q; E267D; T314N; and G317E (see, e.g., U.S. Pat. No. 9,228,180). In some instances, the hyperactive SB variant may include a K14R substitution mutation. The substitution mutations may be relative to the reference sequence of SB transposase shown in SEQ ID NO: 518.

SB TBSs are also known in the art (see, e.g., International Patent Application Publication No. WO98/40510 and U.S. Pat. No. 6,613,752). These TBSs and/or biologically active variants thereof may be used in the nucleic acids of the invention.

Targeting Moieties

To promote transposition to specific regions of a target nucleic acid (e.g., DNA), a transposase present in a composition of the invention (e.g., a TSC) may be targeted to particular nucleotide sequences using a targeting moiety, which can result in biased or targeted transposition of transposable nucleic acids present in a TSC. Any suitable targeting moiety known in the art or described herein may be used, so long as it can be operably linked to the transposase. The targeting moiety may be a fusion partner in a fusion protein that includes a transposase. For example, a fusion protein can include a transposase and a targeting moiety and may optionally include an intervening linker. The targeting moiety may be located N-terminally or C-terminally relative to the transposase. In other examples, the targeting moiety may be covalently or non-covalently conjugated to the transposase. The targeting moiety may be naturally occurring or engineered.

The targeting moiety may be a polypeptide that includes a DNA binding domain (DBD) that confers binding preference or specificity to a defined nucleotide sequence. For example, DBDs may include zinc finger motifs, which are well-known in the art, including but not limited to the zinc finger DBDs Sp1, ZNF202, Gal4, Jazz, E2C, Zif268, and TetR. The zinc finger motif may be derived, for example, from a Cyst-Hist type zinc finger. Fusion proteins that include transposases and zinc finger motifs are known in the art. For example, fusion proteins that include Sleeping Beauty (SB) transposase and a zinc finger DBD have been constructed using the DBD of Sp1, ZNF202, Jazz, E2C, Gal4, or TetR (see, e.g., Wilson et al., *FEBS Letters* 579:6205-9, 2005, Ivics et al., *Mol. Ther.* 5(6):1137-44, 2007; and Yant et al., *Nucleic Acids Res.* 35(7):e50, 2007). The piggyBac and Mos1 transposases have each been fused to the DBD of Gal4 (see, e.g., Maragathavally et al., *FASEB J.* 20(11):1880-2, 2006 and Wu et al., *Proc. Natl. Acad. Sci.*

*USA* 103(41):15008-13, 2006). In another example, the ISY100 transposase has been fused to the DBD of Zif268 (see, e.g., Feng et al., *Nucleic Acids Res.* 38(4):1204-1216).

Zinc finger motifs can be engineered to bind to a desired DNA sequence. A known "recognition code" that relates the amino acids of a single zinc finger motif to its associated DNA target can be utilized as a guide for the design of zinc finger motif DBDs that bind to particular DNA sequences, for example, using modular assembly (see, e.g., Bhakta et al., *Methods Mol. Biol.* 649:3-30, 2010). Alternatively, selection-based approaches (e.g., phage display or bacterial two-hybrid systems) can be used to obtain zinc finger motifs that bind to particular DNA sequences (see, e.g., Maeder et al., *Mol. Cell.* 31:294-301, 2008). A DBD may include, for example, 2, 3, 4, 5, 6, 7, 8, 9, 10, or more zinc finger motifs.

Other DBDs that may be used include DBDs belonging to transcriptional regulators (see, e.g., Szabo et al., *FEBS Letters* 550(1-3):46-50, 2003 and Imre et al., *FEMS Microbiology Letters* 317(1):52-9, 2011) and transcription activator-like effectors (TAL effectors), which are type III effector proteins that are secreted by *Xanthomonas* species and can bind to promoter sequences in the host plant. Like zinc finger motifs, TAL effectors can be engineered to bind to specific DNA sequences (see, e.g., Boch et al., *Science* 326(5959):1509-1512, 2009). Other types of DBDs are known in the art and can be used as targeting moieties, including, for example, helix-turn-helix motifs, leucine zipper domains, winged helix domains, winged helix turn helix domains, helix-loop-helix domains, and HMG box domains.

In some embodiments, the targeting moiety may include an RNA- or DNA-guided endonuclease, including but not limited to Cas9, Cpf1, C2c2, and Argonaute. In preferred embodiments, the RNA- or DNA-guided endonuclease is nuclease-deficient or nuclease-null. For example, the transposase may be fused to a RNA- or DNA-guided endonuclease in a fusion protein.

The Cas9 protein (CRISPR-associated protein 9), which is derived from type II CRISPR (clustered regularly interspaced short palindromic repeats) systems, is an RNA-guided DNA endonuclease that can be programmed to target new sites by modifying its guide RNA sequence (see, e.g., Wang et al., *Annu Rev Biochem* 85:227-64, 2016; and U.S. Pat. No. 8,795,965). In some instances, a nuclease-deficient or nuclease-null Cas9 (e.g., dCas9, which includes point mutations in two catalytic residues (D10A and H840A) of Cas9) may be utilized in the context of the invention as a targeting moiety that can be utilized in vitro. Previous work has established that Cas9 fusion proteins can be utilized for a variety of applications, including transcriptional activation, targetable DNA methylation, and enhanced specificity of DNA cleavage (see, e.g., Mali et al., *Nat Biotechnol.* 31(9):833-8, 2013; Vojta et al., *Nucleic Acids Res.* 44(12): 5615-28, 2016; Guilinger et al., *Nat. Biotechnol.* 32(6):577-82, 2014; U.S. Pat. No. 9,388,430; and U.S. Patent Application Publication Nos. 2015/0291965 and 2016/0177304).

Cpf1 or C2c2 can also be used instead of Cas9 in the context of the invention. Cpf1 is distinct from Cas9 in that it is a single RNA-guided endonuclease lacking trans-activating crRNA (tracrRNA), but with comparable targeting specificity to Cas9 (see, e.g., Zetsche et al., *Cell* 163(3): 759-71, 2015; Kleinstiver et al., *Nat. Biotechnol.* 34(8):869-74, 2016; Kim et al., *Nat. Biotechnol.* 34(8):863-8, 2016; and U.S. Patent Application Publication No. 2016/0208243). C2c2 is a programmable RNA-guided RNA endonuclease that targets single-stranded RNA, with nuclease activity that, like Cas9 and Cpf1, can be made nuclease-deficient (see, e.g., Abudayyeh et al., *Science* 353(6299):aaf5573, 2016). In some instances, Argonaute can be utilized. Prokaryotic Argonaute variants have been described that act as DNA-guided DNA endonucleases, with inactivating mutations also described (see, e.g., Swarts et al., *Nature* 507(7491): 258-61, 2014; Miyoshi et al., *Nat. Commun.* 7:11846, 2016; and Gao et al., *Nat. Biotechnol.* 34(7):768-73, 2016).

In some embodiments, the transposase may be targeted to defined nucleotide sequences by non-covalent binding to a polypeptide that includes a sequence-specific DBD. Some DNA-modifying enzymes naturally utilize such protein interactions for targeted transposition. For example, in the Ty5 retrotransposon system, the yeast Ty5 integrase is targeted to specific regions of genomic DNA by the DNA binding protein Sir4p. The specificity of Ty5 integration can be altered by fusing alternate DBDs to Sir4p (see, e.g., Zhu et al., *Proc. Natl. Acad. Sci. USA* 100(10):5891-5, 2003). In situations where a transposase does not naturally interact with a DNA binding partner, additional components or domains may be fused or conjugated to the transposase and/or DNA binding protein to promote protein-protein interactions. Further, the DBD of the interacting protein may be modified to confer the desired target sequence specificity.

In another embodiment, the targeting moiety may include a DNA or RNA oligonucleotide with a nucleotide sequence that is at least partially complementary to a sequence present in the target nucleic acid (e.g., DNA). Hybridization of the oligonucleotide to the target nucleic acid could target the transposase to the target sequence. An oligonucleotide targeting moiety may be covalently or non-covalently conjugated to the transposase, for example, by modifying both the oligonucleotide and transposase with complementary coupling moieties. Oligonucleotides and proteins can be conjugated using a variety of coupling approaches, including any of the approaches outlined in Mao et al., *Chem. Soc. Rev.* 40:5730-44, 2011. For example, methods of covalent conjugation may include site-specific coupling of thiol-modified oligonucleotides by disulfide bond formation to a transposase engineered with either an accessible cysteine residue (see, e.g., Corey et al., *J. Am. Chem. Soc.* 111(22):8523-5, 1989) or an alpha-thioester (see, e.g., Takeda et al., *Bioorg. Med. Chem. Lett.* 14(10):2407-10, 2004). Examples of non-covalent oligo-protein conjugation methods include, but are not limited to, streptavidin-biotin, Ni-NTA-hexahistidine, and antibody-hapten based coupling methods.

Tethered Synaptic Complexes and Methods of Making the Same

The invention provides TSCs as well as methods of making TSCs. In general, the methods involve contacting a nucleic acid of the invention that includes one or more TBSs with transposases that are able to bind one or more of the TBSs to form subunits of the TSC, where the TBSs have been engineered to be co-tethered via a multivalent scaffold.

As described herein, TSCs in the current invention can be used to form physical bridges between distal locations on the same target DNA molecule, which can be exploited, for example, to determine linkage and phasing information. TSCs can be designed so that the DNA termini in any given TSC subunit will attach at the same target DNA location, but the nearest synaptic complex to which the first synaptic complex is tethered ligates DNA at a distal location usually in the same target DNA molecule. In nature, the distance between TBSs on a nucleic acid molecule needs to be large enough to permit successful transposition of a protein-encoding transposon (e.g., encoding proteins for antibiotic resistance and transposase) because it confers properties necessary for survival of the host. If two terminal TBSs present on a nucleic acid molecule are too close together, constraints on nucleic acid (e.g., DNA) bending will prevent the transposases bound to termini on the same molecule from forming a synaptic complex. However, there is no such steric constraint on synaptic formation between terminal TBSs present on different nucleic molecules, which is a property that can be exploited to make TSCs.

If identical transposase binding sites are positioned sufficiently close to one another, the precise geometry and DNA bending associated with dimerization and synaptic complex formation is sterically favored between neighboring transposable nucleic acid molecules in a TSC. The length (e.g., in bp) between terminal TBSs on a nucleic acid molecule can be varied in order to promote oligomerization and synaptic complex between neighboring nucleic acid molecules in a TSC. A skilled artisan will appreciate that, in some cases, the length may vary between different types of transposases, but routine approaches can be used to determine whether a given length is suitable for use in making TSCs. For example, 64 bp of DNA separating two Tn5 TBSs on a plasmid DNA dramatically inhibited IS50 transposition activity in vivo in *E. coli* (Goryshin et al., *Proc. Natl. Acad. Sci. USA* 91:10834-10838, 1994). Similarly, in a preferred embodiment, we have discovered that distal transposition is promoted when TSCs are formed in vitro from transposase protein preparations and synthetic transposable nucleic acid molecules carrying two closely spaced TBSs.

Many transposases have been shown to distort nearby DNA conformation upon binding to the TBS. With respect to Tn5 transposase, for example, the bending angle on DNA is approximately 119° and centers near the first and third nucleotide of the 19 bp transposase binding site (Jilk et al., *J. Bacteriol.* 178:1671-1679, 1996). To one of ordinary skill in the art, it would be understood that the relative three-dimensional (3-D) orientation of the reactive ends of a transposable nucleic acid can be modified by changing the distance between the transposase binding sites because the pitch and length of the DNA helix influences the orientation of the reactive ends in 3-D space. One would predict that as the distance between TBSs is reduced to less than 100 bp, the rigidity of double-stranded DNA will eventually prevent the interaction of the TBSs present on both ends of the same DNA molecule. This model is consistent with observations in vivo made by Goryshin (ibid) who described a striking periodic relationship between the DNA length separating the TBSs on plasmid DNA and the IS50 transposition frequency for lengths between 66 and 174 bp, with the transposition activity maxima corresponding to 10.5 bp intervals, which is identical to the helical repeat length of various linear DNAs in solution. This suggests that in the context of TSCs, the average distance linking distal transposition events in target DNA can be modulated by changing the relative 3-D orientation of the reactive ends on the face of the tethered synaptic complexes (e.g., by modifying the distance between transposase binding sites).

Methods by which the average distance between distal transposition events can be controlled can also broadly include methods known to increase the rigidity or diffusion of nucleic acids, such as by adding a molecule that increases the rigidity of the spacer region (linking segment) separating TBSs on transposable nucleic acid, including, but not limited to the following classes of molecules with known DNA binding properties: nucleic acid stains and nucleic acid intercalators (e.g., acridine dyes (e.g., acridine orange) and ethidium bromide), certain antibiotics, or DNA binding proteins by modifying the nucleic acid content between TBSs on a transposable nucleic acid with biotin, and then adding streptavidin protein to bind the biotin-modified spacer region, thereby decreasing the flexibility of the spacer region separating transposase binding sites; by adding molecules known to bind, precipitate, and/or condense DNA into toroidal structures, such as histones or histone-like proteins, protamine, spermidine, hexamine cobalt chloride, polyethylene glycol, and the like; by immobilization of extended tethered synaptic complexes on a solid substrate; or by synthesizing a transposable nucleic acid on a solid or semi-solid surface.

When the use of longer nucleic acids for separating transposase binding sites is desired, a TSC could show unwanted transposase activity toward itself rather than toward target DNA. It also will be understood to one skilled in the art that there are means by which the TSC can be modified to make it resistant to unwanted transposase activity. Exemplary, non-limiting ways that a TSC can be rendered more resistant to transposase include the following: the TSC could contain a nucleotide analog resistant to transposase; the TSC could be designed having an overall G+C composition of less than 30%, which, in the case of Tn5 transposase, is known to be transposase-resistant; the TSC could be designed to be rich in sequences known to be a poor substrate for one or more transposases; the TSC could be made partly single stranded; the TSC could be coated with a DNA binding protein; if biotinylated, the nucleic acid between transposase binding sites could be coated with streptavidin or avidin protein; or the TSC could be immobilized to a solid substrate, or synthesized in situ to prevent unwanted transposition into TSC DNA.

As one of ordinary skill in the art will appreciate, synthetic analogs of nucleic acids can substitute for naturally-occurring nucleic acids in many molecular biology procedures, including all the procedures and compositions described herein. Incorporation of modified bases and/or nuclease recognition sites can allow for optional separation of the TBSs later in any of the procedures. Any of the methods of making TSCs described herein may involve use of nucleic acids that include nucleic acid analogs, modified bases, and/or nuclease recognition sites.

TSCs can be used immediately after they are made, or stored for later use (e.g., for days, weeks, months, or years). The TSCs can be stored at any suitable temperature (e.g., about −80° C., about −20° C., about 0° C., about 15° C., about 20° C., about 25° C., about 37° C., or higher). The TSCs may be stored in any suitable storage buffer, which may include one or more additional components, such as stabilizing agents, cryoprotectants (e.g., glycerol or sucrose), anti-microbial agents, nuclease inhibitors, and the like. Storage buffers for nucleic acids and proteins (e.g., transposases) are known in the art.

TSCs can be prepared using transposable nucleic acid of different lengths for different levels of spatial resolution; or the ordering of the TSCs can be influenced by the order of addition of TSC subunits to transposase (or transposase to subunits). The length of TSCs can be adjusted, for example, by adding transposable nucleic acids each carrying a TBS at only one terminus. Terminating the TSCs in this manner also can serve to minimize or prevent undesired polymerization of distinct subpools of TSCs. TSCs of a particular length can be separated from lower weight nucleic acids that fail to form high molecular weight TSCs using a variety of separation methods known to those skilled in molecular biology, including but not limited to gel filtration, ultrafiltration, preparative gel electrophoresis, chromatography, or by selectively precipitating or by binding polymers of the desired length to a solid substrate using polyethylene glycol or similar compounds.

The ease with which transposase activity is reconstituted in vitro from a few components is why simpler transposases such as Tn5 transposase are often preferred over transposases requiring substantially longer DNA binding sites and/or several accessory proteins to reconstitute transposase activity. However, a skilled artisan will appreciate that the disclosure of the present invention allows a skilled artisan to use any suitable transposase, TBS, and, if relevant, accessory protein(s) to make TSCs falling within the scope of the invention.

Affinity Binding Pairs

The compositions of the invention may include affinity binding pairs. Affinity binding pairs may be used to link two or more moieties non-covalently. For example, a multivalent core (e.g., a water soluble multivalent core) may include one or more affinity binding pairs that link the multivalent core to nucleic acids containing TBSs. Any suitable affinity binding pair known in the art or described herein may be used. Exemplary, non-limiting affinity binding pairs include biotin-biotin binding protein (e.g., biotin-streptavidin, biotin-avidin, and biotin-NeutrAvidin™), ligand-receptor, antigen-antibody or antigen binding fragment, hapten-anti-hapten, and Ig binding protein-Ig. Components of affinity binding pairs can be conjugated to compositions of the invention (e.g., artificial nucleic acids (e.g., artificial nucleic acids containing TBSs)), or multivalent cores (e.g., water soluble multivalent cores) using approaches described herein or others known in the art.

Biotin-biotin binding proteins are well-characterized affinity binding pairs. Biotin or biologically active variants and analogues thereof may be used. Avidin and other biotin binding proteins bind with considerable affinity to biotin. Exemplary biotin binding proteins include avidin, streptavidin, NeutrAvidin™ (a deglycosylated version of avidin), CaptAvidin™, and the like. The biotin binding protein may be, for example, tetrameric, dimeric, or monomeric. Biotin and biotin binding proteins can be conjugated using routine approaches to nucleic acids, proteins, or non-nucleotide chemical moieties (e.g., a polymer, e.g., a polyether such as polyethylene glycol (PEG)). For example, a variety of amine-reactive, sulfhydryl-reactive, carboxyl-reactive, carbohydrate/aldehyde-reactive, photo-reactive, and other biotinylation reagents are commercially available. Biotin binding proteins, including avidin, streptavidin, and NeutrAvidin™, are commercially available and can be conjugated using routine approaches to nucleic acids, proteins, or non-nucleotide chemical moieties (e.g., a polymer, e.g., a polyether such as polyethylene glycol (PEG)).

The binding pair may be a ligand-receptor binding pair. A wide variety of receptors and their corresponding ligands are known in the art. The binding pair may include a fragment of a receptor that binds to a ligand. The receptor can be, for example, a cytokine receptors (e.g., vascular endothelial growth factor (VEGF) receptors (e.g., VEGFR-1 and VEGFR-2), tumor necrosis factor (TNF) receptors (e.g., TNF receptor 2), and the like). Soluble receptors, including engineered soluble receptors that include extracellular binding portions of receptors fused to Fc regions, are known in the art (e.g., etanercept, a soluble TNF receptor 2 protein that binds to TNF, and aflibercept, a soluble VEGF receptor that binds to VEGF).

A wide variety of antibodies and the antigens to which they bind are known in the art, and any suitable antigen-antibody or antigen binding fragment thereof may be used in the invention. Exemplary antigen-antibody (or antigen binding fragment) binding pairs include digoxigenin/anti-digoxigenin; 2,4-dinitrophenyl (DNP)-triethylene glycol (TEG)/anti-DNP antibodies; fluorescein/anti-fluorescein antibodies; and the like.

A number of Ig binding proteins are known in the art and can be used in the invention, for example, protein A, protein G, protein L, protein M, binding immunoglobulin protein (BiP), and immunoglobulin-binding protein 1 (IGBP1), or biologically active variants thereof. An Ig binding protein may bind to the Fc region of an immunoglobulin, or a fragment thereof.

Conjugation Approaches

Any suitable conjugation approach may be used to covalently link compositions of the invention. For example, nucleic acids containing TBSs may be conjugated to multivalent cores (e.g., water soluble multivalent cores). A variety of conjugation reactions are known in the art and can be used in the context of the invention, for example, a cycloaddition (e.g., an azide-alkyne Huisgen cycloaddition (e.g., a copper(I)-catalyzed azide-alkyne cycloaddition (CuAAC) or a strain-promoted azide-alkyne cycloaddition (SPAAC))), amide or thioamide bond formation, a pericyclic reaction, a Diels-Alder reaction, sulfonamide bond formation, alcohol or phenol alkylation, a condensation reaction, disulfide bond formation, or a nucleophilic substitution.

In some instances, a composition of the invention may include a conjugating moiety. A conjugating moiety includes at least one functional group that is capable of undergoing a conjugation reaction, for example, any conjugation reaction described in the preceding paragraph. The conjugation moiety can include, without limitation, a 1,3-diene, an alkene, an alkylamino, an alkyl halide, an alkyl pseudohalide, an alkyne, an amino, an anilido, an aryl, an azide, an aziridine, a carboxyl, a carbonyl, an episulfide, an epoxide, a heterocycle, an organic alcohol, an isocyanate group, a maleimide, a succinimidyl ester, a sulfosuccinimidyl ester, a sulfhydryl, a thiol, or a thioisocyanate group.

Methods of Using Tethered Synaptic Complexes

The compositions and methods of the invention are useful in a wide variety of applications, such as applications in which it is desirable to introduce nucleic acid sequences (for example, containing identifiable sequence tags and/or primer binding sites) into a target nucleic acid (e.g., DNA, such as genomic DNA), including, for example, preparation of libraries for nucleic acid sequencing. In general, the TSCs of the invention may be used in methods that can involve combining a target nucleic acid (e.g., DNA, such as genomic DNA) with one or more compositions of the invention under conditions suitable for transposition of transposable nucleic acid molecules at distal sites in the target nucleic acid. A primary mode by which the compositions and methods of the present invention differ from others known in the art is that after combining a target nucleic acid such as DNA with a TSC, each transposable nucleic acid molecule that tethers two synaptic complexes in the TSC is covalently attached at distal locations in the target DNA in two distinct molecular transposition events. In contrast, current practices typically attach two adapter molecules at the same location in the target DNA in a single molecular transposition event. An advantage of attaching one transposable nucleic acid molecule to two distal locations is that the probability of attachment is related to the distance between the attachment sites in the target DNA. Establishing direct linkages between local and distal sites on the same DNA molecule reveals the organization of DNA on a scale that far exceeds the read length limitations of current DNA sequencing technologies.

The broad utility of the present invention extends to many areas of nucleic acid (e.g., DNA) sequencing. One example of the utility of the invention is in allowing for information regarding the phasing of mutations as having arisen either in cis or in trans with respect to a target DNA or reference sequence of interest.

Any of the methods of the invention in which TSCs are brought into contact with target DNA can include a step of modifying the target DNA to bring normally distant sites into an orientation where TSCs can more readily covalently bridge one distal site in the target DNA and another. One clear challenge addressed by the present invention is overcoming the natural propensity of transposases to form a synaptic complex with the nearest available transposase binding site to ligate transposable DNA to opposing strands at precisely the same location in the target DNA molecule. The nearest available transposase binding site is normally present on the same DNA molecule. By generating TSCs in which the TBSs are present at regular intervals, the range of potential molecular interactions is reduced, thereby increasing the reliability with which certain behaviors can be predicted. If one simultaneously restrains the range of movement of the target DNA (e.g., by binding it to a substrate or scaffold or exposing it to an agent that causes DNA supercoiling, condensation, or precipitation), it is expected that the combined effects result in a more highly ordered system with properties that can be modified to suit the needs of the application. For example, if the target DNA was less than 10 kilobases in length, one could add target DNA to TSCs in a fully extended, native state, because the target DNA compaction would be unnecessary to detect linked, long-range transposition events over such a relatively short span. Regardless, any of the TSCs described herein can include a plurality of synaptic complexes that are about equidistant from one another, and these TSCs or any others can be used in methods that include a step of restraining the range of movement of the target DNA.

In some preferred embodiments, the action of a TSC on target DNA that has altered topological properties due to the presence of binding, precipitating or condensing agents, will have enhanced utility due to the fact that such agents may cause sites that are ordinarily more distal in a target DNA molecule to come within closer physical co-proximity.

The compositions of the invention (e.g., nucleic acids and TSCs) can be used in a number of transposition methods, for example, for use in preparing libraries for sequencing. Exemplary methods are described further below.

An example of a one-step transposition method may include one or more (e.g., 1, 2, 3, 4, or all 5) of the following steps: (a) adding a TSC to a target DNA; (b) adding DNA polymerase to fill in gaps in DNA; (c) enriching for library fragments carrying long distance linkage information (e.g., by amplifying by polymerase chain reaction (PCR) or any suitable method); (d) sequencing library fragments in parallel (e.g., using NGS); and (e) identifying linkages between library fragments conveyed by transposed nucleic acid sequences (e.g., identifiable sequence tags).

Any of the methods described herein may include use of a TSC and use of soluble transposomes, e.g., to fragment DNA and add priming sites for library preparation. See, e.g., FIG. 15. Any suitable soluble transposomes can be used, e.g., any suitable tagmentation reagent (e.g., Illumina NEXTERA™).

An example of a two-step transposition method may include one or more (e.g., 1, 2, 3, 4, 5, or all 6) of the following steps: (a) adding a TSC to a target DNA; (b) adding a conventional transposase reagent to add priming sites for amplification-based (e.g., PCR) enrichment of products of linked, but separate transposition events; (c) adding DNA polymerase to fill-in gaps in DNA; (d) enrich for library fragments carrying long distance linkage information; (e) sequencing library fragments in parallel (e.g., using NGS); and (f) identifying linkages between library fragments conveyed by transposed nucleic acid sequences (e.g., identifiable sequence tags).

An example of an alternate two-step transposition method that involves use of a first transposase and a second transposase may include one or more (e.g., 1, 2, 3, 4, 5, 6, or all 7) of the following steps: (a) adding a first transposase to a nucleic acid that includes a TBS at each terminus to form synaptic complexes (leaving out the second transposase); (b) adding synaptic complexes prepared in the previous step to target DNA to initiate a first transposition reaction and allow to proceed to completion, wherein the majority of the first transposase and synaptic complexes are consumed; (c) adding the second transposase to the products of the first transposition reaction to initiate a second transposition reaction; (d) adding DNA polymerase to fill-in gaps in DNA; (e) enriching for DNA fragments carrying long distance linkage information, for example, using amplification by PCR; (f) sequencing library fragments in parallel; and (g) identifying linkages between library fragments conveyed by transposed nucleic acid sequences (e.g., identifiable sequence tags).

An example of an alternate two-step transposition method that involves use of a first transposase and a second transposase may include one or more (e.g., 1, 2, 3, 4, 5, 6, or all 7) of the following steps: (a) adding a first transposase to a multivalent transposase reagent having a first population of artificial nucleic acids that include TBSs that can be bound by the first transposase and a second population of artificial nucleic acids that include TBSs that can be bound by the second transposase to form synaptic complexes (leaving out the second transposase); (b) adding synaptic complexes prepared in the previous step to target DNA to initiate a first transposition reaction and allow to proceed to completion, wherein the majority of the first transposase and synaptic complexes are consumed; (c) adding the second transposase to the products of the first transposition reaction to initiate a second transposition reaction; (d) adding DNA polymerase to fill-in gaps in DNA; (e) enriching for DNA fragments carrying long distance linkage information, for example, using amplification by PCR; (f) sequencing library fragments in parallel; and (g) identifying linkages between library fragments conveyed by transposed nucleic acid sequences (e.g., identifiable sequence tags).

An exemplary rationale for the alternate two-step transposition method described in the preceding paragraph is that the average distance between transposed nucleic acids (e.g., identifiable sequence tags) inserted into target DNA can be controlled by adjusting the concentration of the first synaptic complex reagent relative to the concentration of the target DNA (where higher relative concentration of the first synaptic complex reagent or lower concentration of target DNA will result in closer spacing of the inserted transposable nucleic acid molecules). The synaptic complex will insert at a single site in target DNA in the first step because the TBS at one end remains free until the second transposase is added. After completion of the first transposition reaction, the second transposase is added, and the free ends on the transposed nucleic acids form active synaptic complexes with the second transposase and a second transposition reaction proceeds, attaching the other end of the transposed nucleic acid in target DNA locations proximal to the insertions catalyzed by the first transposition step.

An example of a three-step transposition method that involves use of a first transposase and a second transposase may include one or more (e.g., 1, 2, 3, 4, 5, 6, 7, 8, or all 9) of the following steps: (a) adding the first transposase protein to bind two nucleic acid molecules together through TBSs to form synaptic complexes (the second transposase protein is temporarily withheld); (b) adding the synaptic complexes prepared in the previous step to target DNA to initiate a first transposition reaction and allowing the reaction to proceed to completion where the first transposase and synaptic complexes are consumed; (c) adding the second transposase to the products of the first transposition reaction to initiate a second transposition reaction; (d) optionally adding a nuclease to cleave the transposed nucleic acid at specific locations (e.g., a cleavage site); (e) adding a conventional transposase reagent (e.g., a tagmentation reagent such as Illumina NEXTERA™) to add priming sites for PCR enrichment of products of linked, but separate transposition events in a third transposition reaction; (f) adding DNA polymerase to fill-in gaps in DNA; (g) enriching for library fragments carrying long distance linkage information, for example, using amplification by PCR; (h) sequencing library fragments in parallel; and (i) identifying linkages between library fragments conveyed by transposed nucleic acid sequences (e.g., identifiable sequence tags).

The present invention is broadly useful for the purpose of determining the distance separating linked DNA molecules. A single nucleic acid molecule can be made (e.g., synthesized) carrying at least one fully-formed TBS for one transposase and a partially- or fully-formed TBS for the same or a different transposase, as described above. In this particular embodiment of a two-step transposition reaction, the transposable nucleic acid preparation is incubated with a first transposase protein to form a first mixture of synaptic complexes, and then added to a target DNA sample to initiate a first round of transposition events. Adding more synaptic complex to a fixed amount of target DNA will cause the average distance separating transposition events to be smaller. After the first transposition reaction, a DNA polymerase and deoxynucleotide triphosphates (dNTPs) are added, causing DNA extension to complete the formation of a second transposase binding site on the same adaptor. If a different transposase protein is to be used for the second transposition step (described below), then a nucleic acid with a fully formed transposase binding site for the second transposase can be used from the beginning of the procedure. To prepare additional synaptic complexes from nucleic acids that are already inserted into target DNA, more transposase is added after completion of the first transposition reaction and after the transposase binding sites for the second transposition step are made active. The second transposition reaction is initiated by adding a second DNA sample to the second active synaptic complexes under conditions that are suitable for the activity of the second transposase. The second transposition reaction links the first DNA sample to a second DNA sample.

In another example of a two-step transposition method, the first and second DNA samples are target and reference samples, respectively. The target DNA sample can be synthetic or natural DNA from any source, whether from plant, animal, microbe, virus, the environment, or, of unknown provenance. The reference DNA sample can also be from a synthetic or natural source where all or some of the reference DNA sequence is known. The reference DNA can serve several purposes in molecular biology techniques; for example, as an easily accessible reservoir of highly diverse index sequences for DNA labeling and DNA sequencing; for identifying remotely linked and immediately adjacent DNA library fragments generated from the same target DNA molecule via covalent linkage to reference DNA of known DNA sequence and length; for quantifying the diversity of a population of DNA fragments; for appending DNA with uniquely indexed sequences priming sites for amplification; and for approximating the distance separating two or more transposition events on the same target molecule by using the known distance between insertion sites on the reference DNA as a "measuring stick."

One of ordinary skill in the art appreciates that either target DNA or a reference DNA can serve as substrate for the first transposition. In another embodiment, the reference DNA sample is supplied as a ready-to-use formulation in a kit, where the reference DNA reagent has already undergone the first transposition and has already been complexed with the second transposase, so that a kit end-user could mix a target DNA sample with the reference DNA reagent provided in the kit to initiate the next transposition reaction. This form of reference DNA, complexed with fully functional transposase is known as "activated reference DNA."

In another aspect, the reference DNA is designed and produced to suit the needs of a particular DNA sequencing application. When the target DNA sample is large and complex, as is the case for human genomic DNA, the reference DNA can be selected or designed to offer a very large number of unique insertion sites so that with sufficient sequencing depth adjacent library fragments can be confidently identified by transposition of a synaptic complex into a unique site on the reference DNA. For any given target DNA sample, the length of the unique reference DNA (in bp) offered should typically exceed the number of target molecules that one intends to sequence by two or more orders of magnitude. Inserting mixed bases at certain points or interspersed at regular intervals in known reference DNA is a means by which one can generate a large diversity of reference DNA quickly and inexpensively for DNA sequencing. Although known DNA from a natural source could serve as a suitable DNA substrate for preparing reference DNA, synthetic reference DNA has clear advantages because the desirable properties for DNA sequencing can be altered at will.

In yet another embodiment, a reference DNA sample is immobilized to constrain its movement while reacting with target DNA sample. For example, biotinylated reference DNA can be immobilized on streptavidin paramagnetic beads through specific sites to orient the reference DNA for productive interaction with solution phase target DNA. Target DNA can also be immobilized or condensed before reacting with activated reference DNA.

In another aspect, a collection of reference DNA samples can be arrayed in a dense format on a solid substrate in some recognizable pattern. The pattern of immobilized reference DNA can be created by one of, or a combination of, the many methods widely known to practitioners of molecular biology and to manufacturers of laboratory products, and especially known to manufacturers of microarrays and DNA sequencing platforms, such as methods for depositing beads or small droplets onto a solid surface or into microwells; for applying DNA or beads carrying DNA onto a surface for immobilization by pipetting, spotting, spraying, acoustic dispensing, or piezoelectric dispensing; or for synthesis of DNA directly on a surface. Next, a solution of target DNA molecules is applied to the surface of immobilized reference DNA by pipetting, spotting, flooding, or by flowing a solution through a microfluidic path (or by any of the other methods mentioned previously). In this embodiment, the addresses of the reference DNA samples are either known before the target DNA is applied to the immobilized reference; determined through DNA sequencing before or after the target DNA is applied to the immobilized reference; or determined by some other method or combination of methods known to molecular biologists for interrogating the relative position of DNA content, such as by hybridization of labeled oligonucleotides to the reference DNA or target DNA, or by polymerase extension of oligonucleotides from nucleic acids bound to the surface. In some instances, the immobilized target DNA sample can substitute for the immobilized reference DNA in these examples, while in other instances solution phase reference DNA could be applied to immobilized target DNA. When a reference DNA molecule (for example, an *E. coli* genomic DNA) is prepared as a tethered synaptic complex preserving its natural order and inserted via transposition at multiple sites along a target DNA molecule, the reference DNA sequence can serve as an identifiable sequence tag at known positions in the reference with known distances between the identifiable sequence tags and thereby conveys useful information about the ordering of the target DNA sequence.

In another example, activated reference DNA can be mixed with target DNA under conditions where the transposition reaction does not proceed (e.g., by withholding magnesium ions). It has been demonstrated that active transposases complexed with DNA (e.g., TSCs) are stable, but reference DNA could also be stored in an inactive form to which a transposase is added at some later point before use. The mixture of target DNA and activated DNA mixture can be co-condensed by the addition of agents (e.g., polyethylene glycol, spermine, protamine, manganese, hexamine cobalt chloride, and the like) known to form DNA toroids or to precipitate DNA. By co-spooling two or more molecules into toroids, or by co-precipitating the DNA mixture, the activated reference and target DNA would be brought into close proximity for transposition. The DNA toroids or precipitates can be collected by centrifugation, filtration, binding to solid surface, or by another method for immobilization and removal of excess condensing/precipitation agents.

In a preferred embodiment, the reference DNA is relatively free of undesirable repeat sequences, regions of extreme base composition (e.g., low or high GC bias), insertional hotspots for transposases, homopolymer sequences, or any other DNA sequence that could interfere with the reliable production of reference DNA or of DNA sequencing.

In any of the embodiments described herein, the identifiable sequence tags on the two strands of each transposed nucleic acid can be, for example, continuous or discontinuous complementary randomers, which, after the so-called index read step in DNA sequencing, can be used to detect linkages between distal sites in target DNA bridged by a single transposed nucleic acid (FIG. 5), wherein detection of a repeated sequence in target DNA immediately downstream of the insertion site in different library fragments provides evidence that a neighboring pair of subunits in a TSC were attached to opposite strands at that location in target DNA in the same transposition event. The positions of the index and duplicated sequences correspond to known locations within the transposed DNA and target sequences, and as such, these positions can be queried automatically. If there is reference sequence information available for the expected target DNA sequence, then sequence data extending well beyond the duplicated sequence can support higher confidence long virtual sequencing reads.

The TSCs of the invention have a number of unanticipated advantages. For example, TSCs exhibit a strong transposition proximity bias that is likely due to the rafting behavior of TSCs combined with the tendency of transposase protein to remain tightly bound to the transposed nucleic acid after transposition, which greatly increases the likelihood that transposable nucleic acid molecules from the same TSC will attach to the same DNA molecule multiple times. Also, the reverse complement of an identifiable sequence tag linking distal transposition events can be copied during a fill in step with DNA polymerase. Further, TSCs can be assembled in separate subpools with unique identifiers (e.g., identifiable sequence tags), allowing easier identification of target DNA islands within DNA sequencing datasets based on the rafting behavior of distinct TSC subpools.

Library Preparation and Sequencing Methods

The compositions (e.g., TSCs) and methods described herein can be used, for example, to prepare target nucleic acids (e.g., DNA) for sequencing, for example, for library preparation. The invention also provides methods of sequencing target nucleic acids (e.g., DNA). Any suitable sequencing technique described herein or known in the art can be used in the context of the invention. The methods to determine the nucleotide sequence of a target nucleic acid can be automated (e.g., in a fully automated device). The methods preferably employ NGS approaches. These methods and their applications are described in additional detail below. See, e.g., FIGS. 15 and 17.

Methods of preparing a target nucleic acid (e.g., DNA) for sequencing may include combining a TSC of the invention with a target nucleic acid under conditions and for a time sufficient for the TSC to carry out a transposition event. The method may further include fragmenting the target nucleic acid and optionally adding a polynucleotide to the resulting ends of the nucleic acid fragments. Typically the reaction will occur in buffered solution compatible with transposition, of which many are known in the art (e.g., N-Tris (hydroxymethyl)methyl-3-aminopropanesulfonic acid (TAPS)-based buffers, see Picelli et al., *Genome Res.* 24:2033, 2014). The buffered solution will typically include any necessary cofactors, such as a divalent metal cation (e.g., magnesium cations). A skilled artisan appreciates that the exact conditions and time of the reaction may vary depending, for example, on the TSC (e.g., the transposase(s) that are used), the target nucleic acid, and the sequencing approach used. These conditions can be readily determined based on the present disclosure and routine approaches known in the art.

Any suitable method for fragmenting nucleic acids may be used, for example, physical fragmentation (e.g., sonification, acoustic shearing, nebulization, needle shearing, and hydrodynamic shearing), enzymatic fragmentation (e.g., using a nuclease (e.g., an endonuclease, such as DNaseI, a restriction endonuclease (e.g., EcoRI, BamHI, EcoRV, and ClaI), RNAseIII, a transposase (e.g., Tn5), and the like), chemical fragmentation (e.g., using heat and a divalent metal cation such as magnesium or zinc, which may be used for fragmentation of long RNA fragments). The fragmentation may be random or non-random. For example, restriction endonucleases typically cleave DNA at specific sequences, while other enzymes, such as DNAseI, typically fragment DNA with relatively low sequence specificity. Fragmentation can result in fragments having a desired length (e.g., an average length for a population of fragments), for example, of about 10 bp, about 50 bp, about 100 bp, about 200 bp, about 300 bp, about 400 bp, about 500 bp, about 600 bp, about 700 bp, about 800 bp, about 900 bp, about 1000 bp, about 2000 bp, about 3000 bp, about 4000 bp, about 5000 bp, or higher.

In most transposase-based fragmenting methods, target DNA is treated with a purified transposase enzyme (e.g., Tn5) complexed with short synthetic oligonucleotides (e.g., containing transposase binding sites and other sequences of interest such as primer binding sites and/or identifiable sequence tags) to promote molecular transposition events producing a plurality of DNA fragments, instead of integrating a transposon into a target DNA. The methods in which purified transposases are used as reagents in artificial transpositions to prepare libraries for NGS are sometimes referred to as "tagmentation." Tagmentation reagents are commercially available (e.g., Illumine NEXTERA™) or can be produced using standard approaches (see, e.g., Picelli et al., *Genome Res.* 24:2033, 2014).

Any suitable method for adding a polynucleotide to the resulting ends of the nucleic acid fragments may be used. For example, the method may include enzymatically "polishing" the ends of DNA fragments (e.g., using a DNA polymerase such as the DNA polymerase I Klenow fragment, T7 polymerase, Taq, Pfu, and the like) to permit ligation of adapter DNA, which may be followed by ligating different adapter sequences onto the polished DNAs (for example, using DNA ligase) that allow random fragments of the original source DNA to be subsequently amplified efficiently and without bias. In another example, tagmentation approaches may result in addition of an adapter or barcode onto the ends of each fragment.

Methods of sequencing a target nucleic acid may include one or more (e.g., 1, 2, 3, 4, or all 5) of the following steps: combining a TSC with a target nucleic acid under conditions and for a time sufficient for the TSC to carry out a transposition event; (b) fragmenting the target nucleic acid and adding a polynucleotide to the resulting ends of the nucleic acid fragments; (c) selecting DNA fragments comprising a nucleic acid sequence resulting from the transposition event; (d) amplifying the selected fragments; and (e) sequencing the amplified fragments. In particular embodiments, (b) may include random sharing and adapter ligation (also known as "shotgun adaptation") or tagmentation. The selecting of (c) may include selecting nucleic acid fragments that include an identifiable sequence tag. Any suitable method may be used for amplifying selected fragments, including, for example, polymerase chain reaction (PCR), multiple displacement amplification (MDA), ligase chain reaction (LCR), loop mediated isothermal amplification (LAMP), rolling circle amplification (RCA), or strand displacement amplification (SDA). Other amplification methods are known in the art and may be used in the invention. The sequencing of (e) may include any suitable sequencing approach, preferably an NGS sequencing approach such as sequencing-by-synthesis (SBS), sequencing-by-ligation (SBL), and nanopore sequencing. Exemplary sequencing approaches are described in more detail below. Any of the methods may further include (f) analyzing the sequenced fragments to identify fragments of the target nucleic acid that can be linked due to the presence of a nucleic acid sequence resulting from the transposition event.

In some instances, SBS may be utilized in the context of the invention. SBS techniques generally involve the enzymatic extension of a nascent nucleic acid strand through the iterative addition of nucleotides against a template strand. SBS techniques can utilize nucleotide monomers that have a terminator moiety or those that lack any terminator moieties. Some exemplary types of SBS that do not utilize a terminator moiety include ion semiconducting sequencing and pyrosequencing (see, e.g., Margulies et al., *Nature* 437(7057):376-80, 2005; Rothberg et al., *Nat. Biotechnol.* 10(26)1117-24, 2005; Merriman et al., *Electrophoresis* 23(33):3397-417, 2012; and U.S. Pat. Nos. 7,323,305; 8,546,128; 8,574,835; 8,673,627; 8,748,102; and 8,765,380). In pyrosequencing approaches, a desired DNA sequence is able to be determined by light emitted upon incorporation of the next complementary nucleotide, relying on the detection of pyrophosphate release on nucleotide incorporation. In ion semiconducting sequencing approaches, detection is based on the release of hydrogen ions during the polymerization of DNA.

For SBS techniques that utilize nucleotide monomers having a terminator moiety, the terminator can be irreversible under the sequencing conditions used as in traditional Sanger sequencing, which utilizes dideoxynucleotides, or the terminator can be reversible (see, e.g., U.S. Pat. Nos. 5,750,341; 6,255,475; and 6,355,431). In such an embodiment, the DNA to be sequenced is modified to enable attachment to a flow cell via complementary sequences. As the DNA is amplified, fluorescently tagged nucleotides are added to the DNA strand, with one base added per amplification round as a result of a reversible terminator on every nucleotide, and light emission is detected by a camera.

SBS techniques that involve real-time monitoring of DNA polymerase activity can also be used. For example, in SMRT™ sequencing, a zero-mode waveguide (ZMW) is utilized, wherein the ZMW is a structure that creates an observation volume small enough to observe a fluorescent signal emitted when a single nucleotide of DNA is incorporated into the nascent strand (see, e.g., Levene et al., *Science* 299(5607):682-6, 2003; Eid et al., *Science* 323 (5910):133-8, 2009; Chin et al., *Nat. Methods* 6(10):563-9, 2013; and U.S. Pat. Nos. 7,181,122; 7,302,146; and 7,313,308). In such embodiments, the illumination can be restricted to a zeptoliter-scale volume around a surface-tethered polymerase such that incorporation of fluorescently labeled nucleotides can be observed with low background.

SBL techniques can also be used in the context of the invention. Examples of SBL include, without limitation, polony sequencing and sequencing by oligonucleotide ligation and detection (SOLiD™) (see, e.g., Mitra et al., *Anal., Biochem.* 320(1):55-65, 2003; Shendure et al., *Science* 309 (5741):1728-32, 2005; Cloonan et al., *Nat. Methods* 5(7): 613-9, 2008; and U.S. Pat. No. 9,243,290). SBL uses the DNA ligase enzyme to identify the nucleotide present at a given location in a DNA sequence, relying on DNA ligase's mismatch sensitivity instead of second strand synthesis. Detection of fluorescently-labeled probe oligonucleotides is typically performed with each cycle of ligation.

Nanopore sequencing can also be used. Nanopore sequencing is a real-time DNA sequencing technique in which target nucleic acids pass through a nanopore (see, e.g., Cockroft et al., *J. Am. Chem. Soc.* 3(130):818-20, 2008; Feng et al., *Genomics Proteomics Bioinformatics* 1(13):4-16, 2015; Fuller et al., *Proc. Natl. Acad. Sci. USA* 19(113): 5233-8, 2016; U.S. Pat. No. 7,001,792; and U.S. Patent Application Publication Nos. 2011/0177493 and 2016/0076092). The nanopore can be a synthetic pore or biological membrane protein. As the target nucleic acid passes through the nanopore, each base-pair can be identified by measuring fluctuations in the electrical conductance of the pore.

The compositions (e.g., nucleic acids and TSCs) and methods described herein can be used in any sequencing application, particularly those in which incorporation of defined nucleic acid sequences (e.g., identifiable sequence tag(s)) into a target nucleic acid (e.g., DNA) is desired. The compositions and methods can be used to obtain fully phased, resolved sequence information and can overcome the length limitation imposed by most NGS instruments. Exemplary, non-limiting applications of the present invention include whole-genome sequencing, single-cell genome sequencing, exome sequencing, RNA sequencing (RNA-seq), genome-wide haplotype sequencing, epigenomics, and transcriptomics. Additional applications of next-generation sequencing are also known in the art, and the compositions and methods of the invention may be used in any suitable application.

In some instances, the compositions (e.g., nucleic acids and TSCs) and methods described herein may be utilized in whole-genome or whole-exome sequencing, for example, for identifying disease-causing genetic variations, including indels, non-synonymous variants, or splice-site variants (see, e.g., Cirulli et al., *Nat. Rev. Genet.* 11(6):415-25, 2010). In some embodiments, the invention can be utilized in high-throughput RNA sequencing (RNA-seq), with specific applications including gene expression profiling and splice junction analysis (see, e.g., Li et al., *Nat. Biotechnol.* 32(9): 915-25, 2014). In still other embodiments, the compositions (e.g., nucleic acids and TSCs) and methods may be utilized in genome-wide haplotype sequencing, with specific applications including mutation phase assessment (see, e.g., Snyder et al., *Nat. Rev. Genet.* 16(6):344-58, 2015). As an example, the compositions and methods of the invention can be used to obtain phase-resolved human leukocyte antigen (HLA) typing.

In other instances, the compositions (e.g., nucleic acids and TSCs) and methods described herein may be utilized in epigenomic applications, including chromatin immunoprecipitation followed by high-throughput sequencing (ChIP-seq), DNA methylation analysis through bisulfite sequencing, and chromatin footprinting (see, e.g., Zentner et al., *Nat. Rev. Genet.* 15(12):814-27, 2014; Park, *Nat. Rev. Genet.* 10(10):669-80, 2009; Brunner et al., *Genome Res.* 19(6): 1044-56, 2009; and Buenrostro et al., *Nat. Methods* 10(12) 1213-8, 2013). In other embodiments, the compositions (e.g., nucleic acids and TSCs) and methods described herein may be utilized in single-cell genome sequencing, with specific applications including de novo assembly of genomes, copy number variant detection, and single nucleotide variant detection (see, e.g., Gawad et al., *Nat. Rev. Genet.* 17(3):175-88, 2016).

Target Nucleic Acids

Any target nucleic acid may be combined with a composition of the invention (e.g., a TSC), for example, for library preparation and sequencing. For example, the target nucleic acid may be DNA, RNA, peptide nucleic acid, morpholino nucleic acid, locked nucleic acid, glycerol nucleic acid, hybrids thereof, and mixtures thereof. The target nucleic acid can be of any suitable length, e.g., about 10 bp, about 20 bp, about 50 bp, about 100 bp, about 200 bp, about 500 bp, about 1000 bp, about 5000 bp, about 10,000 bp, about 20,000 bp, about 50,000 bp, about 100,000 bp, about 250,000 bp, about 500,000 bp, about 750,000 bp, about 1 million bp, about 5 million bp, about 10 million bp, about 15 million bp, about 20 million bp, or more. The target nucleic acid may include any sequence, and may include homopolymer sequences or repeat sequences. The repeat sequences can be of any of a number of lengths, e.g., about 2, about 5, about 6, about 7, about 8, about 9, about 10, about 12, about 15, about 20, about 25, about 30, about 35, about 40, about 45, about 50, about 100, about 250, about 500, about 1000 nucleotides, or more. Repeat sequences may be repeated contiguously or non-contiguously, for example, 2, 3, 4, 5, 6, 7, 8, 9, 10, 20, 30, or more times.

The target nucleic acid may be a single target nucleic acid, or there may be a plurality of target nucleic acid (e.g., tens, hundreds, thousands, millions, or more) target nucleic acids. Each member of the plurality of target nucleic acids may be the same, or each member may be different. The target nucleic acid can be synthetic or natural DNA from any source, whether from a plant, an animal (particularly a mammal such as a human), a microbe (e.g., from prokaryotes such as a bacterium (e.g., *Escherichia coli, Staphylococcus aureus*) or an archaeon, or from a eukaryote such as a fungus (e.g., budding yeast)), a virus, the environment, or, of unknown provenance. The target nucleic acid(s) may represent at least a portion of an organism's genome (e.g., at least about 1%, 5%, 10%, 20%, 25%, 30%, 40%, 50%, 75%, 80%, 90%, 95%, 99%, or 100% of the organism's genome). The target nucleic acid may be a chromosome. The target nucleic acid may include genomic DNA or cDNAs from a single cell. The target nucleic acid may include nucleic acids from a plurality of haplotypes.

Kits

The invention provides kits that include one or more compositions of the invention (e.g., nucleic acids, multivalent transposase reagents, and TSCs). The kits may include one or more additional reagents that are useful, for example, for carrying out the methods of the invention. The kit may include one or more containers for holding the components of the kit (e.g., tubes (e.g., microcentrifuge tubes), plates (e.g., microtiter plates), trays, packaging materials, and the like. The kit may also include instructions (e.g., printed instructions for using the kit).

A kit may include any of the nucleic acids described herein. For example, an exemplary kit may include an artificial nucleic acid that includes a first end comprising a first TBS. In some embodiments, a kit may include an artificial nucleic acid that includes a first end comprising a first TBS, a second end comprising a second TBS, and a linking segment disposed between the first TBS and the second TBS. In some embodiments, wherein upon binding of a first transposase to the first TBS and a second transposase to the second TBS, the first transposase does not oligomerize with the second transposase. The kit may also include a purified transposase that binds to the first TBS or the second TBS. The nucleic acid and purified transposase(s) can be present in the same container or in different containers. In some instances, the artificial nucleic acid includes an identifiable sequence tag. The kit may include artificial nucleic acids each having the same identifiable sequence tag. In other examples, the kit may include a plurality of artificial nucleic acids, in which each member has a different identifiable sequence tag and/or TBS. A kit may also include any of the preceding artificial nucleic acids, a first transposase, and optionally, a second transposase, wherein the first transposase binds to the first TBS and the second optional transposase binds to a second TBS.

A kit may also include any of the multivalent transposase reagents described herein. For example, a kit may include a multivalent transposase reagent that includes a multivalent core (e.g., a water soluble multivalent core) and three or more artificial nucleic acids linked to the multivalent core, where each artificial nucleic acid includes a first end that includes a TBS.

In a further example, a kit may include a TSC. Any of the TSCs described herein may be included in a kit. The TSC may include, for example, between three and one thousand synaptic complexes. In some instances, each artificial nucleic acid in the TSC includes an identifiable sequence tag. Each identifiable sequence tag in the TSC may be identical, or the TSC may include a plurality of different identifiable sequence tags. In some embodiments, each identifiable sequence tag in the TSC is different. In some instances, the kit includes a plurality of TSCs. In some instances, each of the plurality of TSCs includes an 1ST. In some instances, the plurality of TSCs includes a plurality of different ISTs. In one embodiment, at least two TSCs each include a single IST that differs from that of the other TSC. For example, in some instances, the kit includes a plurality of TSCs, where each of the plurality includes an artificial nucleic acid sequence selected from the group consisting of SEQ NO. 1 to SEQ NO. 480, as described below in Example 1.

Any of the preceding kits may include one or more additional reagents. For example, the one or more additional reagents may include a soluble transposome, a cofactor, a buffered solution, and/or a reference nucleic acid. The cofactor may be a divalent metal cation (e.g., a magnesium cation). Any of the kits may also include a reagent for nucleic acid sequencing, which may include, for example, oligonucleotide primer(s), a substrate, an enzyme (e.g., a DNA polymerase), a mixture of nucleotides, and/or a reference nucleic acid.

EXAMPLES

The following example is a representative demonstration by which a scaffolded multivalent TSC reagent can be prepared and used.

Figure 5:
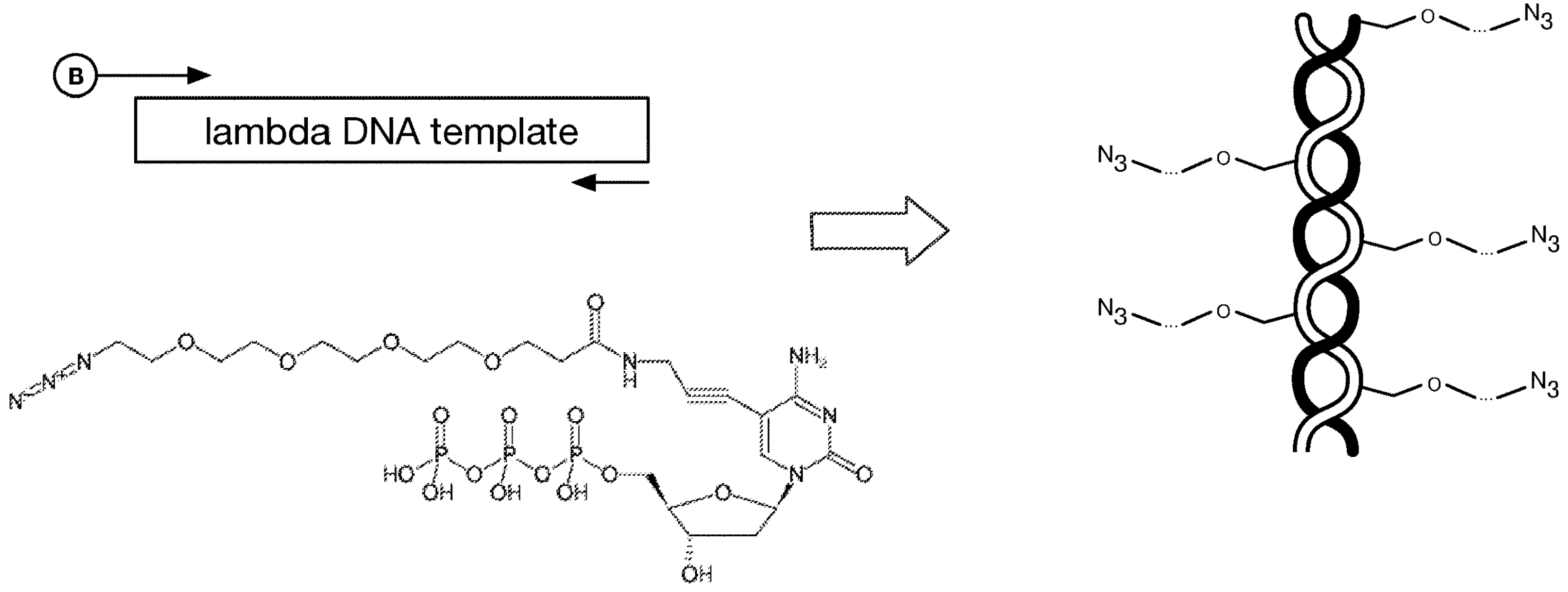
FIG. 5 illustrates the use of an azide-modified dCTP to produce a dsDNA scaffold having a number of azide base modifications.

Step 1:

A DNA-based multivalent core with modified nucleotides for tethering synaptic complexes was produced, as shown in FIG. 5 and described in detail below.

1. A 308 bp multivalent core molecule was amplified by PCR from bacteriophage lambda DNA (New England Biolabs) substituting 5-Azido-PEG4-dCTP for dCTP. The full sequence of the 308 bp lambda DNA amplicon is as follows:

```
                                      (SEQ ID NO: 481)
5'_CTGGCGGCTATCCAGTACAGCGCCGTACCAAGATAACGCGTGCTGG

TTTCAACCTGTCTGATATCCGCAATCTGCTTTTCCGAGAACCAGAACTC

AAACTGTACCGTCGGGTCATAAACGGCAAGATGCGGCGTGGCGGTTATC

TGAAAATAGCCCGGCGTCAGCTCAATCCTCGACGGTGCTGCCGGTGCGG

CAATCCGGAACGATACCGACGCCGGATCGCCCTGCTGCCCCCACGCATT

TACCGCCCGGACTGTCAGCCTGTAGTTCCCCAGCGCCAGTTGCGTGAAG

CGGTATGTGGTTTCCGT_3'
```

a. Next, the following components were combined in a final PCR reaction volume of 110 μl: 55 pmol of LAM_10245_F primer (5'-CTGGCGGC-TATCCAGTACAG (SEQ ID NO: 482)); 55 pmol of LAM_10552_R primer (5'-ACGGAAACCACAT-ACCGCTT (SEQ ID NO: 483)); 200 μM each of dGTP, dATP, dTTP, and 5-Azido-PEG4-dCTP (5-Azido-PEG4-2'-deoxycytidine-5'-triphosphate, Jena Biosciences); 2.75 Units of OneTaq DNA polymerase (New England Biolabs); and 11 ng of lambda DNA.
   b. Thermal cycling conditions used for the PCR were as follows:
      i. 94° C. for 30 sec
      ii. 94° C. for 20 sec
      iii. 55° C. for 20 sec
      iv. 68° C. for 20 sec
      v. Cycled to step ii 21 more times
      vi. 68° C. for 5 min
      vii. Held at 10° C.
2. Next was added 20 units of exonuclease I (New England Biolabs) to the PCR to digest unincorporated primers.
3. The above reaction mixture was incubated at 37° C. for 15 min, 80° C. for 20 min, and finally, at 60° C. for 10 min.
4. The reaction was then concentrated and diafiltered the exonuclease-treated 308 bp multivalent core using an Amicon Ultra-4 centrifugal ultrafiltration device (3,000 NMWL) (Millipore) to remove unincorporated 5-Azido-PEG4-dCTP, residual digestion products, and other low molecular weight reaction components.
5. Added the concentrated 308 bp multivalent core preparation to a Montage SEQ 96 cleanup plate (Millipore).
6. Filtered on a MultiScreen vacuum manifold (Millipore) until the wells appeared empty, and then added 100 μl of ultrapure water per well.
7. Filtered on the vacuum manifold again until the wells appeared empty.

Figure 6:
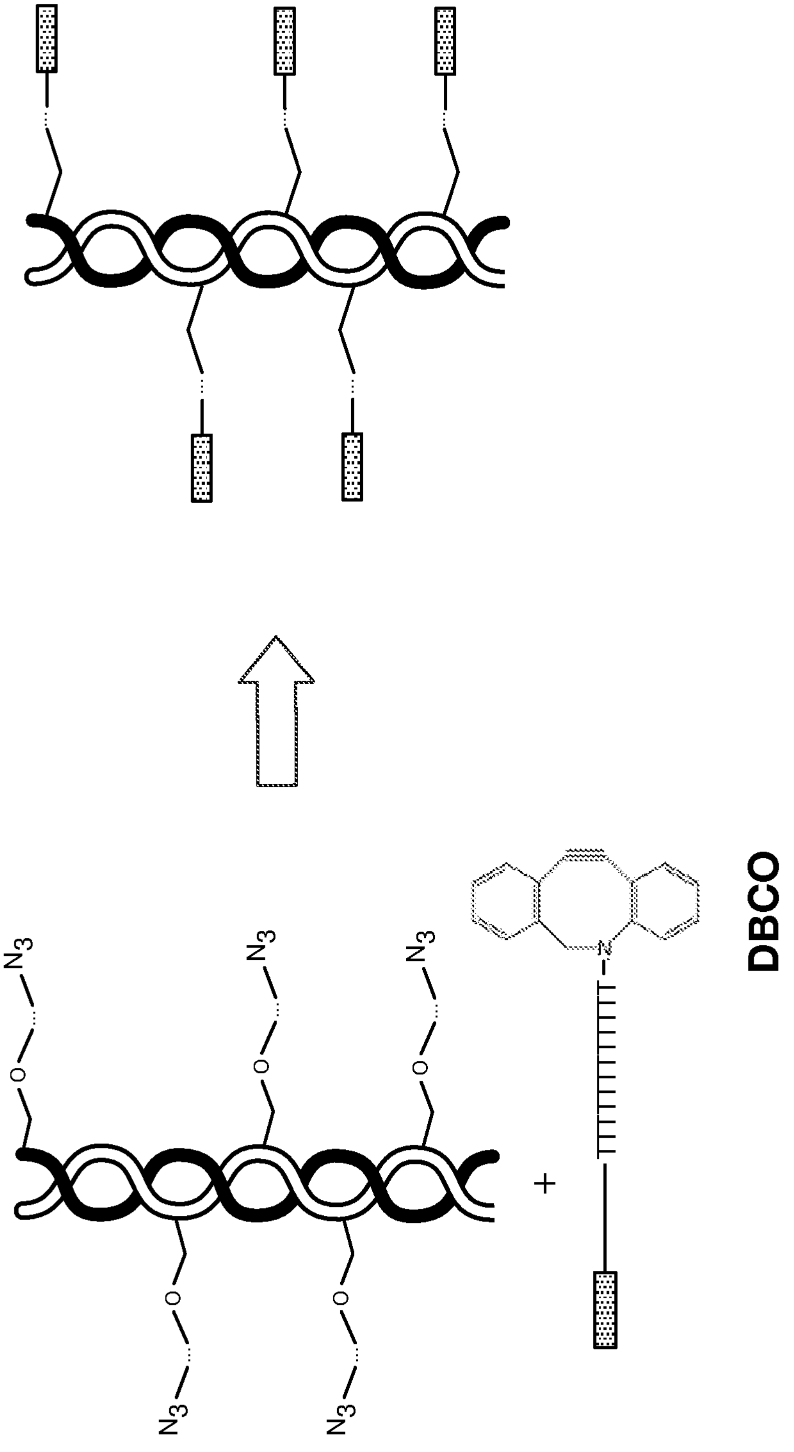
FIG. 6 illustrates the reaction of a DBCO-modified oligonucleotide with an azide-modified dsDNA substrate, for the purpose of scaffolding the addition of TBS-containing adapters.

Step 2:

Next, a 5'-DBCO-labeled poly-T TAG1 splint primer was reacted with the 5-Azido-PEG4-dCTP-modified 308 bp multivalent core (i.e., universal scaffold) from above, using click chemistry (i.e., SPAAC), as shown in FIG. 6, and described in detail below:

1. In the well of the Montage SEQ 96 cleanup plate described above, resuspended the concentrated 308 bp multivalent core in 40 μl of a 1.5-fold molar excess of 5'-DBCO (Dibenzocyclooctyl)-labeled poly-T TAG1 splint primer (5'-DBCO-TTTTTTTTTTTT-CAAGCAGAAGACGGCATACGAGAT (SEQ ID NO: 484)) with respect to moles of 5-Azido-PEG4-dCTP present in the 308 bp multivalent core, and then, filtered on the vacuum manifold again until all wells appeared empty (served to concentrate the reagents on the surface of the ultrafiltration membrane and increased the click chemistry reaction rate).
2. Incubated the concentrated reagents together at room temperature for 2 hours to permit the click chemistry reaction to proceed.
3. Dissolved the reaction product (each multivalent core molecule covalently linked to multiple copies of 5'-DBCO-labeled poly-T TAG1 splint primer) in 100 μl of 10 mM Tris-HCl, pH 8.0 (The oligonucleotides linked to the multivalent core served as forward primers during the PCR on the multivalent core described below).

Figure 7:
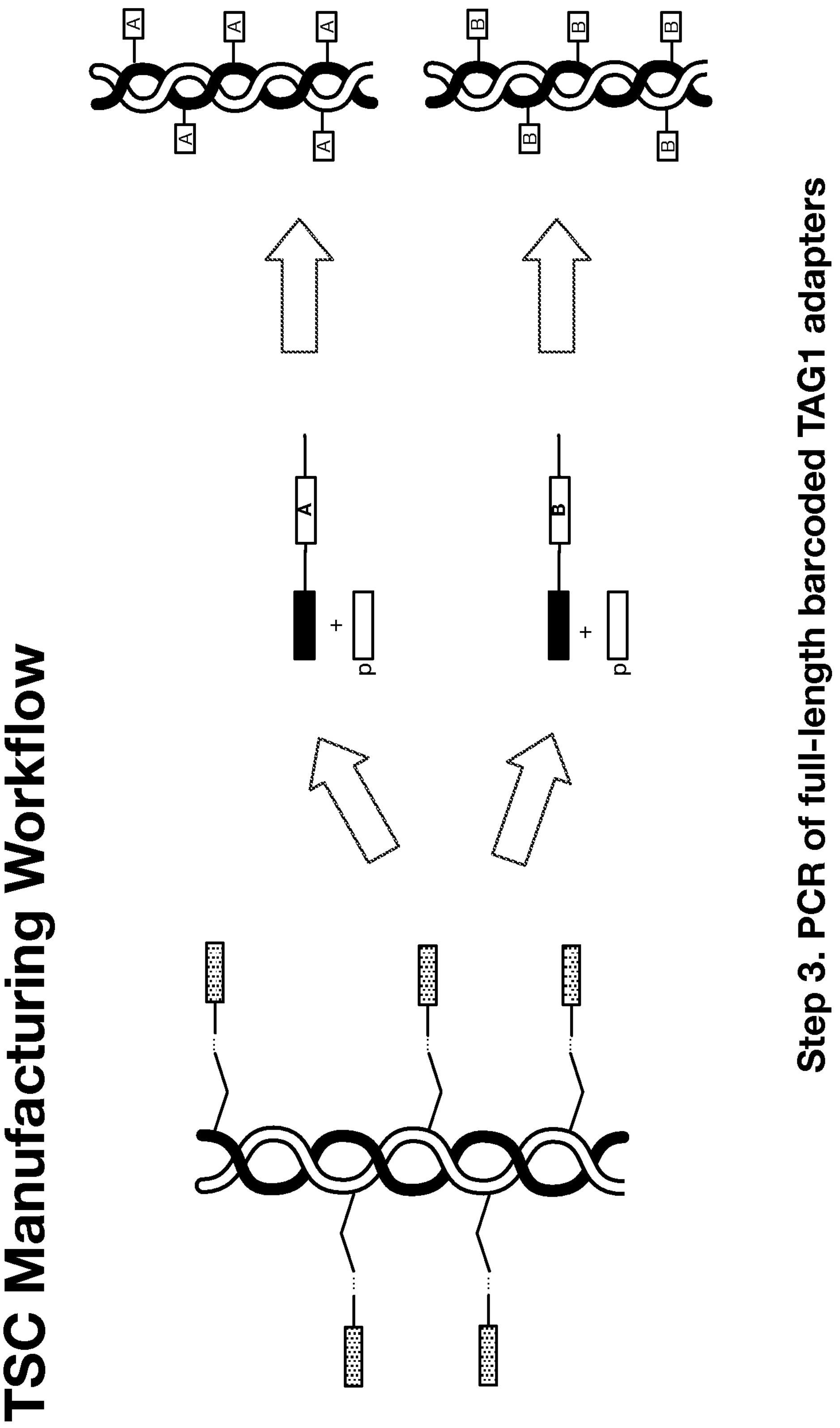
FIG. 7 illustrates the synthesis of multivalent barcoded TSC scaffolds via anchored PCR on a dsDNA substrate with covalently attached adapter sequences.

Step 3:

PCR of full-length barcoded TAG1 adapters on the multivalent core as shown in FIG. 7, and described in detail below:

1. Combined 125 fmol of template oligonucleotide (n=480 templates with different barcodes), 5 pmol multivalent core with covalently attached 5'-DBCO (Dibenzocyclooctyl) oligonucleotide prepared in the steps described above, 5 pmol TAG1-revcom-5P-primer (5'-P-CTGTCTCTTATACA-CATCTCCGAGCCCACGAGAC (SEQ ID NO: 485)), and 2×Q5 HotStart DNA Polymerase Master Mix (New England Biolabs) in a total reaction volume of 10 μl in 96 separate wells on five 96-well PCR plates (n=480 PCR reactions) (PCR served to amplify full length (80 bp) adapters on the multivalent core in each well (5'-TTTTTTTTTTTTCAAGCAGAAGACGGCATACGAGATNNNNNNNNNNGTCTCGTGGGCTCGGAGATGTGTATAAGAGACAG (SEQ ID NO: 486))).

The following sequences represent a list of all 480 template sequences used to produce full-length barcoded TAG1 adapters on the multivalent core by PCR, using the above described methods.

SEQ ID NO: 1
CAAGCAGAAGACGGCATACGAGATGTACCATGTGGTCTCGTGGGCTCGGA

GATG

SEQ ID NO: 2
CAAGCAGAAGACGGCATACGAGATGTTGCTTCCAGTCTCGTGGGCTCGGA

GATG

SEQ ID NO: 3
CAAGCAGAAGACGGCATACGAGATGTCGGTTGTTGTCTCGTGGGCTCGGA

GATG

SEQ ID NO: 4
CAAGCAGAAGACGGCATACGAGATGTGCTGTTGTGTCTCGTGGGCTCGGA

GATG

SEQ ID NO: 5
CAAGCAGAAGACGGCATACGAGATGTCTTGGATGGTCTCGTGGGCTCGGA

GATG

SEQ ID NO: 6
CAAGCAGAAGACGGCATACGAGATGTGCTTCGAAGTCTCGTGGGCTCGGA

GATG

SEQ ID NO: 7
CAAGCAGAAGACGGCATACGAGATGTCTCTACTCGTCTCGTGGGCTCGGA

GATG

SEQ ID NO: 8
CAAGCAGAAGACGGCATACGAGATGTGAACATCGGTCTCGTGGGCTCGGA

GATG

SEQ ID NO: 9
CAAGCAGAAGACGGCATACGAGATGTTGACGCATGTCTCGTGGGCTCGGA

GATG

SEQ ID NO: 10
CAAGCAGAAGACGGCATACGAGATGTGAGCTTGTGTCTCGTGGGCTCGGA

GATG

SEQ ID NO: 11
CAAGCAGAAGACGGCATACGAGATGTATGCCTGTGTCTCGTGGGCTCGGA

GATG

SEQ ID NO: 12
CAAGCAGAAGACGGCATACGAGATGTTCTTGACGGTCTCGTGGGCTCGGA

GATG

SEQ ID NO: 13
CAAGCAGAAGACGGCATACGAGATCTAGAACGAGGTCTCGTGGGCTCGGA

GATG

SEQ ID NO: 14
CAAGCAGAAGACGGCATACGAGATCTGACATGGTGTCTCGTGGGCTCGGA

GATG

-continued

SEQ ID NO: 15
CAAGCAGAAGACGGCATACGAGATCTTCACGTTCGTCTCGTGGGCTCGGA

GATG

SEQ ID NO: 16
CAAGCAGAAGACGGCATACGAGATCTTTGGTGAGGTCTCGTGGGCTCGGA

GATG

SEQ ID NO: 17
CAAGCAGAAGACGGCATACGAGATCTTGTGAAGCGTCTCGTGGGCTCGGA

GATG

SEQ ID NO: 18
CAAGCAGAAGACGGCATACGAGATCTTGGAGAGTGTCTCGTGGGCTCGGA

GATG

SEQ ID NO: 19
CAAGCAGAAGACGGCATACGAGATCTGTGAGCTTGTCTCGTGGGCTCGGA

GATG

SEQ ID NO: 20
CAAGCAGAAGACGGCATACGAGATCTTTGTGTGCGTCTCGTGGGCTCGGA

GATG

SEQ ID NO: 21
CAAGCAGAAGACGGCATACGAGATCTCTTCGTTCGTCTCGTGGGCTCGGA

GATG

SEQ ID NO: 22
CAAGCAGAAGACGGCATACGAGATCTCGTTGAGTGTCTCGTGGGCTCGGA

GATG

SEQ ID NO: 23
CAAGCAGAAGACGGCATACGAGATCTCCATACGTGTCTCGTGGGCTCGGA

GATG

SEQ ID NO: 24
CAAGCAGAAGACGGCATACGAGATCTATGACCAGGTCTCGTGGGCTCGGA

GATG

SEQ ID NO: 25
CAAGCAGAAGACGGCATACGAGATTGGAGTGGTTGTCTCGTGGGCTCGGA

GATG

SEQ ID NO: 26
CAAGCAGAAGACGGCATACGAGATTGCGCATGATGTCTCGTGGGCTCGGA

GATG

SEQ ID NO: 27
CAAGCAGAAGACGGCATACGAGATTGACCATCCAGTCTCGTGGGCTCGGA

GATG

SEQ ID NO: 28
CAAGCAGAAGACGGCATACGAGATTGTAGTTGCGGTCTCGTGGGCTCGGA

GATG

SEQ ID NO: 29
CAAGCAGAAGACGGCATACGAGATTGTATTCCGGGTCTCGTGGGCTCGGA

GATG

SEQ ID NO: 30
CAAGCAGAAGACGGCATACGAGATTGTACCAGGAGTCTCGTGGGCTCGGA

GATG

-continued

SEQ ID NO: 31
CAAGCAGAAGACGGCATACGAGATTGCTGCACTTGTCTCGTGGGCTCGGA
GATG

SEQ ID NO: 32
CAAGCAGAAGACGGCATACGAGATTGTGGATCACGTCTCGTGGGCTCGGA
GATG

SEQ ID NO: 33
CAAGCAGAAGACGGCATACGAGATTGGCAATGGAGTCTCGTGGGCTCGGA
GATG

SEQ ID NO: 34
CAAGCAGAAGACGGCATACGAGATTGTCCGTATGGTCTCGTGGGCTCGGA
GATG

SEQ ID NO: 35
CAAGCAGAAGACGGCATACGAGATTGACTCAGACGTCTCGTGGGCTCGGA
GATG

SEQ ID NO: 36
CAAGCAGAAGACGGCATACGAGATTGAAGTGTCGGTCTCGTGGGCTCGGA
GATG

SEQ ID NO: 37
CAAGCAGAAGACGGCATACGAGATAGAACTGAGCGTCTCGTGGGCTCGGA
GATG

SEQ ID NO: 38
CAAGCAGAAGACGGCATACGAGATAGCTGTGTTGGTCTCGTGGGCTCGGA
GATG

SEQ ID NO: 39
CAAGCAGAAGACGGCATACGAGATAGTCCTTAGCGTCTCGTGGGCTCGGA
GATG

SEQ ID NO: 40
CAAGCAGAAGACGGCATACGAGATAGGATTGGAGGTCTCGTGGGCTCGGA
GATG

SEQ ID NO: 41
CAAGCAGAAGACGGCATACGAGATAGACGTTCAGGTCTCGTGGGCTCGGA
GATG

SEQ ID NO: 42
CAAGCAGAAGACGGCATACGAGATAGGCGTTCTAGTCTCGTGGGCTCGGA
GATG

SEQ ID NO: 43
CAAGCAGAAGACGGCATACGAGATAGATTGCGTGGTCTCGTGGGCTCGGA
GATG

SEQ ID NO: 44
CAAGCAGAAGACGGCATACGAGATAGGTCGGTAAGTCTCGTGGGCTCGGA
GATG

SEQ ID NO: 45
CAAGCAGAAGACGGCATACGAGATAGAGAGGTTGGTCTCGTGGGCTCGGA
GATG

SEQ ID NO: 46
CAAGCAGAAGACGGCATACGAGATAGTTGAGGCAGTCTCGTGGGCTCGGA
GATG

-continued

SEQ ID NO: 47
CAAGCAGAAGACGGCATACGAGATAGTCTGCTCTGTCTCGTGGGCTCGGA
GATG

SEQ ID NO: 48
CAAGCAGAAGACGGCATACGAGATAGTGGAGTTGGTCTCGTGGGCTCGGA
GATG

SEQ ID NO: 49
CAAGCAGAAGACGGCATACGAGATTCGCCTTGTTGTCTCGTGGGCTCGGA
GATG

SEQ ID NO: 50
CAAGCAGAAGACGGCATACGAGATTCTGCCTCTTGTCTCGTGGGCTCGGA
GATG

SEQ ID NO: 51
CAAGCAGAAGACGGCATACGAGATTCCTGACACAGTCTCGTGGGCTCGGA
GATG

SEQ ID NO: 52
CAAGCAGAAGACGGCATACGAGATTCAGATGAGGGTCTCGTGGGCTCGGA
GATG

SEQ ID NO: 53
CAAGCAGAAGACGGCATACGAGATTCAGGCATAGGTCTCGTGGGCTCGGA
GATG

SEQ ID NO: 54
CAAGCAGAAGACGGCATACGAGATTCCTATCGCAGTCTCGTGGGCTCGGA
GATG

SEQ ID NO: 55
CAAGCAGAAGACGGCATACGAGATTCATAGCGGTGTCTCGTGGGCTCGGA
GATG

SEQ ID NO: 56
CAAGCAGAAGACGGCATACGAGATTCTAGCCGAAGTCTCGTGGGCTCGGA
GATG

SEQ ID NO: 57
CAAGCAGAAGACGGCATACGAGATTCATACTCCGGTCTCGTGGGCTCGGA
GATG

SEQ ID NO: 58
CAAGCAGAAGACGGCATACGAGATTCTTGCAGACGTCTCGTGGGCTCGGA
GATG

SEQ ID NO: 59
CAAGCAGAAGACGGCATACGAGATTCGGTATAGGGTCTCGTGGGCTCGGA
GATG

SEQ ID NO: 60
CAAGCAGAAGACGGCATACGAGATTCTCACAGCAGTCTCGTGGGCTCGGA
GATG

SEQ ID NO: 61
CAAGCAGAAGACGGCATACGAGATACATGGCGAAGTCTCGTGGGCTCGGA
GATG

SEQ ID NO: 62
CAAGCAGAAGACGGCATACGAGATACACCTGGAAGTCTCGTGGGCTCGGA
GATG

-continued

SEQ ID NO: 63
CAAGCAGAAGACGGCATACGAGATACTGACTGACGTCTCGTGGGCTCGGA
GATG

SEQ ID NO: 64
CAAGCAGAAGACGGCATACGAGATACTACGGTTGGTCTCGTGGGCTCGGA
GATG

SEQ ID NO: 65
CAAGCAGAAGACGGCATACGAGATACCCTTGATCGTCTCGTGGGCTCGGA
GATG

SEQ ID NO: 66
CAAGCAGAAGACGGCATACGAGATACATGGTCCAGTCTCGTGGGCTCGGA
GATG

SEQ ID NO: 67
CAAGCAGAAGACGGCATACGAGATACCCAAGCAAGTCTCGTGGGCTCGGA
GATG

SEQ ID NO: 68
CAAGCAGAAGACGGCATACGAGATACCAGCGATTGTCTCGTGGGCTCGGA
GATG

SEQ ID NO: 69
CAAGCAGAAGACGGCATACGAGATACAACGACGTGTCTCGTGGGCTCGGA
GATG

SEQ ID NO: 70
CAAGCAGAAGACGGCATACGAGATACGAGCAGTAGTCTCGTGGGCTCGGA
GATG

SEQ ID NO: 71
CAAGCAGAAGACGGCATACGAGATACGCCAGTATGTCTCGTGGGCTCGGA
GATG

SEQ ID NO: 72
CAAGCAGAAGACGGCATACGAGATACCTGAGATCGTCTCGTGGGCTCGGA
GATG

SEQ ID NO: 73
CAAGCAGAAGACGGCATACGAGATCACCATTCACGTCTCGTGGGCTCGGA
GATG

SEQ ID NO: 74
CAAGCAGAAGACGGCATACGAGATCATTCTCTCGGTCTCGTGGGCTCGGA
GATG

SEQ ID NO: 75
CAAGCAGAAGACGGCATACGAGATCAGGACCTATGTCTCGTGGGCTCGGA
GATG

SEQ ID NO: 76
CAAGCAGAAGACGGCATACGAGATCAGGATCTTCGTCTCGTGGGCTCGGA
GATG

SEQ ID NO: 77
CAAGCAGAAGACGGCATACGAGATCAACACACTCGTCTCGTGGGCTCGGA
GATG

SEQ ID NO: 78
CAAGCAGAAGACGGCATACGAGATCAGATGTGTGGTCTCGTGGGCTCGGA
GATG

-continued

SEQ ID NO: 79
CAAGCAGAAGACGGCATACGAGATCACCTGTCATGTCTCGTGGGCTCGGA
GATG

SEQ ID NO: 80
CAAGCAGAAGACGGCATACGAGATCACTAGGTGAGTCTCGTGGGCTCGGA
GATG

SEQ ID NO: 81
CAAGCAGAAGACGGCATACGAGATCAGAAGAGGTGTCTCGTGGGCTCGGA
GATG

SEQ ID NO: 82
CAAGCAGAAGACGGCATACGAGATCAGTCTTGCAGTCTCGTGGGCTCGGA
GATG

SEQ ID NO: 83
CAAGCAGAAGACGGCATACGAGATCATAGGATGCGTCTCGTGGGCTCGGA
GATG

SEQ ID NO: 84
CAAGCAGAAGACGGCATACGAGATCAGTTCATGGGTCTCGTGGGCTCGGA
GATG

SEQ ID NO: 85
CAAGCAGAAGACGGCATACGAGATGACTCCATGTGTCTCGTGGGCTCGGA
GATG

SEQ ID NO: 86
CAAGCAGAAGACGGCATACGAGATGAAACCTCCTGTCTCGTGGGCTCGGA
GATG

SEQ ID NO: 87
CAAGCAGAAGACGGCATACGAGATGAGATTACCGGTCTCGTGGGCTCGGA
GATG

SEQ ID NO: 88
CAAGCAGAAGACGGCATACGAGATGAACCGCATAGTCTCGTGGGCTCGGA
GATG

SEQ ID NO: 89
CAAGCAGAAGACGGCATACGAGATGATGGCACTAGTCTCGTGGGCTCGGA
GATG

SEQ ID NO: 90
CAAGCAGAAGACGGCATACGAGATGAGTCCACATGTCTCGTGGGCTCGGA
GATG

SEQ ID NO: 91
CAAGCAGAAGACGGCATACGAGATGAAACGTGGAGTCTCGTGGGCTCGGA
GATG

SEQ ID NO: 92
CAAGCAGAAGACGGCATACGAGATGAACTAGGAGGTCTCGTGGGCTCGGA
GATG

SEQ ID NO: 93
CAAGCAGAAGACGGCATACGAGATGATACGCCTTGTCTCGTGGGCTCGGA
GATG

SEQ ID NO: 94
CAAGCAGAAGACGGCATACGAGATGACAATGTGGGTCTCGTGGGCTCGGA
GATG

-continued

SEQ ID NO: 95
CAAGCAGAAGACGGCATACGAGATGAACTCTCGAGTCTCGTGGGCTCGGA
GATG

SEQ ID NO: 96
CAAGCAGAAGACGGCATACGAGATGACATCGTGAGTCTCGTGGGCTCGGA
GATG

SEQ ID NO: 97
CAAGCAGAAGACGGCATACGAGATGTGTCCTTCTGTCTCGTGGGCTCGGA
GATG

SEQ ID NO: 98
CAAGCAGAAGACGGCATACGAGATGTTGTACCGTGTCTCGTGGGCTCGGA
GATG

SEQ ID NO: 99
CAAGCAGAAGACGGCATACGAGATGTTGCACCAAGTCTCGTGGGCTCGGA
GATG

SEQ ID NO: 100
CAAGCAGAAGACGGCATACGAGATGTGGAGATGAGTCTCGTGGGCTCGGA
GATG

SEQ ID NO: 101
CAAGCAGAAGACGGCATACGAGATGTCTTGCTGTGTCTCGTGGGCTCGGA
GATG

SEQ ID NO: 102
CAAGCAGAAGACGGCATACGAGATGTCACTGACAGTCTCGTGGGCTCGGA
GATG

SEQ ID NO: 103
CAAGCAGAAGACGGCATACGAGATGTCAGGAGATGTCTCGTGGGCTCGGA
GATG

SEQ ID NO: 104
CAAGCAGAAGACGGCATACGAGATGTCGGCTAATGTCTCGTGGGCTCGGA
GATG

SEQ ID NO: 105
CAAGCAGAAGACGGCATACGAGATGTTCCGTGAAGTCTCGTGGGCTCGGA
GATG

SEQ ID NO: 106
CAAGCAGAAGACGGCATACGAGATGTTTACGGCTGTCTCGTGGGCTCGGA
GATG

SEQ ID NO: 107
CAAGCAGAAGACGGCATACGAGATGTATGGTTGCGTCTCGTGGGCTCGGA
GATG

SEQ ID NO: 108
CAAGCAGAAGACGGCATACGAGATGTGTACCTTGGTCTCGTGGGCTCGGA
GATG

SEQ ID NO: 109
CAAGCAGAAGACGGCATACGAGATCTGGAATTGCGTCTCGTGGGCTCGGA
GATG

SEQ ID NO: 110
CAAGCAGAAGACGGCATACGAGATCTTGGCATGTGTCTCGTGGGCTCGGA
GATG

-continued

SEQ ID NO: 111
CAAGCAGAAGACGGCATACGAGATCTTGGTACAGGTCTCGTGGGCTCGGA
GATG

SEQ ID NO: 112
CAAGCAGAAGACGGCATACGAGATCTAGTCAGGAGTCTCGTGGGCTCGGA
GATG

SEQ ID NO: 113
CAAGCAGAAGACGGCATACGAGATCTTTGGTCTCGTCTCGTGGGCTCGGA
GATG

SEQ ID NO: 114
CAAGCAGAAGACGGCATACGAGATCTAGGCTTCTGTCTCGTGGGCTCGGA
GATG

SEQ ID NO: 115
CAAGCAGAAGACGGCATACGAGATCTATCGCCATGTCTCGTGGGCTCGGA
GATG

SEQ ID NO: 116
CAAGCAGAAGACGGCATACGAGATCTGCTATCCTGTCTCGTGGGCTCGGA
GATG

SEQ ID NO: 117
CAAGCAGAAGACGGCATACGAGATCTATCCAGAGGTCTCGTGGGCTCGGA
GATG

SEQ ID NO: 118
CAAGCAGAAGACGGCATACGAGATCTGCTTCTTGGTCTCGTGGGCTCGGA
GATG

SEQ ID NO: 119
CAAGCAGAAGACGGCATACGAGATCTGTAGGAGTGTCTCGTGGGCTCGGA
GATG

SEQ ID NO: 120
CAAGCAGAAGACGGCATACGAGATCTCCAGTGTTGTCTCGTGGGCTCGGA
GATG

SEQ ID NO: 121
CAAGCAGAAGACGGCATACGAGATTGCGCTAGTAGTCTCGTGGGCTCGGA
GATG

SEQ ID NO: 122
CAAGCAGAAGACGGCATACGAGATTGGGTAGTGTGTCTCGTGGGCTCGGA
GATG

SEQ ID NO: 123
CAAGCAGAAGACGGCATACGAGATTGTCGCGATAGTCTCGTGGGCTCGGA
GATG

SEQ ID NO: 124
CAAGCAGAAGACGGCATACGAGATTGCTGATCGTGTCTCGTGGGCTCGGA
GATG

SEQ ID NO: 125
CAAGCAGAAGACGGCATACGAGATTGGTTGCGATGTCTCGTGGGCTCGGA
GATG

SEQ ID NO: 126
CAAGCAGAAGACGGCATACGAGATTGTTCGCAGTGTCTCGTGGGCTCGGA
GATG

-continued

SEQ ID NO: 127
CAAGCAGAAGACGGCATACGAGATTGCGAGACTAGTCTCGTGGGCTCGGA

GATG

SEQ ID NO: 128
CAAGCAGAAGACGGCATACGAGATTGGAGATACGGTCTCGTGGGCTCGGA

GATG

SEQ ID NO: 129
CAAGCAGAAGACGGCATACGAGATTGTTACCGAGGTCTCGTGGGCTCGGA

GATG

SEQ ID NO: 130
CAAGCAGAAGACGGCATACGAGATTGGATTCAGCGTCTCGTGGGCTCGGA

GATG

SEQ ID NO: 131
CAAGCAGAAGACGGCATACGAGATTGTCGCTGTTGTCTCGTGGGCTCGGA

GATG

SEQ ID NO: 132
CAAGCAGAAGACGGCATACGAGATTGTGCCATTCGTCTCGTGGGCTCGGA

GATG

SEQ ID NO: 133
CAAGCAGAAGACGGCATACGAGATAGGTCCTAAGGTCTCGTGGGCTCGGA

GATG

SEQ ID NO: 134
CAAGCAGAAGACGGCATACGAGATAGGACGAATGGTCTCGTGGGCTCGGA

GATG

SEQ ID NO: 135
CAAGCAGAAGACGGCATACGAGATAGAAGTCCGTGTCTCGTGGGCTCGGA

GATG

SEQ ID NO: 136
CAAGCAGAAGACGGCATACGAGATAGGAAGGTTCGTCTCGTGGGCTCGGA

GATG

SEQ ID NO: 137
CAAGCAGAAGACGGCATACGAGATAGGATTGCTCGTCTCGTGGGCTCGGA

GATG

SEQ ID NO: 138
CAAGCAGAAGACGGCATACGAGATAGGAGATGTCGTCTCGTGGGCTCGGA

GATG

SEQ ID NO: 139
CAAGCAGAAGACGGCATACGAGATAGACACGGTTGTCTCGTGGGCTCGGA

GATG

SEQ ID NO: 140
CAAGCAGAAGACGGCATACGAGATAGAGTCGCTTGTCTCGTGGGCTCGGA

GATG

SEQ ID NO: 141
CAAGCAGAAGACGGCATACGAGATAGCTAACTCGGTCTCGTGGGCTCGGA

GATG

SEQ ID NO: 142
CAAGCAGAAGACGGCATACGAGATAGACGACAGAGTCTCGTGGGCTCGGA

GATG

-continued

SEQ ID NO: 143
CAAGCAGAAGACGGCATACGAGATAGAGCAAGCAGTCTCGTGGGCTCGGA

GATG

SEQ ID NO: 144
CAAGCAGAAGACGGCATACGAGATAGGAACGCTTGTCTCGTGGGCTCGGA

GATG

SEQ ID NO: 145
CAAGCAGAAGACGGCATACGAGATTCGTATTGGCGTCTCGTGGGCTCGGA

GATG

SEQ ID NO: 146
CAAGCAGAAGACGGCATACGAGATTCCGCAATCTGTCTCGTGGGCTCGGA

GATG

SEQ ID NO: 147
CAAGCAGAAGACGGCATACGAGATTCGTGCTTACGTCTCGTGGGCTCGGA

GATG

SEQ ID NO: 148
CAAGCAGAAGACGGCATACGAGATTCAACCTTGGGTCTCGTGGGCTCGGA

GATG

SEQ ID NO: 149
CAAGCAGAAGACGGCATACGAGATTCGGAAGCTAGTCTCGTGGGCTCGGA

GATG

SEQ ID NO: 150
CAAGCAGAAGACGGCATACGAGATTCGTTACGCAGTCTCGTGGGCTCGGA

GATG

SEQ ID NO: 151
CAAGCAGAAGACGGCATACGAGATTCCGACGTTAGTCTCGTGGGCTCGGA

GATG

SEQ ID NO: 152
CAAGCAGAAGACGGCATACGAGATTCAGCGTGTTGTCTCGTGGGCTCGGA

GATG

SEQ ID NO: 153
CAAGCAGAAGACGGCATACGAGATTCACCTTCTCGTCTCGTGGGCTCGGA

GATG

SEQ ID NO: 154
CAAGCAGAAGACGGCATACGAGATTCCATTGCCTGTCTCGTGGGCTCGGA

GATG

SEQ ID NO: 155
CAAGCAGAAGACGGCATACGAGATTCATCTTCGGGTCTCGTGGGCTCGGA

GATG

SEQ ID NO: 156
CAAGCAGAAGACGGCATACGAGATTCTGACTTCGGTCTCGTGGGCTCGGA

GATG

SEQ ID NO: 157
CAAGCAGAAGACGGCATACGAGATACAACTGGTGGTCTCGTGGGCTCGGA

GATG

SEQ ID NO: 158
CAAGCAGAAGACGGCATACGAGATACTCAAGGACGTCTCGTGGGCTCGGA

GATG

-continued

SEQ ID NO: 159
CAAGCAGAAGACGGCATACGAGATACATTCGAGGGTCTCGTGGGCTCGGA
GATG

SEQ ID NO: 160
CAAGCAGAAGACGGCATACGAGATACGGCTATTGGTCTCGTGGGCTCGGA
GATG

SEQ ID NO: 161
CAAGCAGAAGACGGCATACGAGATACCCGTATCTGTCTCGTGGGCTCGGA
GATG

SEQ ID NO: 162
CAAGCAGAAGACGGCATACGAGATACGGATACCAGTCTCGTGGGCTCGGA
GATG

SEQ ID NO: 163
CAAGCAGAAGACGGCATACGAGATACCGATGCTTGTCTCGTGGGCTCGGA
GATG

SEQ ID NO: 164
CAAGCAGAAGACGGCATACGAGATACTCTAACGCGTCTCGTGGGCTCGGA
GATG

SEQ ID NO: 165
CAAGCAGAAGACGGCATACGAGATACATGTAGCGGTCTCGTGGGCTCGGA
GATG

SEQ ID NO: 166
CAAGCAGAAGACGGCATACGAGATACCAATCGACGTCTCGTGGGCTCGGA
GATG

SEQ ID NO: 167
CAAGCAGAAGACGGCATACGAGATACGAGGACTTGTCTCGTGGGCTCGGA
GATG

SEQ ID NO: 168
CAAGCAGAAGACGGCATACGAGATACGGTGATTCGTCTCGTGGGCTCGGA
GATG

SEQ ID NO: 169
CAAGCAGAAGACGGCATACGAGATCATAACGAGGGTCTCGTGGGCTCGGA
GATG

SEQ ID NO: 170
CAAGCAGAAGACGGCATACGAGATCACACGTTGTGTCTCGTGGGCTCGGA
GATG

SEQ ID NO: 171
CAAGCAGAAGACGGCATACGAGATCATGTTCGAGGTCTCGTGGGCTCGGA
GATG

SEQ ID NO: 172
CAAGCAGAAGACGGCATACGAGATCATCTCTAGGGTCTCGTGGGCTCGGA
GATG

SEQ ID NO: 173
CAAGCAGAAGACGGCATACGAGATCAGTGCCATAGTCTCGTGGGCTCGGA
GATG

SEQ ID NO: 174
CAAGCAGAAGACGGCATACGAGATCATTAAGCGGGTCTCGTGGGCTCGGA
GATG

-continued

SEQ ID NO: 175
CAAGCAGAAGACGGCATACGAGATCAGAAGTTGGGTCTCGTGGGCTCGGA
GATG

SEQ ID NO: 176
CAAGCAGAAGACGGCATACGAGATCATACACGCTGTCTCGTGGGCTCGGA
GATG

SEQ ID NO: 177
CAAGCAGAAGACGGCATACGAGATCACAGTGAAGGTCTCGTGGGCTCGGA
GATG

SEQ ID NO: 178
CAAGCAGAAGACGGCATACGAGATCACTACAGTGGTCTCGTGGGCTCGGA
GATG

SEQ ID NO: 179
CAAGCAGAAGACGGCATACGAGATCAGTGGTGTTGTCTCGTGGGCTCGGA
GATG

SEQ ID NO: 180
CAAGCAGAAGACGGCATACGAGATCACTTCACCAGTCTCGTGGGCTCGGA
GATG

SEQ ID NO: 181
CAAGCAGAAGACGGCATACGAGATGAAAGAGCCAGTCTCGTGGGCTCGGA
GATG

SEQ ID. NO: 182
CAAGCAGAAGACGGCATACGAGATGAAGGTCACTGTCTCGTGGGCTCGGA
GATG

SEQ ID NO: 183
CAAGCAGAAGACGGCATACGAGATGAAACCGTTCGTCTCGTGGGCTCGGA
GATG

SEQ ID NO: 184
CAAGCAGAAGACGGCATACGAGATGAAGCGGAATGTCTCGTGGGCTCGGA
GATG

SEQ ID NO: 185
CAAGCAGAAGACGGCATACGAGATGAAAGCCACAGTCTCGTGGGCTCGGA
GATG

SEQ ID NO: 186
CAAGCAGAAGACGGCATACGAGATGACTTACAGCGTCTCGTGGGCTCGGA
GATG

SEQ ID NO: 187
CAAGCAGAAGACGGCATACGAGATGAGCGATAGTGTCTCGTGGGCTCGGA
GATG

SEQ ID NO: 188
CAAGCAGAAGACGGCATACGAGATGAGAACACACGTCTCGTGGGCTCGGA
GATG

SEQ ID NO: 189
CAAGCAGAAGACGGCATACGAGATGACAACACCTGTCTCGTGGGCTCGGA
GATG

SEQ ID NO: 190
CAAGCAGAAGACGGCATACGAGATGAACACCAGTGTCTCGTGGGCTCGGA
GATG

-continued

SEQ ID NO: 191
CAAGCAGAAGACGGCATACGAGATGAGCTGACTAGTCTCGTGGGCTCGGA
GATG

SEQ ID NO: 192
CAAGCAGAAGACGGCATACGAGATGAGAGACGATGTCTCGTGGGCTCGGA
GATG

SEQ ID NO: 193
CAAGCAGAAGACGGCATACGAGATGTTGGTCCTTGTCTCGTGGGCTCGGA
GATG

SEQ ID NO: 194
CAAGCAGAAGACGGCATACGAGATGTCTTAGGACGTCTCGTGGGCTCGGA
GATG

SEQ ID NO: 195
CAAGCAGAAGACGGCATACGAGATGTTCGCATTGGTCTCGTGGGCTCGGA
GATG

SEQ ID NO: 196
CAAGCAGAAGACGGCATACGAGATGTCTAGCAAGGTCTCGTGGGCTCGGA
GATG

SEQ ID NO: 197
CAAGCAGAAGACGGCATACGAGATGTGGTCTTAGGTCTCGTGGGCTCGGA
GATG

SEQ ID NO: 198
CAAGCAGAAGACGGCATACGAGATGTACGGTCTTGTCTCGTGGGCTCGGA
GATG

SEQ ID NO: 199
CAAGCAGAAGACGGCATACGAGATGTACGACTTGGTCTCGTGGGCTCGGA
GATG

SEQ ID NO: 200
CAAGCAGAAGACGGCATACGAGATGTTGCGAACTGTCTCGTGGGCTCGGA
GATG

SEQ ID NO: 201
CAAGCAGAAGACGGCATACGAGATGTGGACAATCGTCTCGTGGGCTCGGA
GATG

SEQ ID NO: 202
CAAGCAGAAGACGGCATACGAGATGTTTCTCGACGTCTCGTGGGCTCGGA
GATG

SEQ ID NO: 203
CAAGCAGAAGACGGCATACGAGATGTTAAGTGGCGTCTCGTGGGCTCGGA
GATG

SEQ ID NO: 204
CAAGCAGAAGACGGCATACGAGATGTATCGGTGTGTCTCGTGGGCTCGGA
GATG

SEQ ID NO: 205
CAAGCAGAAGACGGCATACGAGATCTGCTGTAAGGTCTCGTGGGCTCGGA
GATG

SEQ ID NO: 206
CAAGCAGAAGACGGCATACGAGATCTGTGAAGTGGTCTCGTGGGCTCGGA
GATG

-continued

SEQ ID NO: 207
CAAGCAGAAGACGGCATACGAGATCTAAGGCGTTGTCTCGTGGGCTCGGA
GATG

SEQ ID NO: 208
CAAGCAGAAGACGGCATACGAGATCTTCACTCTGGTCTCGTGGGCTCGGA
GATG

SEQ ID NO: 209
CAAGCAGAAGACGGCATACGAGATCTGTCTAGGTGTCTCGTGGGCTCGGA
GATG

SEQ ID NO: 210
CAAGCAGAAGACGGCATACGAGATCTCCTTGTAGGTCTCGTGGGCTCGGA
GATG

SEQ ID NO: 211
CAAGCAGAAGACGGCATACGAGATCTCATTCGGTGTCTCGTGGGCTCGGA
GATG

SEQ ID NO: 212
CAAGCAGAAGACGGCATACGAGATCTGATGCACTGTCTCGTGGGCTCGGA
GATG

SEQ ID NO: 213
CAAGCAGAAGACGGCATACGAGATCTTGTGCGTTGTCTCGTGGGCTCGGA
GATG

SEQ ID NO: 214
CAAGCAGAAGACGGCATACGAGATCTCCAATAGGGTCTCGTGGGCTCGGA
GATG

SEQ ID NO: 215
CAAGCAGAAGACGGCATACGAGATCTGTTCGGTTGTCTCGTGGGCTCGGA
GATG

SEQ ID NO: 216
CAAGCAGAAGACGGCATACGAGATCTTGGTAGCTGTCTCGTGGGCTCGGA
GATG

SEQ ID NO: 217
CAAGCAGAAGACGGCATACGAGATTGGTATGCTGGTCTCGTGGGCTCGGA
GATG

SEQ ID NO: 218
CAAGCAGAAGACGGCATACGAGATTGCGCTTAACGTCTCGTGGGCTCGGA
GATG

SEQ ID NO: 219
CAAGCAGAAGACGGCATACGAGATTGCTCCTAGAGTCTCGTGGGCTCGGA
GATG

SEQ ID NO: 220
CAAGCAGAAGACGGCATACGAGATTGCTTCTGAGGTCTCGTGGGCTCGGA
GATG

SEQ ID NO: 221
CAAGCAGAAGACGGCATACGAGATTGAGCAGATGGTCTCGTGGGCTCGGA
GATG

SEQ ID NO: 222
CAAGCAGAAGACGGCATACGAGATTGCCGTAAGAGTCTCGTGGGCTCGGA
GATG

-continued

SEQ ID NO: 223
CAAGCAGAAGACGGCATACGAGATTGTTGATCCGGTCTCGTGGGCTCGGA
GATG

SEQ ID NO: 224
CAAGCAGAAGACGGCATACGAGATTGTGCAGGTAGTCTCGTGGGCTCGGA
GATG

SEQ ID NO: 225
CAAGCAGAAGACGGCATACGAGATTGCAGGTTAGGTCTCGTGGGCTCGGA
GATG

SEQ ID NO: 226
CAAGCAGAAGACGGCATACGAGATTGTACGCTACGTCTCGTGGGCTCGGA
GATG

SEQ ID NO: 227
CAAGCAGAAGACGGCATACGAGATTGCCAGGATAGTCTCGTGGGCTCGGA
GATG

SEQ ID NO: 228
CAAGCAGAAGACGGCATACGAGATTGCGTGTGTAGTCTCGTGGGCTCGGA
GATG

SEQ ID NO: 229
CAAGCAGAAGACGGCATACGAGATAGGTTGTAGCGTCTCGTGGGCTCGGA
GATG

SEQ ID NO: 230
CAAGCAGAAGACGGCATACGAGATAGCAGTCTTCGTCTCGTGGGCTCGGA
GATG

SEQ ID NO: 231
CAAGCAGAAGACGGCATACGAGATAGAGCACTTCGTCTCGTGGGCTCGGA
GATG

SEQ ID NO: 232
CAAGCAGAAGACGGCATACGAGATAGACTCGTTGGTCTCGTGGGCTCGGA
GATG

SEQ ID NO: 233
CAAGCAGAAGACGGCATACGAGATAGTAGGTAGGGTCTCGTGGGCTCGGA
GATG

SEQ ID NO: 234
CAAGCAGAAGACGGCATACGAGATAGGTCTGATCGTCTCGTGGGCTCGGA
GATG

SEQ ID NO: 235
CAAGCAGAAGACGGCATACGAGATAGACAGCTCAGTCTCGTGGGCTCGGA
GATG

SEQ ID NO: 236
CAAGCAGAAGACGGCATACGAGATAGCCGATGTAGTCTCGTGGGCTCGGA
GATG

SEQ ID NO: 237
CAAGCAGAAGACGGCATACGAGATAGCTGTTGACGTCTCGTGGGCTCGGA
GATG

SEQ ID NO: 238
CAAGCAGAAGACGGCATACGAGATAGTAGCGTCTGTCTCGTGGGCTCGGA
GATG

-continued

SEQ ID NO: 239
CAAGCAGAAGACGGCATACGAGATAGAACCGAAGGTCTCGTGGGCTCGGA
GATG

SEQ ID NO: 240
CAAGCAGAAGACGGCATACGAGATAGCTTACCTGGTCTCGTGGGCTCGGA
GATG

SEQ ID NO: 241
CAAGCAGAAGACGGCATACGAGATTCAGTTACGGGTCTCGTGGGCTCGGA
GATG

SEQ ID NO: 242
CAAGCAGAAGACGGCATACGAGATTCCATCCTCTGTCTCGTGGGCTCGGA
GATG

SEQ ID NO: 243
CAAGCAGAAGACGGCATACGAGATTCGTAACGACGTCTCGTGGGCTCGGA
GATG

SEQ ID NO: 244
CAAGCAGAAGACGGCATACGAGATTCGTCGAAGAGTCTCGTGGGCTCGGA
GATG

SEQ ID NO: 245
CAAGCAGAAGACGGCATACGAGATTCCAGTTCTGGTCTCGTGGGCTCGGA
GATG

SEQ ID NO: 246
CAAGCAGAAGACGGCATACGAGATTCGGTGTCTTGTCTCGTGGGCTCGGA
GATG

SEQ ID NO: 247
CAAGCAGAAGACGGCATACGAGATTCACATTGCGGTCTCGTGGGCTCGGA
GATG

SEQ ID NO: 248
CAAGCAGAAGACGGCATACGAGATTCACGGAACAGTCTCGTGGGCTCGGA
GATG

SEQ ID NO: 249
CAAGCAGAAGACGGCATACGAGATTCCCTGATTGGTCTCGTGGGCTCGGA
GATG

SEQ ID NO: 250
CAAGCAGAAGACGGCATACGAGATTCACGGATTCGTCTCGTGGGCTCGGA
GATG

SEQ ID NO: 251
CAAGCAGAAGACGGCATACGAGATTCTTGACAGGGTCTCGTGGGCTCGGA
GATG

SEQ ID NO: 252
CAAGCAGAAGACGGCATACGAGATTCTGTGGTACGTCTCGTGGGCTCGGA
GATG

SEQ ID NO: 253
CAAGCAGAAGACGGCATACGAGATACACTCCATCGTCTCGTGGGCTCGGA
GATG

SEQ ID NO: 254
CAAGCAGAAGACGGCATACGAGATACTCGAAGGTGTCTCGTGGGCTCGGA
GATG

-continued

SEQ ID NO: 255
CAAGCAGAAGACGGCATACGAGATACAGTCTGTGGTCTCGTGGGCTCGGA
GATG

SEQ ID NO: 256
CAAGCAGAAGACGGCATACGAGATACCTAGGCATGTCTCGTGGGCTCGGA
GATG

SEQ ID NO: 257
CAAGCAGAAGACGGCATACGAGATACAACAACCGGTCTCGTGGGCTCGGA
GATG

SEQ ID NO: 258
CAAGCAGAAGACGGCATACGAGATACCGTTGCAAGTCTCGTGGGCTCGGA
GATG

SEQ ID NO: 259
CAAGCAGAAGACGGCATACGAGATACGCTACGTTGTCTCGTGGGCTCGGA
GATG

SEQ ID NO: 260
CAAGCAGAAGACGGCATACGAGATACGACAAGAGGTCTCGTGGGCTCGGA
GATG

SEQ ID NO: 261
CAAGCAGAAGACGGCATACGAGATACTCGAGTGAGTCTCGTGGGCTCGGA
GATG

SEQ ID NO: 262
CAAGCAGAAGACGGCATACGAGATACAGGTTCGAGTCTCGTGGGCTCGGA
GATG

SEQ ID NO: 263
CAAGCAGAAGACGGCATACGAGATACCGTCAATGGTCTCGTGGGCTCGGA
GATG

SEQ ID NO: 264
CAAGCAGAAGACGGCATACGAGATACCGAGTATGGTCTCGTGGGCTCGGA
GATG

SEQ ID NO: 265
CAAGCAGAAGACGGCATACGAGATCATCCTACCTGTCTCGTGGGCTCGGA
GATG

SEQ ID NO: 266
CAAGCAGAAGACGGCATACGAGATCAAGCCAAGTGTCTCGTGGGCTCGGA
GATG

SEQ ID NO: 267
CAAGCAGAAGACGGCATACGAGATCAGCGTCATTGTCTCGTGGGCTCGGA
GATG

SEQ ID NO: 268
CAAGCAGAAGACGGCATACGAGATCACAGAATCGGTCTCGTGGGCTCGGA
GATG

SEQ ID NO: 269
CAAGCAGAAGACGGCATACGAGATCAATCGATCGGTCTCGTGGGCTCGGA
GATG

SEQ ID NO: 270
CAAGCAGAAGACGGCATACGAGATCATGAGGTGTGTCTCGTGGGCTCGGA
GATG

-continued

SEQ ID NO: 271
CAAGCAGAAGACGGCATACGAGATCAGACGATCTGTCTCGTGGGCTCGGA
GATG

SEQ ID NO: 272
CAAGCAGAAGACGGCATACGAGATCACAACGGATGTCTCGTGGGCTCGGA
GATG

SEQ ID NO: 273
CAAGCAGAAGACGGCATACGAGATCAAGTCGACAGTCTCGTGGGCTCGGA
GATG

SEQ ID NO: 274
CAAGCAGAAGACGGCATACGAGATCAGATCGAGTGTCTCGTGGGCTCGGA
GATG

SEQ ID NO: 275
CAAGCAGAAGACGGCATACGAGATCATCAGACGAGTCTCGTGGGCTCGGA
GATG

SEQ ID NO: 276
CAAGCAGAAGACGGCATACGAGATCACACCACTAGTCTCGTGGGCTCGGA
GATG

SEQ ID NO: 277
CAAGCAGAAGACGGCATACGAGATGACTCTGGTTGTCTCGTGGGCTCGGA
GATG

SEQ ID NO: 278
CAAGCAGAAGACGGCATACGAGATGATACCACAGGTCTCGTGGGCTCGGA
GATG

SEQ ID NO: 279
CAAGCAGAAGACGGCATACGAGATGAGACTTAGGGTCTCGTGGGCTCGGA
GATG

SEQ ID NO: 280
CAAGCAGAAGACGGCATACGAGATGATCTGAGAGGTCTCGTGGGCTCGGA
GATG

SEQ ID NO: 281
CAAGCAGAAGACGGCATACGAGATGAGTTCTCGTGTCTCGTGGGCTCGGA
GATG

SEQ ID NO: 282
CAAGCAGAAGACGGCATACGAGATGAGCTTAGCTGTCTCGTGGGCTCGGA
GATG

SEQ ID NO: 283
CAAGCAGAAGACGGCATACGAGATGAGTGGATAGGTCTCGTGGGCTCGGA
GATG

SEQ ID NO: 284
CAAGCAGAAGACGGCATACGAGATGACATAACGGGTCTCGTGGGCTCGGA
GATG

SEQ ID NO: 285
CAAGCAGAAGACGGCATACGAGATGAACCTAAGGGTCTCGTGGGCTCGGA
GATG

SEQ ID NO: 286
CAAGCAGAAGACGGCATACGAGATGATCGACATCGTCTCGTGGGCTCGGA
GATG

-continued

SEQ ID NO: 287
CAAGCAGAAGACGGCATACGAGATGAGCTCTGTAGTCTCGTGGGCTCGGA
GATG

SEQ ID NO: 288
CAAGCAGAAGACGGCATACGAGATGAACTGCTAGGTCTCGTGGGCTCGGA
GATG

SEQ ID NO: 289
CAAGCAGAAGACGGCATACGAGATGTAGAGCCTTGTCTCGTGGGCTCGGA
GATG

SEQ ID NO: 290
CAAGCAGAAGACGGCATACGAGATGTTGCTTGGTGTCTCGTGGGCTCGGA
GATG

SEQ ID NO: 291
CAAGCAGAAGACGGCATACGAGATGTATCACACGGTCTCGTGGGCTCGGA
GATG

SEQ ID NO: 292
CAAGCAGAAGACGGCATACGAGATGTGTTGTTCGGTCTCGTGGGCTCGGA
GATG

SEQ ID NO: 293
CAAGCAGAAGACGGCATACGAGATGTTGCGTAGAGTCTCGTGGGCTCGGA
GATG

SEQ ID NO: 294
CAAGCAGAAGACGGCATACGAGATGTCATGGAACGTCTCGTGGGCTCGGA
GATG

SEQ ID NO: 295
CAAGCAGAAGACGGCATACGAGATGTCTGTTAGGGTCTCGTGGGCTCGGA
GATG

SEQ ID NO: 296
CAAGCAGAAGACGGCATACGAGATGTGGTACTACGTCTCGTGGGCTCGGA
GATG

SEQ ID NO: 297
CAAGCAGAAGACGGCATACGAGATGTGCCACTTAGTCTCGTGGGCTCGGA
GATG

SEQ ID NO: 298
CAAGCAGAAGACGGCATACGAGATGTTATCAGCGGTCTCGTGGGCTCGGA
GATG

SEQ ID NO: 299
CAAGCAGAAGACGGCATACGAGATGTCTTCGACTGTCTCGTGGGCTCGGA
GATG

SEQ ID NO: 300
CAAGCAGAAGACGGCATACGAGATGTCGAAGAACGTCTCGTGGGCTCGGA
GATG

SEQ ID NO: 301
CAAGCAGAAGACGGCATACGAGATCTCACCTTACGTCTCGTGGGCTCGGA
GATG

SEQ ID NO: 302
CAAGCAGAAGACGGCATACGAGATCTACATAGGCGTCTCGTGGGCTCGGA
GATG

-continued

SEQ ID NO: 303
CAAGCAGAAGACGGCATACGAGATCTTGTCTGCTGTCTCGTGGGCTCGGA
GATG

SEQ ID NO: 304
CAAGCAGAAGACGGCATACGAGATCTCAGTCCAAGTCTCGTGGGCTCGGA
GATG

SEQ ID NO: 305
CAAGCAGAAGACGGCATACGAGATCTGTCTCCTTGTCTCGTGGGCTCGGA
GATG

SEQ ID NO: 306
CAAGCAGAAGACGGCATACGAGATCTCAACCTAGGTCTCGTGGGCTCGGA
GATG

SEQ ID NO: 307
CAAGCAGAAGACGGCATACGAGATCTAACGTCTGGTCTCGTGGGCTCGGA
GATG

SEQ ID NO: 308
CAAGCAGAAGACGGCATACGAGATCTCCTCAGTTGTCTCGTGGGCTCGGA
GATG

SEQ ID NO: 309
CAAGCAGAAGACGGCATACGAGATCTCCTACTGAGTCTCGTGGGCTCGGA
GATG

SEQ ID NO: 310
CAAGCAGAAGACGGCATACGAGATCTGCATACAGGTCTCGTGGGCTCGGA
GATG

SEQ ID NO: 311
CAAGCAGAAGACGGCATACGAGATCTGTTAAGGCGTCTCGTGGGCTCGGA
GATG

SEQ ID NO: 312
CAAGCAGAAGACGGCATACGAGATCTTTGCGAAGGTCTCGTGGGCTCGGA
GATG

SEQ ID NO: 313
CAAGCAGAAGACGGCATACGAGATTGTTGGCTTGGTCTCGTGGGCTCGGA
GATG

SEQ ID NO: 314
CAAGCAGAAGACGGCATACGAGATTGATGCACGAGTCTCGTGGGCTCGGA
GATG

SEQ ID NO: 315
CAAGCAGAAGACGGCATACGAGATTGGGCAAGTTGTCTCGTGGGCTCGGA
GATG

SEQ ID NO: 316
CAAGCAGAAGACGGCATACGAGATTGGGACTGTTGTCTCGTGGGCTCGGA
GATG

SEQ ID NO: 317
CAAGCAGAAGACGGCATACGAGATTGTGTTGTGGGTCTCGTGGGCTCGGA
GATG

SEQ ID NO: 318
CAAGCAGAAGACGGCATACGAGATTGTCCAATCGGTCTCGTGGGCTCGGA
GATG

-continued

SEQ ID NO: 319
CAAGCAGAAGACGGCATACGAGATTGCTGCGTATGTCTCGTGGGCTCGGA
GATG

SEQ ID NO: 320
CAAGCAGAAGACGGCATACGAGATTGGAAGGAAGGTCTCGTGGGCTCGGA
GATG

SEQ ID NO: 321
CAAGCAGAAGACGGCATACGAGATTGCTGGAGTAGTCTCGTGGGCTCGGA
GATG

SEQ ID NO: 322
CAAGCAGAAGACGGCATACGAGATTGTCCTGCTAGTCTCGTGGGCTCGGA
GATG

SEQ ID NO: 323
CAAGCAGAAGACGGCATACGAGATTGCGTTATGCGTCTCGTGGGCTCGGA
GATG

SEQ ID NO: 324
CAAGCAGAAGACGGCATACGAGATTGCTACTTGGGTCTCGTGGGCTCGGA
GATG

SEQ ID NO: 325
CAAGCAGAAGACGGCATACGAGATAGAGTTGGCTGTCTCGTGGGCTCGGA
GATG

SEQ ID NO: 326
CAAGCAGAAGACGGCATACGAGATAGAGGTGTACGTCTCGTGGGCTCGGA
GATG

SEQ ID NO: 327
CAAGCAGAAGACGGCATACGAGATAGCGATAGAGGTCTCGTGGGCTCGGA
GATG

SEQ ID NO: 328
CAAGCAGAAGACGGCATACGAGATAGATAAGGCGGTCTCGTGGGCTCGGA
GATG

SEQ ID NO: 329
CAAGCAGAAGACGGCATACGAGATAGGTAGTCAGGTCTCGTGGGCTCGGA
GATG

SEQ ID NO: 330
CAAGCAGAAGACGGCATACGAGATAGCAAGCAGTGTCTCGTGGGCTCGGA
GATG

SEQ ID NO: 331
CAAGCAGAAGACGGCATACGAGATAGTGTCCAGAGTCTCGTGGGCTCGGA
GATG

SEQ ID NO: 332
CAAGCAGAAGACGGCATACGAGATAGTCGTTCGTGTCTCGTGGGCTCGGA
GATG

SEQ ID NO: 333
CAAGCAGAAGACGGCATACGAGATAGTCTTCTGCGTCTCGTGGGCTCGGA
GATG

SEQ ID NO: 334
CAAGCAGAAGACGGCATACGAGATAGCTGAAGCTGTCTCGTGGGCTCGGA
GATG

-continued

SEQ ID NO: 335
CAAGCAGAAGACGGCATACGAGATAGCATGAGGAGTCTCGTGGGCTCGGA
GATG

SEQ ID NO: 336
CAAGCAGAAGACGGCATACGAGATAGACTGTGTCGTCTCGTGGGCTCGGA
GATG

SEQ ID NO: 337
CAAGCAGAAGACGGCATACGAGATTCGGCGTTATGTCTCGTGGGCTCGGA
GATG

SEQ ID NO: 338
CAAGCAGAAGACGGCATACGAGATTCTGTAGCCAGTCTCGTGGGCTCGGA
GATG

SEQ ID NO: 339
CAAGCAGAAGACGGCATACGAGATTCCGACCATTGTCTCGTGGGCTCGGA
GATG

SEQ ID NO: 340
CAAGCAGAAGACGGCATACGAGATTCATGACGTCGTCTCGTGGGCTCGGA
GATG

SEQ ID NO: 341
CAAGCAGAAGACGGCATACGAGATTCTACATCGGGTCTCGTGGGCTCGGA
GATG

SEQ ID NO: 342
CAAGCAGAAGACGGCATACGAGATTCGTCACTGTGTCTCGTGGGCTCGGA
GATG

SEQ ID NO: 343
CAAGCAGAAGACGGCATACGAGATTCGATAGGCTGTCTCGTGGGCTCGGA
GATG

SEQ ID NO: 344
CAAGCAGAAGACGGCATACGAGATTCTTGTCGGTGTCTCGTGGGCTCGGA
GATG

SEQ ID NO: 345
CAAGCAGAAGACGGCATACGAGATTCAGACCGTAGTCTCGTGGGCTCGGA
GATG

SEQ ID NO: 346
CAAGCAGAAGACGGCATACGAGATTCCGAACTGTGTCTCGTGGGCTCGGA
GATG

SEQ ID NO: 347
CAAGCAGAAGACGGCATACGAGATTCCACTAGCTGTCTCGTGGGCTCGGA
GATG

SEQ ID NO: 348
CAAGCAGAAGACGGCATACGAGATTCTCTCGTGTGTCTCGTGGGCTCGGA
GATG

SEQ ID NO: 349
CAAGCAGAAGACGGCATACGAGATACGCCTATCAGTCTCGTGGGCTCGGA
GATG

SEQ ID NO: 350
CAAGCAGAAGACGGCATACGAGATACGATAGCGAGTCTCGTGGGCTCGGA
GATG

-continued

SEQ ID NO: 351
CAAGCAGAAGACGGCATACGAGATACTCGAACCAGTCTCGTGGGCTCGGA
GATG

SEQ ID NO: 352
CAAGCAGAAGACGGCATACGAGATACAGTGCAGTGTCTCGTGGGCTCGGA
GATG

SEQ ID NO: 353
CAAGCAGAAGACGGCATACGAGATACTGTGACTGGTCTCGTGGGCTCGGA
GATG

SEQ ID NO: 354
CAAGCAGAAGACGGCATACGAGATACGGTTGATGGTCTCGTGGGCTCGGA
GATG

SEQ ID NO: 355
CAAGCAGAAGACGGCATACGAGATACTAGACGTGGTCTCGTGGGCTCGGA
GATG

SEQ ID NO: 356
CAAGCAGAAGACGGCATACGAGATACAGAAGCGTGTCTCGTGGGCTCGGA
GATG

SEQ ID NO: 357
CAAGCAGAAGACGGCATACGAGATACCGTAGGTTGTCTCGTGGGCTCGGA
GATG

SEQ ID NO: 358
CAAGCAGAAGACGGCATACGAGATACCAGAGTGTGTCTCGTGGGCTCGGA
GATG

SEQ ID NO: 359
CAAGCAGAAGACGGCATACGAGATACTGCTCATGGTCTCGTGGGCTCGGA
GATG

SEQ ID NO: 360
CAAGCAGAAGACGGCATACGAGATACTCATGGTGGTCTCGTGGGCTCGGA
GATG

SEQ ID NO: 361
CAAGCAGAAGACGGCATACGAGATCACGTACGAAGTCTCGTGGGCTCGGA
GATG

SEQ ID NO: 362
CAAGCAGAAGACGGCATACGAGATCACTTAGTGGGTCTCGTGGGCTCGGA
GATG

SEQ ID NO: 363
CAAGCAGAAGACGGCATACGAGATCACCAAGACTGTCTCGTGGGCTCGGA
GATG

SEQ ID NO: 364
CAAGCAGAAGACGGCATACGAGATCACGTGATCAGTCTCGTGGGCTCGGA
GATG

SEQ ID NO: 365
CAAGCAGAAGACGGCATACGAGATCAGGAAGGATGTCTCGTGGGCTCGGA
GATG

SEQ ID NO: 366
CAAGCAGAAGACGGCATACGAGATCAACCTCTGTGTCTCGTGGGCTCGGA
GATG

-continued

SEQ ID NO: 367
CAAGCAGAAGACGGCATACGAGATCAAAGAAGGCGTCTCGTGGGCTCGGA
GATG

SEQ ID NO: 368
CAAGCAGAAGACGGCATACGAGATCAGTTGACCTGTCTCGTGGGCTCGGA
GATG

SEQ ID NO: 369
CAAGCAGAAGACGGCATACGAGATCACAAGGTCTGTCTCGTGGGCTCGGA
GATG

SEQ ID NO: 370
CAAGCAGAAGACGGCATACGAGATCAGTCATCGAGTCTCGTGGGCTCGGA
GATG

SEQ ID NO: 371
CAAGCAGAAGACGGCATACGAGATCAACATCCTGGTCTCGTGGGCTCGGA
GATG

SEQ ID NO: 372
CAAGCAGAAGACGGCATACGAGATCACCAAGTTGGTCTCGTGGGCTCGGA
GATG

SEQ ID NO: 373
CAAGCAGAAGACGGCATACGAGATGACTCATTGCGTCTCGTGGGCTCGGA
GATG

SEQ ID NO: 374
CAAGCAGAAGACGGCATACGAGATGATGATCGGAGTCTCGTGGGCTCGGA
GATG

SEQ ID NO: 375
CAAGCAGAAGACGGCATACGAGATGATGCGCTTAGTCTCGTGGGCTCGGA
GATG

SEQ ID NO: 376
CAAGCAGAAGACGGCATACGAGATGAGTGTTCCTGTCTCGTGGGCTCGGA
GATG

SEQ ID NO: 377
CAAGCAGAAGACGGCATACGAGATGACTTGTCGAGTCTCGTGGGCTCGGA
GATG

SEQ ID NO: 378
CAAGCAGAAGACGGCATACGAGATGACTCGTCTTGTCTCGTGGGCTCGGA
GATG

SEQ ID NO: 379
CAAGCAGAAGACGGCATACGAGATGAGTGTGACAGTCTCGTGGGCTCGGA
GATG

SEQ ID NO: 380
CAAGCAGAAGACGGCATACGAGATGACTGGTTCTGTCTCGTGGGCTCGGA
GATG

SEQ ID NO: 381
CAAGCAGAAGACGGCATACGAGATGAGCACAACTGTCTCGTGGGCTCGGA
GATG

SEQ ID NO: 382
CAAGCAGAAGACGGCATACGAGATGACATGGCTAGTCTCGTGGGCTCGGA
GATG

-continued

SEQ ID NO: 383
CAAGCAGAAGACGGCATACGAGATGACTCATCAGGTCTCGTGGGCTCGGA
GATG

SEQ ID NO: 384
CAAGCAGAAGACGGCATACGAGATGATGATACGCGTCTCGTGGGCTCGGA
GATG

SEQ ID NO: 385
CAAGCAGAAGACGGCATACGAGATGTGATCCATGGTCTCGTGGGCTCGGA
GATG

SEQ ID NO: 386
CAAGCAGAAGACGGCATACGAGATGTCCGACTATGTCTCGTGGGCTCGGA
GATG

SEQ ID NO: 387
CAAGCAGAAGACGGCATACGAGATGTTTCAGGAGGTCTCGTGGGCTCGGA
GATG

SEQ ID NO: 388
CAAGCAGAAGACGGCATACGAGATGTATCTCGCTGTCTCGTGGGCTCGGA
GATG

SEQ ID NO: 389
CAAGCAGAAGACGGCATACGAGATGTAGCTCCTAGTCTCGTGGGCTCGGA
GATG

SEQ ID NO: 390
CAAGCAGAAGACGGCATACGAGATGTCGCTCTATGTCTCGTGGGCTCGGA
GATG

SEQ ID NO: 391
CAAGCAGAAGACGGCATACGAGATGTGGATTCGTGTCTCGTGGGCTCGGA
GATG

SEQ ID NO: 392
CAAGCAGAAGACGGCATACGAGATGTATGCCAACGTCTCGTGGGCTCGGA
GATG

SEQ ID NO: 393
CAAGCAGAAGACGGCATACGAGATGTGACTATGCGTCTCGTGGGCTCGGA
GATG

SEQ ID NO: 394
CAAGCAGAAGACGGCATACGAGATGTATATGCGCGTCTCGTGGGCTCGGA
GATG

SEQ ID NO: 395
CAAGCAGAAGACGGCATACGAGATGTAGGAGGAAGTCTCGTGGGCTCGGA
GATG

SEQ ID NO: 396
CAAGCAGAAGACGGCATACGAGATGTATGGAAGGGTCTCGTGGGCTCGGA
GATG

SEQ ID NO: 397
CAAGCAGAAGACGGCATACGAGATCTGGTTGTCAGTCTCGTGGGCTCGGA
GATG

SEQ ID NO: 398
CAAGCAGAAGACGGCATACGAGATCTGATGAGACGTCTCGTGGGCTCGGA
GATG

-continued

SEQ ID NO: 399
CAAGCAGAAGACGGCATACGAGATCTTCGTGGATGTCTCGTGGGCTCGGA
GATG

SEQ ID NO: 400
CAAGCAGAAGACGGCATACGAGATCTGGACTAGAGTCTCGTGGGCTCGGA
GATG

SEQ ID NO: 401
CAAGCAGAAGACGGCATACGAGATCTAATGGACGGTCTCGTGGGCTCGGA
GATG

SEQ ID NO: 402
CAAGCAGAAGACGGCATACGAGATCTCTCAGAGTGTCTCGTGGGCTCGGA
GATG

SEQ ID NO: 403
CAAGCAGAAGACGGCATACGAGATCTGGATGTAGGTCTCGTGGGCTCGGA
GATG

SEQ ID NO: 404
CAAGCAGAAGACGGCATACGAGATCTCAAGTGCAGTCTCGTGGGCTCGGA
GATG

SEQ ID NO: 405
CAAGCAGAAGACGGCATACGAGATCTTTAGGTCGGTCTCGTGGGCTCGGA
GATG

SEQ ID NO: 406
CAAGCAGAAGACGGCATACGAGATCTTCTAGCTGGTCTCGTGGGCTCGGA
GATG

SEQ ID NO: 407
CAAGCAGAAGACGGCATACGAGATCTGGTCAGATGTCTCGTGGGCTCGGA
GATG

SEQ ID NO: 408
CAAGCAGAAGACGGCATACGAGATCTGTAGCATCGTCTCGTGGGCTCGGA
GATG

SEQ ID NO: 409
CAAGCAGAAGACGGCATACGAGATTGTCGGTTACGTCTCGTGGGCTCGGA
GATG

SEQ ID NO: 410
CAAGCAGAAGACGGCATACGAGATTGCGGATTGAGTCTCGTGGGCTCGGA
GATG

SEQ ID NO: 411
CAAGCAGAAGACGGCATACGAGATTGAATACGCGGTCTCGTGGGCTCGGA
GATG

SEQ ID NO: 412
CAAGCAGAAGACGGCATACGAGATTGACCAGCTTGTCTCGTGGGCTCGGA
GATG

SEQ ID NO: 413
CAAGCAGAAGACGGCATACGAGATTGCTCGATACGTCTCGTGGGCTCGGA
GATG

SEQ ID NO: 414
CAAGCAGAAGACGGCATACGAGATTGTCAACTGGGTCTCGTGGGCTCGGA
GATG

-continued

SEQ ID NO: 415
CAAGCAGAAGACGGCATACGAGATTGACCGTAGTGTCTCGTGGGCTCGGA
GATG

SEQ ID NO: 416
CAAGCAGAAGACGGCATACGAGATTGCCGGAATTGTCTCGTGGGCTCGGA
GATG

SEQ ID NO: 417
CAAGCAGAAGACGGCATACGAGATTGCGTCTTGTGTCTCGTGGGCTCGGA
GATG

SEQ ID NO: 418
CAAGCAGAAGACGGCATACGAGATTGGAATCCGAGTCTCGTGGGCTCGGA
GATG

SEQ ID NO: 419
CAAGCAGAAGACGGCATACGAGATTGACGATGACGTCTCGTGGGCTCGGA
GATG

SEQ ID NO: 420
CAAGCAGAAGACGGCATACGAGATTGCGTATTCGGTCTCGTGGGCTCGGA
GATG

SEQ ID NO: 421
CAAGCAGAAGACGGCATACGAGATAGAAGTCGAGGTCTCGTGGGCTCGGA
GATG

SEQ ID NO: 422
CAAGCAGAAGACGGCATACGAGATAGAGTGTTGGGTCTCGTGGGCTCGGA
GATG

SEQ ID NO: 423
CAAGCAGAAGACGGCATACGAGATAGCAGGTATCGTCTCGTGGGCTCGGA
GATG

SEQ ID NO: 424
CAAGCAGAAGACGGCATACGAGATAGTATCGGTCGTCTCGTGGGCTCGGA
GATG

SEQ ID NO: 425
CAAGCAGAAGACGGCATACGAGATAGTCTCCGATGTCTCGTGGGCTCGGA
GATG

SEQ ID NO: 426
CAAGCAGAAGACGGCATACGAGATAGCACACATGGTCTCGTGGGCTCGGA
GATG

SEQ ID NO: 427
CAAGCAGAAGACGGCATACGAGATAGCCACTTCTGTCTCGTGGGCTCGGA
GATG

SEQ ID NO: 428
CAAGCAGAAGACGGCATACGAGATAGGAGTCTCTGTCTCGTGGGCTCGGA
GATG

SEQ ID NO: 429
CAAGCAGAAGACGGCATACGAGATAGCATACCACGTCTCGTGGGCTCGGA
GATG

SEQ ID NO: 430
CAAGCAGAAGACGGCATACGAGATAGAAGGACACGTCTCGTGGGCTCGGA
GATG

-continued

SEQ ID NO: 431
CAAGCAGAAGACGGCATACGAGATAGGAATCGTGGTCTCGTGGGCTCGGA
GATG

SEQ ID NO: 432
CAAGCAGAAGACGGCATACGAGATAGTCAGGCTTGTCTCGTGGGCTCGGA
GATG

SEQ ID NO: 433
CAAGCAGAAGACGGCATACGAGATTCTAGAGCTCGTCTCGTGGGCTCGGA
GATG

SEQ ID NO: 434
CAAGCAGAAGACGGCATACGAGATTCGTGTCTGAGTCTCGTGGGCTCGGA
GATG

SEQ ID NO: 435
CAAGCAGAAGACGGCATACGAGATTCGCATGTCTGTCTCGTGGGCTCGGA
GATG

SEQ ID NO: 436
CAAGCAGAAGACGGCATACGAGATTCAATGCCTCGTCTCGTGGGCTCGGA
GATG

SEQ ID NO: 437
CAAGCAGAAGACGGCATACGAGATTCGATCGTACGTCTCGTGGGCTCGGA
GATG

SEQ ID NO: 438
CAAGCAGAAGACGGCATACGAGATTCACCAATGCGTCTCGTGGGCTCGGA
GATG

SEQ ID NO: 439
CAAGCAGAAGACGGCATACGAGATTCGCTGGATTGTCTCGTGGGCTCGGA
GATG

SEQ ID NO: 440
CAAGCAGAAGACGGCATACGAGATTCTGGCTATCGTCTCGTGGGCTCGGA
GATG

SEQ ID NO: 441
CAAGCAGAAGACGGCATACGAGATTCAACGGTCAGTCTCGTGGGCTCGGA
GATG

SEQ ID NO: 442
CAAGCAGAAGACGGCATACGAGATTCGTACTCTCGTCTCGTGGGCTCGGA
GATG

SEQ ID NO: 443
CAAGCAGAAGACGGCATACGAGATTCCGTGTACTGTCTCGTGGGCTCGGA
GATG

SEQ ID NO: 444
CAAGCAGAAGACGGCATACGAGATTCTGAAGACGGTCTCGTGGGCTCGGA
GATG

SEQ ID NO: 445
CAAGCAGAAGACGGCATACGAGATACCTTCCGTAGTCTCGTGGGCTCGGA
GATG

SEQ ID NO: 446
CAAGCAGAAGACGGCATACGAGATACCACAAGTCGTCTCGTGGGCTCGGA
GATG

-continued

SEQ ID NO: 447
CAAGCAGAAGACGGCATACGAGATACCGGTCATAGTCTCGTGGGCTCGGA
GATG

SEQ ID NO: 448
CAAGCAGAAGACGGCATACGAGATACACGCCTAAGTCTCGTGGGCTCGGA
GATG

SEQ ID NO: 449
CAAGCAGAAGACGGCATACGAGATACTGAGCTAGGTCTCGTGGGCTCGGA
GATG

SEQ ID NO: 450
CAAGCAGAAGACGGCATACGAGATACTAATGCCGGTCTCGTGGGCTCGGA
GATG

SEQ ID NO: 451
CAAGCAGAAGACGGCATACGAGATACGATACTGGGTCTCGTGGGCTCGGA
GATG

SEQ ID NO: 452
CAAGCAGAAGACGGCATACGAGATACAACAGGACGTCTCGTGGGCTCGGA
GATG

SEQ ID NO: 453
CAAGCAGAAGACGGCATACGAGATACATCCGGTAGTCTCGTGGGCTCGGA
GATG

SEQ ID NO: 454
CAAGCAGAAGACGGCATACGAGATACAAGCGCATGTCTCGTGGGCTCGGA
GATG

SEQ ID NO: 455
CAAGCAGAAGACGGCATACGAGATACACTGAGGTGTCTCGTGGGCTCGGA
GATG

SEQ ID NO: 456
CAAGCAGAAGACGGCATACGAGATACGTAGAGCAGTCTCGTGGGCTCGGA
GATG

SEQ ID NO: 457
CAAGCAGAAGACGGCATACGAGATCATTCCAAGGGTCTCGTGGGCTCGGA
GATG

SEQ ID NO: 458
CAAGCAGAAGACGGCATACGAGATCACCTTCCTTGTCTCGTGGGCTCGGA
GATG

SEQ ID NO: 459
CAAGCAGAAGACGGCATACGAGATCAGCAATTCGGTCTCGTGGGCTCGGA
GATG

SEQ ID NO: 460
CAAGCAGAAGACGGCATACGAGATCATCGTAGTCGTCTCGTGGGCTCGGA
GATG

SEQ ID NO: 461
CAAGCAGAAGACGGCATACGAGATCATTCAGCCTGTCTCGTGGGCTCGGA
GATG

SEQ ID NO: 462
CAAGCAGAAGACGGCATACGAGATCAAGGAACCTGTCTCGTGGGCTCGGA
GATG

-continued

SEQ ID NO: 463
CAAGCAGAAGACGGCATACGAGATCAAGTTCGTCGTCTCGTGGGCTCGGA
GATG

SEQ ID NO: 464
CAAGCAGAAGACGGCATACGAGATCAGTCAGTTGGTCTCGTGGGCTCGGA
GATG

SEQ ID NO: 465
CAAGCAGAAGACGGCATACGAGATCAAGGATCTGGTCTCGTGGGCTCGGA
GATG

SEQ ID NO: 466
CAAGCAGAAGACGGCATACGAGATCAAAGCACTGGTCTCGTGGGCTCGGA
GATG

SEQ ID NO: 467
CAAGCAGAAGACGGCATACGAGATCATCCGAGTTGTCTCGTGGGCTCGGA
GATG

SEQ ID NO: 468
CAAGCAGAAGACGGCATACGAGATCATGAACCTGGTCTCGTGGGCTCGGA
GATG

SEQ ID NO: 469
CAAGCAGAAGACGGCATACGAGATGAGCCATAACGTCTCGTGGGCTCGGA
GATG

SEQ ID NO: 470
CAAGCAGAAGACGGCATACGAGATGATTGGACGTGTCTCGTGGGCTCGGA
GATG

SEQ ID NO: 471
CAAGCAGAAGACGGCATACGAGATGATTCCTGTGGTCTCGTGGGCTCGGA
GATG

SEQ ID NO: 472
CAAGCAGAAGACGGCATACGAGATGAGCACGTAAGTCTCGTGGGCTCGGA
GATG

SEQ ID NO: 473
CAAGCAGAAGACGGCATACGAGATGACATCTACGGTCTCGTGGGCTCGGA
GATG

SEQ ID NO: 474
CAAGCAGAAGACGGCATACGAGATGATACTGCGTGTCTCGTGGGCTCGGA
GATG

SEQ ID NO: 475
CAAGCAGAAGACGGCATACGAGATGATATGGCAGGTCTCGTGGGCTCGGA
GATG

SEQ ID NO: 476
CAAGCAGAAGACGGCATACGAGATGAACAGCAACGTCTCGTGGGCTCGGA
GATG

SEQ ID NO: 477
CAAGCAGAAGACGGCATACGAGATGAGTTAGACGGTCTCGTGGGCTCGGA
GATG

SEQ ID NO: 478
CAAGCAGAAGACGGCATACGAGATGATTGCCACTGTCTCGTGGGCTCGGA
GATG

-continued

SEQ ID NO: 479
CAAGCAGAAGACGGCATACGAGATGATTCGTTGGGTCTCGTGGGCTCGGA

GATG

SEQ ID NO: 480
CAAGCAGAAGACGGCATACGAGATGAAGCTTGAGGTCTCGTGGGCTCGGA

GATG

2. The following thermal cycling conditions were used for amplifying full length adapters on the multivalent core:
   1. 98° C. for 30 sec
   2. 98° C. for 5 sec
   3. 62° C. for 10 sec
   4. 72° C. for 20 sec
   5. Cycled to step 2 for 11 more times
   6. 72° C. for 2 min
   7. Held at 10° C.

Figure 8:
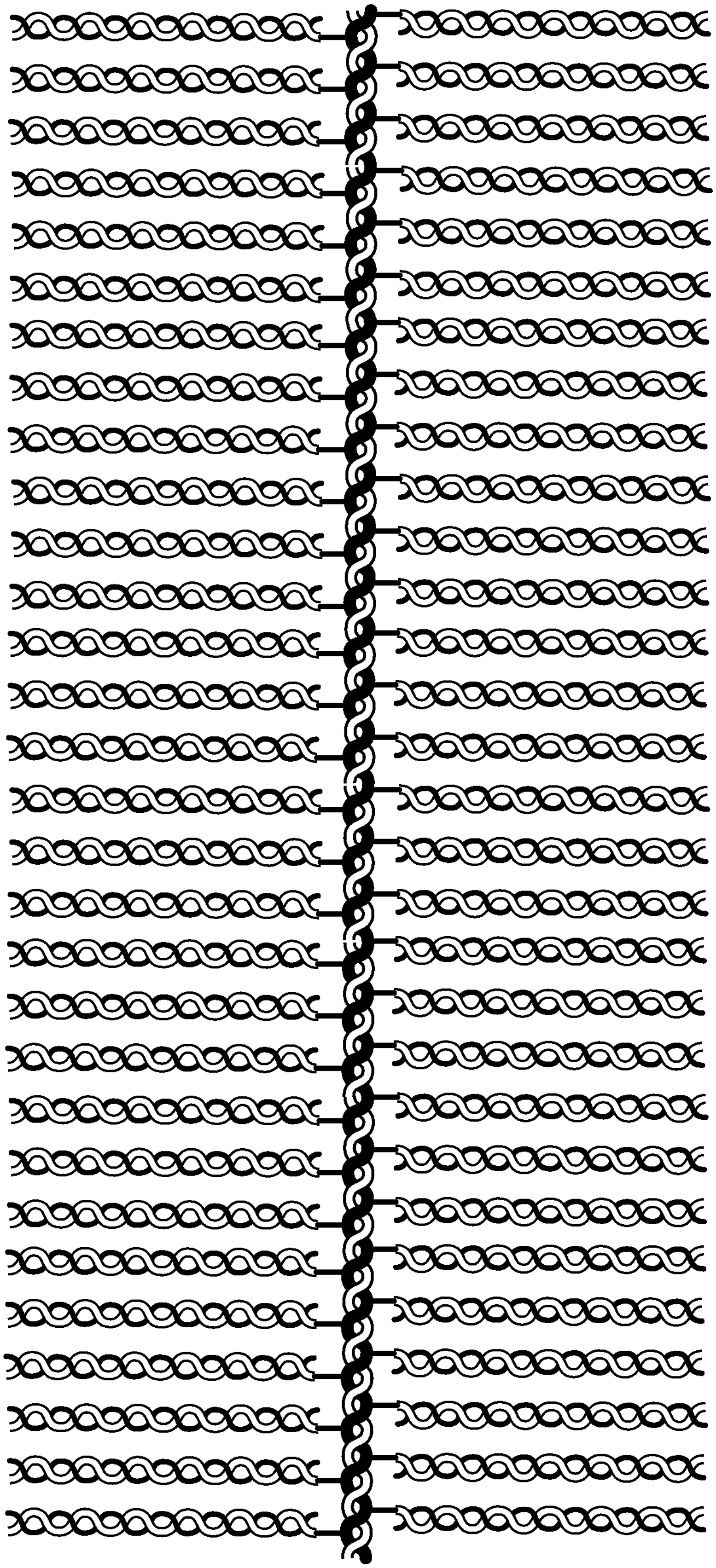
FIG. 8 illustrates the scaffolded product of anchored PCR used for making TSC scaffolds.

FIG. 8 shows a schematic representation of resulting 80 bp TAG1 adapters covalently attached to the multivalent core through the PCR. The tethered TAG1 adapters also carried the Illumina P7 primer sequence (5'-CAAGCAGAAGACGGCATACGAG (SEQ ID NO: 487)), which later permitted library amplification and cluster formation on Illumina sequencing flow cells.

3. After PCR, each reaction (n=480) was then diluted to 100 μl in a final concentration of 0.25× Exonuclease Reaction Buffer (New England Biolabs), 5 mM magnesium chloride, and 0.04 units/μl of exonuclease I enzyme (New England Biolabs) to digest the unincorporated primers.
4. Then the exonuclease I digestions were incubated at 37° C. for 15 min; at 80° C. for 20 min to heat-inactivate the enzyme, and then finally, at 60 C for 10 min.
5. A subset of exonuclease I-digested PCR reactions were electrophoresed on agarose gels, and quantified by PicoGreen assay (Thermo) to determine the amount of dsDNA (i.e., full length adapter) that was amplified on the multivalent core.
6. Then was added 90 μl from each exonuclease I digest to a separate well of a MultiScreen PCRμ96 ultrafiltration plate (Millipore).
7. The above reaction was filtered on the MultiScreen vacuum manifold until the wells appeared empty, and then added 90 μl of 10 mM Tris-HCl, pH 8.0.
8. Filtered again until the wells were empty.
9. Resuspended each purified digest in 60 μl of 10 mM Tris-HCl, pH 8.0.
10. Transferred 50 μl from each well of the MultiScreen PCRμ96 ultrafiltration plate to a clean 96-well PCR plate.
11. Diluted each reaction to a final volume of 55 μl containing a final concentration of 0.3× exonuclease I buffer and 0.09 units/μl of lambda exonuclease enzyme (New England Biolabs).
12. Incubated the lambda exonuclease digest at 37° C. for 30 min to make the adapters on the multivalent core single-stranded, and then at 75° C. for 10 min to inactivate the lambda exonuclease.
13. Added 32.3 fmol of TNS.MEDS.UNIV oligonucleotide (5'-P-CTGTCTCTTATACACATCT (SEQ ID NO: 488)) to the ssDNA on the multivalent core in a final volume of 60 μl of 80 mM Tris-HCl, pH 8.0 and 10 mM EDTA.
14. Denatured the mixture at 95° C. for 2 min, and then cooled slowly to room temperature to anneal TNS.MEDS.UNIV oligonucleotide to the single-stranded adapters on the multivalent core.

Formation of Tethered Synaptic Complexes (TSCs) on the Multivalent Core:

1. In five 96-well PCR plates (n=480 wells), 1.5 pmol of Tn5 transposase was combined with 0.65 pmol of tethered adapters (on the multivalent core) in 1× transposase binding buffer (130 mM NaCl; 12.5 mM Tris-HCl, pH 8.0; 7.5% glycerol; 7.5% DMSO; 0.05% Triton X-100; 10.7 mM $CaCl_2$); 12.9 ng/μl acetylated bovine serum albumin) in a total volume of 95 μl, and incubated at room temperature for one hour to form synaptic complexes tethered to each multivalent core.
2. Pooled equal volumes of each tethered synaptic complex (n=480) into a single tube.

Use of Tethered Synaptic Complexes (TSCs) to Prepare Libraries:

1. In one well of an 8-well PCR strip tube (USA Scientific), added 1 fmol of pooled tethered synaptic complexes (n=480) to 1 ng of human DNA in a volume of 20 μl of 1× reaction buffer.
2. Incubated at 37° C. for 9 hours.
3. Added 125 fmol of T2T (untethered synaptic complexes carrying Illumina P5 primer sequence (5'-AATGATACGGCGACCACCGAG (SEQ ID NO: 489)) to permit library amplification and cluster formation on Illumina sequencing flow cells). The full length sequence of single-stranded T2T was (5'-AATGATACGGCGACCACCGAGATCTACACACACAGCTTCGTCGGCAGCGTCAGATGTGT ATAAGAGACAG (SEQ ID NO: 490)), and was annealed to TNS.MEDS.UNIV oligonucleotide (5'-P-CTGTCTCTTATACACATCT (SEQ ID NO: 491)) before addition of Tn5 transposase to form synaptic complexes.
4. After adding T2T, incubated at 55° C. for 15 min; and then held at 25° C. for 5 min.
5. Added 11.6 μl of a stop solution containing 1% SDS and 75 mM EDTA (pH 8); and then heat-inactivated the T2T reaction at 68° C. for 10 min.
6. Diluted the stopped T2T reaction to 50 μl with ultrapure water.
7. Added 40 μl of room temperature MAGwise magnetic beads (seqWell), and mixed thoroughly by pipetting.
8. Incubated for 5 min at room temperature to bind DNA fragments to magnetic beads.
9. Collected magnetic beads on the inner wall of the container by placing the 8-well PCR strip on a 96S Super Magnet plate (Alpaqua) for 3 min.
10. While the 8-well PCR strip remained on the magnet plate, pipetted off the supernatant fluid, and discarded.
11. Gently washed the bead pellet twice with 120 μl of 80% ethanol while the 8-well PCR strip remained on the magnet plate, and removed the supernatant fluid by pipetting after each wash.
12. After air-drying the bead pellet for 5 min, thoroughly resuspended the beads in 25 μl of 10 mM Tris-HCl, pH 8.0.
13. Added 25 μl of Kapa HiFi HotStart 2× ReadyMix (Kapa Biosystems), and mixed thoroughly with resuspended beads by pipetting.
14. Incubated at 72° C. for 10 min to fill-in the termini of the library fragments, and then at 95° C. to denature the library fragments.

15. While the sample was denaturing at 95° C., added 2 μl of 10 μM P5 primer (5'-AATGATACGGCGACCACCGAG (SEQ ID NO: 492)) and 2 μl of 10 μM P7 primer (5'-CAAGCAGAAGACGGCATACGAG (SEQ ID NO: 493)) to the reaction.
16. Amplified library for 18 cycles of PCR using the following thermal cycling conditions:
    1. 95° C. for 3 min
    2. 98° C. for 20 sec
    3. 64° C. for 45 sec
    4. 72° C. for 30 sec
    5. Cycled to step 2 for 17 more times
    6. 72° C. for 2 min
    7. Held at 4° C.
17. Diluted to 100 μl with ultrapure water and transferred to a clean 1.5 ml LoBind tube (Eppendorf).
18. Added 77.5 μl of room temperature MAGwise magnetic beads (seqWell), and mixed thoroughly by pipetting.
19. Incubated for 5 min at room temperature to bind DNA to magnetic beads.
20. Collected magnetic beads on inner wall of tube by placing the 8-well PCR strip on a magnetic tube rack for 3 min.
21. While still in the magnetic tube rack, pipetted off the supernatant fluid, and discarded.
22. Gently washed the bead pellet twice with 400 μl of 80% ethanol while on the magnetic tube rack, and discarded the supernatant fluid after each wash.
23. After air-drying for 5 min, removed the tube from the magnetic tube rack, and resuspended the magnetic beads in 28 μl of 10 mM Tris-HCl, pH 8.0.
24. Eluted for 5 min at room temperature.
25. Returned the tube to the magnetic tube rack and waited 3 min to pellet the magnetic beads.
26. Transferred the purified library (eluate) to a clean 1.5 ml LoBind tube.
27. Repeated steps 17-26.
28. Denatured and diluted the purified library for loading on the Illumina NextSeq 500 sequencing platform according to the manufacturer's instructions.

Use of Tethered Synaptic Complexes (TSCs) to Prepare Libraries and Determining the Distance Between Linked Transposition Events:

Human genomic DNA (1.5 ng) was incubated for 30 minutes at 37° C. with approximately 300 fmol of tethered synaptic complexes (TSCs) carrying 5,637 unique i7 barcodes. The reaction was purified using MAGwise paramagnetic beads (seqWell) after heat-inactivation. Next, the purified TSC-treated DNA was digested for 30 minutes at 37° C. with 30 units of truncated exonuclease VIII (New England Biolabs) and 20 units exonuclease I (New England Biolabs). After heat-inactivation, the exonuclease digest was split into 112 separate tagging reactions, which added 112 unique i5 barcodes. Next, the 112 tagging reactions were pooled and purified after heat-inactivation. Thus, the total number of possible barcode combinations was 631,344 (5,637×112). The pooled, purified tagging reactions were PCR-amplified (18 cycles) with P5 and P7 primers to generate an NGS library, and then sequenced on an Illumina NextSeq 500 sequencer using paired end dual index chemistry. Sequencing data were obtained from the sequencer and mapped to the hg38 human reference genome using bowtie2, and indices were mapped to the P5 and P7 adapter repertoire. Mapping coordinates were calculated and used to infer distances between reads having the same barcode for the purpose of identifying linked/phased reads.

Results

Figure 1:
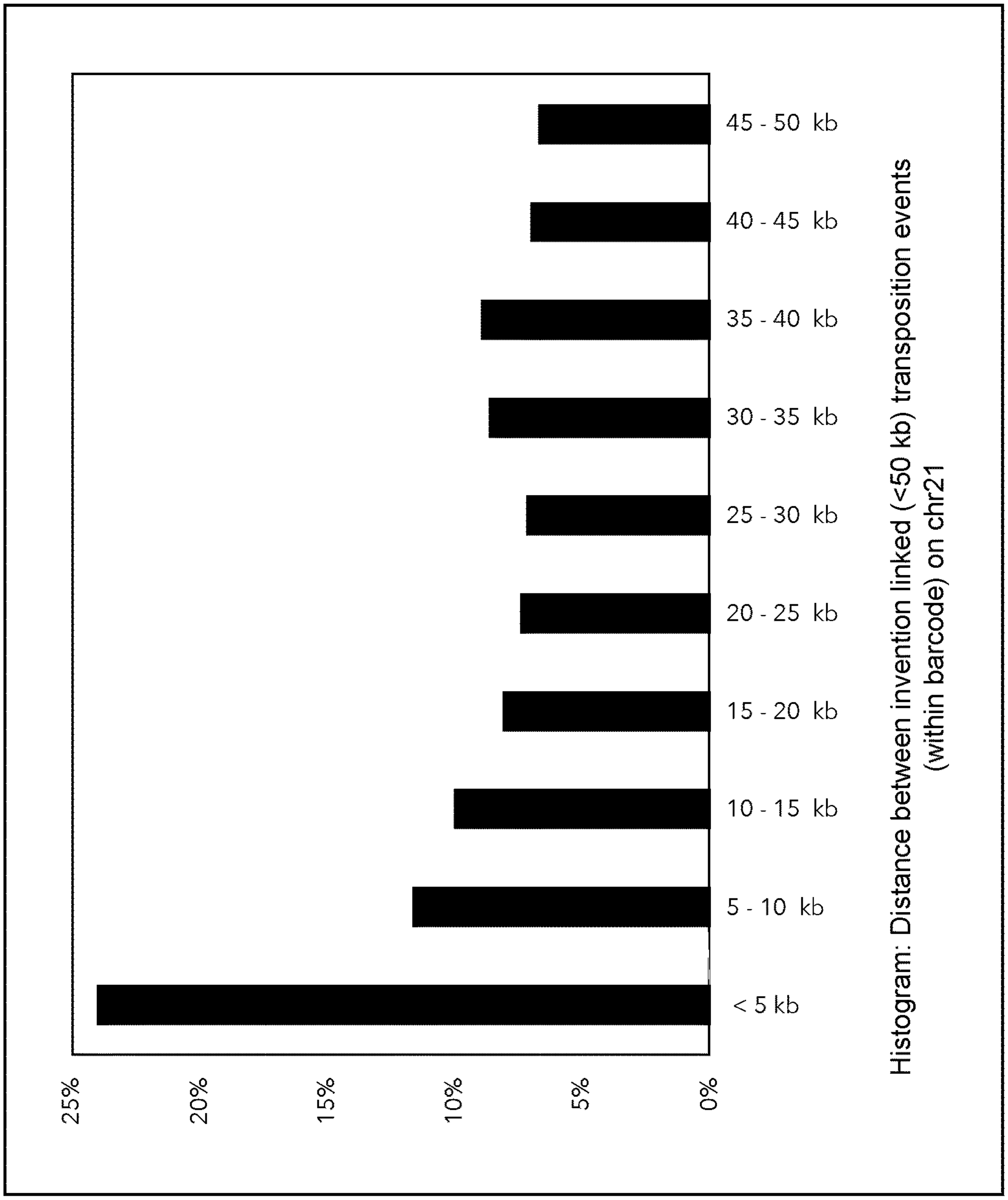
FIG. 1 shows the distribution of distances between adjacent transposition sites on a known reference sample (NA12878 human gDNA) for reads produced by barcoded tethered synaptic complexes (TSCs).
Figure 2:
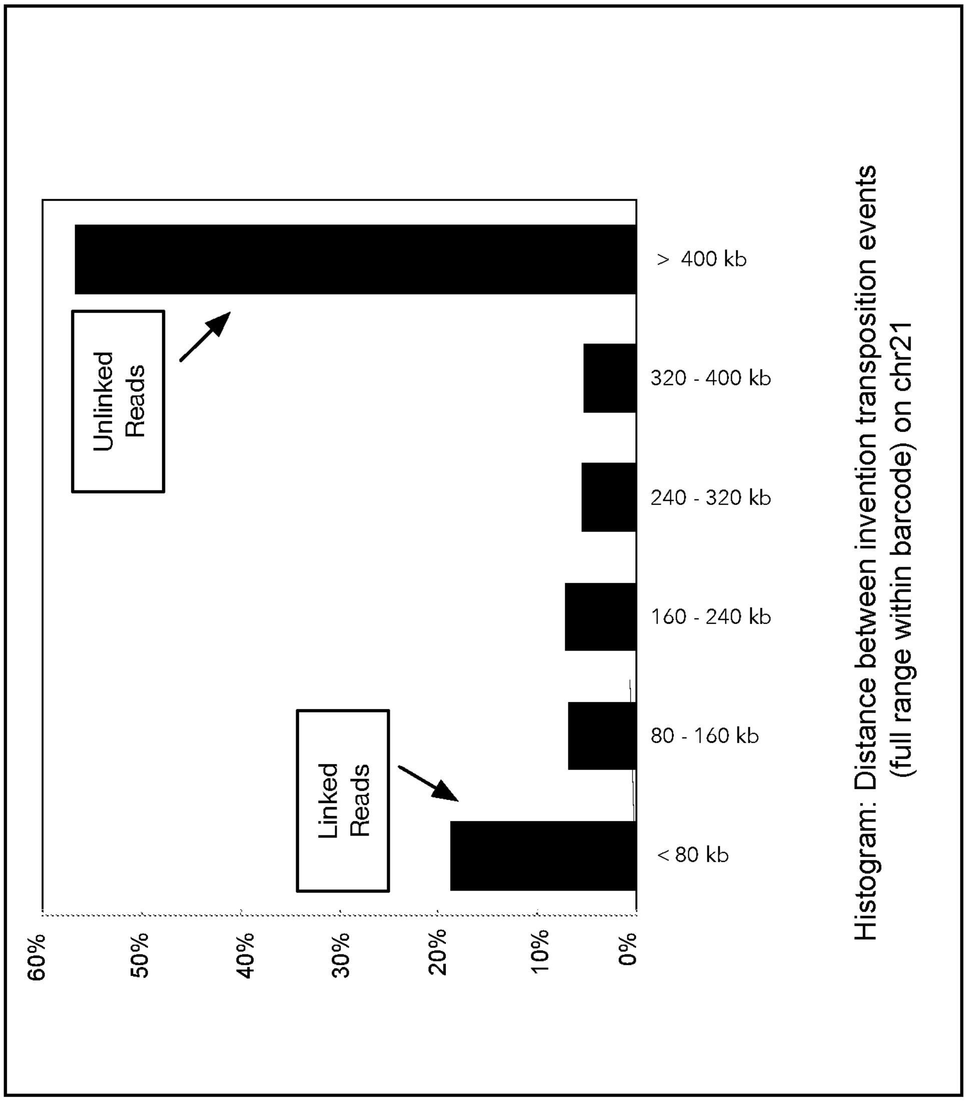
FIG. 2 shows the distribution of adjacent transposition site distances between reads derived by transposition on the same TSC scaffold (linked) versus non-same TSC scaffold (non-linked).
Figure 3:
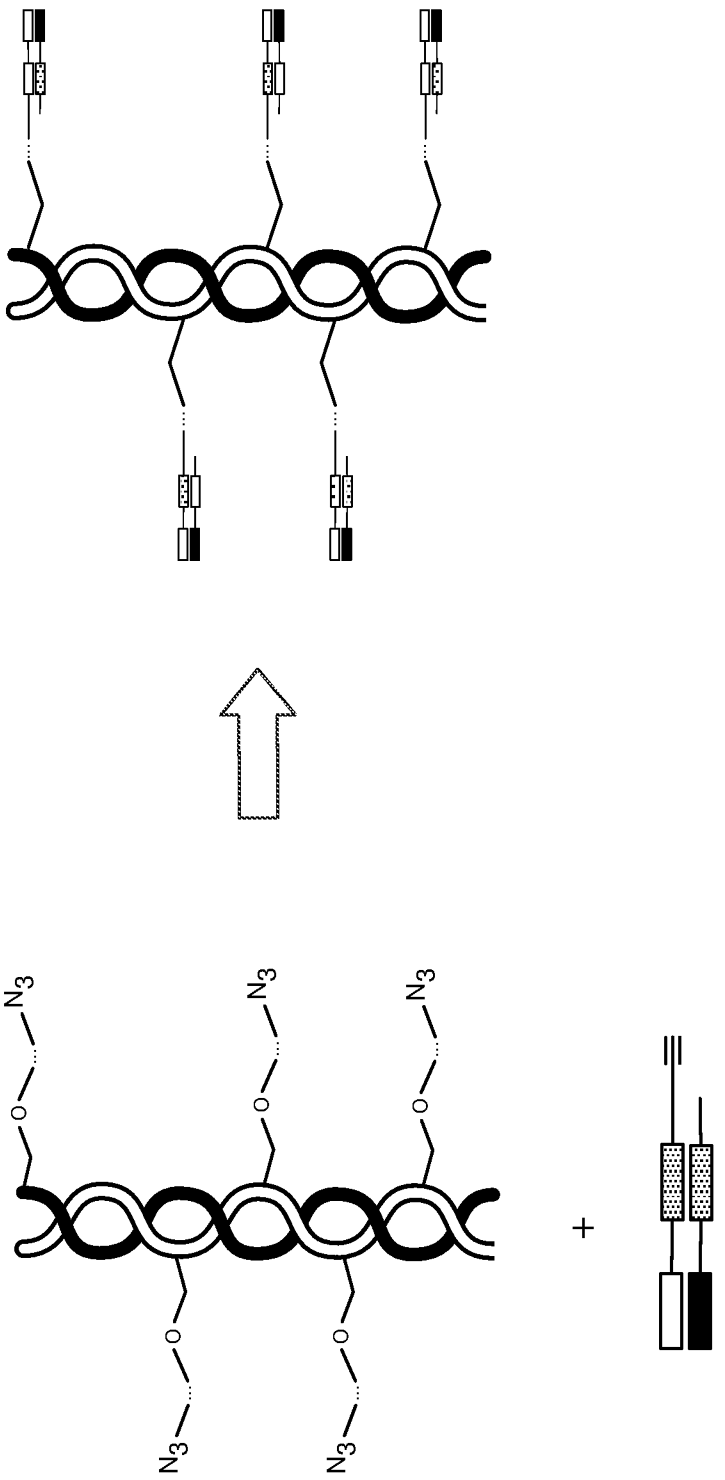
FIG. 3 illustrates a means by which alkynyl-modified TBS-containing adapters are covalently attached to a nucleic acid scaffold having azide modification via click chemistry.
Figure 4:
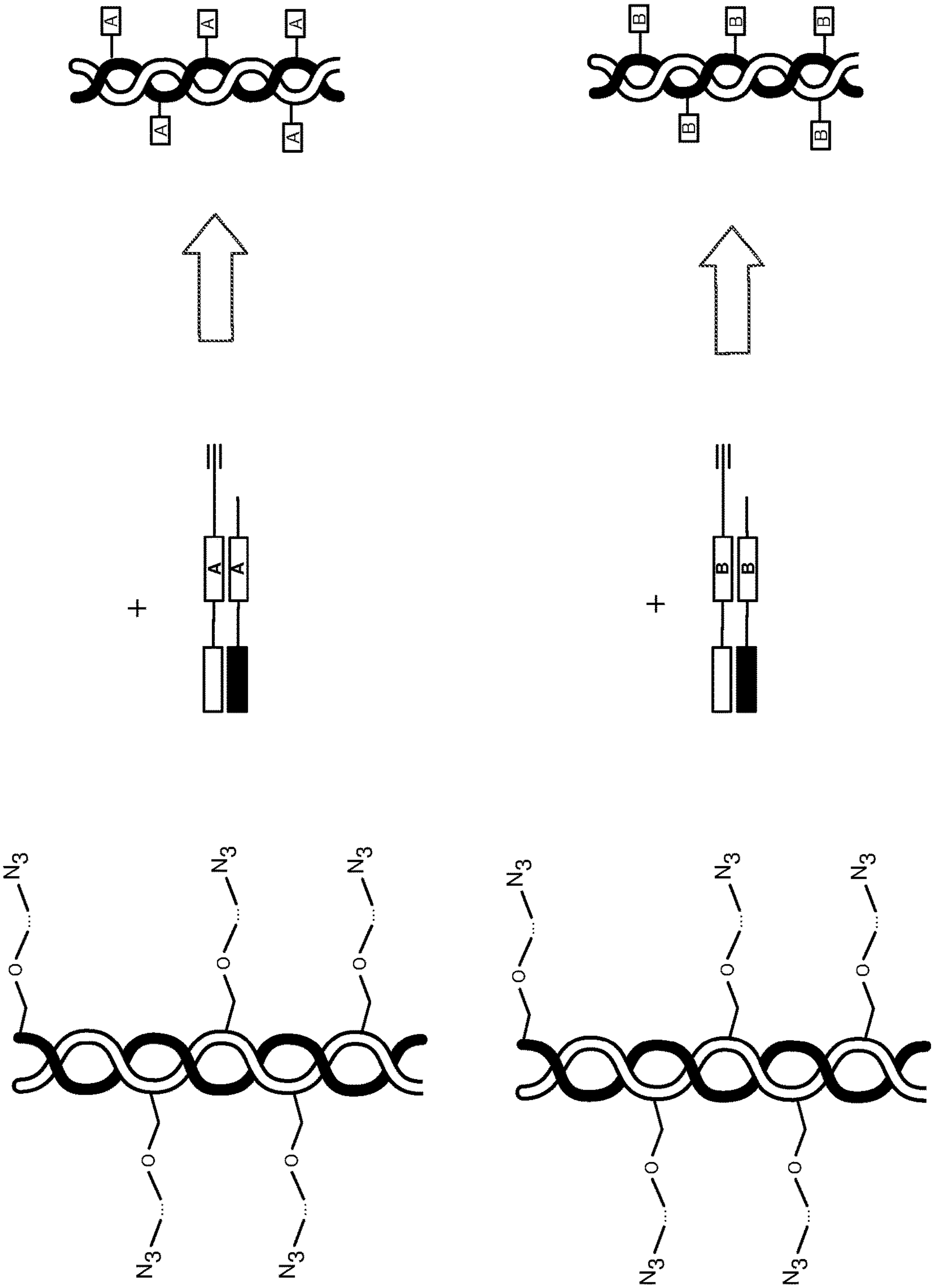
FIG. 4 illustrates the means by which differently-barcoded TSC scaffolds can be produced in the manner of FIG. 3.

Transposase activity semi-randomly inserted barcoded reads from TSCs into discrete target DNA regions where linked reads were identified after sequencing. Linked reads derived from the same target DNA molecule carried the same barcode and typically mapped together at distances of less than 50,000 bp on human genomic reference DNA (FIG. 1). Unlinked reads carried different barcodes or the same the barcode, but when unlinked reads carried the same barcode they were typically separated by 100-1000-fold greater mapping distances than were the linked reads with the same barcodes (FIG. 2).

Figure 16:
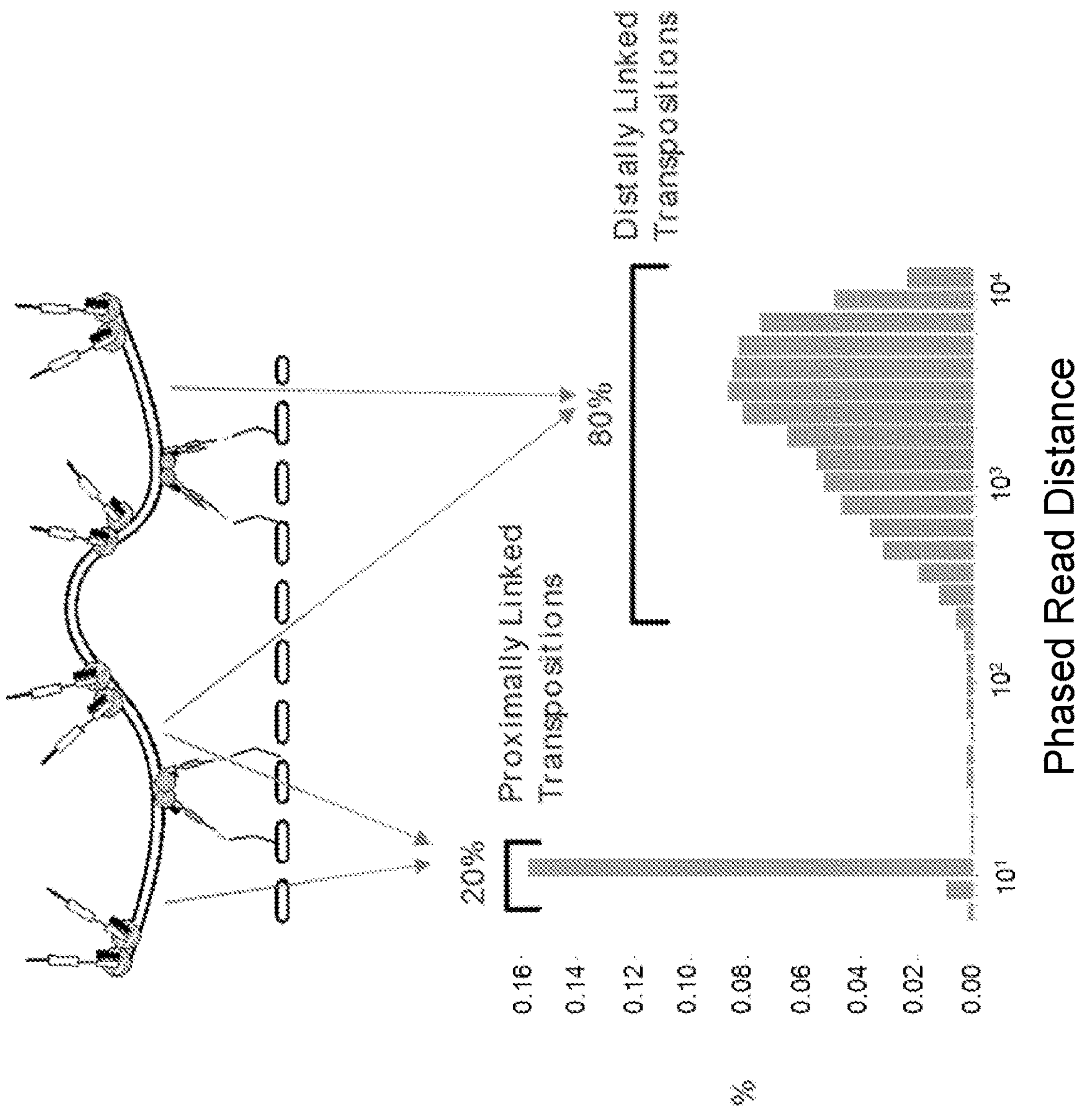
FIG. 16 illustrates the molecular structure of a tethered synaptic complex polymer. Barcoded oligonucleotide adapter molecules are covalently attached to a synthetic scaffold, and transposase proteins are then loaded onto this synthetic structure to create multiple co-bound synaptic complexes. The bottom panel is a graph showing the percentage of transposition events according to the phased read distance. Approximately 20% of the transposition events are proximally linked, and about 80% of the transposition events are distally linked.
Figure 18:
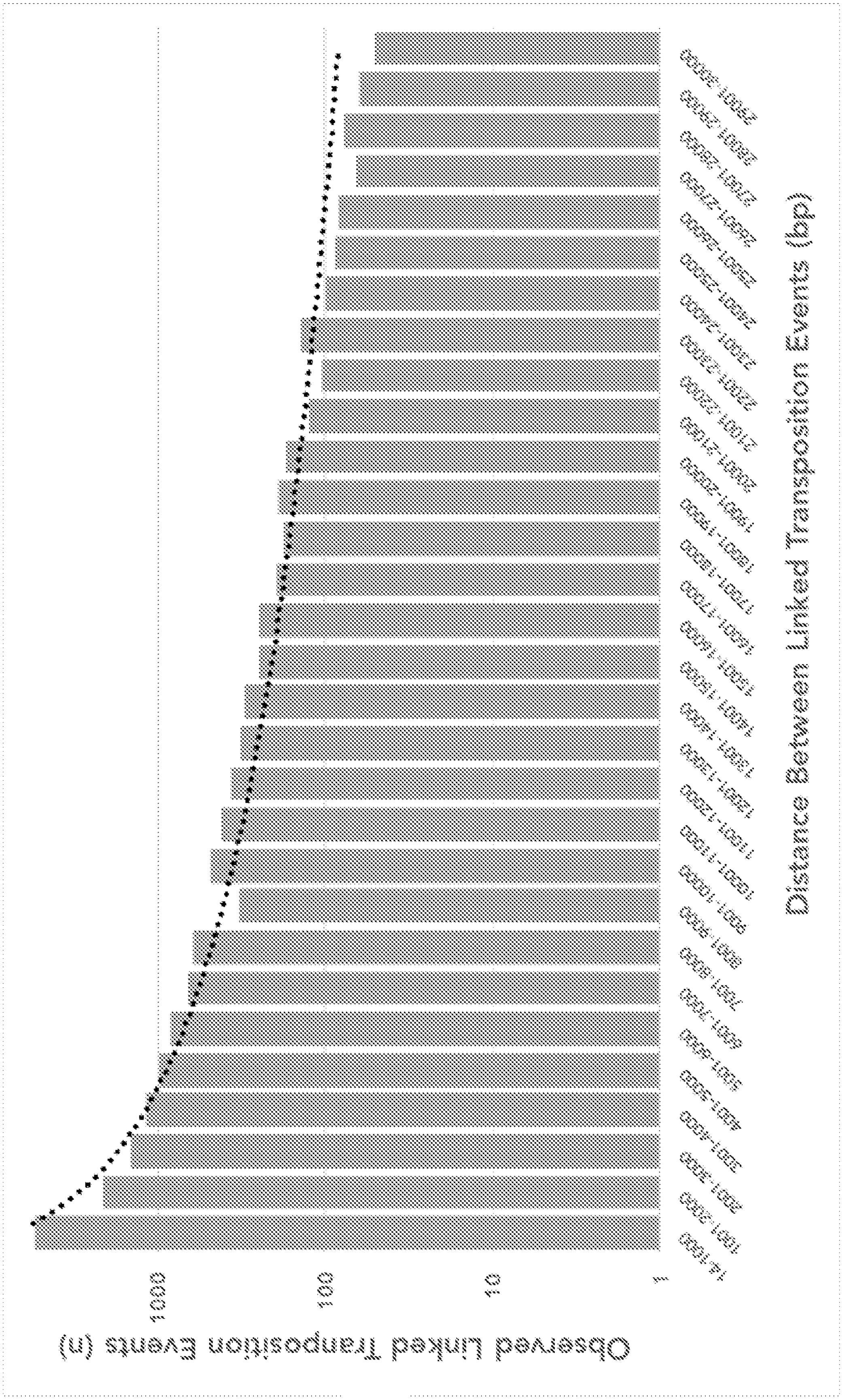
FIG. 18 illustrates the number of observed linked transposition events produced by scaffolded transposition on a human target DNA as a function of the mapping distance (bp) between the linked transposition events.
Figure 19:
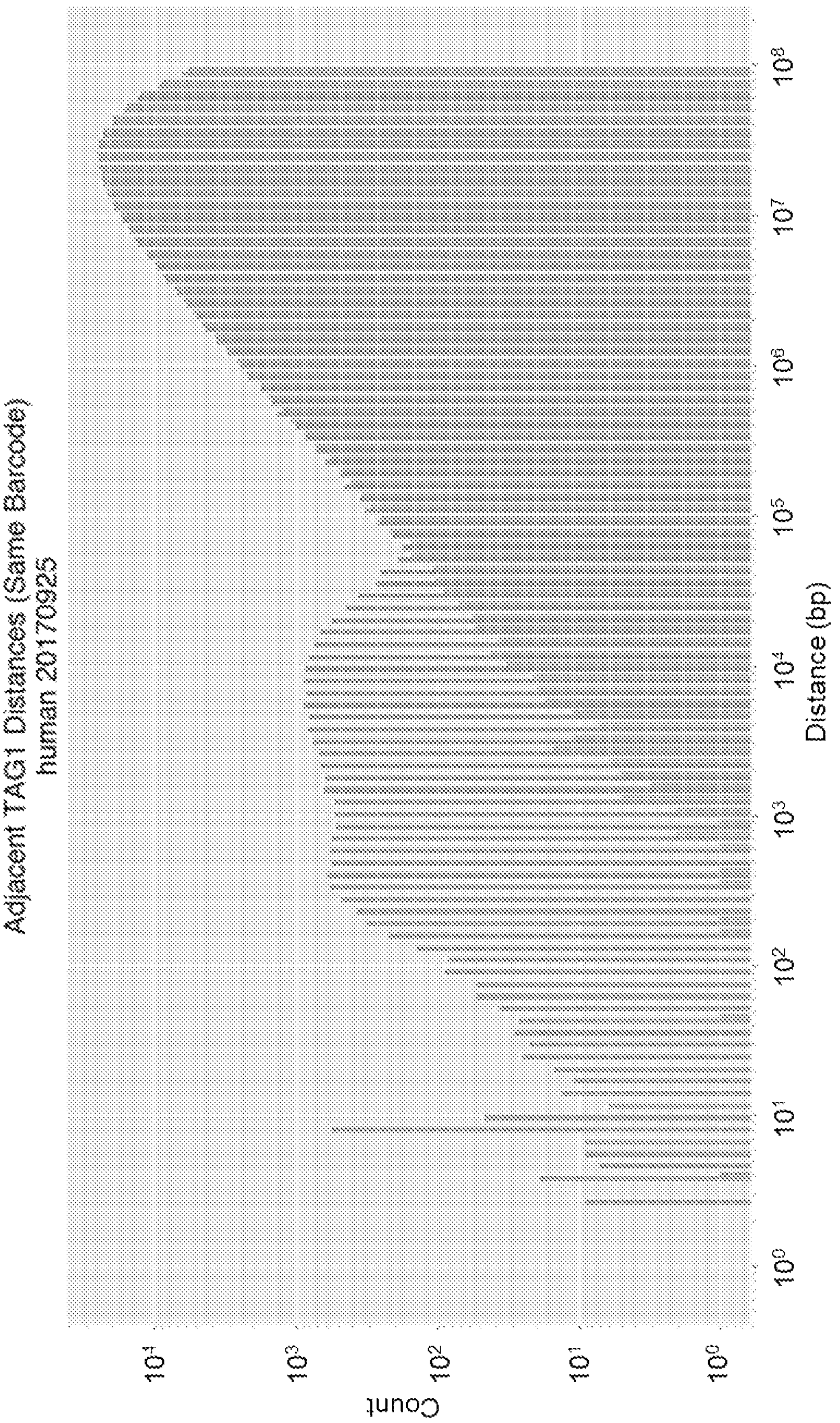
FIG. 19 illustrates the number of transposition events on human target DNA (dark gray bars) as a function of the mapping distance (bp) to the nearest transposition event with the same barcode, as compared to an analysis of the same data set after the barcodes were subjected to random permutation (light gray bars).

Sequencing of a library generated using human DNA treated with TSCs was performed to evaluate the distance between reads with identical barcodes (FIG. 16). Approximately 20% of the transposition events were considered proximally linked, and approximately 80% of the transposition events were considered distally linked. The number of observed transposition events that were linked in a data set as a function of distance is shown in FIG. 18. The number of transposition events on human target DNA as a function of mapping distance to the nearest transposition event with the same barcode, as compared to an analysis of the same data set after the barcodes were subjected to random permutation is shown in FIG. 19. A distinct peak was observed at approximately $10^2$ to $10^4$ bp that was separate from the background as assessed by the random permutation (peak at about $10^7$ to $10^8$ bp).

What is claimed is:

1. A multivalent transposase reagent comprising:
(a) a branched, water soluble multivalent core comprising three linkage sites;
(b) a first artificial nucleic acid comprising a first end comprising a double-stranded transposase binding site (TBS) and a second end covalently or non-covalently linked to a first one of the three linkage sites;
(c) a second artificial nucleic acid comprising a first end comprising a double-stranded TBS and a second end covalently or non-covalently linked to a second one of the three linkage sites; and
(d) a third artificial nucleic acid comprising a first end comprising a double-stranded TBS and a second end covalently or non-covalently linked to a third one of the three linkage sites,
wherein each TBS is transposable.

2. The reagent of claim 1, wherein the first, second, or third artificial nucleic acid is linked to the branched water, soluble multivalent core by a covalent bond resulting from a conjugation reaction.

3. The reagent of claim 2, wherein the conjugation reaction is selected from the group consisting of an azide-alkyne Huisgen cycloaddition, amide or thioamide bond formation, a pericyclic reaction, a Diels-Alder reaction, sulfonamide bond formation, alcohol or phenol alkylation, a condensation reaction, disulfide bond formation, and a nucleophilic substitution.

4. The reagent of claim 1, wherein the first, second, or third artificial nucleic acid is linked non-covalently to the branched, water soluble multivalent core.

5. The reagent of claim 4, wherein the first, second, or third artificial nucleic acid is linked to the branched, water soluble multivalent core by an affinity binding pair.

6. The reagent of claim 1, further comprising a fourth linkage site in the branched water soluble multivalent core and a fourth artificial nucleic acid comprising a first end comprising a transposable, double-stranded TBS and a second end covalently or non-covalently linked to the branched water soluble multivalent core via the fourth linkage site.

7. The reagent of claim 1, further comprising a plurality of additional linkage sites in the branched, water soluble multivalent core and a plurality of additional artificial nucleic acids, each additional artificial nucleic acid comprising a first end comprising a transposable, double-stranded TBS and a second end covalently or non-covalently linked to the branched, water soluble multivalent core via a corresponding linkage site, and each additional artificial nucleic acid being linked to the branched, water soluble multivalent core via the plurality of additional linkage sites.

8. The reagent of claim 1, wherein the branched, water soluble multivalent core is a polymer, a nucleic acid, a peptide, a polypeptide, or a protein.

9. The reagent of claim 8, wherein:

(i) the branched, water soluble multivalent core is a polymer; or (ii) the branched, water soluble multivalent core is a polymer, and the polymer is a polyethylene glycol (PEG)-based polymer.

10. The reagent of claim 9, wherein:

(i) the branched polymer is a star-shaped polymer, a comb polymer, a brush polymer, a hyperbranched polymer, or a dendrimer; or (ii) the PEG-based polymer is a PEG dendrimer or a multi-arm PEG.

11. The reagent of claim 1, wherein each of the first, second, and third artificial nucleic acids of the reagent comprises an identifiable sequence tag (IST).

12. A method of sequencing a target nucleic acid, the method comprising:

(a) combining the reagent of claim 1 with a target nucleic acid under conditions and for a time sufficient for the reagent to carry out a transposition event;

(b) fragmenting the target nucleic acid and optionally adding a polynucleotide to the resulting ends of the nucleic acid fragments;

(c) selecting DNA fragments comprising a nucleic acid sequence resulting from the transposition event;

(d) amplifying the selected fragments; and (e) sequencing the amplified fragments.

13. The method of claim 12, wherein:

(i) the fragmenting of (b) comprises tagmentation or random shearing and adapter ligation;

(ii) the selecting of (c) comprises selecting nucleic acid fragments comprising an IST;

(iii) the amplifying of (d) comprises polymerase chain reaction (PCR), multiple displacement amplification (MDA), ligase chain reaction (LCR), loop mediated isothermal amplification (LAMP), rolling circle amplification (RCA), or strand displacement amplification (SDA); and/or (iv) the sequencing of (e) comprises sequencing by synthesis, sequencing by ligation, or nanopore sequencing.

14. The method of claim 12, further comprising:

(f) analyzing the sequenced fragments to identify fragments of the target nucleic acid that can be linked due to the presence of a nucleic acid sequence resulting from the transposition event.

15. The method of claim 12, wherein:

(i) the target nucleic acid comprises genomic DNA or cDNAs from a single cell;

(ii) the target nucleic acid comprises nucleic acids from a plurality of haplotypes;

(iii) the target nucleic acid is crosslinked via histones or chromatin from single or multiple cells;

(iv) the target nucleic acid has been condensed or optionally treated with one or more condensing agents; and/or (v) the sequence of the amplified fragments is used to perform de novo sequence assembly.

16. A kit comprising the reagent of claim 1 and one or more additional reagents.

17. The kit of claim 16, wherein:

(i) the one or more additional reagents is selected from the group consisting of a soluble transposome, a cofactor, a buffered solution, and a reference DNA; and/or (ii) the kit further comprises a reagent for nucleic acid sequencing.

18. A mixture comprising a plurality of the reagents of claim 1.

19. A library produced by combining the reagent of claim 1 with a target nucleic acid under conditions and for a time sufficient for the reagent to carry out a transposition event.

20. The reagent of claim 7, further comprising a plurality of additional transposases bound to the TBSs of the plurality of additional artificial nucleic acids, wherein pairs of the plurality of additional transposases oligomerize to form synaptic complexes.

21. The reagent of claim 1, further comprising first, second, and third transposases bound to the TBS of the first, second, and third artificial nucleic acids.

22. The reagent of claim 8, wherein the branched, water soluble multivalent core comprises a nucleic acid, and the nucleic acid is a DNA.

23. The reagent of claim 22, wherein the DNA is double-stranded.

24. The reagent of claim 8, wherein the branched, water soluble multivalent core is a protein, and the protein is a multimeric protein.

25. The reagent of claim 24, wherein the multimeric protein is avidin or streptavidin.

26. The reagent of claim 11, wherein the IST of each of the first, second, and third artificial nucleic acid is identical.

* * * * *